(12) United States Patent
Djaballah et al.

(10) Patent No.: US 9,562,019 B2
(45) Date of Patent: Feb. 7, 2017

(54) SUBSTITUTED PYRIDAZINES AS EGFR AND/OR KRAS INHIBITORS

(75) Inventors: Hakim Djaballah, Scarsdale, NY (US); Harold E. Varmus, New York, NY (US); David Shum, Forest Hills, NY (US); Romel Somwar, New York, NY (US); Alexander Chucholowski, San Diego, CA (US); Mohan Santhanam Thiruvazhi, San Diego, CA (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 1049 days.

(21) Appl. No.: 12/520,256

(22) PCT Filed: Dec. 21, 2007

(86) PCT No.: PCT/US2007/088543
§ 371 (c)(1),
(2), (4) Date: Sep. 30, 2009

(87) PCT Pub. No.: WO2008/080056
PCT Pub. Date: Jul. 3, 2008

(65) Prior Publication Data
US 2013/0131062 A1      May 23, 2013

Related U.S. Application Data

(60) Provisional application No. 60/871,181, filed on Dec. 21, 2006.

(51) Int. Cl.
| | |
|---|---|
| C07D 237/10 | (2006.01) |
| C07D 237/04 | (2006.01) |
| C07D 307/68 | (2006.01) |
| C07D 307/71 | (2006.01) |
| C07D 307/85 | (2006.01) |
| C07D 307/92 | (2006.01) |
| C07D 401/04 | (2006.01) |
| C07D 403/04 | (2006.01) |
| C07D 403/12 | (2006.01) |
| C07D 405/04 | (2006.01) |
| C07D 405/06 | (2006.01) |
| C07D 405/12 | (2006.01) |
| C07D 405/14 | (2006.01) |
| C07D 409/14 | (2006.01) |
| C07D 471/04 | (2006.01) |
| C07D 495/04 | (2006.01) |
| C07D 401/14 | (2006.01) |

(Continued)

(52) U.S. Cl.
CPC ........... *C07D 237/04* (2013.01); *C07D 307/68* (2013.01); *C07D 307/71* (2013.01); *C07D 307/85* (2013.01); *C07D 307/92* (2013.01); *C07D 401/04* (2013.01); *C07D 401/14* (2013.01); *C07D 403/04* (2013.01); *C07D 403/12* (2013.01); *C07D 405/04* (2013.01); *C07D 405/06* (2013.01); *C07D 405/10* (2013.01); *C07D 405/12* (2013.01); *C07D 405/14* (2013.01); *C07D 409/14* (2013.01); *C07D 413/04* (2013.01); *C07D 417/10* (2013.01); *C07D 471/04* (2013.01); *C07D 495/04* (2013.01)

(58) Field of Classification Search
CPC .................................................. C07D 237/10
USPC ............ 544/238, 224, 114; 514/252.06, 247, 514/252.01; 546/210, 268.1; 548/152, 548/304.4, 518; 549/70, 398, 416, 505
See application file for complete search history.

(56) References Cited

U.S. PATENT DOCUMENTS

| | | |
|---|---|---|
| 3,045,014 A | 7/1962 | Hensel et al. |
| 3,555,026 A | 1/1971 | Reichender et al. |

(Continued)

FOREIGN PATENT DOCUMENTS

| | | |
|---|---|---|
| DE | 14 20 011 B | 6/1959 |
| DE | 14 20 969 A | 10/1968 |

(Continued)

OTHER PUBLICATIONS

Gridelli, et al., The Oncologist 2007;12:840-849.*

(Continued)

*Primary Examiner* — Douglas M Willis
(74) *Attorney, Agent, or Firm* — Choate, Hall, and Stewart LLP; Brenda Herschbach Jarrell

(57) ABSTRACT

The present invention is directed to pyridazinone compounds of formula (I) and furan compounds of formula (II), pharmaceutical compositions of compounds of formula (I) and (II), kits containing these compounds, methods of syntheses, and a method of treatment of a proliferative disease in a subject by administration of a therapeutically effective amount of a compound of formulae (I) or (II). Both classes of compounds were identified through screening of a collection of small molecule libraries.

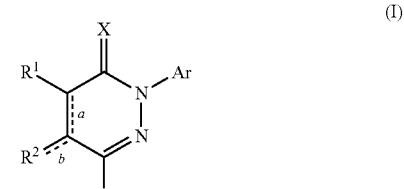

(I)

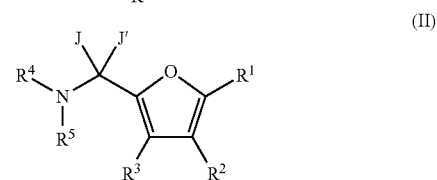

(II)

35 Claims, 39 Drawing Sheets

(51) Int. Cl.
  C07D 405/10       (2006.01)
  C07D 413/04       (2006.01)
  C07D 417/10       (2006.01)

(56) References Cited

U.S. PATENT DOCUMENTS

| | | | |
|---|---|---|---|
| 4,077,797 A | 3/1978 | Fischer et al. | |
| 4,411,691 A | 10/1983 | Rohr et al. | |
| 7,067,540 B2* | 6/2006 | Devadas et al. | 514/348 |
| 2005/0020594 A1* | 1/2005 | Hepperle et al. | 514/247 |

FOREIGN PATENT DOCUMENTS

| | | | |
|---|---|---|---|
| DE | 19 30 002 A | | 12/1970 |
| DE | 25 26 643 A | | 12/1976 |
| EP | 0 003 805 A | | 2/1979 |
| EP | 1043317 A1 | | 10/2000 |
| EP | 1 130 015 A | | 9/2001 |
| GB | 917 849 A | | 2/1963 |
| GB | 1 124 659 A | | 8/1968 |
| GB | 1303 490 | | 6/1970 |
| WO | WO 0009488 | * | 2/2000 |
| WO | WO 03059891 | * | 1/2003 |
| WO | WO 03/059891 | | 7/2003 |
| WO | WO 2006124874 | * | 5/2006 |
| WO | WO 2008/080056 | * | 7/2008 |

OTHER PUBLICATIONS

Mummenthaler, et al., Mol. Pharmaceutics 2011, 8, 2069-2079.*
Bill, et al., PLoS ONE, Jul. 1, 2012, vol. 7, # 7, e41179.*
Jänne, Lung Cancer (2008) 60 (Supplement 2), S3-S9.*
http://www.iupac.org/goldbook/A00123.pdf, downloaded Oct. 29, 2010.*
Wikipedia, Acyl, last modified Mar. 11, 2010.*
Hawley's Condensed Chem. Dict., 14th Ed., 2002.*
Hackh's Chem. Dict., 3rd Ed., 1944, p. 18.*
Jordan, V. C. Nature Reviews: Drug Discovery, 2, 2003, 205.*
Hackam, et al. JAMA, 296(14), 2006, 1731-1732.*
Bell et al., "Inherited susceptibility to lung cancer may be associated with the T790M drug resistance mutation in EGFR" *Nat. Genet.* 37:1315-1316 (2005).
Castle et al., "Pyridazines. III. The Synthesis of Substituted Pyridazines I." *J. Heterocyclic Chem.*, 2:463-472 (1965).
Dury "Neue Wege in der Chemie der Pyridazone" *Angewandte Chemie*, 77(7):282-290 (1965).
Fisher et al., "Induction and apoptotic regression of lung adenocarcinomas by regulation of a K-Ras transgene in the presence and absence of tumor suppressor genes" *Genes Dev.* 15:3249-3262 (2001).
Hensel et al., "Üeber neue Baumwollfarbstoffe" *Angewandte Chemie*, 77(7):303-313 (1965).
International Search Report for PCT/US2007/088543, mailed from the ISA/EP Oct. 30, 2008.
Kim et al., "Efficient N-arylation of Pyridazin-3(2H)-ones" *Tetrahedron Letters*, 45:8781-8784 (2004).
Kobayashi et al., "EGFR mutation and resistance of non-small-cell lung cancer to gefitinib" *N.Eng.J.Med.* 352:786-792 (2005).
Lyga, "The Reaction of 2-Substituted 4, 5-dichloro-3(2H)pyridazinones with alkoxides and Alkylthiolates" *J. Heterocyclic Chem.*, 25:1757-1760 (1988).
Lynch et al., "Activating mutations in the epidermal growth factor receptor underlying responsiveness of non-small-cell lung cancer to gefitinib." *N. Engl. J. Med.* 350:2129-2139 (2004).
Maki et al., "The Ring contraction of Pyridazinones to Pyrazoles" *Chem. and Pharm. Bulletin*, 19(8):1635-1640 (1971).
Maki et al., "Studies of Rearrangement Reaction. Viii. Ring-Contraction From Pyridazinone Derivatives to Pyrazolone Derivatives" *Chem. and Pharm. Bulletin*, 12:176-182 (1964).
Ostrowicz et al., "Vicarious Nucleophile Substitution of Hydrogen in Pyridazines" *Tetrahedron Letters*, 33(33):4787-4790 (1992).
Paez et al., "EGFR mutations in lung cancer: correlation with clinical response to gefitinib therapy" *Science* 304:1497-1500 (2004).
Pao et al., "EGF receptor gene mutations are common in lung cancers from "never smokers" and are associated with sensitivity of tumors to gefitinib and erlotinib" *Proc. Natl. Acad. Sci USA* 101:13306-13311 (2004).
Pao et al., "KRAS Mutations and Primary Resistance of Lung Adenocarcinomas to Gefitinib or Erlotinib" *PLoS Med* 2(1):e17 (2005).
Parkin et al., "Global cancer statistics, 2002" *CA Cancer J. Clin.* 55(2):74-108 (2005).
Politi et al., "Lung adenocarcinomas induced in mice by mutant EGF receptors found in human lung cancers respond to a tyrosine kinase inhibitor or to down-regulation of the receptors" *Genes Dev.* 20:1496-1510 (2006).
Pu et al., "An efficient copper catalysed N-arylation of pyridazinones with a structurally well-defined copper complex" *Tetrahedron Letters*, 47(2):149-153 (2006).
Rodenhuis and Slebos, "The ras oncogenes in human lung cancer" *Am. Rev. Respir. Dis.* 142:S27-30 (1990).
Rodenhuis et al., "Incidence and possible clinical significance of K-ras oncogene activation in adenocarcinoma of the human lung" *Cancer Res.* 48:5738-5741 (1988).
Schreiber "Die Eignung von 4, 5-Dichlor-pyridazinonen-(6)-zur selektiven Umsetzung von Mercaptogruppen" *Hoppe-Zeylers Zeitschrift für Physiologische Chemie* 348:371-377 (1967).
Schober et al., "Pyridazines with Hetero-Atom Substituents in Positions 3 and 5, Part VII. Halog enation of 2-Aryl-5-hydroxy-pyridazin-3(2H)-ones in Position 4" *Monatshefte für Chemie*, 121:565-569 (1990).
Suzuki et al., "Detection of ras gene mutations in human lung cancers by single-strand conformation polymorphism analysis of polymerase chain reaction products" *Oncogene* 5:1037-1043 (1990).
Zhang et al., "Confirmation and prevention of halogen exchange: practical and highly efficient one-pot synthesis of dibromo- and dichloropyridazinones" *Tetrahedron Letters*, 47:8733-8735 (2006).
Pao, William et al., "Acquired Resistance of Lung Adenocarcinomas to Gefitinib or Erlotinib Is Associated with a Second Mutation in the EGFR Kinase Domain," PLOS Medicine, vol. 2, Issue 3, 0225-0235 (Mar. 2005).
Written Opinion for PCT/US2007/088543, 15 pages (Oct. 30, 2008).

* cited by examiner

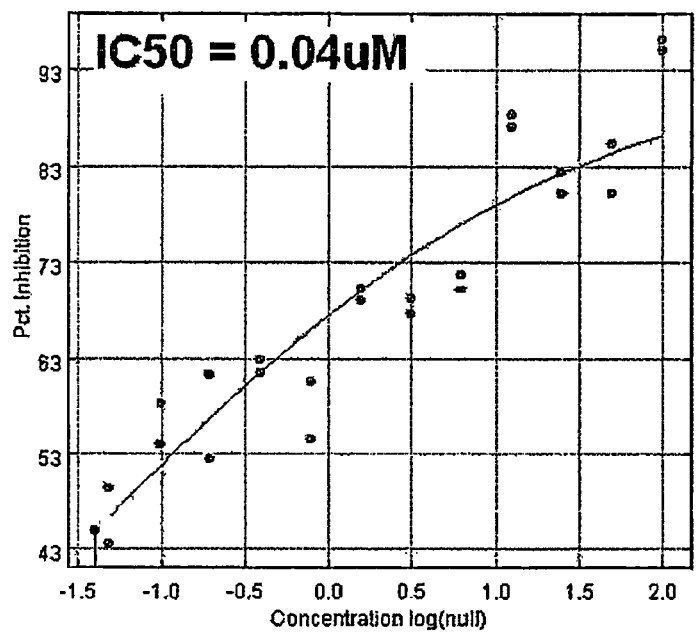
FIGURE 4A. Cell Line H1650
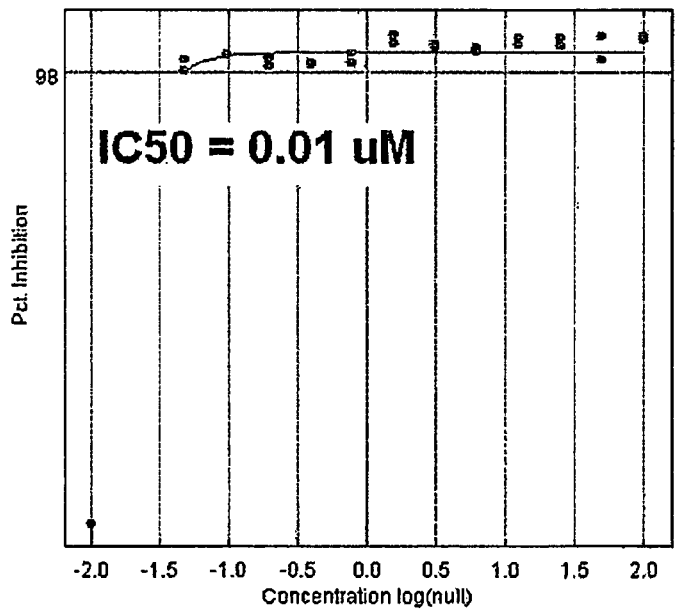
FIGURE 4B. Cell Line H1975

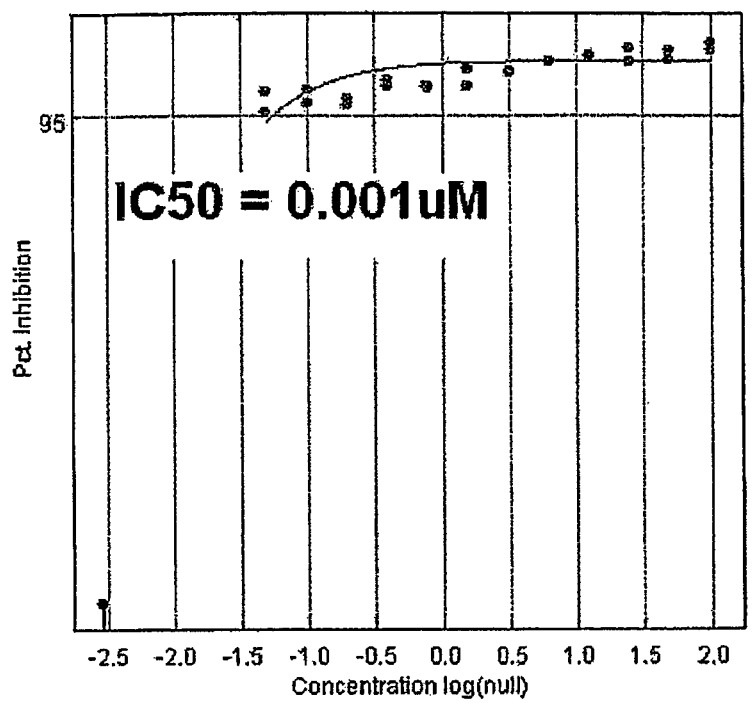
FIGURE 4C. Cell Line 2030
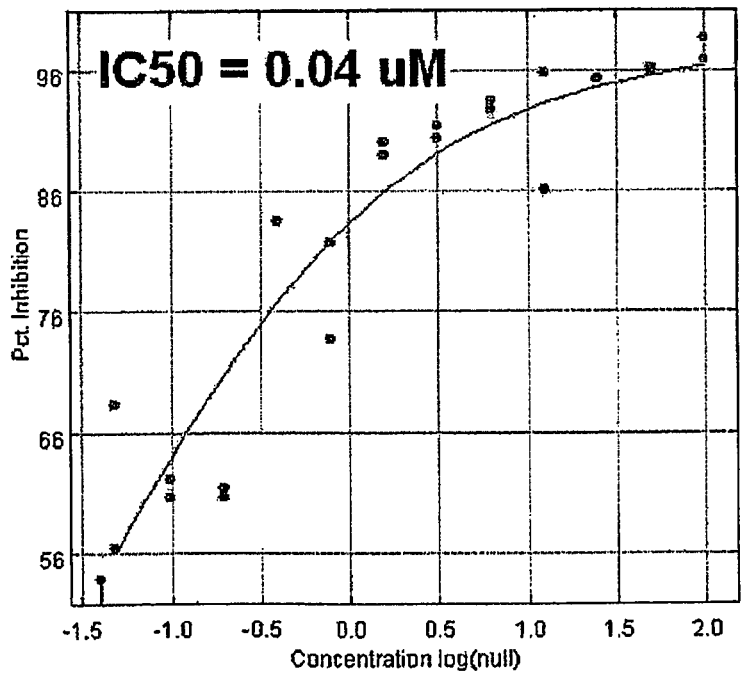
FIGURE 4D. Cell Line 3255

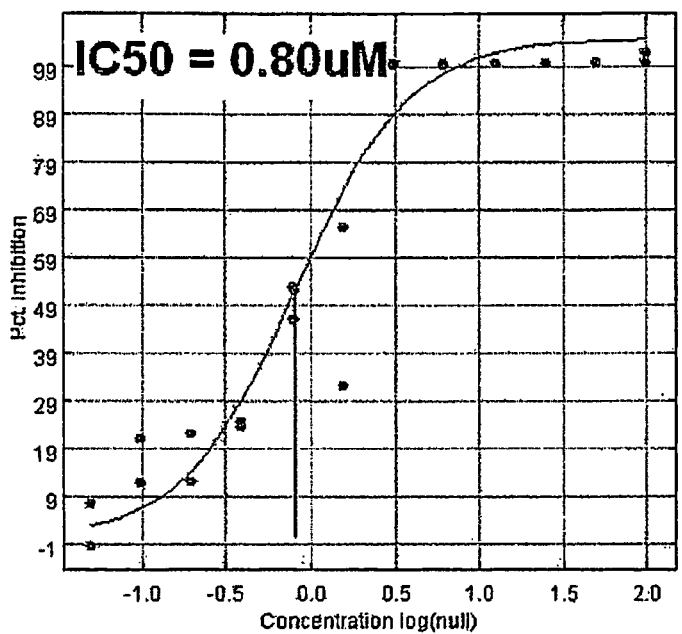
FIGURE 4E. Cell Line NHBE
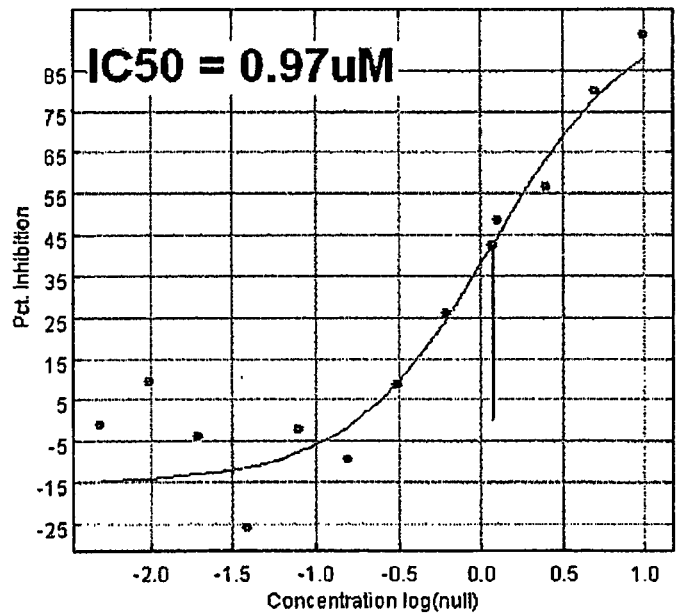
FIGURE 5A. Cell Line H1650

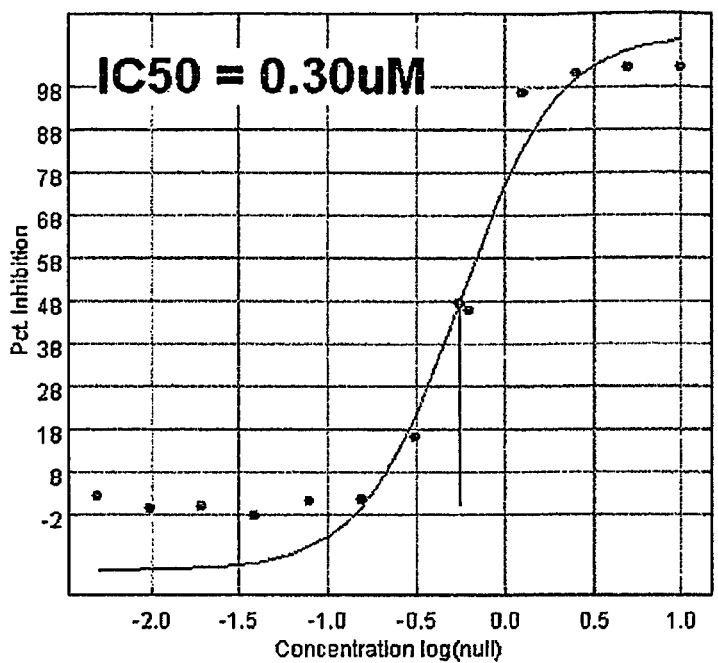
FIGURE 5B. Cell Line 2030
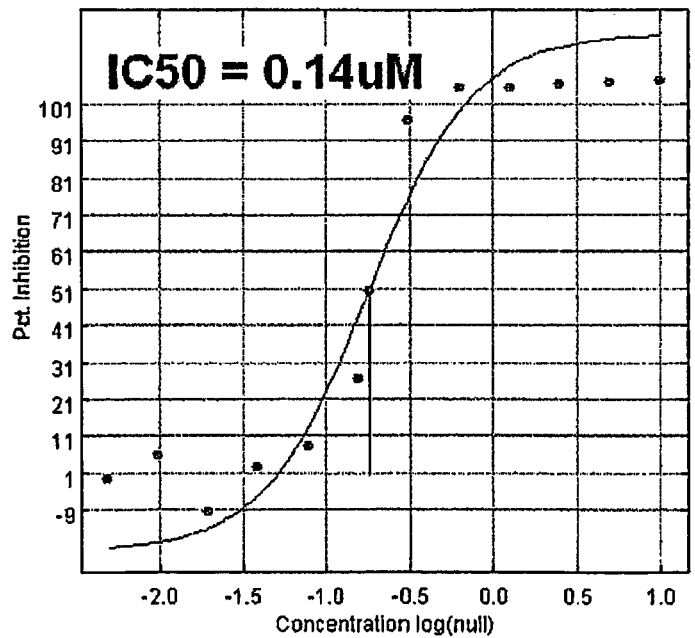
FIGURE 5C. Cell Line H1975

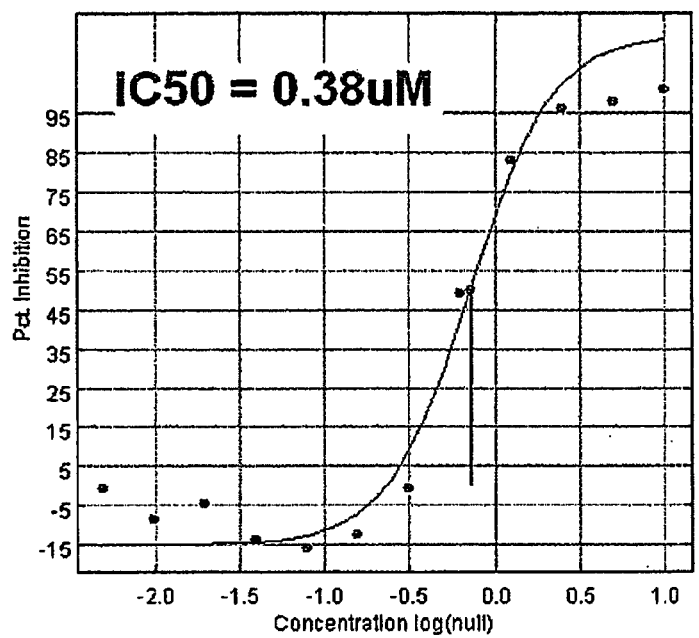
FIGURE 5D. Cell Line 3255
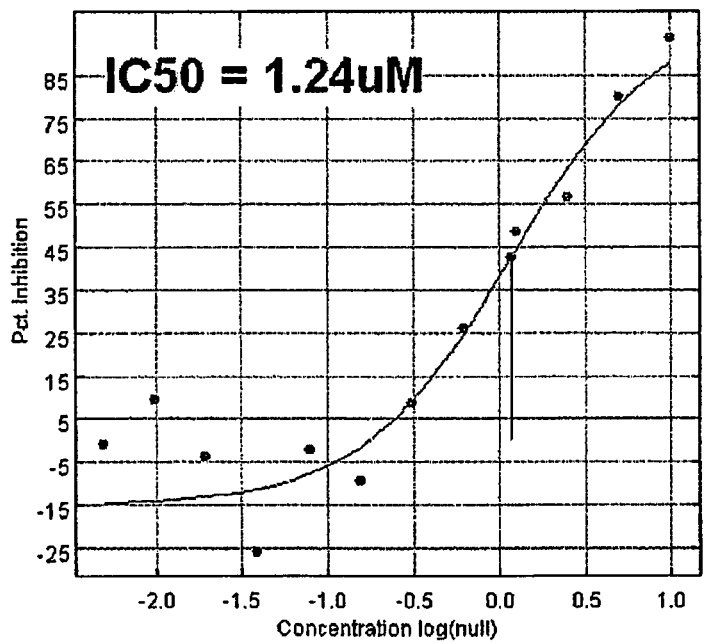
FIGURE 6A. Cell Line H1650

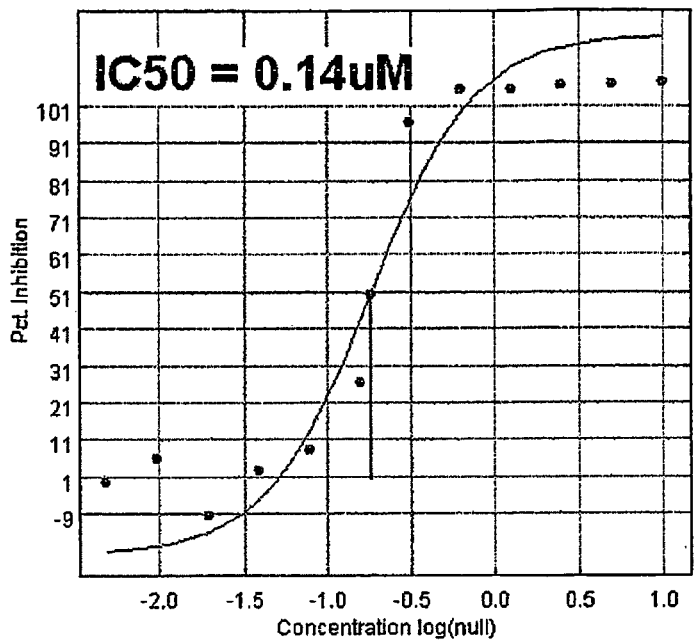
FIGURE 6B. Cell Line H1975
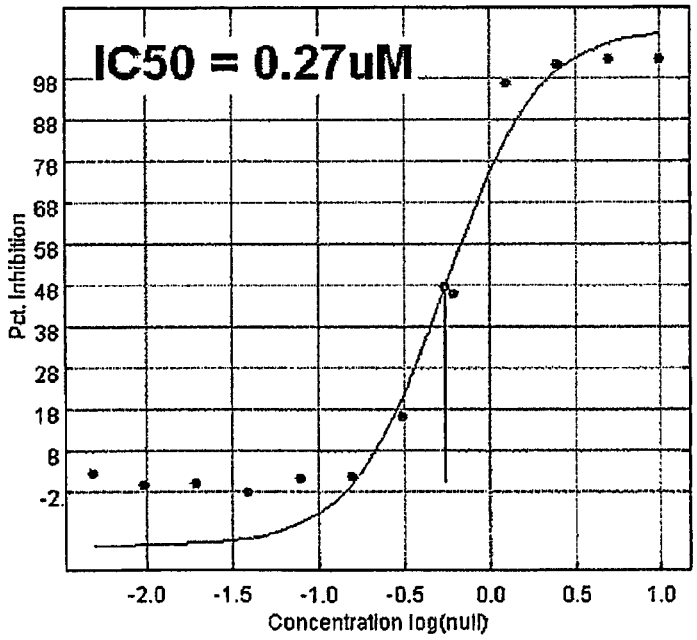
FIGURE 6C. Cell Line 2030

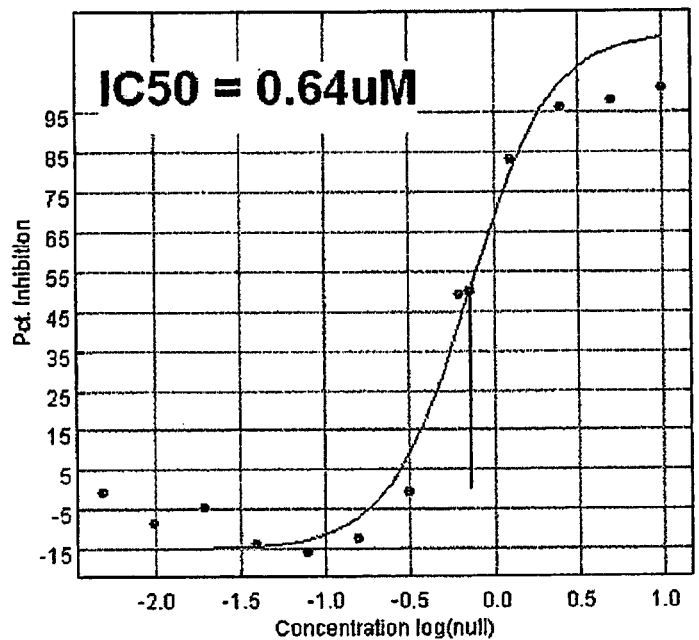
FIGURE 6D. Cell Line 3255
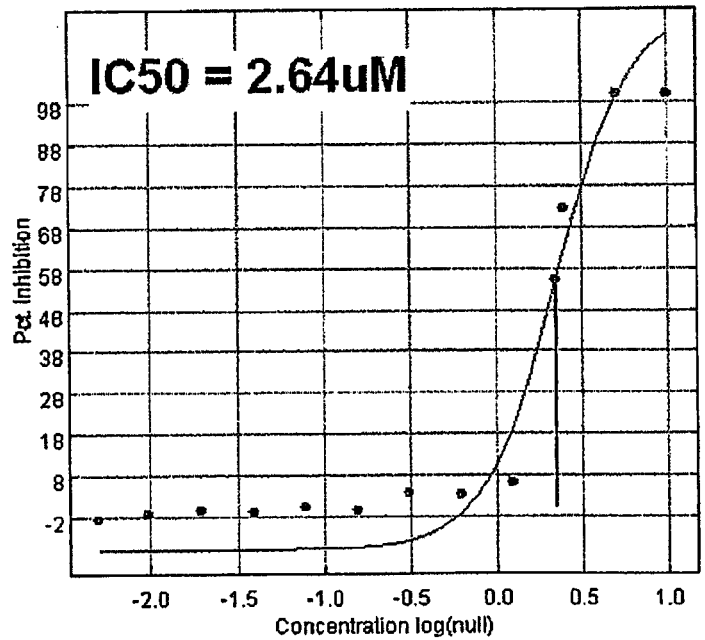
FIGURE 6E. Cell Line NHBE

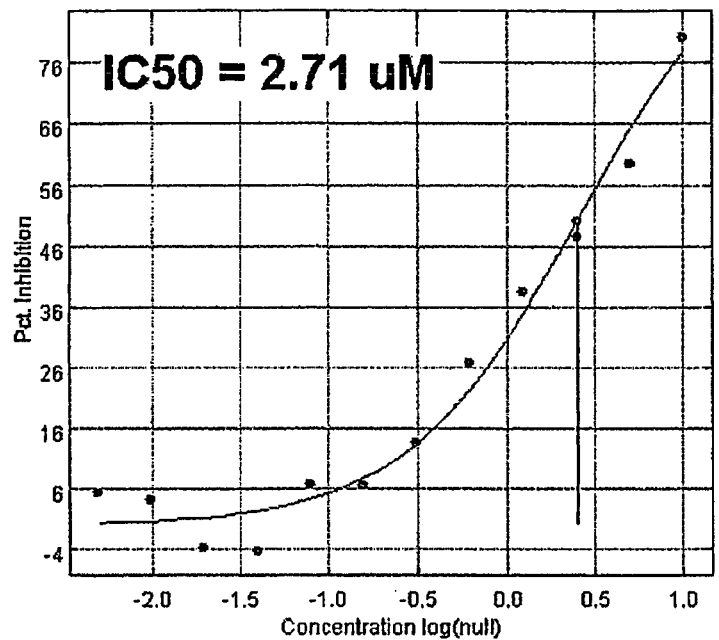
FIGURE 7A. Cell Line H1650
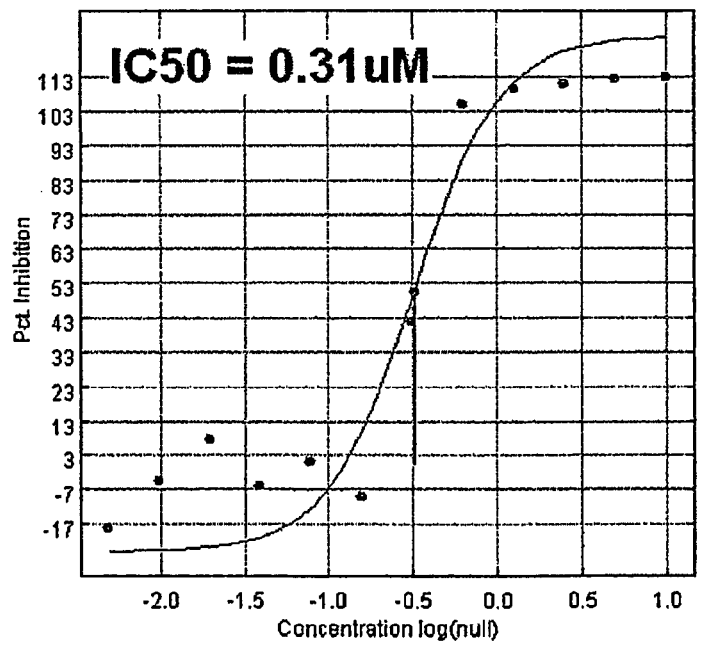
FIGURE 7B. Cell Line H1975

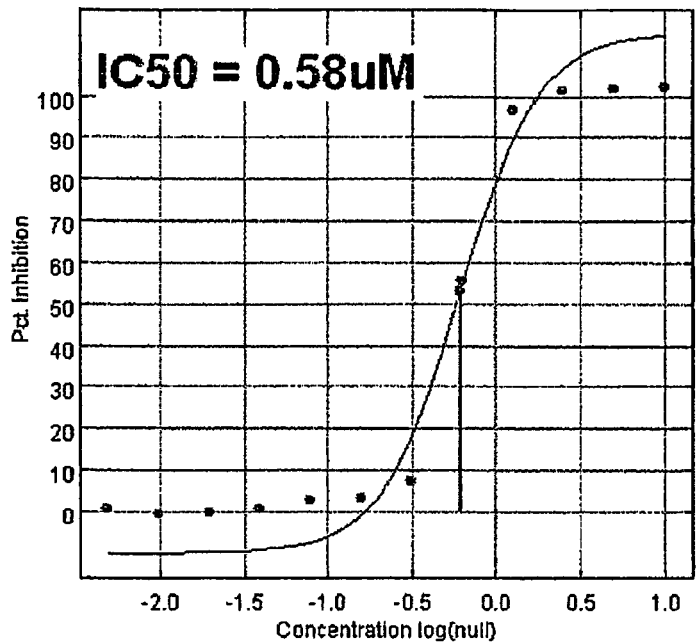
FIGURE 7C. Cell Line 2030
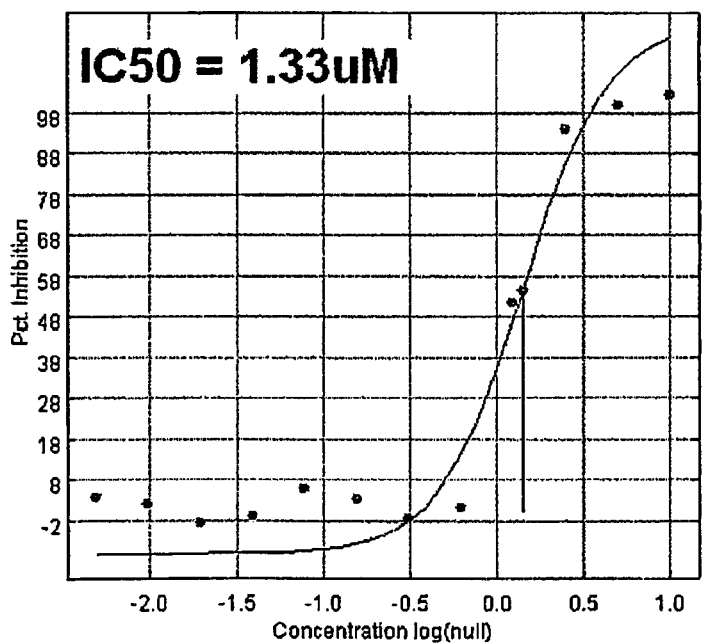
FIGURE 7D. Cell Line 3255

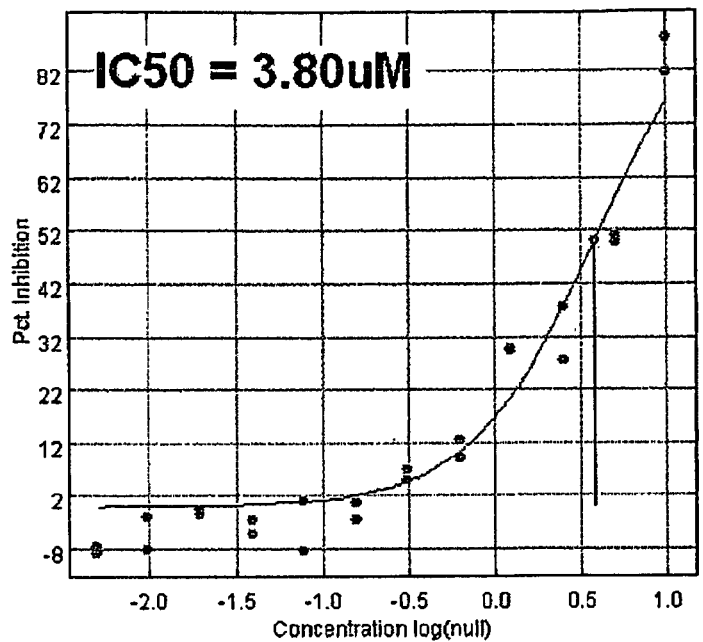
FIGURE 8A. Cell Line H1650
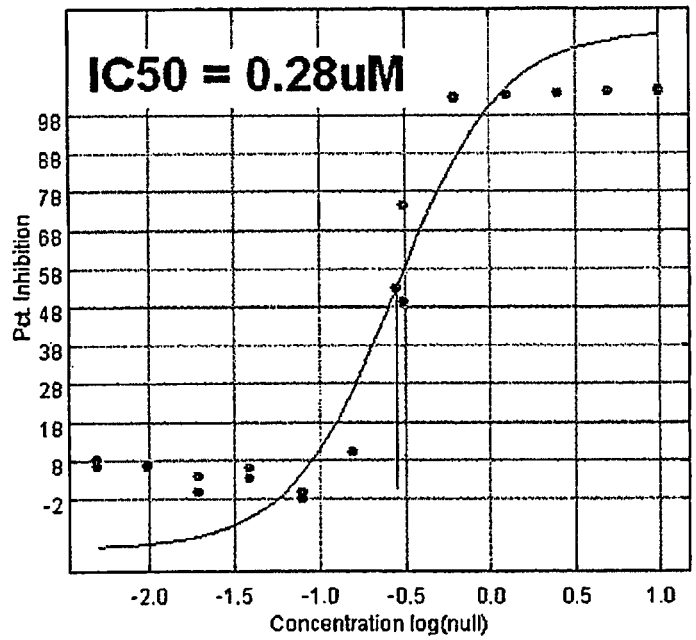
FIGURE 8B. Cell Line H1975

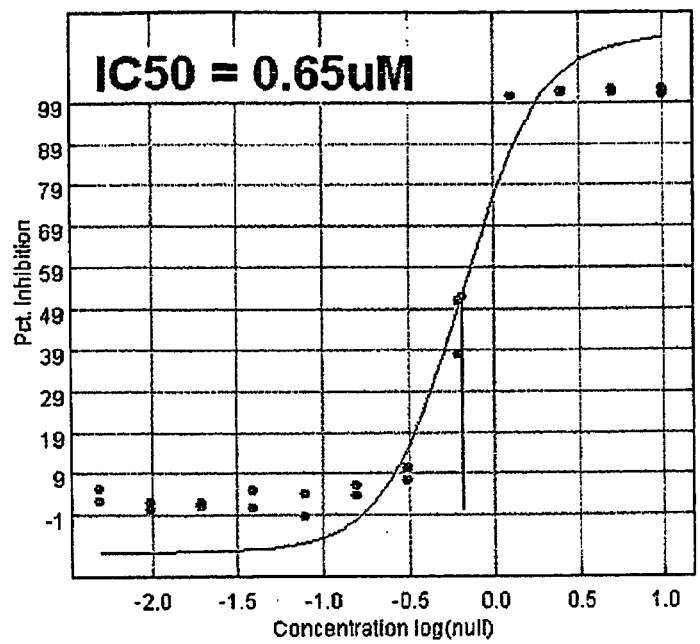
FIGURE 8C. Cell Line 2030
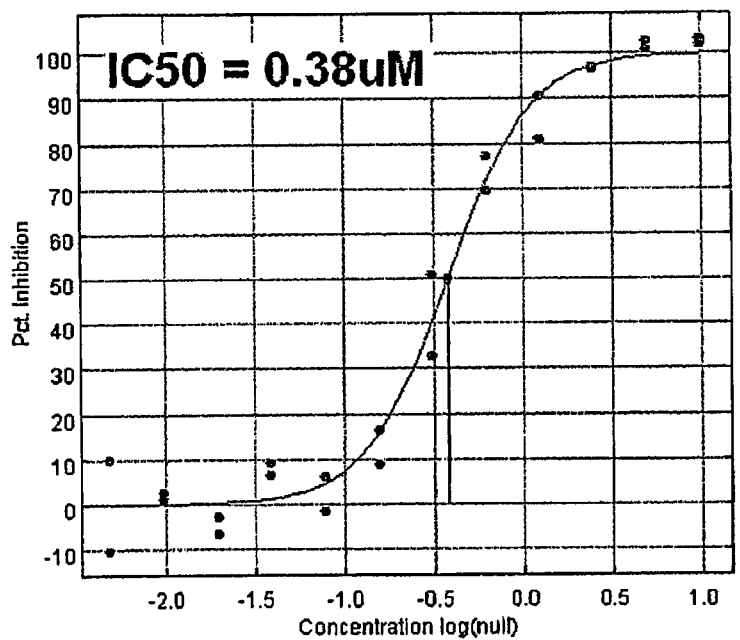
FIGURE 8D. Cell Line 3255

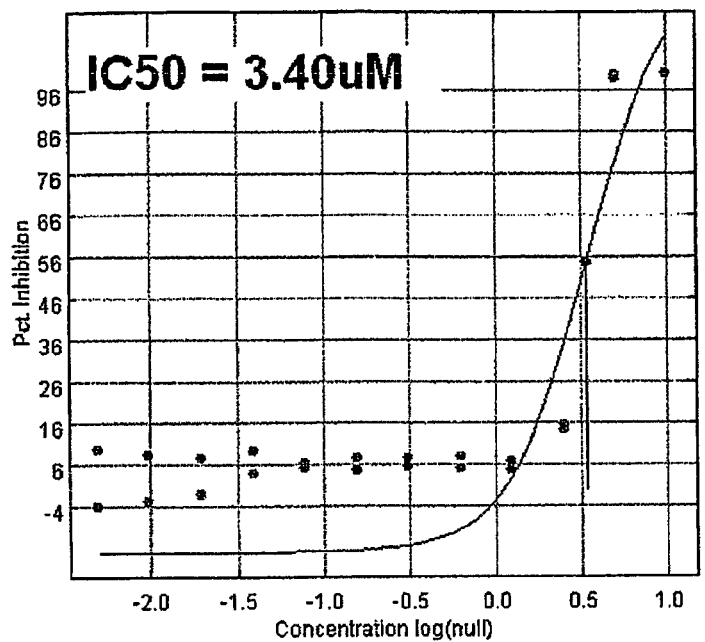
FIGURE 8E. Cell Line NHBE
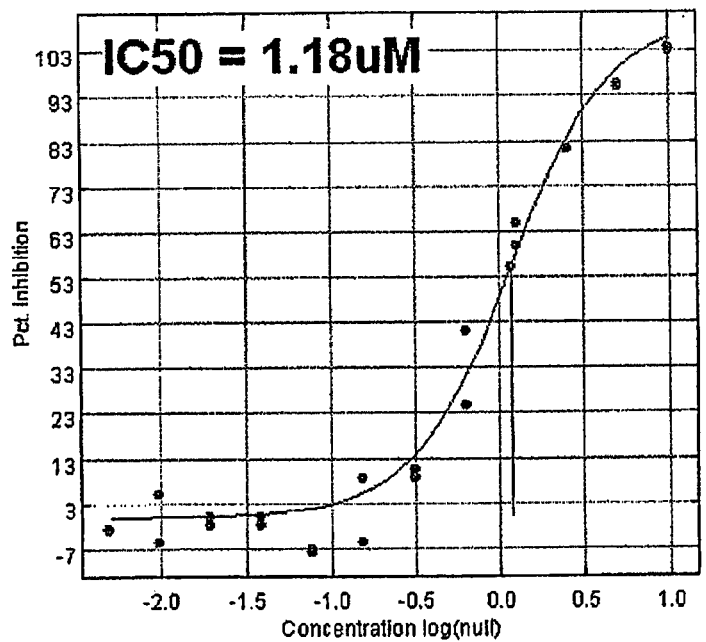
FIGURE 9A. Cell Line H1650

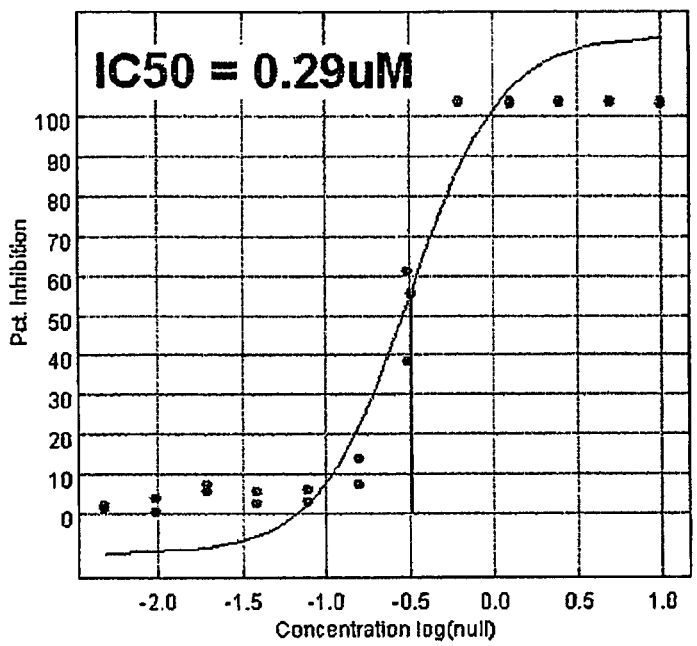
FIGURE 9B. Cell Line H1975
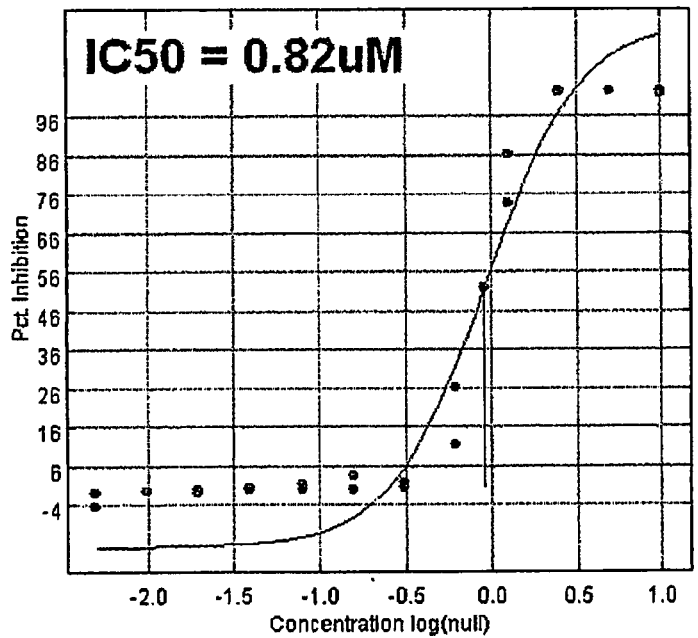
FIGURE 9C. Cell Line 2030

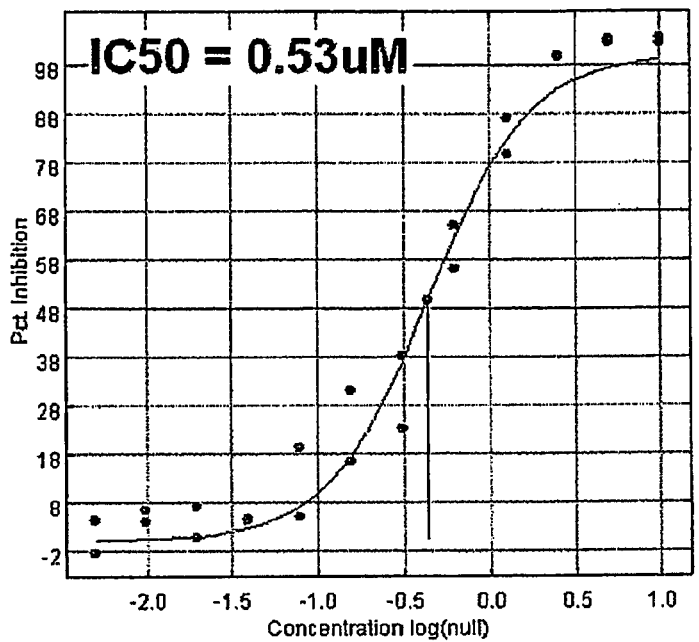
FIGURE 9D. Cell Line 3255
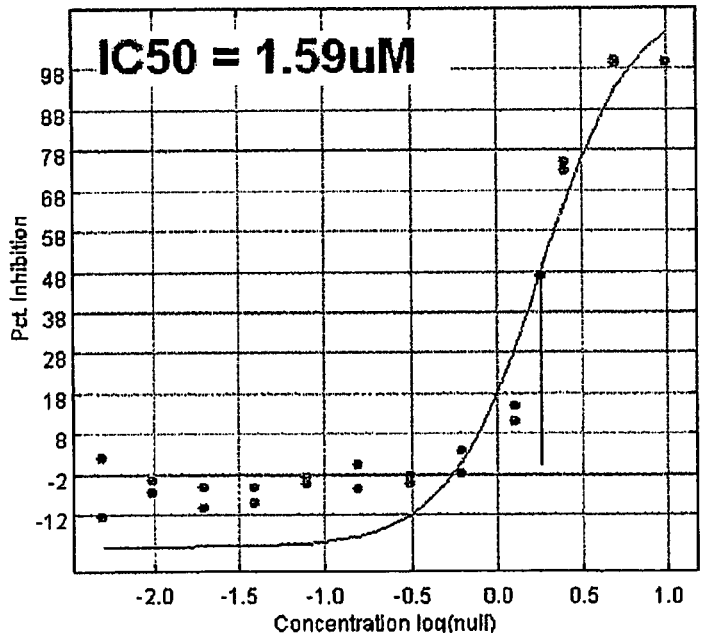
FIGURE 9E. Cell Line NHBE

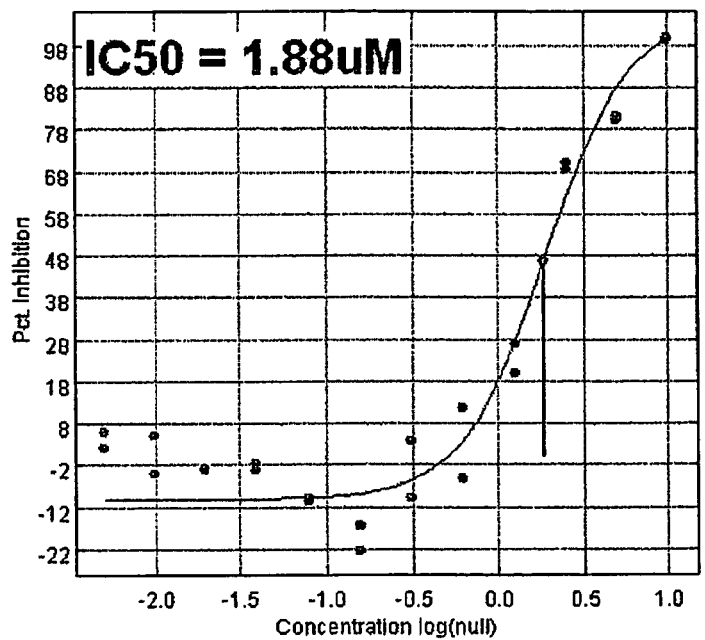
FIGURE 10A. Cell Line H1650
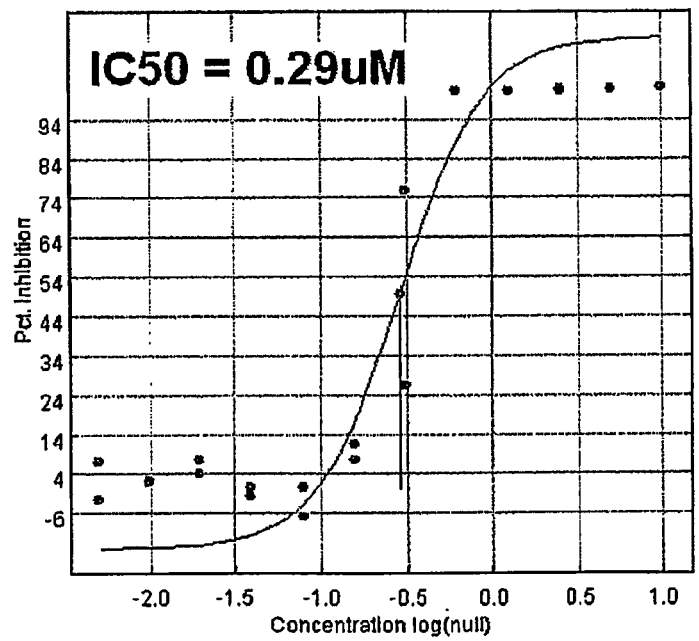
FIGURE 10B. Cell Line H1975

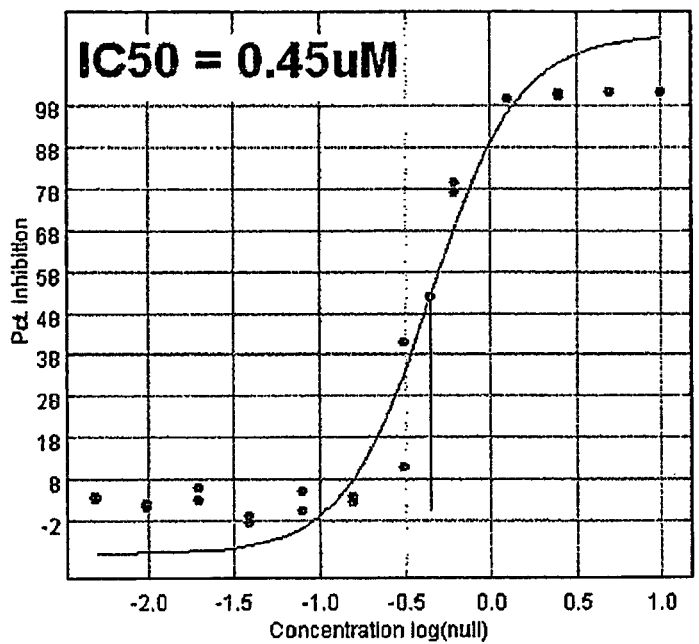
FIGURE 10C. Cell Line 2030
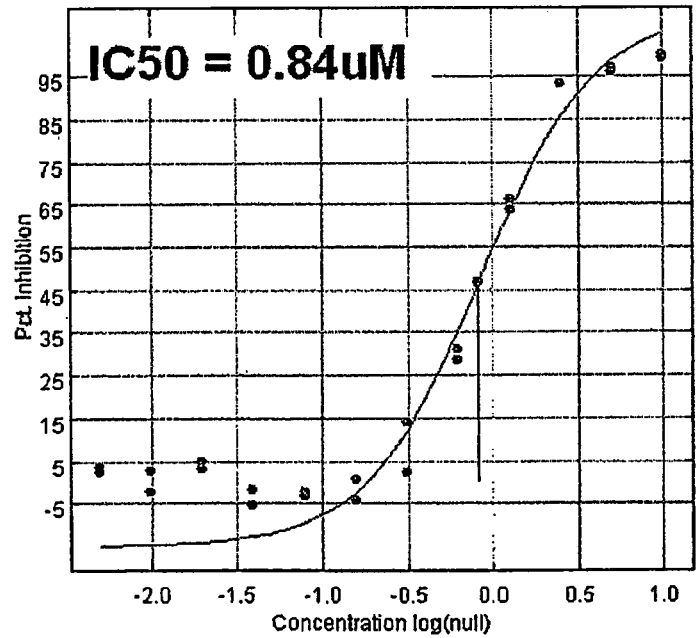
FIGURE 10D. Cell Line 3255

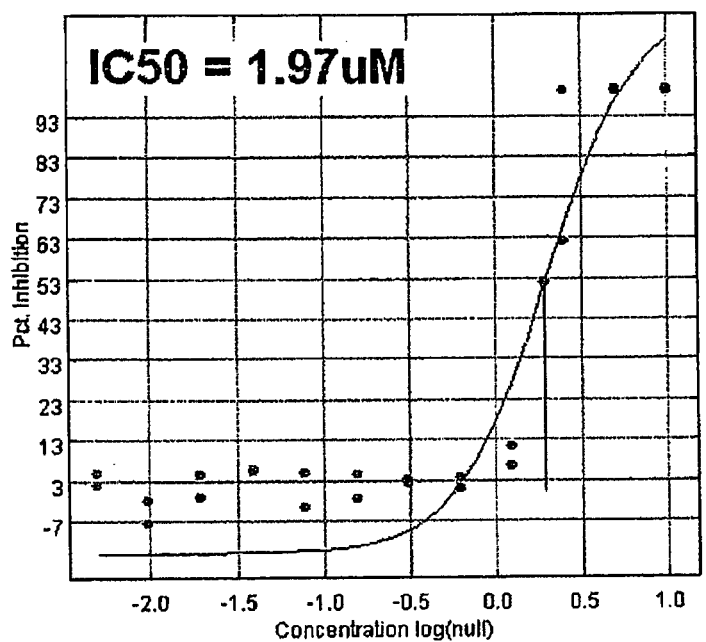
FIGURE 10E. Cell Line NHBE

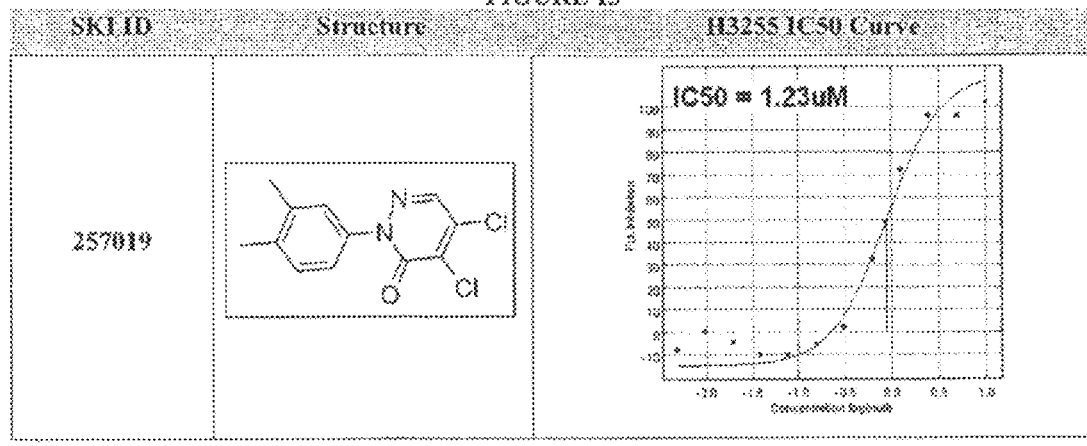
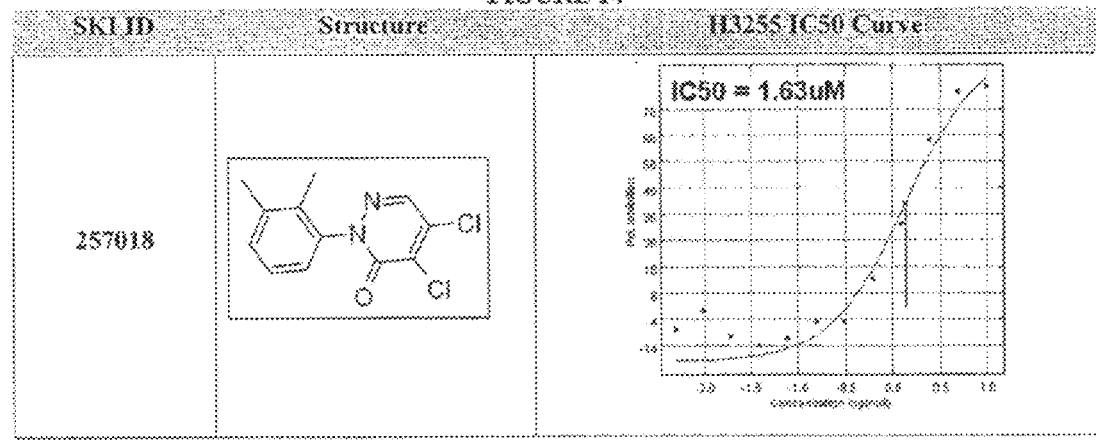

FIGURE 15
| SKI ID | Structure | H3255 IC50 Curve |
|---|---|---|
| 176729 | 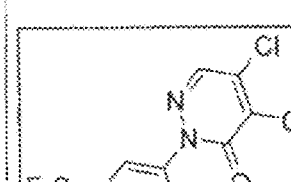 | 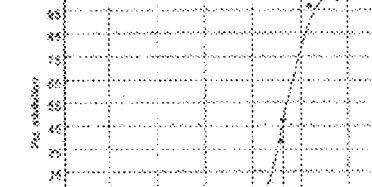 IC50 = 0.73uM |
FIGURE 16
| SKI ID | Structure | H3255 IC50 Curve |
|---|---|---|
| 257015 | 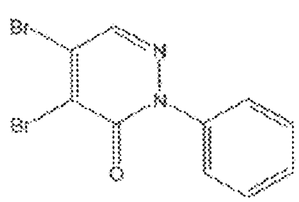 | 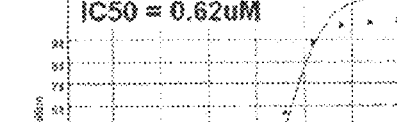 IC50 = 0.62uM |

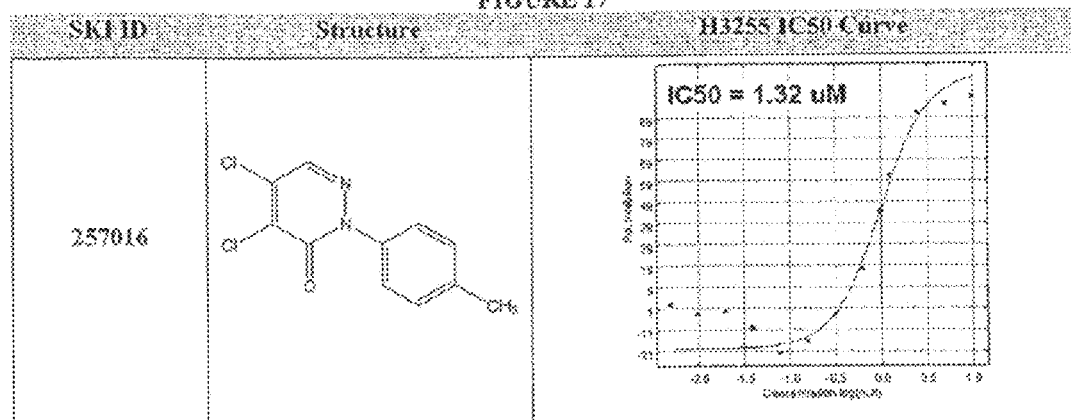
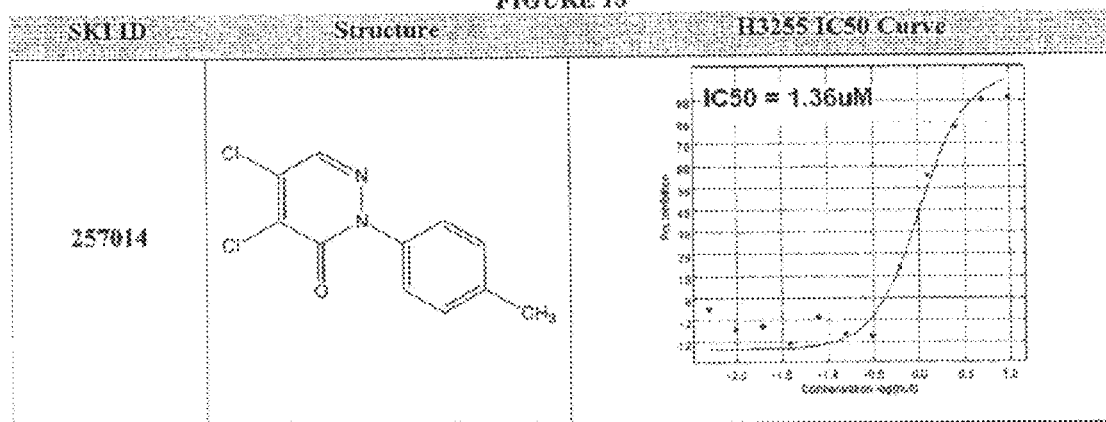

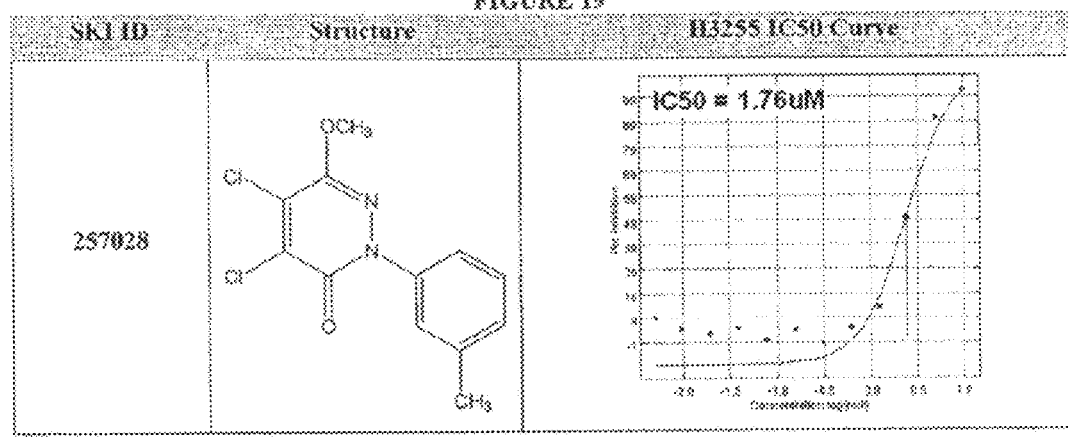
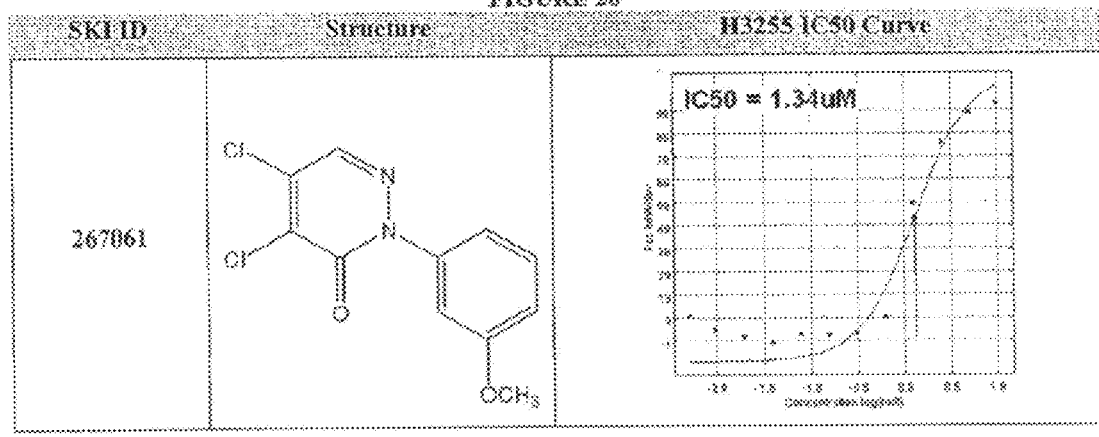

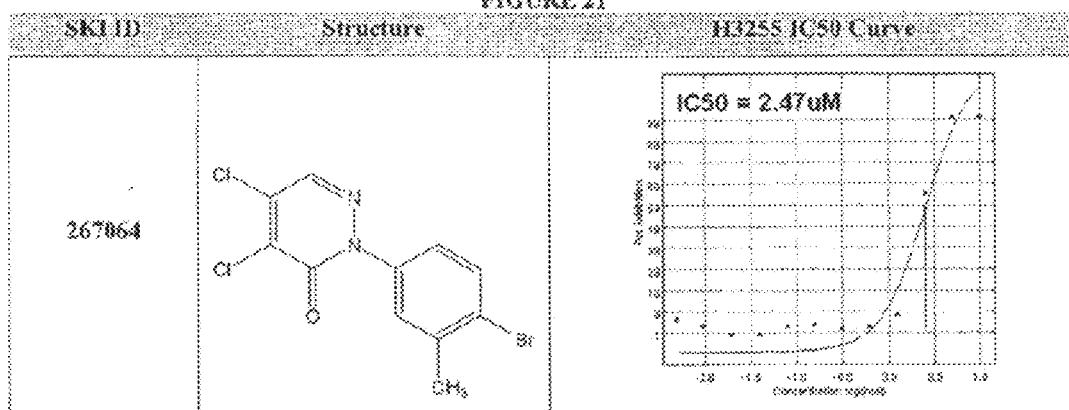
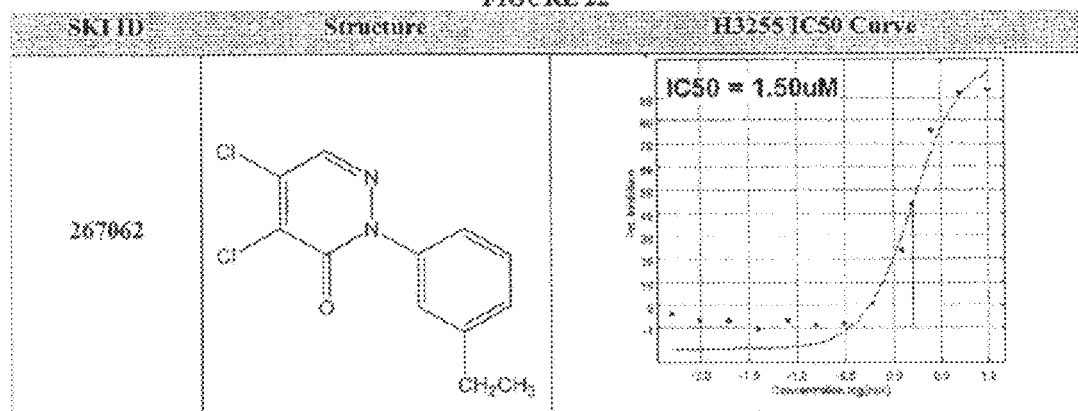

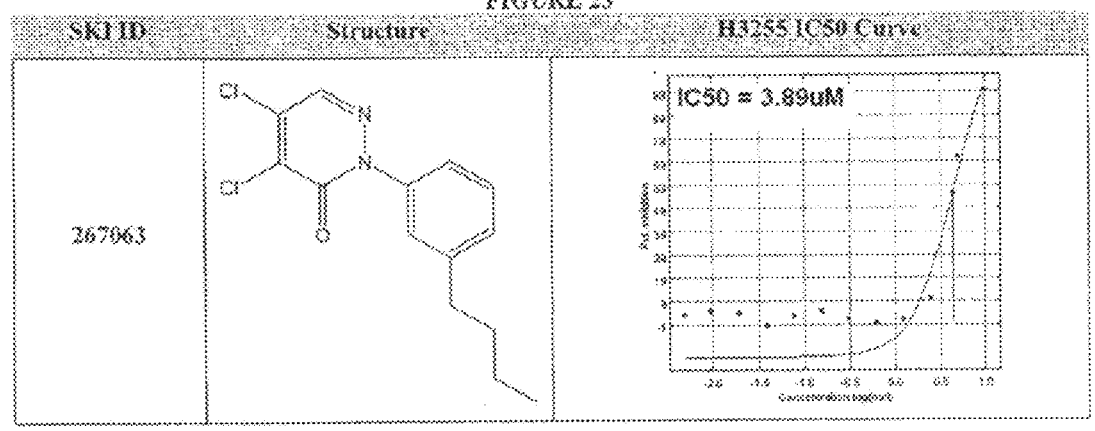
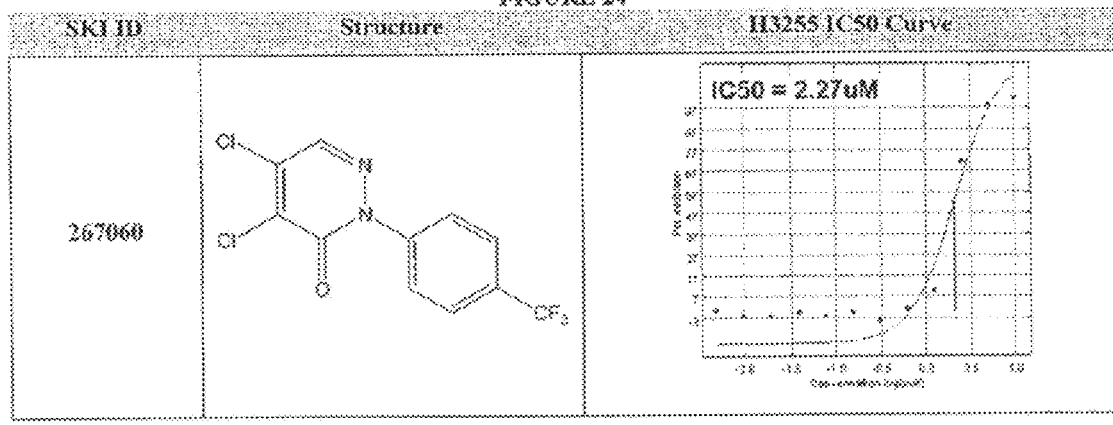

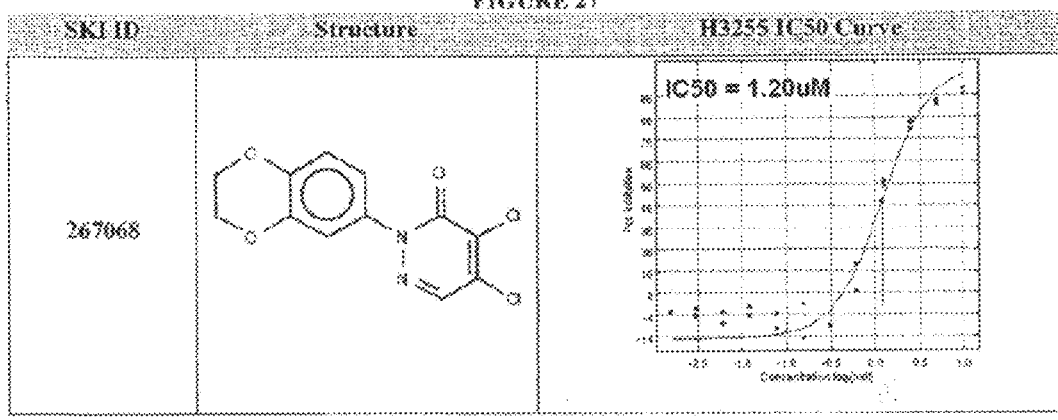
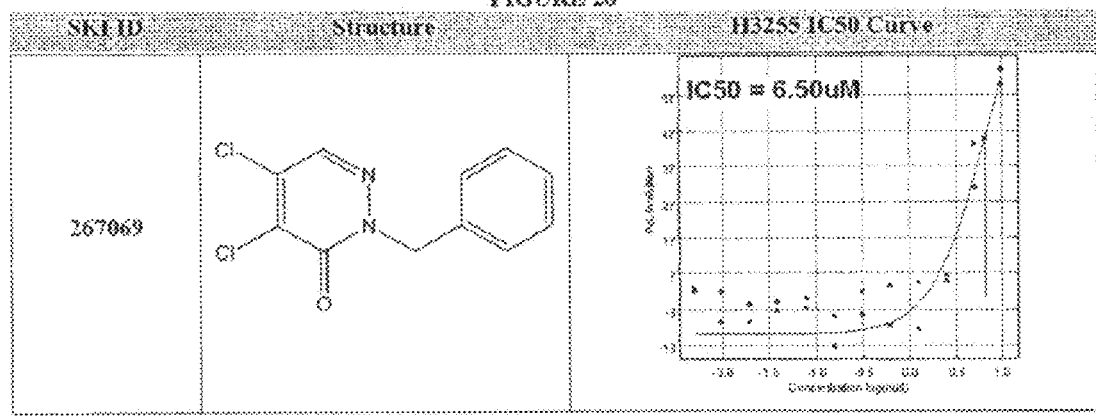

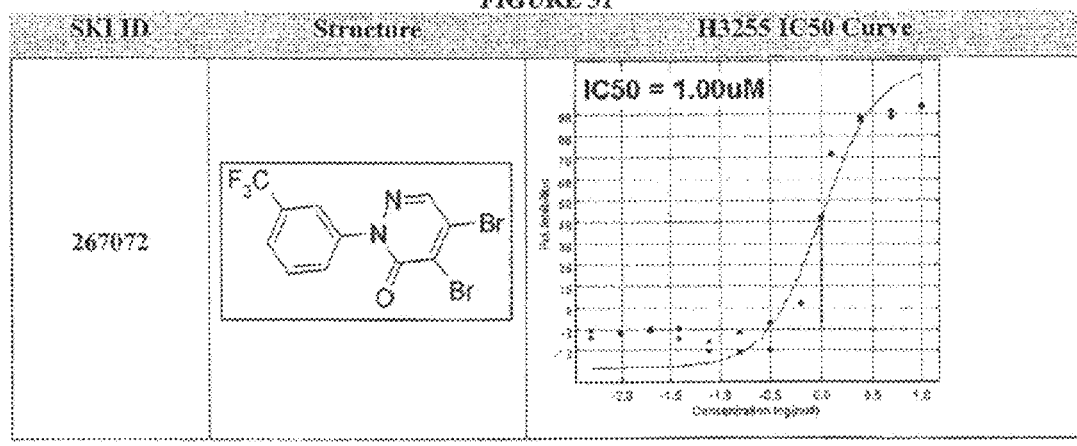
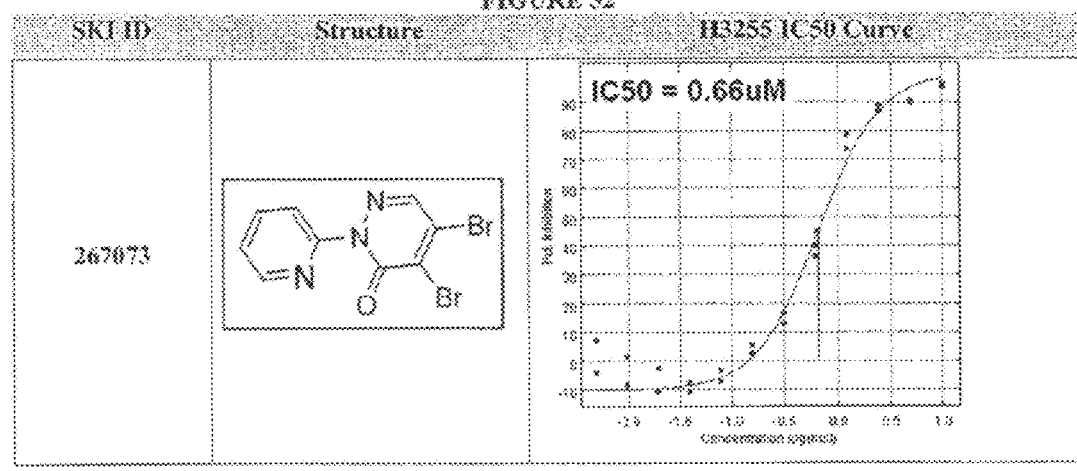

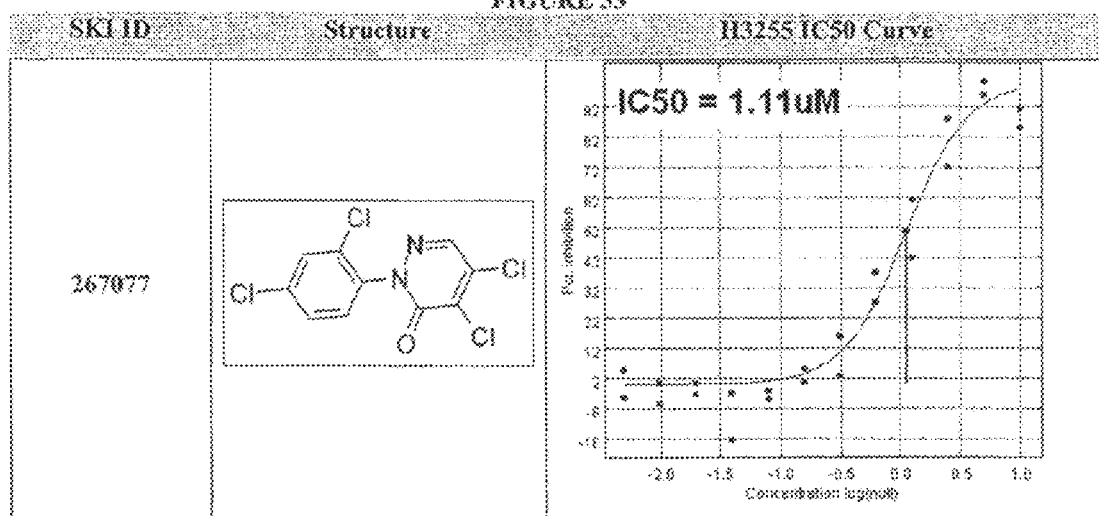
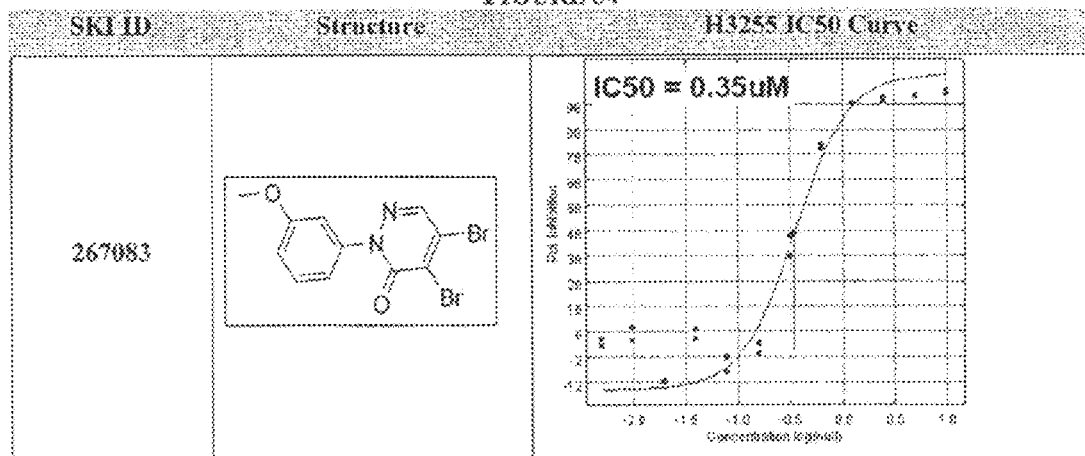

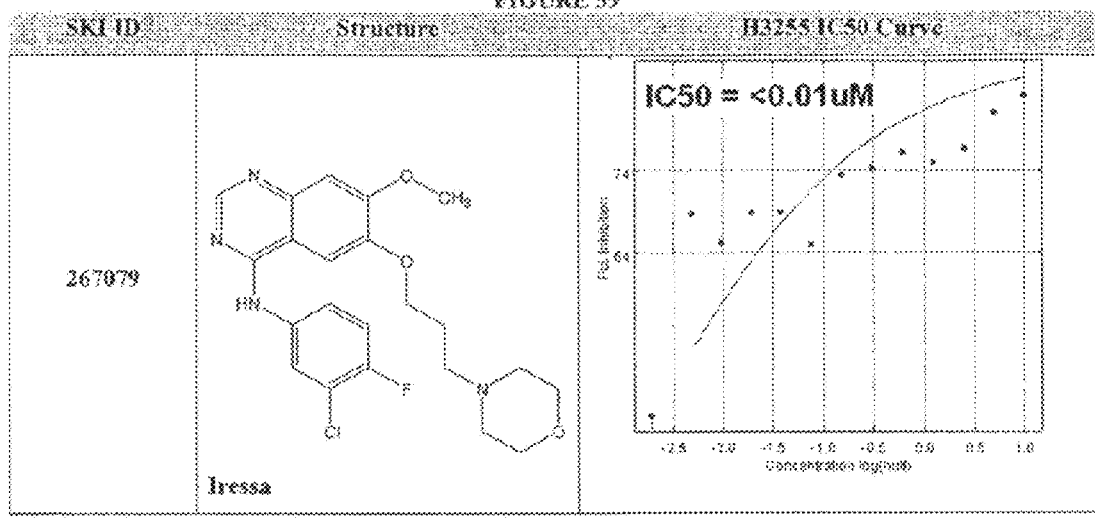
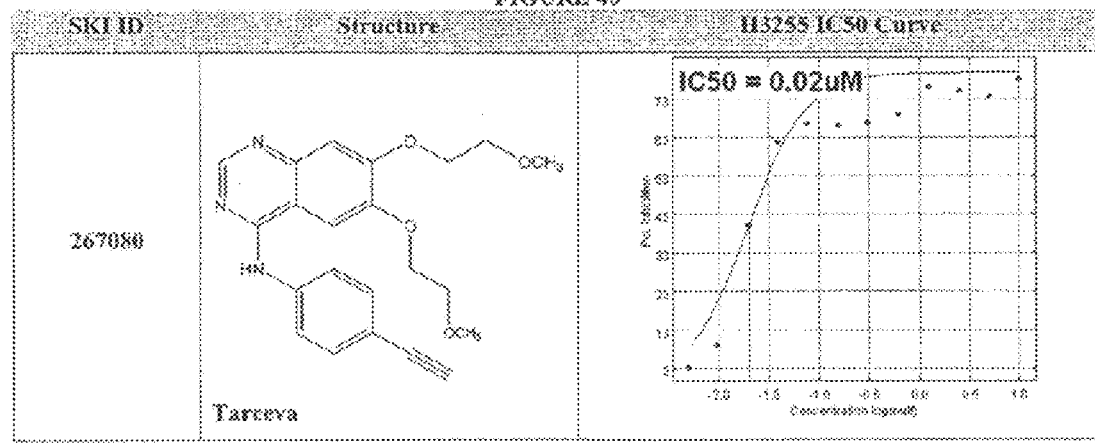

SUBSTITUTED PYRIDAZINES AS EGFR AND/OR KRAS INHIBITORS

CROSS-REFERENCE TO RELATED APPLICATIONS

This application is a U.S. national phase application under 35 U.S.C. §371 of international PCT application no. PCT/US2007/088543, filed Dec. 21, 2007, which claims priority under 35 U.S.C. §119(e) to U.S. provisional application, U.S. Ser. No. 60/871,181, filed Dec. 21, 2006, the entire contents of which are incorporated herein by reference.

BACKGROUND OF THE INVENTION

Lung cancer has been the most common cancer in the world since 1985, with approximately 163,510 deaths expected to occur in 2005 in the United States. Even with current treatments involving surgery, chemotherapy, and/or radiotherapy, overall 5-year survival in the United States is still only approximately 15 percent; in developing countries, 5-year survival rates are about 9 percent (Parkin et al., *CA Cancer J. Clin.* (2005) 55:74-108). The overwhelming majority of lung cancers in both sexes can be attributed to smoking. However, approximately 10% of lung cancers arise in individuals who smoked less than 100 cigarettes in a lifetime ("never smokers").

Several proto-oncogenes encoding components of the ERBB/HER signaling pathway are known to be mutated in lung cancers, almost exclusively in adenocarcinomas. The most common mutations affect the KRAS and EGFR genes. Approximately 15 to 30% of adenocarcinomas have KRAS mutations (Rodenhuis and Slebos, *Am. Rev. Respir. Dis.* (1990) 142:S27-30; Suzuki et al., *Oncogene* (1990) 5:1037-1043), while EGFR mutations are found in about 10% of adenocarcinomas in the United States and in much higher percentages of patients in East Asia (Pao et al., *PLoS Med* (2005) 2:e17). EGFR and KRAS mutations are mutually exclusive, suggesting that they have functionally equivalent or overlapping roles in lung tumorigenesis.

The majority of mutations in KRAS in human lung adenocarcinomas are found in exon 2, leading to missense amino acid substitutions in codons 12 or 13 (Rodenhuis et al., *Cancer Res.* (1988) 48:5738-5741). Nearly 90% of EGFR mutations identified in human lung cancer occur in two "hotspots". Half of these mutations are various multi-nucleotide in-frame deletions that eliminate a highly conserved four amino acid sequence (LREA) encoded in exon 19. The other "hotspot" mutations are point mutations in exon 21 that result in a specific amino acid substitution (i.e., lysine to arginine) at position 858 (L858R). The remaining 10-15% are nucleotide substitutions, deletions, or insertions/duplications found in exons 18-21, outside of the common sites of mutation (Lynch et al., *N Engl. J. Med.* (2004) 350:2129-2139; Paez et al., *Science* (2004) 304:1497-1500; Pao et al., *Proc. Natl. Acad. Sci. USA* (2004) 101:13306-13311).

Most of the somatic mutations in the EGFR described above are associated with sensitivity of human lung tumors to the tyrosine kinase inhibitors gefitinib (IRESSA™, AstraZeneca) and erlotinib (TARCEVA™, OSI Pharmaceuticals, Genentech). Although these two small molecules were developed as inhibitors of the wild type EGFR tyrosine kinase, EGFR with the common mutations in the kinase domain confer an augmented sensitivity to these drugs. To date, gefitinib and erlotinib are the only two targeted agents clinically available for treatment of human non-small cell lung cancer (adenocarcinoma, squamous cell carcinoma and large cell carcinoma).

In most patients who initially respond to erlotinib and gefitinib, the cancer resumes detectable growth within 6 months to two years. This loss of sensitivity to gefitinib and erlotinib arises co-incidentally with a secondary mutation in exon 20 of the EGFR, which leads to substitution of methionine for threonine at position 790 (T790M) in the kinase domain, in addition to the primary drug-sensitive mutation. Activating EGFR mutations (e.g. L858R) seem to occur preferentially in cis with the T790M mutation. This T790M mutation has also recently been identified in a family with a history of adenocarcinoma (Bell et al., *Nat. Genet.* (2005) 37:1315-1316). Biochemical analyses of transfected cells and growth inhibition studies with lung cancer cell lines demonstrated that the T790M mutation confers resistance to the EGFR mutants that were usually sensitive to either gefitinib or erlotinib (Kobayashi et al., *N. Eng. J. Med.* (2005) 352:786-792).

Tumors arising from mutant EGFR require the continuous expression/activity of the oncogene for survival. This is based on the regression of mutant EGFR lung tumors that were treated with erlotinib and gefitinb, and has also been demonstrated for lung tumors arising in mice with controlled expression of oncogenic egfr (Politi et al., *Genes Dev.* (2006) 20:1496-1510) and kras (Fisher et al., *Genes Dev.* (2001) 15:3249-3262). The mutant oncogene may alter a normal cell so that continued expression or function of the oncogene is required to prevent the cell from entering an apoptotic (or differentiation) pathway. Very likely, the protein encoded by the mutant oncogene activates multiple signaling pathways in such a way that sudden loss of a signal dependent on a mutant oncoprotein removes a block to other signals that direct apoptosis or differentiation.

There are currently no approved therapeutic drugs that are effective against lung tumors with the T790M-EGFR mutation. Moreover, there has been no success in developing agents that would target KRAS. Given the high prevalence of KRAS mutations in lung and other cancers, a drug that targets this type of cancer is urgently needed.

SUMMARY OF THE INVENTION

The present invention is directed to pyridazinone and furan-containing compounds, and pharmaceutically acceptable salts, prodrugs, isomers, and tautomers thereof, pharmaceutical compositions, kits, methods of syntheses, and methods of treating proliferative diseases (e.g., neoplasia), such as cancer (e.g., lung cancer), in a subject by administering a therapeutically effective amount of a compound of the present invention, or a pharmaceutically acceptable salt, prodrug, isomer, or tautomer thereof. Furthermore, the compounds of the present invention may target a common effector in the oncogenic EGFR and/or KRAS pathways, and may be so identified using cell-based screens as described herein. Such compounds are effective in the treatment of cancers associated with EGFR and/or KRAS mutations.

In one aspect, the present invention provides pyridazinone compounds having the formula (I):

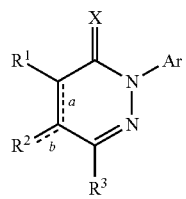

wherein X is oxygen or N(R$^x$); wherein R$^x$ is hydrogen, optionally substituted aliphatic, optionally substituted heteroaliphatic, optionally substituted heterocyclyl, optionally substituted aryl, optionally substituted heteroaryl, optionally substituted acyl, optionally substituted sulfinyl, optionally substituted sulfonyl, optionally substituted hydroxy, or optionally substituted amino;

===== designates a single or double bond represented by a and b; with the proviso that:

when a is a double bond, b is a single bond, and R$^1$, R$^2$, and R$^3$, are, independently, hydrogen, aliphatic, heteroaliphatic, hydroxy, thio, amino, heterocyclic, aryl, heteroaryl, acyl, amido, imido, sulfinyl, sulfonyl, carboxaldehyde, cyano, isocyano, azido, hydrazino, nitro, halo; optionally substituted with oxo, thiooxo, imino, aliphatic, carbocyclic, hydroxy, aliphaticoxy, aryloxy, thio, aliphaticthioxy, arylthioxy, heteroaliphatic, heterocyclic, aryl, arylaliphatic, hctcroaryl, heteroarylaliphatic, acyl, acyloxy, amido, imido, sulfinyl, sulfonyl, amino, aliphaticamino, dialiphaticamino, trialiphaticamino, arylamino, diarylamino, carboxaldehyde, cyano, isocyano, azido, hydrazino, nitro, or halo; or R$^1$ and R$^2$ are joined to form a 5- to 6-membered optionally substituted carbocyclic, optionally substituted heterocyclic, optionally substituted aryl or optionally substituted heteroaryl ring, and R$^3$ is as defined above; or R$^2$ and R$^3$ are joined to form a 5- to 6-membered optionally substituted carbocyclic, optionally substituted heterocyclic, optionally substituted aryl or optionally substituted heteroaryl ring, and R$^1$ is as defined above; or when a is a single bond, b is a double bond, and R$^2$ and the carbon directly attached to R$^2$ form an (=O), (=S), or (=NR$^y$) group, wherein R$^y$ is hydrogen, aliphatic, heteroaliphatic, hydroxy, thio, amino, heterocyclic, aryl, heteroaryl, acyl, amido, imido, sulfinyl, sulfonyl, carboxaldehyde, cyano, isocyano, azido, hydrazino, nitro, halo; optionally substituted with oxo, thiooxo, imino, aliphatic, carbocyclic, hydroxy, aliphaticoxy, aryloxy, thio, aliphaticthioxy, arylthioxy, heteroaliphatic, heterocyclic, aryl, arylaliphatic, heteroaryl, heteroarylaliphatic, acyl, acyloxy, amido, imido, sulfinyl, sulfonyl, amino, aliphaticamino, dialiphaticamino, trialiphaticamino, arylamino, diarylamino, carboxaldehyde, cyano, isocyano, azido, hydrazino, nitro, or halo; and R$^1$ and R$^3$ are, independently, hydrogen, aliphatic, heteroaliphatic, hydroxy, thio, amino, heterocyclic, aryl, heteroaryl, acyl, amido, imido, sulfinyl, sulfonyl, carboxaldehyde, cyano, isocyano, azido, hydrazino, nitro, halo; optionally substituted with oxo, thiooxo, imino, aliphatic, carbocyclic, hydroxy, aliphaticoxy, aryloxy, thio, aliphaticthioxy, arylthioxy, heteroaliphatic, heterocyclic, aryl, arylaliphatic, heteroaryl, heteroarylaliphatic, acyl, acyloxy, amido, imido, sulfinyl, sulfonyl, amino, aliphaticamino, dialiphaticamino, trialiphaticamino, arylamino, diarylamino, carboxaldehyde, cyano, isocyano, azido, hydrazino, nitro, or halo;

Ar is a group selected from aryl, heteroaryl, aliphatic optionally substituted with aryl or heteroaryl, or heteroaliphatic optionally substituted with aryl or heteroaryl, each group optionally substituted with aliphatic, heteroaliphatic, carbocyclic, hydroxy, aliphaticoxy, aryloxy, thio, aliphaticthioxy, arylthioxy, heteroaliphatic, heterocyclic, aryl, arylaliphatic, heteroaryl, heteroarylaliphatic, acyl, acyloxy, amido, imido, sulfinyl, sulfonyl, amino, aliphaticamino, dialiphaticamino, trialiphaticamino, arylamino, diarylamino, carboxaldehyde, cyano, isocyano, azido, hydrazino, nitro, or halo;

and pharmaceutically acceptable salts, prodrugs, isomers, or tautomers, thereof.

The present invention also provides methods of synthesizing compounds of formula (I).

In another aspect, the present invention provides furan-containing compounds having the formula (II):

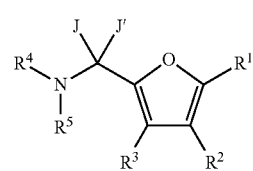

wherein each instance of R$^1$, R$^2$, and R$^3$ is, independently, hydrogen, aliphatic, heteroaliphatic, hydroxy, thio, amino, heterocyclic, aryl, heteroaryl, acyl, amido, imido, sulfinyl, sulfonyl, carboxaldehyde, cyano, isocyano, azido, hydrazino, nitro, halo; optionally substituted with oxo, thiooxo, imino, aliphatic, carbocyclic, hydroxy, aliphaticoxy, aryloxy, thio, aliphaticthioxy, arylthioxy, heteroaliphatic, heterocyclic, aryl, arylaliphatic, heteroaryl, heteroarylaliphatic, acyl, acyloxy, amido, imido, sulfinyl, sulfonyl, amino, aliphaticamino, dialiphaticamino, trialiphaticamino, arylamino, diarylamino, carboxaldehyde, cyano, isocyano, azido, hydrazino, nitro, or halo; or R$^1$ and R$^2$ are joined to form a 5- or 6-membered optionally substituted carbocyclic, optionally substituted heterocyclic, optionally substituted aryl, or optionally substituted heteroaryl ring, and R$^3$ is as defined above;

each instance of R$^4$ and R$^5$ is, independently, hydrogen, aliphatic, heteroaliphatic, hydroxy, thio, amino, heterocyclic, aryl, heteroaryl, acyl, amido, imido, sulfinyl, sulfonyl, carboxaldehyde, hydrazino; optionally substituted with oxo, thiooxo, imino, aliphatic, carbocyclic, hydroxy, aliphaticoxy, aryloxy, thio, aliphaticthioxy, arylthioxy, heteroaliphatic, heterocyclic, aryl, arylaliphatic, heteroaryl, heteroarylaliphatic, acyl, acyloxy, amido, imido, sulfinyl, sulfonyl, amino, aliphaticamino, dialiphaticamino, trialiphaticamino, arylamino, diarylamino, carboxaldehyde, cyano, isocyano, azido, hydrazino, nitro, or halo; or R$^4$ and R$^5$ are joined to form an 5- or 6-membered optionally substituted heterocyclic or optionally substituted heteroaryl ring;

J and J', together, form an oxo (=O), thiooxo (=S), or imino (=NR$^{N5}$) group, wherein R$^{N5}$ is hydrogen, optionally substituted hydroxy, optionally substituted amino, optionally substituted aryl, optionally substituted sulfonyl, optionally substituted heteroaryl, optionally substituted acyl, optionally substituted aliphatic, or optionally substituted heteroaliphatic; or each instance of J and J' is, independently, hydrogen, optionally substituted aliphatic or optionally substituted heteroaliphatic, and pharmaceutically acceptable salts, prodrugs, isomers, or tautomers, thereof.

In another aspect, the present invention provides pharmaceutical compositions comprising a therapeutically effective amount of a compound of formula (I), or a compound of formula (II) (or pharmaceutically acceptable salts, prodrugs, isomers, or tautomers thereof), and at least one pharmaceutically acceptable excipient.

In another aspect, the present invention provides kits comprising at least one compound of formula (I), or at least one compound of formula (II) (or pharmaceutically acceptable salts, prodrugs, isomers, or tautomers, thereof). A kit of the invention can include additional solvents, buffers, or excipients for pre-mixing before oral or parental administration, means for oral or parental administration, or additional chemotherapeutic agents.

The present invention also provides a method of treating proliferative diseases in a subject by administering a therapeutically effective amount of a compound of formula (I), or by administering a therapeutically effective amount of a compound of formula (II) (or a pharmaceutically acceptable salt, prodrug, isomer, or tautomer thereof). In certain embodiments, the proliferative disease is cancer. In certain embodiments, the cancer is renal cancer, bladder cancer, liver cancer, testicular cancer, ovarian cancer, colorectal cancer, prostate cancer, pancreatic cancer, lung cancer, breast cancer, brain cancer, bone cancer, stomach cancer, oral cancer, skin cancer, blood cancer, or leukemia. In certain embodiments the cancer is associated with EGFR and/or KRAS mutations. In certain embodiments, the cancer is lung cancer. In certain embodiments, the lung cancer is human non-small cell lung cancer (adenocarcinoma, squamous cell carcinoma, and large cell carcinoma).

BRIEF DESCRIPTION OF THE FIGURES

FIGS. 4A-4E. $IC_{50}$ Curves of Primary HTS Data for SKI 104122.

FIGS. 5A-5D. $IC_{50}$ Curves of SKI 104122 (repeated).

FIGS. 6A-6E. $IC_{50}$ Curves for Resynthesized SKI 104122.

FIGS. 7A-7D. $IC_{50}$ Curves for Resynthesized SKI 104122

FIGS. 8A-8E. $IC_{50}$ Curves for Resynthesized SKI 104122.

FIGS. 9A-9E. $IC_{50}$ Curves for Resynthesized SKI 104122.

FIGS. 10A-10E. $IC_{50}$ Curves for Resynthesized SKI 104122.

FIGS. 11-40. $IC_{50}$ curves for active pyridazinone compounds against the H3255 cell line.

DEFINITIONS

Chemical Definitions

Figure 1:
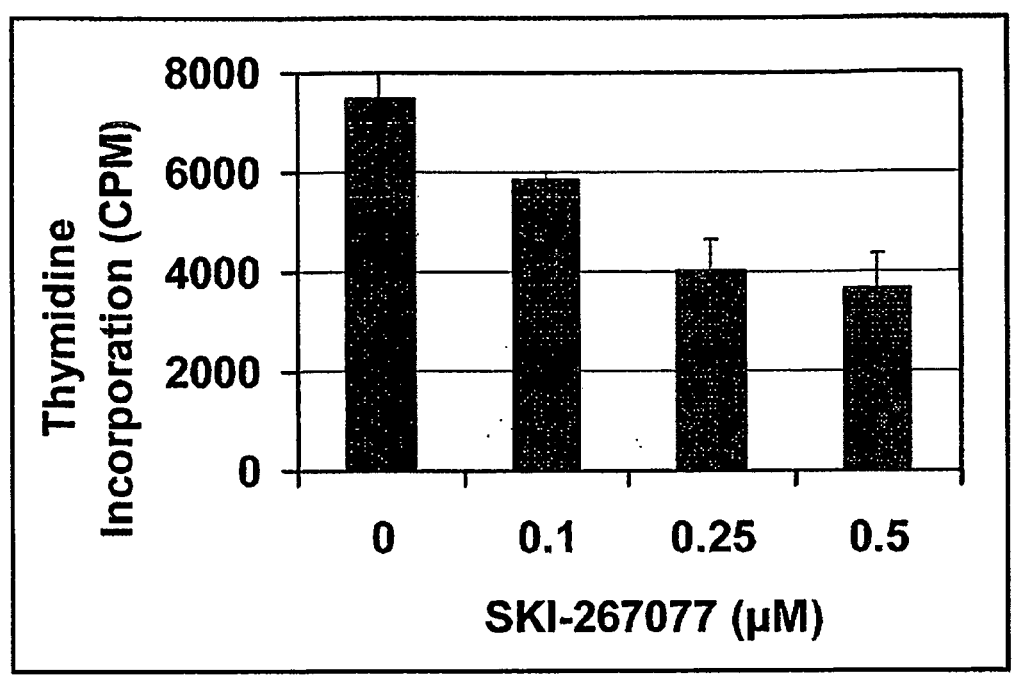
FIG. 1. SKI-267077 blocks DNA synthesis. H2030 cells were treated with the indicated concentration of SKI-267077 for 24 h and then the incorporation of $^3$H-thymidine into DNA was determined FIGS. 2A-2B. SKI-267077 induces cell cycle arrest. H2030 cells were treated with SKI-267077 for 24 h. Cell cycle progression was analyzed by FACS analysis.

Definitions of specific functional groups and chemical terms are described in more detail below. For purposes of this invention, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry, $5^{th}$* Edition, John Wiley & Sons, Inc., New York, 2001; Larock, *Comprehensive Organic Transformations*, VCH Publishers, Inc., New York, 1989; Carruthers, *Some Modern Methods of Organic Synthesis, $3^{rd}$* Edition, Cambridge University Press, Cambridge, 1987; the entire contents of each of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Where an isomer/enantiomer is preferred, it may, in some embodiments be provided substantially free of the corresponding enantiomer, and may also be referred to as "optically enriched." Thus, an "optically-enriched" isomer/enantiomer refers to a compound which is isolated or separated via separation techniques or prepared free of the corresponding isomer/enantiomer. "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds.

Examples of substituents are defined herein, and include, but are not limited to, aliphatic, carbocyclic, alkyl, alkenyl, alkynyl, aliphaticoxy, alkyloxy, alkenyloxy, alkynyloxy, aliphaticthioxy, alkylthioxy, alkenylthioxy, alkynylthioxy, heteroaliphatic, heterocyclic, aryl, heteroaryl, acyl, amido, imido, sulfinyl, sulfonyl, aliphaticamino, dialiphaticamino, trialiphaticamino, arylamino, diarylamino, carboxaldehyde, cyano, isocyano, amino, azido, hydrazino nitro, oxo, thiooxo, imino, hydroxy, thio, halo, aryloxy, arylthioxy, and arylamino; wherein any of the substituents described above and herein may be substituted or unsubstituted, branched or unbranched, cyclic or acyclic, which result in the formation of a stable moiety. These substituents recited above may be optionally substituted by additional substituents, such as oxo, thioxo, or imino, or may be optionally substituted by any of the substituents recited above, given that the combination results in a stable moiety. Exemplary substituent combinations include, for example, perfluoroaliphatic, perfluoroaliphaticoxy, aminoaliphatic, hydroxyaliphatic, thioaliphatic, arylaliphatic, heteroarylaliphatic, arylaliphaticthioxy, arylaliphaticoxy, arylaliphaticamino, heteroaliphaticoxy, heteroaliphaticthioxy, heteroaliphaticamino; Additional examples of generally applicable substituents are illustrated by the specific embodiments and in the Examples as described herein.

The term "stable moiety," as used herein, preferably refers to a moiety which possess stability sufficient to allow manufacture, and which maintains its integrity for a sufficient period of time to be useful for the purposes detailed herein.

The term "aliphatic," as used herein, includes both saturated and unsaturated, nonaromatic, straight chain (i.e., unbranched), branched, acyclic, cyclic, or polycyclic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "alkyl" is used to indicate those alkyl groups (cyclic, acyclic, substituted, unsubstituted, branched or unbranched) having 1-6 carbon atoms. Substituents include, but are not limited to, any of the substituents described herein, that result in the formation of a stable moiety.

The term "carbocyclic," "carbocycle," or "carbocycyl," as used herein, refers to a cyclic aliphatic group, such as a cycloalkyl, cycloalkenyl, and cycloalkynyl, which may be substituted or unsubstituted. Substituents include, but are not limited to, any of the substituents described herein, that result in the formation of a stable moiety.

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-10 carbon atoms. In another embodiment, the alkyl group employed contains 1-8 carbon atoms. In still other embodiments, the alkyl group contains 1-6 carbon atoms. In yet another embodiments, the alkyl group contains 1-4 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substitutents. Substituents include, but are not limited to, any of the substituents described herein, that result in the formation of a stable moiety.

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 1-20 carbon atoms. In some embodiments, the alkenyl group employed in the invention contains 1-10 carbon atoms. In another embodiment, the alkenyl group employed contains 1-8 carbon atoms. In still other embodiments, the alkenyl group contains 1-6 carbon atoms. In yet another embodiments, the alkenyl group contains 1-4 carbons. Alkenyl groups include, for example, ethenyl, propenyl, butenyl, 1-methyl-2-buten-1-yl, and the like, which may bear one or more substituents. Substituents include, but are not limited to, any of the substituents described herein, that result in the formation of a stable moiety.

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 1-20 carbon atoms. In some embodiments, the alkynyl group employed in the invention contains 1-10 carbon atoms. In another embodiment, the alkynyl group employed contains 1-8 carbon atoms. In still other embodiments, the alkynyl group contains 1-6 carbon atoms. Representative alkynyl groups include, but are not limited to, ethynyl, 2-propynyl (propargyl), 1-propynyl, and the like, which may bear one or more substituents. Substituents include, but are not limited to, any of the substituents described herein, that result in the formation of a stable moiety.

The term "aliphaticoxy," as used herein, refers to an aliphatic group, defined herein, attached to the parent molecular moiety through an oxygen atom. In certain embodiments, the aliphatic group contains 1-20 aliphatic carbon atoms. In certain other embodiments, the aliphatic group employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples include, but are not limited to, methoxy, ethoxy, propoxy, isopropoxy, n-butoxy, tert-butoxy, i-butoxy, sec-butoxy, neopentoxy, n-hexoxy, and the like, which may bear one or more substituents. Substituents include, but are not limited to, any of the above-listed substituents, and that result in the formation of a stable moiety.

The terms "alkyloxy," "alkenyloxy" and "alkynyloxy" refer to an alkyl, alkenyl and alkynyl group, respectively, attached to the parent molecular moiety through an oxygen atom.

The terms "aliphaticthioxy," as used herein, refer to an aliphatic group attached to the parent molecular moiety through a sulfur atom. In certain embodiments, the aliphatic group contains 1-20 aliphatic carbon atoms. In certain other embodiments, the aliphatic group contains 1-10 aliphatic carbon atoms. In yet other embodiments, the aliphatic group contains 1-8 aliphatic carbon atoms. In still other embodiments, the aliphatic group contains 1-6 aliphatic carbon atoms. In yet other embodiments, the aliphatic group contain 1-4 aliphatic carbon atoms. Examples of aliphaticthioxy moieties include, but are not limited to, methylthio, ethylthio, propylthio, isopropylthio, n-butylthio, and the like.

The terms "alkylthioxy," "alkenylthioxy" and "alkynylthioxy" refer to an alkyl, alkenyl, and alkynyl group, respectively, attached to the parent molecular moiety through a sulfur atom.

The term "heteroaliphatic," as used herein, refers to an aliphatic moiety, as defined herein, that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. Substituents include, but are not limited to, any of the substituents described herein, that result in the formation of a stable moiety.

The term "heterocyclic," or "heterocyclyl," as used herein, refers to an non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, piperidinyl, piperazinyl, azocanyl, thiaranyl, thietanyl, tetrahydrothiophenyl, dithiolanyl, thiacyclohexanyl, oxiranyl, oxetanyl, tetrahydropuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety.

The term "aryl," as used herein, refer to stable aromatic mono- or polycyclic ring system having 3-20 ring atoms, of which all ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Substituents include, but are not limited to, any of the substituents described herein, that result in the formation of a stable moiety.

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Substituents include, but are not limited to, any of the substituents described herein, that result in the formation of a stable moiety.

The term "acyl," as used herein, refers to a group having the general formula —C(=O)R, where R is hydrogen, halogen, hydroxy, thio, amino, aliphatic, carbocyclic, heteroaliphatic, alkyl, alkenyl, alkynyl, aryl, alkyloxy, alkylthioxy, alkylamino, dialkylamino, arylamino, diarylamino, aryl, heteroaryl, or heterocycyl. Exemplary acyl groups include aldehydes, carboxylic acids, ketones (such as an acetyl group [—(C=O)CH$_3$], esters, amides, carbonates, carbamates, and ureas.

The term "acyloxy," as used herein, refers to an acyl group of the formula (—OC(=O)R), where R may be hydrogen, hydroxy, thio, amino, aliphatic, carbocyclic, heteroaliphatic, alkyl, alkenyl, alkynyl, aryl, aliphaticoxy, aliphaticthioxy, aliphaticamino, dialiphaticamino, arylamino, diarylamino, aryl, heteroaryl, or heterocycyl.

The term "amide," or "amido," as used herein, refers to an acyl group having the general formula —C(=O)N(R)(R), —N(H)C(=O)(R), or —N(R)C(=O)(R), where each instance of R is, hydrogen, hydroxy, thio, amino, aliphatic, carbocyclic, heteroaliphatic, alkyl, alkenyl, alkynyl, aryl, alkyloxy, alkylthioxy, alkylamino, dialkylamino, arylamino, di arylamino, aryl, heteroaryl, or heterocycyl.

The term "imide," or "imido," as used herein, refers to a group having the general formula —C(=NR)R, —OC(=NH)R, —OC(=NR)R, —C(=NH)R, —N(H)C(=NH)R, —N(H)C(=NR)R, —N(R)C(=NH)R, or —N(R)C(=NR)R, where each instance of R is, independently, aliphatic, heteroaliphatic, aryl, heteroaryl or heterocyclyl.

The term "sulfinyl," as used herein, refers to a group of the formula R—S(=O)— where there is one double bond between the sulfur and oxygen, and where R may be aliphatic, aryl, alkoxy, hydroxy, thiol, alkylthioxy, amino, alkylamino, dialkylamino, aryl, heteroaryl, or heterocyclyl. The term "aliphaticsulfinyl" refers to a sulfinyl group where R may be aliphatic, heterocyclyl, or heteroaliphatic. The term "arylsulfinyl" refers to a sulfinyl group where R may be aryl or heteroaryl.

The term "sulfonyl," as used herein, refers to an organic radical (or functional group) obtained from an sulfonic acid by the removal of the hydroxyl group. Sulfonyl groups can be written as having the general formula R—S(=O)$_2$—, where there are two double bonds between the sulfur and oxygen, and where R may be aliphatic, heteroaliphatic, aryl, alkyloxy, hydroxy, thiol, alkylthioxy, amino, alkylamino, dialkylamino, aryl, heteroaryl, or heterocyclic. The term "aliphaticsulfonyl" refers to a sulfonyl group where R may be aliphatic, heteroaliphatic, or heterocyclic. The term "arylsulfonyl" refers to a sulfonyl group where R may be aryl or heteroaryl. The names of sulfonyl groups typically end in -syl, such as tosyl (toluene sulfonyl, $CH_3C_6H_4SO_2$—), mesyl (methyl sulfonyl, $CH_3SO_2$—), etc.

The terms "aliphaticamino," "dialiphaticamino," and "trialiphaticamino," as used herein, refers to one, two, or three, respectively, aliphatic, heterocyclyl or heteroaliphatic groups, as previously defined, attached to the parent molecular moiety through a nitrogen atom. The term "aliphaticamino" refers to a group having the structure —NHR' wherein R' is an aliphatic, heterocyclyl or heteroaliphatic group, as previously defined; and the term "dialiphaticamino" refers to a group having the structure —NR'R", wherein R' and R" are each independently selected from the group consisting of aliphatic, heterocyclyl or heteroaliphatic groups. The term "trialiphaticamino" refers to a group having the structure —NR'R"R'", wherein R', R", and R'" are each independently selected from the group consisting of aliphatic, heterocyclyl or heteroaliphatic groups. In certain embodiments, the R', R", or R'" groups contain 1-20 carbon atoms. In certain other embodiments, the R', R", or R'" groups contain 1-10 carbon atoms. In yet other embodiments, the R', R", or R'" groups contain 1-8 carbon atoms. In still other embodiments, the R', R", or R'" groups contain 1-6 carbon atoms. In yet other embodiments, the R', R", or R'" groups contain 1-4 carbon atoms. Additionally, R', R", and/or R'" taken together may optionally be joined to form a five to six membered ring system. Examples include, but are not limited to, methylamino, dimethylamino, ethylamino, diethylamino, diethylaminocarbonyl, methylethylamino, iso-propylamino, piperidino, piperazinyl, pyrrolidinyl, trimethylamino, and propylamino. In certain embodiments, the R', R", or R'" groups are substituted by independent replacement of one or more of the hydrogen atoms thereon with one or more substituents. Substituents include, but are not limited to, any of the substituents described herein, that result in the formation of a stable moiety.

The terms "arylamino," and "diarylamino," as used herein, refers to one, or two, respectively, aryl or heteroaryl groups, as previously defined, attached to the parent molecular moiety through a nitrogen atom. The term "arylamino" refers to a group having the structure —NHR' wherein R' is an aryl or heteroaryl group, as previously defined; and the term "diarylamino" refers to a group having the structure —NR'R", wherein R' and R" are each independently selected from the group consisting of aryl and heteroaryl. In certain embodiments, the R' or R" groups are substituted by independent replacement of one or more of the hydrogen atoms thereon with one or more substituents. Substituents include, but are not limited to, any of the substituents described herein, that result in the formation of a stable moiety.

The term "perfluoroaliphatic," as used herein, refers to an aliphatic group, as defined herein, that has only fluorine substituents. Such perfluoroaliphatic include trifluoromethyl (—CF$_3$).

The term "perfluoroaliphaticoxy," as used herein, refers to a perfluoroaliphatic group, as defined herein, that is attached to the parent group through an oxygen atom.

The terms "carboxaldehyde," or "carboxyaldehyde," as used herein, refers to an acyl group of the formula —CHO.

The term "cyano," as used herein, refers to a group of the formula (—CN).

The term "isocyano," as used herein, refers to a group of the formula (—NC).

The term "amino," as used herein, refers to a group of the formula (—NH$_2$).

The term "azido," as used herein, refers to a group of the formula (—N$_3$).

The term "hydrazino," as used herein, refers to a group of the formula [(—N(R'")—N(R')(R")], wherein each instance of R', R", or R'", is a hydrogen, or a substituent. Substituents include, but are not limited to, any of the substituents described herein, that result in the formation of a stable moiety.

The term "nitro," as used herein, refers to a group of the formula (—NO$_2$).

The term "oxo," as used herein, refers to a group of the formula (=O)

The term "thiooxo," as used herein, refers to a group of the formula (=S).

The term "imino," as used herein, refers to a group of the formula (=NR'), wherein R' is a hydrogen, or a substituent. Substituents include, but are not limited to, any of the substituents described herein, that result in the formation of a stable moiety.

The term "hydroxy," or "hydroxyl," as used herein, refers to a group of the formula (—OH).

The term "thio," or "thiol," as used herein, refers to a group of the formula (—SH).

The terms "halo" and "halogen" as used herein refer to an atom selected from fluorine (fluoro), chlorine (chloro), bromine (bromo), and iodine (iodo).

The term "aminoaliphatic," as used herein, refers to an amino group, as defined herein, attached to the parent molecular moiety through an aliphatic group.

The term "hydroxyaliphatic," as used herein, refers to a hydroxy group, as defined herein, attached to the parent molecular moeity through an aliphatic group.

The term "thioaliphatic," as used herein, refers to a thio group, as defined herein, attached to the parent molecular moiety through an aliphatic group.

The term "arylaliphatic," as used herein, refers to an aryl group, as defined herein, attached to the parent molecular moeity through an aliphatic group.

The term "heteroarylaliphatic" as used herein, refers to a heteroaryl group, as defined herein, attached to the parent molecular moiety through an aliphatic group.

The term "aryloxy," as used herein, refers to an aryl group, as defined herein, attached to the parent molecular moiety through an oxygen atom.

The term "arylthioxy," as used herein, refers to an aryl group, as defined herein, attached to the parent molecular moiety through a sulfur atom.

The term "arylamino," as used herein, refers to an aryl group, as defined herein, attached to the parent molecular moiety through a nitrogen atom —(N)(R')—, wherein R' is a hydrogen, or a substituent. Substituents include, but are not limited to, any of the substituents described herein, that result in the formation of a stable moiety.

The term "arylaliphaticthioxy," as used herein, refers to an arylaliphatic group, as defined herein, attached to the parent molecular moiety through a sulfur atom.

The term "arylaliphaticoxy," as used herein, refers to an arylaliphatic group, as defined herein, attached to the parent molecular moiety through an oxygen atom.

The term "arylaliphaticamino," as used herein, refers to an arylaliphatic group, as defined herein, attached to the parent molecular moiety through a nitrogen atom —(N)(R')—, wherein R' is a hydrogen, or a substituent. Substituents include, but are not limited to, any of the substituents described herein, that result in the formation of a stable moiety.

The term "heteroaliphaticoxy," as used herein, refers to a heteroaliphatic group, as defined herein, attached to the parent molecular moiety through an oxygen atom.

The term "heteroaliphaticthioxy," as used herein, refers to a heteroaliphatic group, as defined herein, attached to the parent molecular moiety through a sulfur atom.

The term "heteroaliphaticamino," as used herein, refers to a heteroaliphatic group, as defined herein, attached to the parent molecular moiety through a nitrogen atom —(N)(R')(R"), wherein R' and R" is, independently, a hydrogen, or a substituent. Substituents include, but are not limited to, any of the substituents described herein, that result in the formation of a stable moiety.

The term "Ph," as used herein, refers to a phenyl group.

The term "Ar," as used herein, refers to an aryl or a heteroaryl group.

General Terms

The term "neoplasia," or "neoplastic," or "neoplasm," as used herein, refers to the abnormal growth of tissue in a subject, and may be either benign or malignant.

The presently claimed invention is directed to the treatment of neoplasia in a subject. In certain embodiments, the neoplasia is a tumor. Tn certain embodiments, the neoplasia is a benign tumor. In certain embodiments, the neoplasia is a malignant tumor (i.e., cancer).

By the term "tumor" is meant a neoplastic growth of cells which may be either benign or malignant.

The term "proliferative disease" as used herein refers to any disease associated with an undesired and/or abnormal proliferation of cells. The cells may be any type of cell found in the subject. The proliferation may be due to any cause (e.g., any genetic mutation, any signal). Examples of proliferative diseases include cancer, neoplasms, inflammatory diseases, autoimmune diseases, graft-vs.-host disease, diabetic retinopathy, and benign tumors.

By the term "cancer" is meant a malignant neoplasm. Cancers are classified by the type of cell that resembles the tumor and, therefore, the tissue presumed to be the origin of the tumor; e.g., carcinoma: malignant tumors derived from epithelial cells, and represents the most common cancers, including breast, prostate, lung and colon cancer; lymphoma and leukemia: malignant tumors derived from blood and bone marrow cells; sarcoma: malignant tumors derived from connective tissue, or mesenchymal cells; mesothelioma: tumors derived from the mesothelial cells lining the peritoneum and the pleura; glioma: tumors derived from glia, the most common type of brain cell; germinoma: tumors derived from germ cells, normally found in the testicle and ovary; choriocarcinoma: malignant tumors derived from the placenta. In certain embodiments, the presently claimed invention is directed to the treatment of prostate cancer, lung cancer, breast cancer, brain cancer, bone cancer, stomach cancer, oral cancer, skin cancer (melanoma), colorectal cancer, bladder cancer, pancreatic cancer, endometrial cancer, ovarian cancer, endometrial cancer, cutaneous melanoma, leukemia, non-Hodgkin's lymphoma, Wilms' tumor, lymphomas, rhabdomyosarcoma (arising from muscle), retinoblastoma, osteosarcoma, or Ewing's sarcoma, in a subject.

The term "subject," as used herein, refers to any animal. In certain embodiments, the subject is a mammal. In certain embodiments, the term "subject", as used herein, refers to a human (e.g., a man, a woman, or a child).

The terms "administer," "administering," or "administration," as used herein, refer to either directly administering a compound or composition to a patient, or administering a prodrug derivative or analog of the compound to the patient, which will form an equivalent amount of the active compound or substance within the patient's body.

The terms "treat" or "treating," as used herein, refers to partially or completely alleviating, inhibiting, preventing, ameliorating, and/or relieving the condition.

The terms "effective amount" and "therapeutically effective amount," as used herein, refer to the amount of a compound of the presently claimed invention that, when administered to a patient, is effective to at least partially treat a condition from which the subject is suffering. Conditions include, but are not limited to, renal cancer, bladder cancer, liver cancer, testicular cancer, ovarian cancer, colorectal cancer, prostate cancer, pancreatic cancer, lung cancer, breast cancer, brain cancer, bone cancer, stomach cancer, oral cancer, skin cancer, blood cancer, leukemia, non-Hodgkin's lymphoma, Wilms' tumor, lymphomas, rhabdomyosarcoma, retinoblastoma, osteosarcoma, Ewing's sarcoma, or any other disorder as described herein. To be "therapeutically effective," against tumors or cancers, as used herein, is meant reducing the neoplasm, or slowing or halting the growth or spread of the neoplasm, e.g., tumor or cancer, in a subject diagnosed or suffering from a tumor or cancer.

The term "pharmaceutically acceptable salts" or "pharmaceutically acceptable salt" includes acid addition salts, that is salts derived from treating a compound of the presently claimed invention with an organic or inorganic acid such as, for example, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluencsulfonic, salicylic, benzoic, or similarly known acceptable acids. Where a compound the presently claimed invention contains a substituent with acidic properties, for instance, phenolic hydroxyl, the term also includes salts derived from bases, for example, sodium salts.

The term "prodrug," as used herein, is meant a compound which is administered to a subject in an inactive (or significantly less active) form. Once administered, the prodrug is metabolised in vivo, for example, by deacylation, dephosphorylation, hydrolysis, or epimerization, into a more active compound.

The term "isomers," as used herein, is meant two or more organic compounds that are configurational isomers (e.g., isomers that are constitutionally identical but differ by a 3D distribution of groups in space). Configurational isomers include geometric isomers (e.g., cis, trans, E, Z) and stereoisomers (e.g., enantiomers, diastereomers, atropisomers).

The term "tautomers," as used herein, is meant two or more organic compounds generated from each other by a formal migration of a hydrogen atom, and accompanied by an exchange of valencies between a single bond and an adjacent double bond, i.e., a tautomerization reaction. Tautomers include keto-enol, amide-imidic, lactam-lactim, enamine-imine, and enamine-imine. In solutions where tautomerization is possible, a chemical equilibrium of the tautomers will be reached. The exact ratio of the tautomers depends on several factors, including temperature, solvent, and pH.

DETAILED DESCRIPTION OF CERTAIN EMBODIMENTS OF THE INVENTION

The present invention is directed to pyridazinone and furan-containing compounds, and pharmaceutically acceptable salts, prodrugs, isomers, and tautomers, thereof, pharmaceutical compositions, kits, methods of syntheses, and methods of treating proliferative diseases, such as cancer (e.g., lung cancer), in a subject by administering a therapeutically effective amount of a compound of the present invention, or a pharmaceutically acceptable salt, prodrug, isomer, or tautomer, thereof.

Furthermore, the compounds of the present invention may target a common effector in the oncogenic EGFR and/or KRAS pathways, and may be so identified using cell-based screens as described herein. Such compounds are effective in the treatment of cancers that are associated with EGFR and/or KRAS mutations.

Compounds of Formula (I)

Pyridazinone compounds of the present invention correspond to compounds of formula (I) as depicted below:

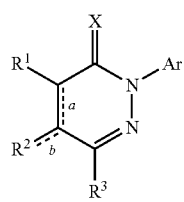

(I)

wherein X is oxygen or $NR^x$;

$R^x$ is hydrogen, optionally substituted aliphatic, optionally substituted heteroaliphatic, optionally substituted heterocyclyl, optionally substituted aryl, optionally substituted heteroaryl, optionally substituted acyl, optionally substituted sulfinyl, optionally substituted sulfonyl, optionally substituted hydroxy, or optionally substituted amino;

═══ designates a single or double bond represented by a and b; with the proviso that:

(i) when a is a double bond, b is a single bond, and $R^1$, $R^2$, and $R^3$, are, independently, hydrogen, aliphatic, heteroaliphatic, hydroxy, thio, amino, heterocyclic, aryl, heteroaryl, acyl, amido, imido, sulfinyl, sulfonyl, carboxaldehyde, cyano, isocyano, azido, hydrazino, nitro, halo; optionally substituted with oxo, thiooxo, imino, aliphatic, carbocyclic, hydroxy, aliphaticoxy, aryloxy, thio, aliphaticthioxy, arylthioxy, heteroaliphatic, heterocyclic, aryl, arylaliphatic, heteroaryl, heteroarylaliphatic, acyl, acyloxy, amido, imido, sulfinyl, sulfonyl, amino, aliphaticamino, dialiphaticamino, trialiphaticamino, arylamino, diarylamino, carboxaldehyde, cyano, isocyano, azido, hydrazino, nitro, or halo; or $R^1$ and $R^2$ are joined to form a 5- to 6-membered optionally substituted carbocyclic, optionally substituted heterocyclic, optionally substituted aryl or optionally substituted heteroaryl ring, and $R^3$ is as defined above; or $R^2$ and $R^3$ are joined to form a 5- to 6-membered optionally substituted carbocyclic, optionally substituted heterocyclic, optionally substituted aryl or optionally substituted heteroaryl ring, and $R^1$ is as defined above; or (ii) when a is a single bond, b is a double bond, and $R^2$ and the carbon directly attached to $R^2$ form an (═O), (═S), or (═$NR^y$) group, wherein $R^y$ is hydrogen, aliphatic, heteroaliphatic, hydroxy, thio, amino, heterocyclic, aryl, heteroaryl, acyl, amido, imido, sulfinyl, sulfonyl, carboxaldehyde, cyano, isocyano, azido, hydrazino, nitro, halo; optionally substituted with oxo, thiooxo, imino, aliphatic, carbocyclic, hydroxy, aliphaticoxy, aryloxy, thio, aliphaticthioxy, arylthioxy, heteroaliphatic, heterocyclic, aryl, arylaliphatic, heteroaryl, heteroarylaliphatic, acyl, acyloxy, amido, imido, sulfinyl, sulfonyl, amino, aliphaticamino, dialiphaticamino, trialiphaticamino, arylamino, diarylamino, carboxaldehyde, cyano, isocyano, azido, hydrazino, nitro, or halo; and $R^1$ and $R^3$ are, independently, hydrogen, aliphatic, heteroaliphatic, hydroxy, thio, amino, heterocyclic, aryl, heteroaryl, acyl, amido, imido, sulfinyl, sulfonyl, carboxaldehyde, cyano, isocyano, azido, hydrazino, nitro, halo; optionally substituted with oxo, thiooxo, imino, aliphatic, carbocyclic, hydroxy, aliphaticoxy, aryloxy, thio, aliphaticthioxy, arylthioxy, heteroaliphatic, heterocyclic, aryl, arylaliphatic, heteroaryl, heteroarylaliphatic, acyl, acyloxy, amido, imido, sulfinyl, sulfonyl, amino, aliphaticamino, dialiphaticamino, trialiphaticamino, arylamino, diarylamino, carboxaldehyde, cyano, isocyano, azido, hydrazino, nitro, or halo;

Ar is a group selected from aryl, heteroaryl, aliphatic optionally substituted with aryl, aliphatic optionally substituted with heteroaryl, heteroaliphatic optionally substituted with aryl, or heteroaliphatic optionally substituted with heteroaryl, each group optionally substituted with aliphatic, heteroaliphatic, carbocyclic, hydroxy, aliphaticoxy, aryloxy, thio, aliphaticthioxy, arylthioxy, heteroaliphatic, heterocyclic, aryl, arylaliphatic, heteroaryl, heteroarylaliphatic, acyl, acyloxy, amido, imido, sulfinyl, sulfonyl, amino, aliphaticamino, dialiphaticamino, trialiphaticamino, arylamino, diarylamino, carboxaldehyde, cyano, isocyano, azido, hydrazino, nitro, or halo;

and pharmaceutically acceptable salts, prodrugs, isomers, or tautomers, thereof.

In certain embodiments, the compound 4,5-dichloro-2-m-tolyl-2H-pyridazin-3-one (SKI-104122), as depicted below, is specifically excluded from compounds of formula (I):

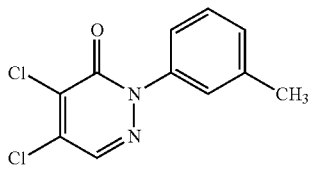 [SMILES: Cc1cccc(-n2ncc(Cl)c(Cl)c2=O)c1]

4,5-dichloro-2-m-tolyl-2H-pyridazin-3-one

In certain embodiments, $R^1$ and $R^2$ are the same, and $R^3$ is hydrogen, halo, optionally substituted acyl, optionally substituted heterocyclic, optionally substituted aryl, optionally substituted heteroaryl, or optionally substituted hydroxy.

In other embodiments, $R^1$ and $R^2$ are both hydrogen.

In other embodiments, $R^1$ and $R^2$ are both chloro. In other embodiments, $R^1$ and $R^2$ are both bromo. In other embodiments, $R^1$ and $R^2$ are both iodo. In other embodiments, $R^1$ and $R^2$ are both fluoro.

In other embodiments, $R^1$ and $R^2$ are both optionally substituted hydroxy. In yet other embodiments, $R^1$ and $R^2$ are both optionally substituted thio. In yet other embodiments, $R^1$ and $R^2$ are both optionally substituted amino.

In yet other embodiments, $R^1$ and $R^2$ are both optionally substituted aliphatic. In yet other embodiments, $R^1$ and $R^2$ are both optionally substituted heterocylic.

In yet other embodiments, $R^1$ and $R^2$ are both cyano.

In certain embodiments, the compounds of formula (I), wherein $R^1$ and $R^2$ are the same, have one of the following structural formulae:

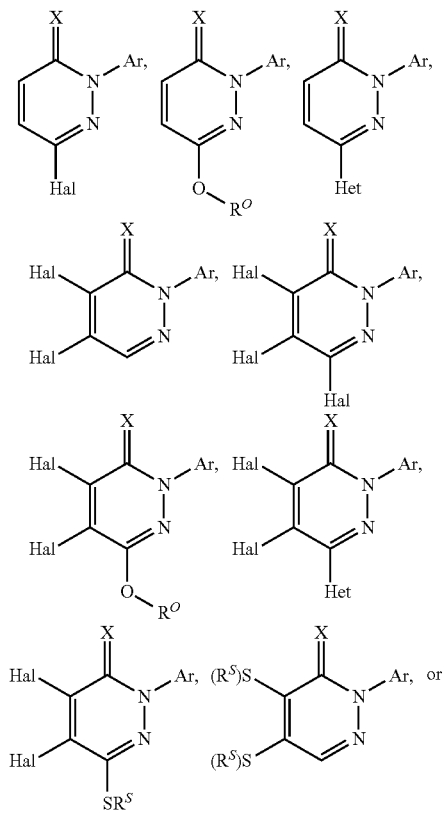

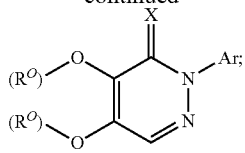

wherein X is oxygen or or $NR^x$; Hal is bromo, chloro, iodo or fluoro; Het is an optionally substituted heterocycyl; each instance of $R^O$ is hydrogen, or an optionally substituted aliphatic, optionally substituted heteroaliphatic, optionally substituted aryl, optionally substituted heteroaryl, optionally substituted acyl, optionally substituted sulfinyl, or optionally substituted sulfonyl, or two $R^O$ groups are joined to form a 5- to 6-membered optionally substituted heterocyclic ring; and each instance of $R^S$ is hydrogen, or an optionally substituted aliphatic, optionally substituted heteroaliphatic, optionally substituted aryl, optionally substituted heteroaryl, optionally substituted acyl, optionally substituted sulfinyl, or optionally substituted sulfonyl, or two $R^S$ groups are joined to form a 5- to 6-membered optionally substituted heterocyclic ring.

In certain embodiments, $R^1$ and $R^2$ are the different, and $R^3$ is hydrogen, halo, optionally substituted acyl, optionally substituted heterocyclic, optionally substituted aryl, optionally substituted heteroaryl, or optionally substituted hydroxy.

In certain embodiments, $R^1$ and $R^2$ are the different, and are selected from the group consisting of hydrogen, halo, cyano, nitro, azido, optionally substituted hydroxy, optionally substituted thio, optionally substituted amino, optionally substituted aliphatic, optionally substituted heteroaliphatic, optionally substituted heterocyclic, optionally substituted aryl, or optionally substituted heteroaryl.

In certain embodiments, compounds of formula (I), wherein $R^1$ and $R^2$ are the different, correspond to the following structural formulae:

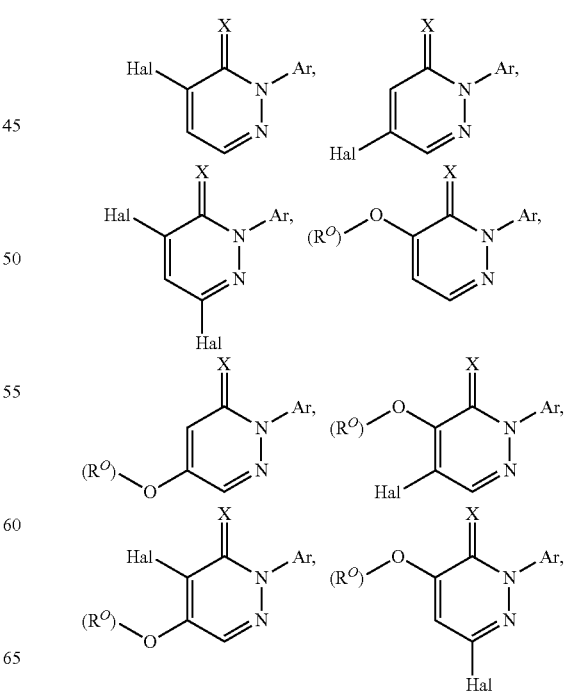

-continued

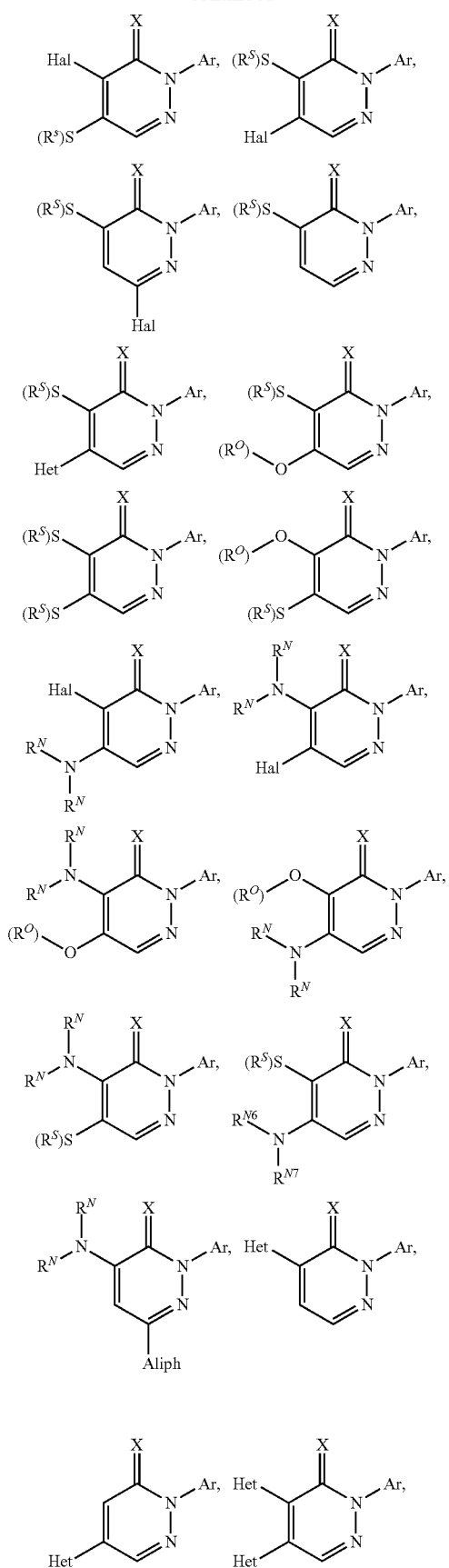

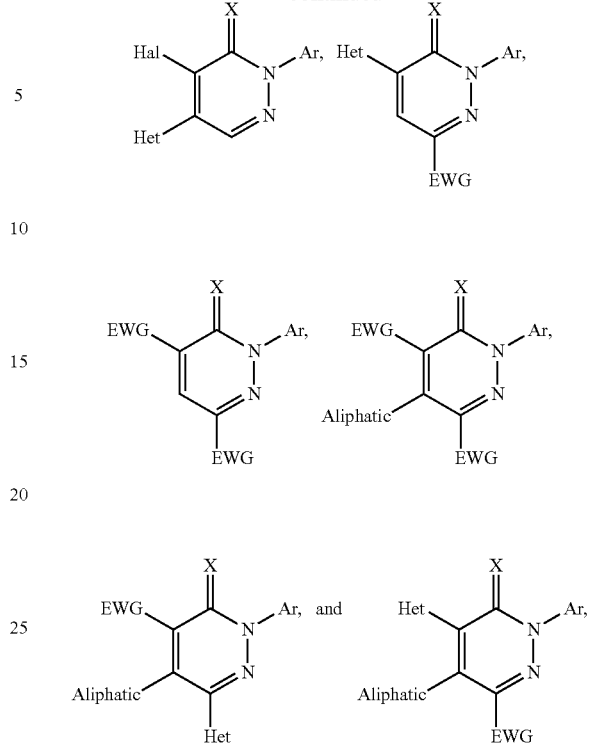

wherein X; Hal; Het; $R^O$; and $R^S$ are as described above; and EWG (electron withdrawing group) is acyl (e.g., carboxylic acid, carboxaldehyde, ester, amide, imide, ketone), nitro, or cyano; Aliphatic is optionally substituted aliphatic; and each instance of $R^N$ is, hydrogen, or an optionally substituted amino, optionally substituted aliphatic, optionally substituted heteroaliphatic, optionally substituted aryl, optionally substituted heteroaryl, optionally substituted acyl, optionally substituted sulfinyl, or optionally substituted sulfonyl, or two $R^N$ groups, both groups present on the same nitrogen, are joined to form a 5- to 6-membered optionally substituted heterocyclic ring, an azido group (—$N_3$), or an optionally substituted hydrazino group.

In certain embodiments, the Ar group of compounds of formula (I) corresponds to an optionally substituted aryl, or an aliphatic group optionally substituted with aryl. Exemplary aryl groups include phenyl, napthyl, and biphenyl. In certain embodiments, the Ar group is an optionally substituted phenyl group.

In certain embodiments, the Ar group of compounds of formula (I) corresponds to an optionally substituted heteroaryl, or an aliphatic group optionally substituted with heteroaryl. Exemplary heteroaryl groups include pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, thiazolynyl, isothiazolyl, thiadiazolynyl, oxazolyl, isoxazolyl, oxadiaziolyl, and oxadiaziolyl. In certain embodiments, the Ar group is an optionally substituted pyridinyl group.

In certain embodiments, the Ar group of compounds of formula (I) correspond to the following structural formula:

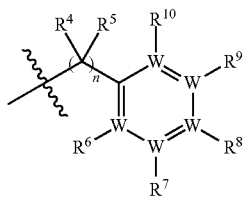

wherein n is 0 or 1;

W is a carbon or nitrogen atom; with the proviso that when W is nitrogen, the group directly attached to nitrogen (e.g., $R^6$, $R^7$, $R^8$, $R^9$, or $R^{10}$) is an electron pair; and when W is a carbon, then the group directly attached to the carbon (e.g., $R^6$, $R^7$, $R^8$, $R^9$, or $R^{10}$) is as defined herein;

each instance of $R^6$, $R^7$, $R^8$, $R^9$, and $R^{10}$ is, independently, hydrogen, aliphatic, heteroaliphatic, hydroxy, thio, amino, heterocyclic, aryl, heteroaryl, acyl, amido, imido, sulfinyl, sulfonyl, carboxaldehyde, cyano, isocyano, azido, hydrazino, nitro, halo; optionally substituted with oxo, thio-oxo, imino, aliphatic, heteroaliphatic, carbocyclic, hydroxy, aliphaticoxy, aryloxy, thio, aliphaticthioxy, arylthioxy, heteroaliphatic, heterocyclic, aryl, arylaliphatic, heteroaryl, heteroarylaliphatic, acyl, acyloxy, amido, imido, sulfinyl, sulfonyl, amino, aliphaticamino, dialiphaticamino, trialiphaticamino, arylamino, diarylamino, carboxaldehyde, cyano, isocyano, azido, hydrazino, nitro, or halo; or $R^6$ and $R^7$ may be joined to form a 5- or 6-membered optionally substituted carbocyclic, optionally substituted heterocyclic, optionally substituted aryl, or optionally substituted heteroaryl ring; $R^7$ and $R^8$ may be joined to form a 5- or 6-membered optionally substituted carbocyclic, optionally substituted heterocyclic, optionally substituted aryl, or optionally substituted heteroaryl ring; $R^8$ and $R^9$ may be joined to form a 5- or 6-membered optionally substituted carbocyclic, optionally substituted heterocyclic, optionally substituted aryl, or optionally substituted heteroaryl ring; or $R^9$ and $R^{10}$ may be joined to form a 5- or 6-membered optionally substituted carbocyclic, optionally substituted heterocyclic, optionally substituted aryl, or optionally substituted heteroaryl ring; and each instance of $R^4$ and $R^5$ is, independently, hydrogen or optionally substituted aliphatic.

In certain embodiments, the Ar group of formula (I) corresponds to the following structural formulae:

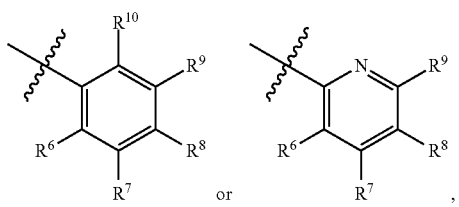

wherein n is 0, and $R^6$, $R^7$, $R^8$, $R^9$, and $R^{10}$ are as described above and herein.

In certain embodiments, when n is 0, $R^7$ is not hydrogen. In certain embodiments, when n is 1, $R^6$, $R^7$, $R^8$, $R^9$, and $R^{10}$ are all hydrogen. In certain embodiments, when $R^8$ is not hydrogen, $R^7$ is also not hydrogen. In certain embodiments, when $R^6$ is not hydrogen, $R^8$ is hydrogen.

In certain embodiments, the Ar group of formula (I) corresponds to the following structural formulae:

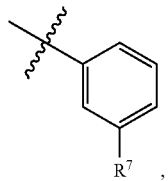

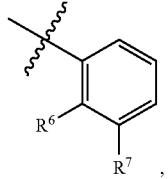

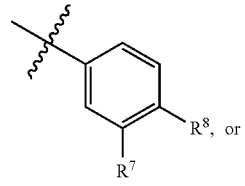

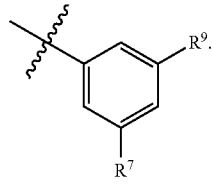

In certain embodiments, for compounds having an Ar group corresponding to structural formula Ia-Ar, $R^7$ is halo, optionally substituted hydroxy, optionally substituted aliphatic, or optionally substituted heteroaliphatic. In certain embodiments, $R^7$ is bromo, chloro, iodo, methyl, ethyl, n-propyl, n-butyl, trifluoromethyl, benzyl, or methoxy.

In certain embodiments, for compounds having an Ar group corresponding to structural formula Ib-Ar, $R^6$ and $R^7$ are, independently, halo, optionally substituted hydroxy, optionally substituted aliphatic, or optionally substituted heteroaliphatic. In certain embodiments, $R^6$ is bromo, chloro, iodo, methyl, ethyl, n-propyl, n-butyl, trifluoromethyl, benzyl, or methoxy, and $R^7$ is bromo, chloro, iodo, methyl, ethyl, n-propyl, n-butyl, trifluoromethyl, benzyl, or methoxy.

In certain embodiments, for compounds having an Ar group corresponding to structural formula Ic-Ar, $R^7$ and $R^8$ are, independently, halo, optionally substituted hydroxy, optionally substituted aliphatic, or optionally substituted heteroaliphatic, or $R^7$ and $R^8$ may be joined to form a 5- or 6-membered optionally substituted carbocyclic, optionally substituted heterocyclic, optionally substituted aryl, or optionally substituted heteroaryl ring. In certain embodiments, $R^7$ is bromo, chloro, iodo, methyl, ethyl, n-propyl, n-butyl, trifluoromethyl, benzyl, or methoxy, and $R^8$ is bromo, chloro, iodo, methyl, ethyl, n-propyl, n-butyl, trifluoromethyl, benzyl, or methoxy.

In certain embodiments, for compounds having an Ar group corresponding to structural formula Id-Ar, $R^7$ and $R^9$ are, independently, halo, optionally substituted hydroxy, optionally substituted aliphatic, optionally substituted heteroaliphatic, optionally substituted aryl, or optionally substituted heteroaryl. In certain embodiments, $R^7$ is bromo, chloro, iodo, fluoro, methyl, ethyl, n-propyl, n-butyl, trifluoromethyl, benzyl, or methoxy, and R$^9$ is bromo, chloro, iodo, fluoro, methyl, ethyl, n-propyl, n-butyl, trifluoromethyl, benzyl, or methoxy.

In certain embodiments, for compounds having an Ar group of formula (I) corresponding to structural formula Ic-Ar, the group corresponds to the following structural formulae:

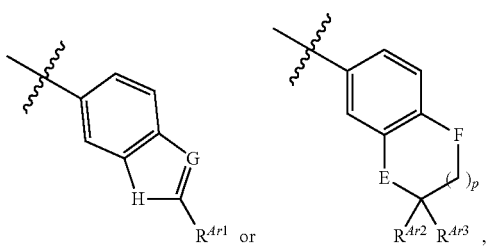

wherein H, E, and F are sulfur, oxygen, —N(H)—, or —CH$_2$—; G is carbon or nitrogen; p is 0 to 1; and R$^{Ar1}$, R$^{Ar2}$, and R$^{Ar3}$, are, independently, hydrogen, optionally substituted heterocyclic, optionally substituted aryl, optionally substituted heteroaryl, optionally substituted heteroaliphatic, or optionally substituted aliphatic.

In certain embodiments, for compounds having an Ar group of formula (I) corresponding to structural formula Ic-Ar, the group corresponds to the following structural formulae:

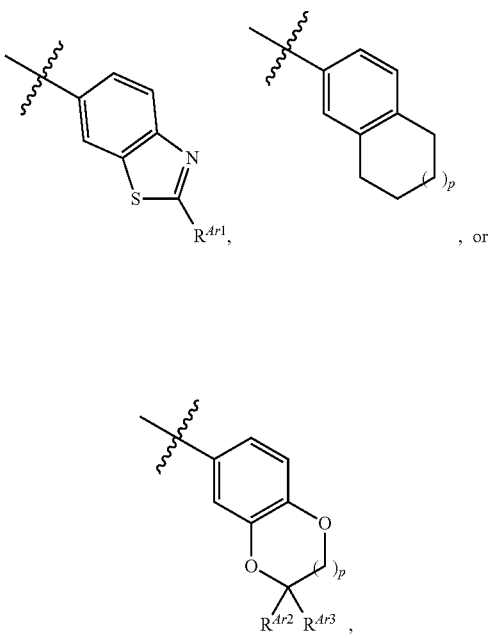

wherein each instance of R$^{Ar1}$, R$^{Ar2}$, and R$^{Ar3}$, is, independently, hydrogen, methyl, ethyl, phenyl, or benzyl, optionally substituted with bromo, chloro, iodo, fluoro, methyl, ethyl, n-propyl, n-butyl, trifluoromethyl, or methoxy.

In certain embodiments, compounds of formula (I) correspond to compounds wherein X is oxygen. Such compounds of formula (I) are exemplified in Table 1:

TABLE 1

Compounds of formula (I)

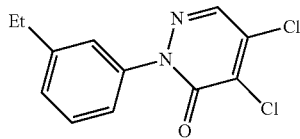 [SMILES: CCc1cccc(-n2ncc(Cl)c(Cl)c2=O)c1] (7a)

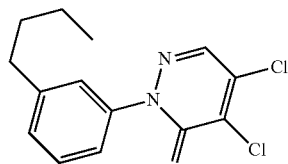 (7b)

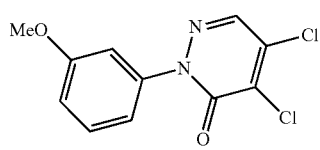 [SMILES: COc1cccc(-n2ncc(Cl)c(Cl)c2=O)c1] (7c)

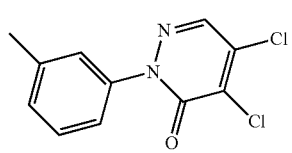 [SMILES: Cc1cccc(-n2ncc(Cl)c(Cl)c2=O)c1] (9a)

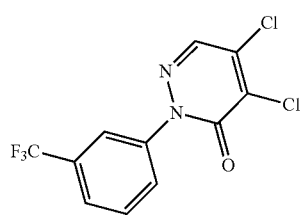 [SMILES: O=c1c(Cl)c(Cl)cnn1-c1cccc(C(F)(F)F)c1] (9b)

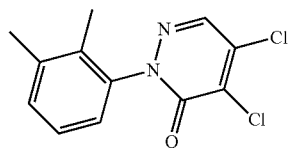 [SMILES: Cc1cccc(-n2ncc(Cl)c(Cl)c2=O)c1C] (9c)

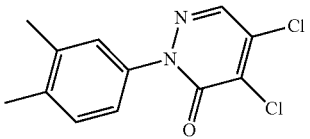 [SMILES: Cc1ccc(-n2ncc(Cl)c(Cl)c2=O)cc1C] (9d)

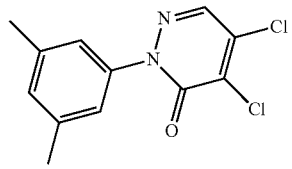 [SMILES: Cc1cc(C)cc(-n2ncc(Cl)c(Cl)c2=O)c1] (9e)

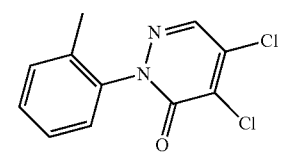 [SMILES: Cc1ccccc1-n1ncc(Cl)c(Cl)c1=O] (9f)

TABLE 1-continued

Compounds of formula (I)

(9g), (9h), (9i), (9j), (9k), (9l), (9m), (9n), (12a), (12b), (12c), (12d), (12e), (14), (15a), (15b), (15c), (16), (17)

TABLE 1-continued

Compounds of formula (I)

(20a), (20b), (21), (22), (23), (29), (30), (31)

TABLE 1-continued
Compounds of formula (I)
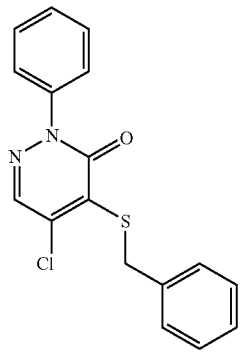
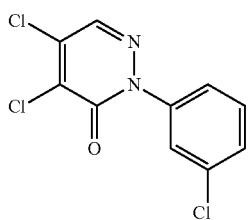 [SMILES: O=c1c(Cl)c(Cl)cnn1-c1cccc(Cl)c1]
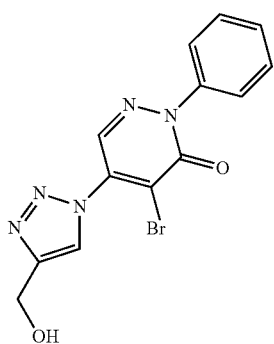 [SMILES: O=c1c(Br)c(-n2cc(CO)nn2)cnn1-c1ccccc1]
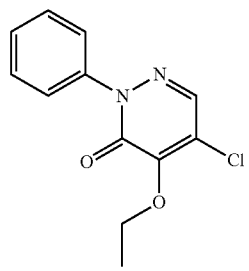 [SMILES: CCOc1c(Cl)cnn(-c2ccccc2)c1=O]
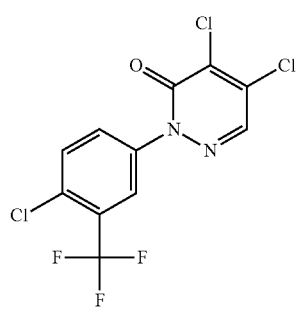 [SMILES: O=c1c(Cl)c(Cl)cnn1-c1ccc(Cl)c(C(F)(F)F)c1]
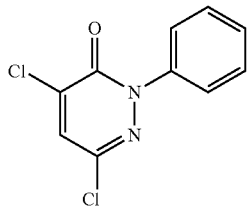 [SMILES: O=c1c(Cl)cc(Cl)nn1-c1ccccc1]
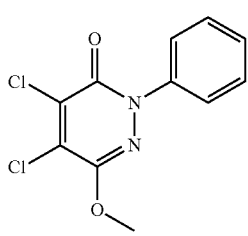 [SMILES: COc1nn(-c2ccccc2)c(=O)c(Cl)c1Cl]
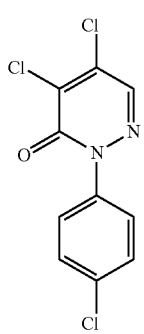
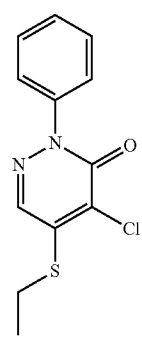
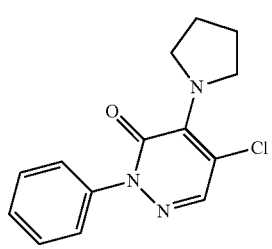 [SMILES: O=c1c(N2CCCC2)c(Cl)cnn1-c1ccccc1]

TABLE 1-continued
Compounds of formula (I)
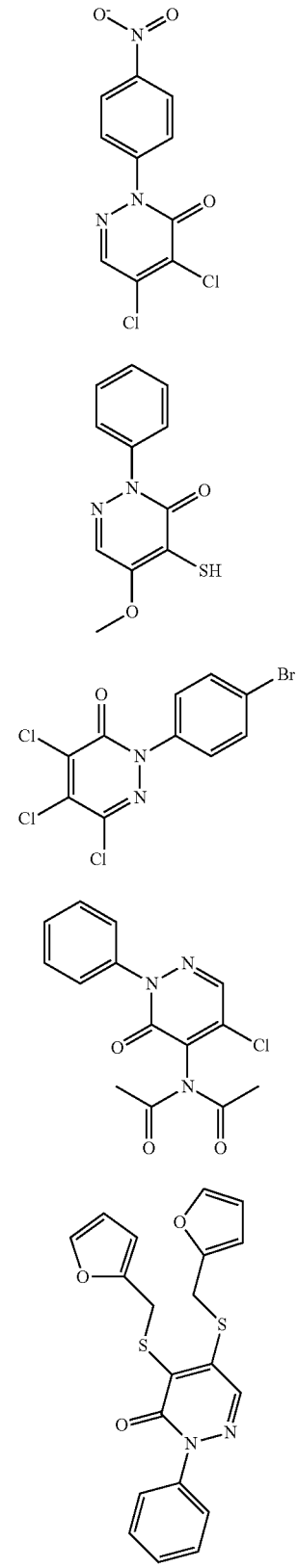
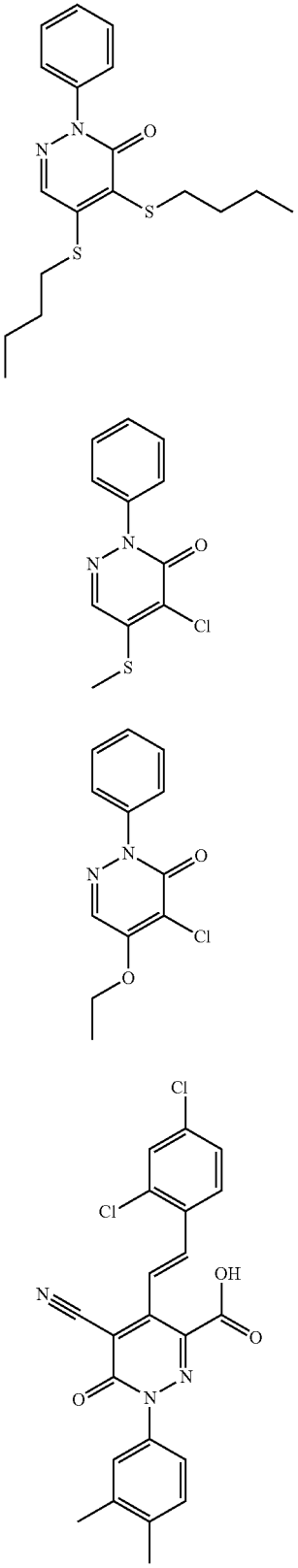

TABLE 1-continued
Compounds of formula (I)
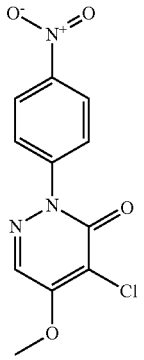 [SMILES: COc1cnn(-c2ccc([N+](=O)[O-])cc2)c(=O)c1Cl]
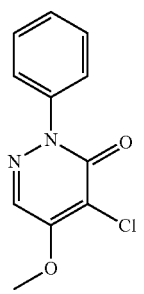 [SMILES: COc1cnn(-c2ccccc2)c(=O)c1Cl]
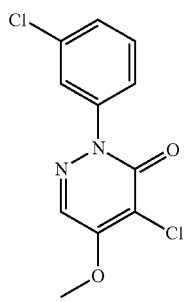 [SMILES: COc1cnn(-c2cccc(Cl)c2)c(=O)c1Cl]
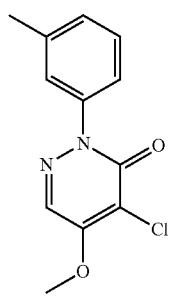
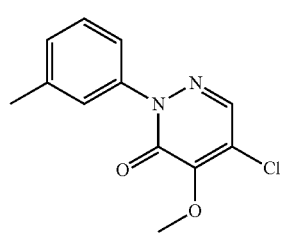 [SMILES: COc1c(Cl)cnn(-c2cccc(C)c2)c1=O]
TABLE 1-continued
Compounds of formula (I)
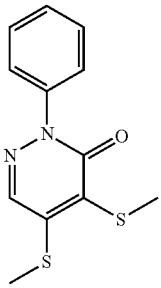 [SMILES: CSc1cnn(-c2ccccc2)c(=O)c1SC]
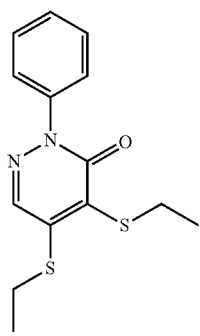
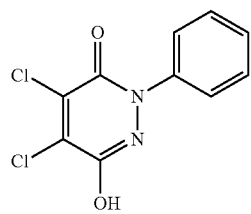 [SMILES: O=c1c(Cl)c(Cl)c(O)nn1-c1ccccc1]
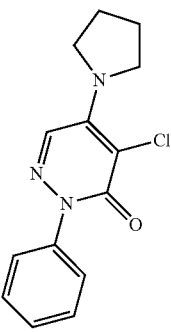
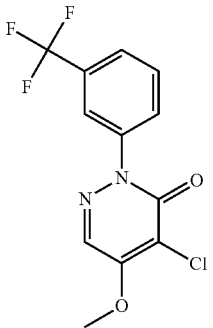 [SMILES: COc1cnn(-c2cccc(C(F)(F)F)c2)c(=O)c1Cl]

TABLE 1-continued
Compounds of formula (I)
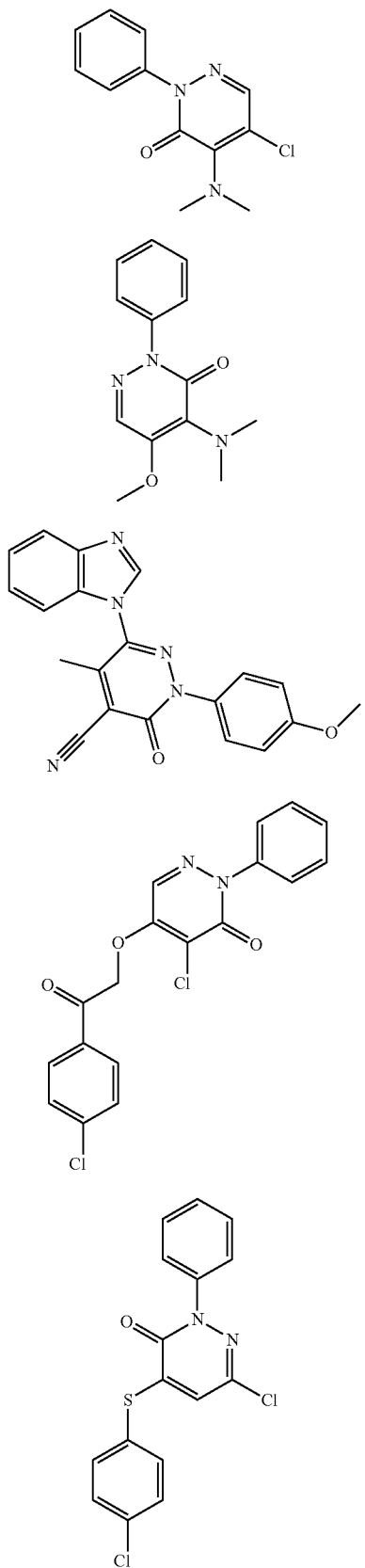
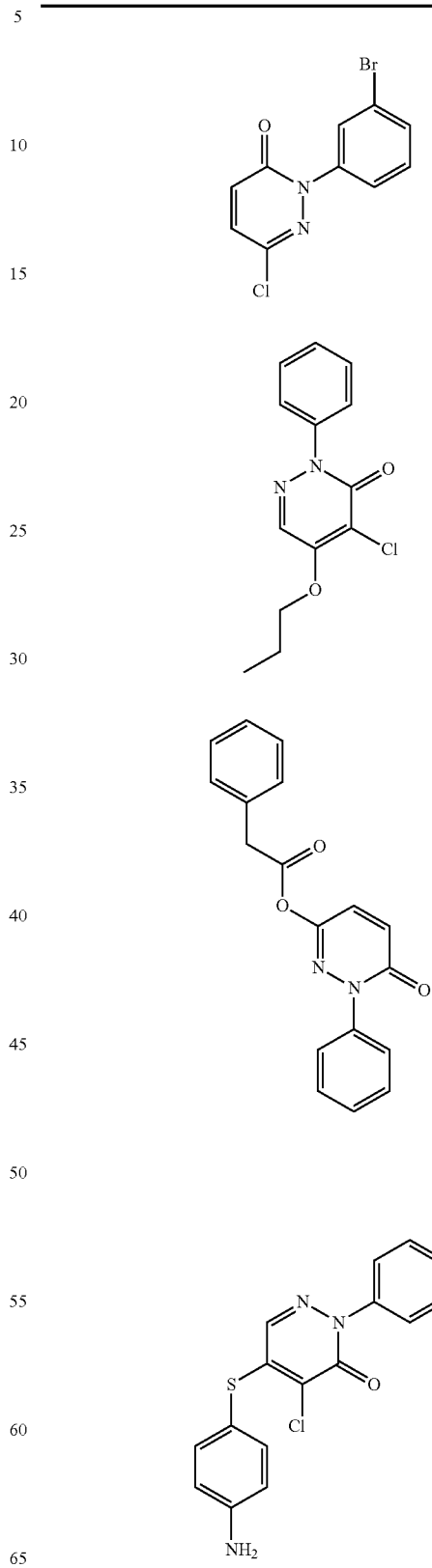

TABLE 1-continued

Compounds of formula (I)

TABLE 1-continued
Compounds of formula (I)
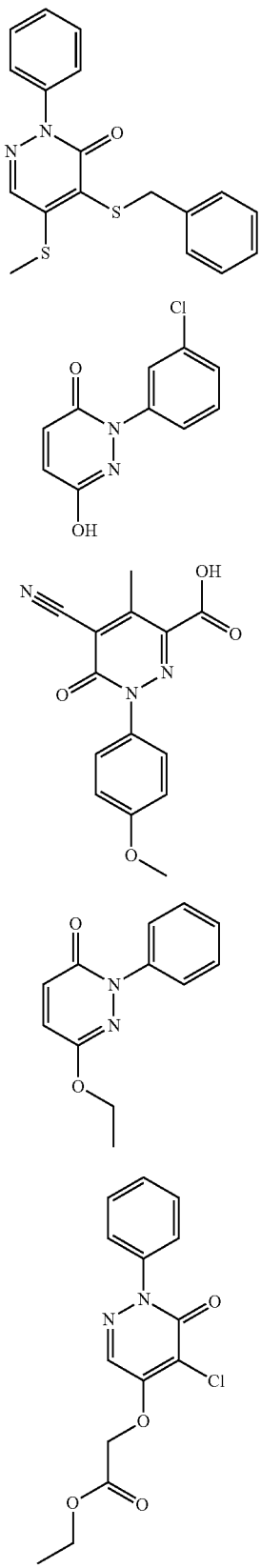
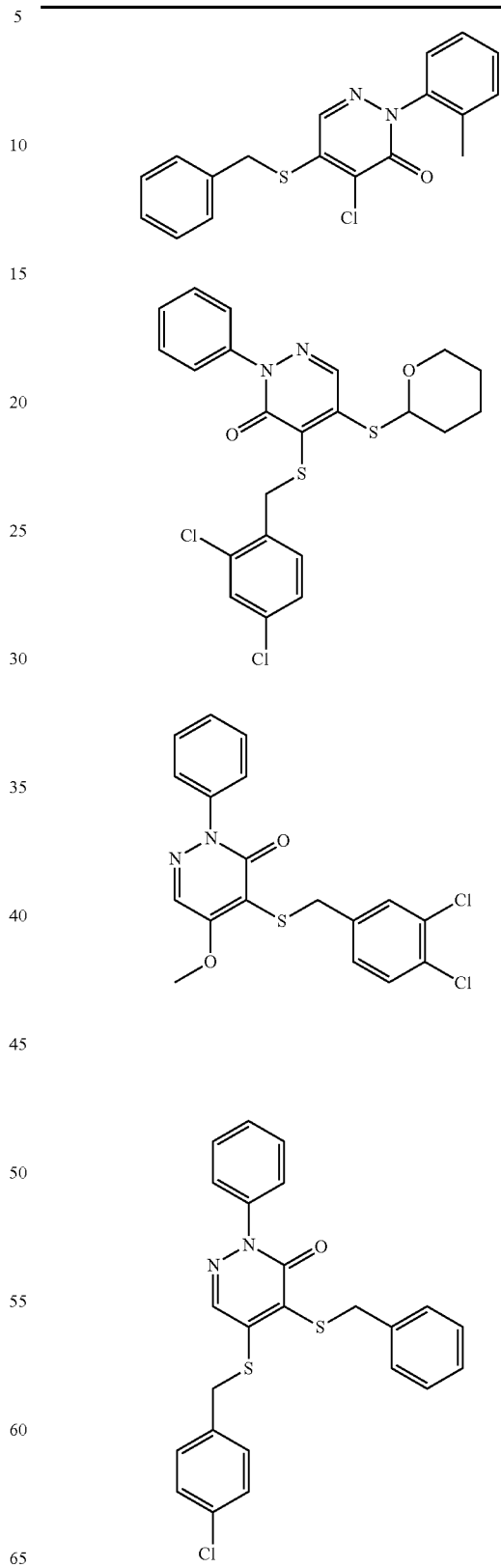

TABLE 1-continued
Compounds of formula (I)
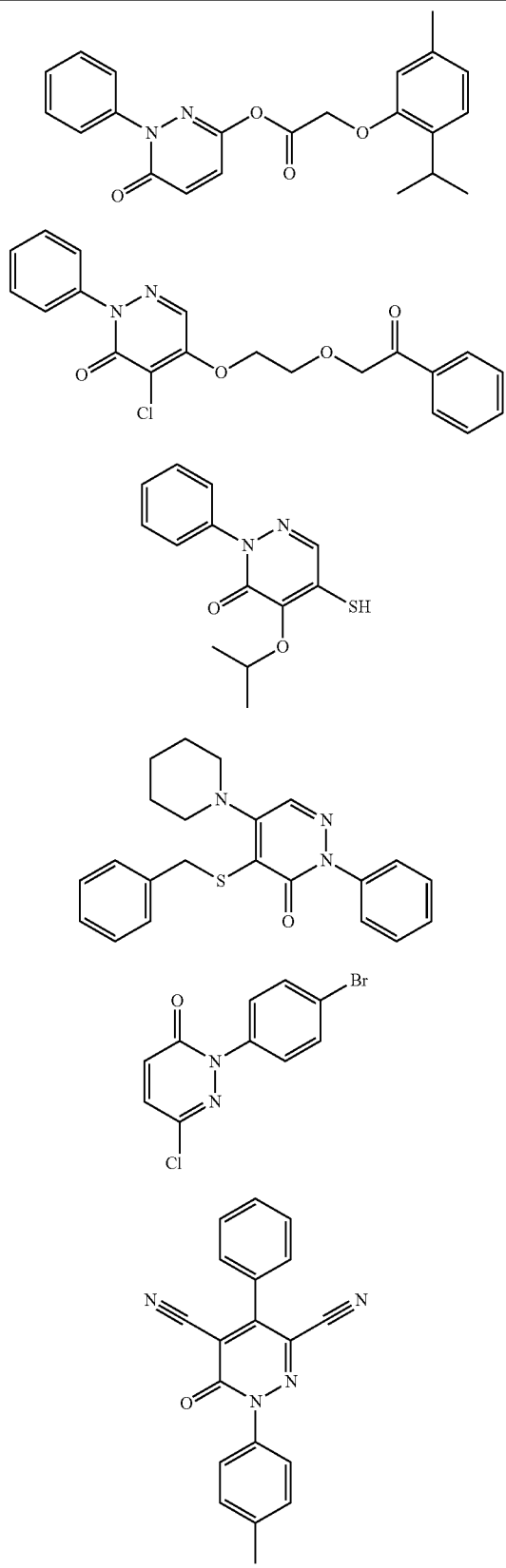
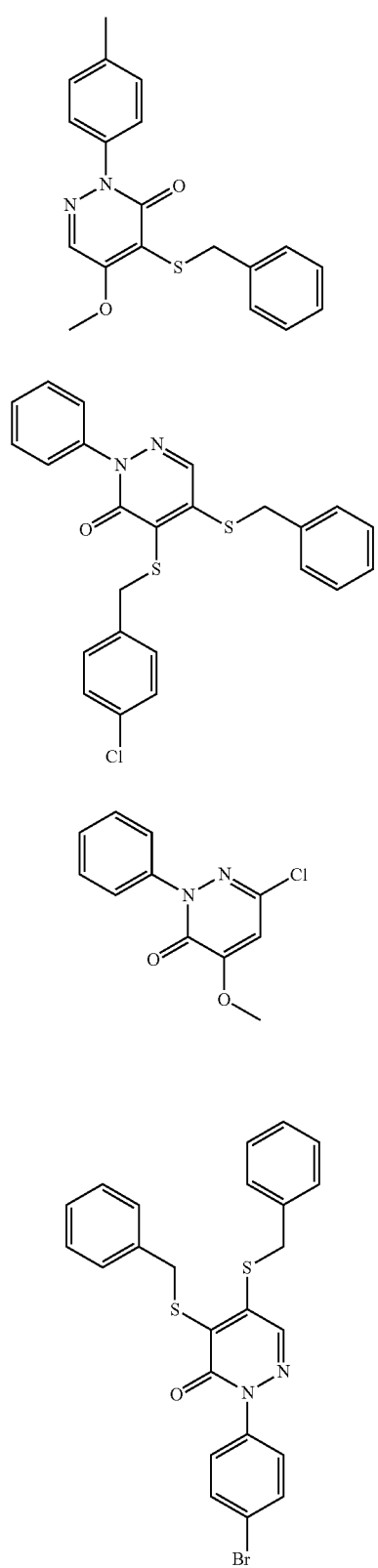

TABLE 1-continued
Compounds of formula (I)
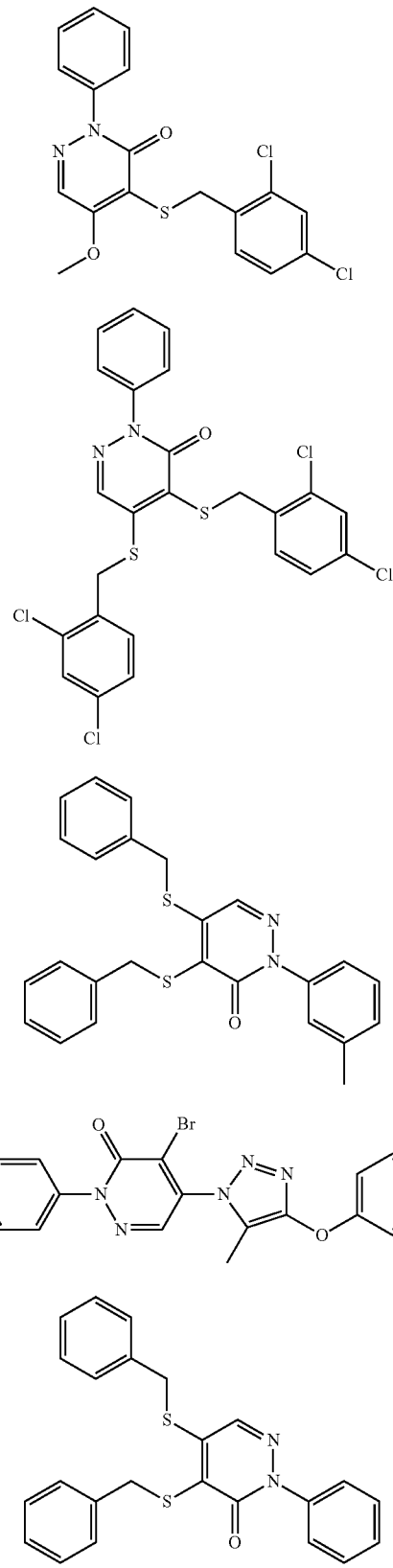
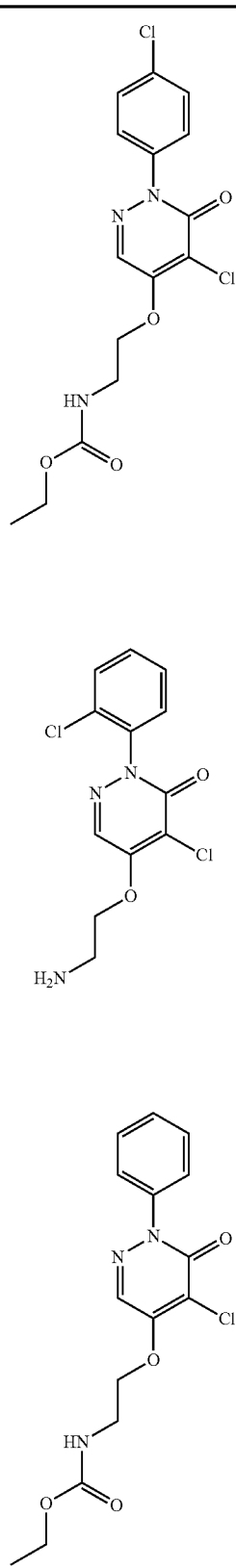

TABLE 1-continued
Compounds of formula (I)
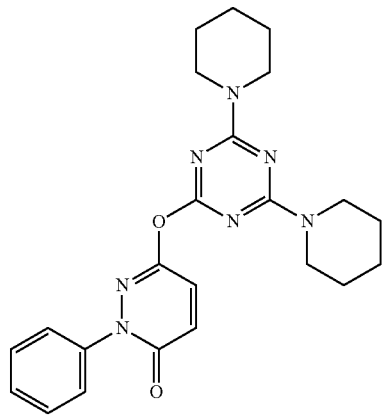 [SMILES: O=c1ccc(Oc2nc(N3CCCCC3)nc(N3CCCCC3)n2)nn1-c1ccccc1]
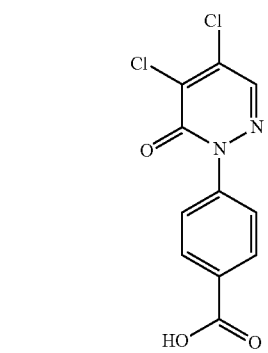
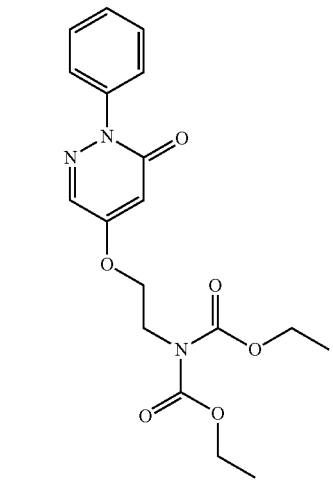 [SMILES: CCOC(=O)N(CCOc1cnn(-c2ccccc2)c(=O)c1)C(=O)OCC]
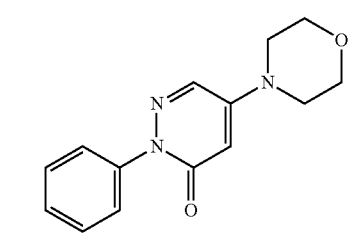
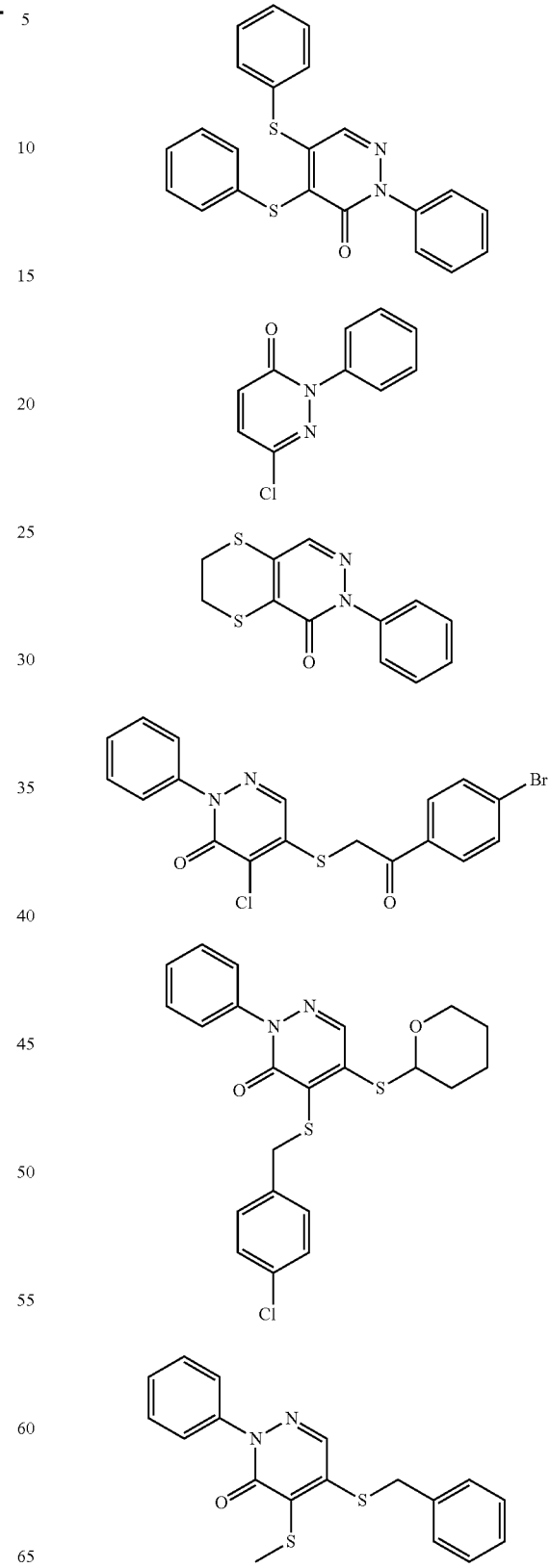

TABLE 1-continued

Compounds of formula (I)

TABLE 1-continued
Compounds of formula (I)
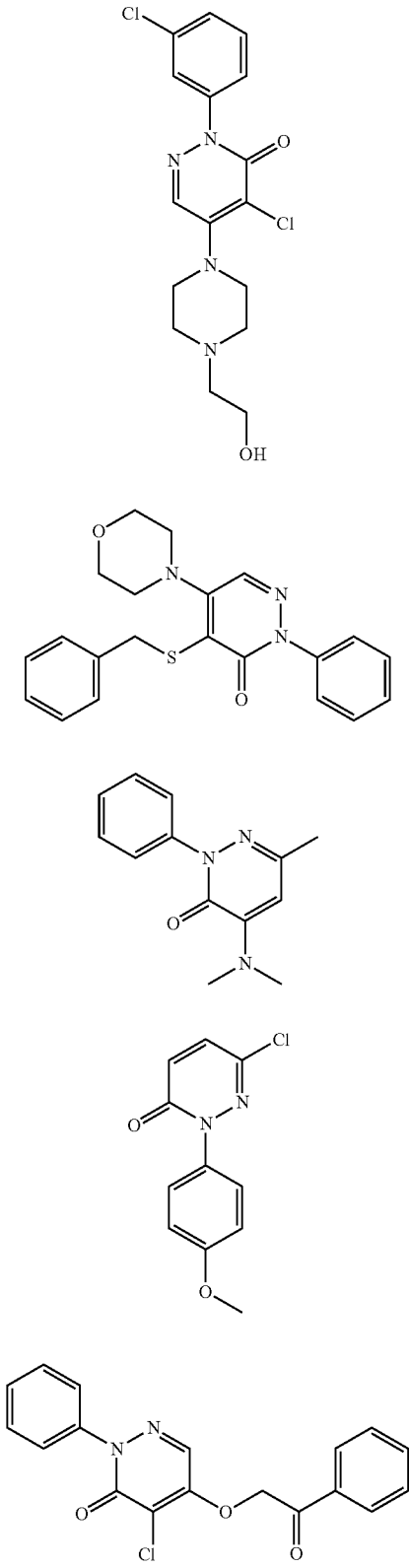
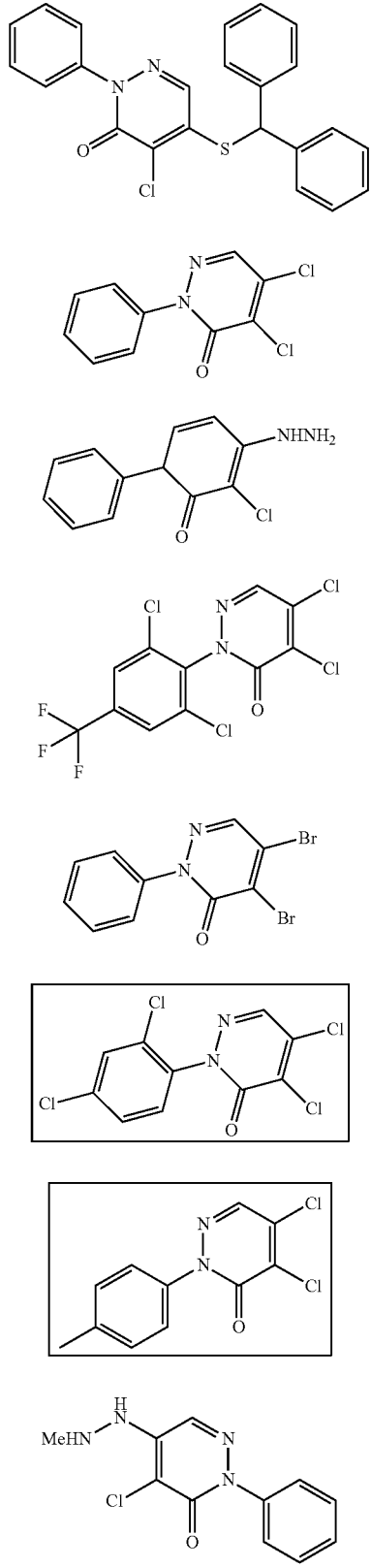

TABLE 1-continued

Compounds of formula (I)

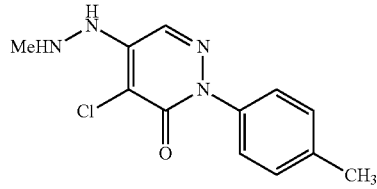 [SMILES: CNNc1cnn(-c2ccc(C)cc2)c(=O)c1Cl]

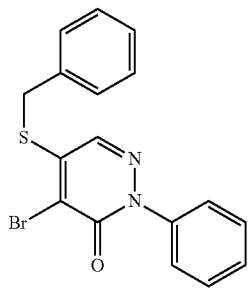

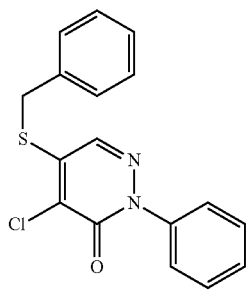 [SMILES: O=c1c(Cl)c(SCc2ccccc2)cnn1-c1ccccc1]

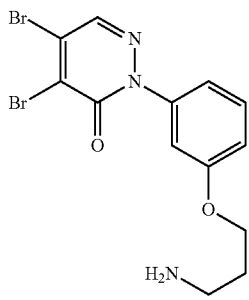 [SMILES: NCCCOc1cccc(-n2ncc(Br)c(Br)c2=O)c1]

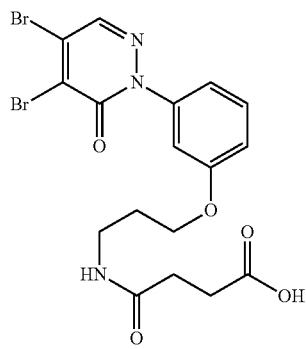 [SMILES: O=C(O)CCC(=O)NCCCOc1cccc(-n2ncc(Br)c(Br)c2=O)c1]

TABLE 1-continued

Compounds of formula (I)

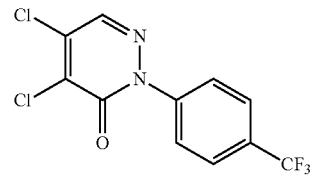 [SMILES: O=c1c(Cl)c(Cl)cnn1-c1ccc(C(F)(F)F)cc1]

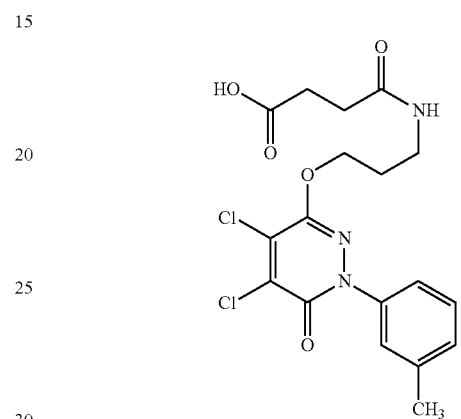

In certain embodiments, compounds of formula (I) correspond to compounds 7a-7c, 9a-9n, 12a-12c, 14, 15a-15c, 16, 17, 20a-20b, 21-23 and 29-31, as depicted above in Table 1. In certain embodiments, compounds of formula (I) correspond to compounds 7a-7c, 9a-9n, 12a-12c, 14, 15a-15c, 16, 17, and 20a-20b.

In certain embodiments, compounds of formula (I) correspond to compounds wherein X is NR$^x$; and wherein R$^x$ is hydrogen, optionally substituted aliphatic, optionally substituted heteroaliphatic, optionally substituted heterocyclyl, optionally substituted aryl, optionally substituted heteroaryl, optionally substituted acyl, optionally substituted sulfinyl, optionally substituted sulfonyl, optionally substituted hydroxy, or optionally substituted amino. In certain embodiments, X is —NH. Such compounds of formula (I) are exemplified in Table 2:

TABLE 2

Compounds of formula (I)

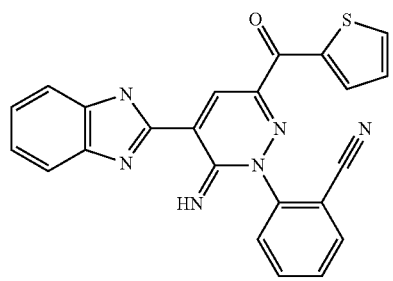 [SMILES: N#Cc1ccccc1-n1nc(C(=O)c2cccs2)cc(-c2nc3ccccc3[nH]2)c1=N]

TABLE 2-continued
Compounds of formula (I)
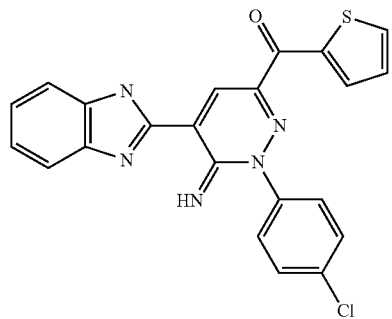 [SMILES: N=c1c(-c2nc3ccccc3[nH]2)cc(C(=O)c2cccs2)nn1-c1ccc(Cl)cc1]
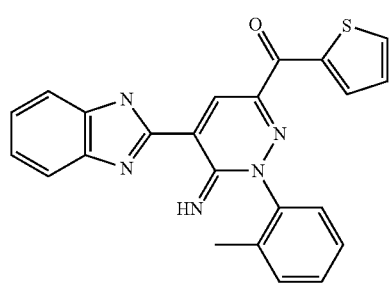 [SMILES: Cc1ccccc1-n1nc(C(=O)c2cccs2)cc(-c2nc3ccccc3[nH]2)c1=N]
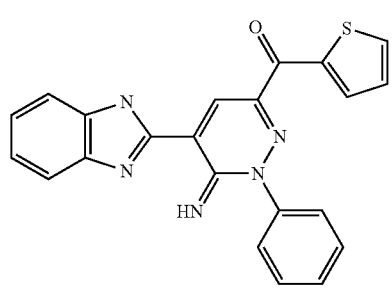
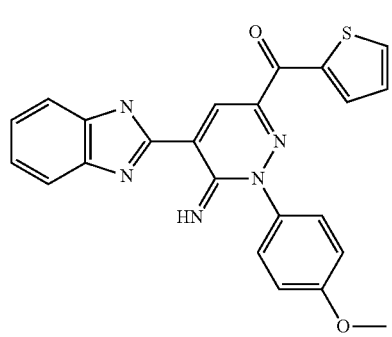
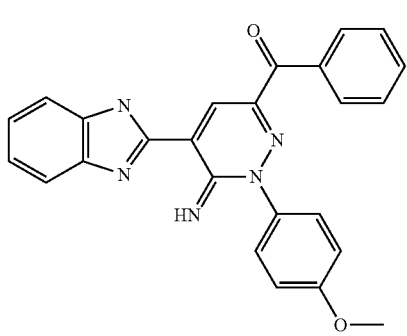 [SMILES: COc1ccc(-n2nc(C(=O)c3ccccc3)cc(-c3nc4ccccc4[nH]3)c2=N)cc1]
TABLE 2-continued
Compounds of formula (I)
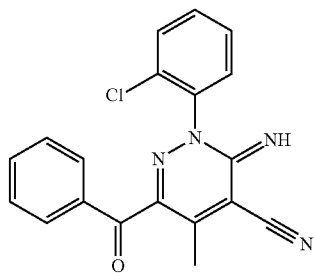 [SMILES: Cc1c(C(=O)c2ccccc2)nn(-c2ccccc2Cl)c(=N)c1C#N]
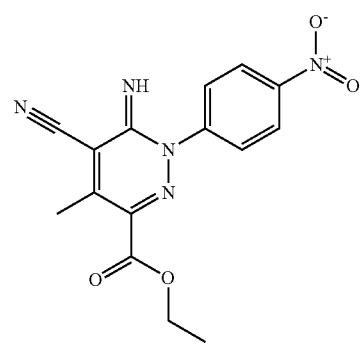 [SMILES: CCOC(=O)c1nn(-c2ccc([N+](=O)[O-])cc2)c(=N)c(C#N)c1C]
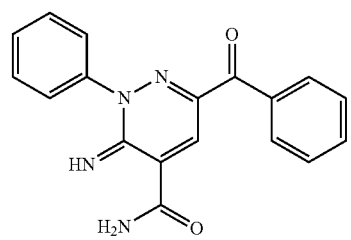 [SMILES: N=c1c(C(N)=O)cc(C(=O)c2ccccc2)nn1-c1ccccc1]
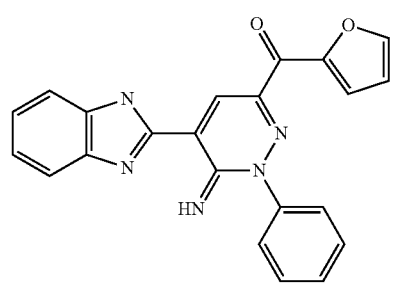
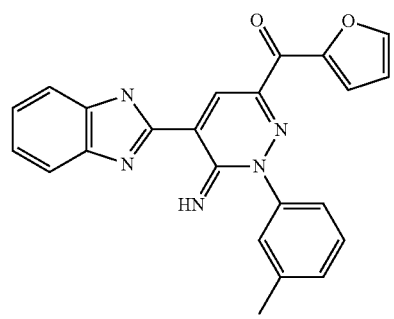 [SMILES: Cc1cccc(-n2nc(C(=O)c3ccco3)cc(-c3nc4ccccc4[nH]3)c2=N)c1]

TABLE 2-continued

Compounds of formula (I)

[Chemical structure: benzimidazole-substituted pyridazinone with furan-2-carbonyl group and 4-methoxyphenyl N-substituent, with =NH]

In certain embodiments, compounds of formula (I) correspond to compounds wherein a is a single bond, b is a double bond, $R^2$ and the carbon directly attached to $R^2$ forms the group (=$NR^y$), and $R^y$ is hydrogen, optionally substituted aliphatic, optionally substituted heteroaliphatic, optionally substituted heterocyclyl, optionally substituted aryl, optionally substituted heteroaryl, optionally substituted acyl, optionally substituted sulfinyl, optionally substituted sulfonyl, optionally substituted hydroxy, or optionally substituted amino. In certain embodiments, $R^y$ is optionally substituted amino. In certain embodiments, $R^y$ is —$NH_2$. In certain embodiments, $R^y$ is —$NH(CH_3)$. Such compounds of formula (I) are exemplified in Table 3:

TABLE 3

Compounds of formula (I)

[Chemical structure: pyridazinone with =NHCH₃, Cl, and 4-methylphenyl substituent]

[Chemical structure: pyridazinone with =NHCH₃, Cl, and phenyl substituent]

[Chemical structure: pyridazinone with =NH₂ (hydrazone), Cl, and phenyl substituent]

Pharmaceutical Compositions of Compounds of Formula (I)

The present invention is also directed to a pharmaceutical composition comprising a therapeutically effective amount of a compound of formula (I), as defined herein, or a pharmaceutically acceptable salt, prodrug, isomer or tautomer thereof, and at least one pharmaceutically acceptable excipient.

Pharmaceutically acceptable excipients are well-known in the art and include, without limitation, purified water, mannitol, sorbit, silicon dioxide, terpenes (e.g., menthol), alcohols (e.g., ethanol, propylene glycol, glycerol and other similar alcohols), organic solvents (e.g., dimethylsulfoxide, dimethylformamide, dimethylacctamide), waxes, saccharides, oligosaccharides and/or polysaccharides (e.g., starch or starch fragments, corn starch, glucose, galactose, lactose, cellulose), dextrins, amino acids, gums (e.g., xanthan gum, locust bean gum, British gum) and the like, or mixtures thereof.

The present invention is also directed to methods of treating a proliferative dsease in a subject by administering to a subject a therapeutically effective amount of a compound of formula (I), or a pharmaceutically acceptable salt, prodrug, isomer or tautomer thereof. The present application also contemplates a method of treating a proliferative disease in a subject by administering to a subject a therapeutically effective amount of a pharmaceutical composition comprising a compound of formula (I), or a pharmaceutically acceptable salt, prodrug, or tautomer thereof, and a pharmaceutically acceptable excipient.

In certain embodiments, the proliferative disease is neoplasia. Neoplasia, as used herein, refers to the abnormal growth of tissue in a subject, and may be either benign or malignant. In certain embodiments, the neoplasia is a tumor. In certain embodiments, the neoplasia is cancer. In certain embodiments, the cancer is renal cancer, bladder cancer, liver cancer, testicular cancer, ovarian cancer, colorectal cancer, prostate cancer, pancreatic cancer, lung cancer, breast cancer, brain cancer, bone cancer, stomach cancer, oral cancer, skin cancer, blood cancer, or leukemia. In certain embodiments, the cancer is non-Hodgkin's lymphoma, Wilms' tumor, lymphomas, rhabdomyosarcoma (arising from muscle), retinoblastoma, osteosarcoma, or Ewing's sarcoma. in certain embodiments, the cancer is lung cancer. In certain embodiments, the lung cancer is human non-small cell lung cancer (adenocarcinoma, squamous cell carcinoma, and large cell carcinoma). In certain embodiments the cancer is associated with EGFR and/or KRAS mutations.

In certain embodiments, compounds of formula (I) are effective against a cancer or a tumor. To be "effective against" tumors or cancers, as used herein, is meant reducing the mass (e.g., a tumor or cancer) or slowing or halting the growth or spread of the mass, in a subject diagnosed or suffering from a tumor or cancer. In certain embodiments, compounds of formula (I) are therapeutically effective against a cancer or a tumor with EGFR and/or KRAS mutations. In certain embodiments compounds of formula (I) are therapeutically effective against a lung cancer or a lung tumor with EGFR and/or KRAS mutations.

The form of administration of a compound of the invention to a subject is not particularly restricted, and can be oral or a parenteral administration using generally employed methods. For example, administration may be enteral (by mouth, by feeding tube, rectally), parenteral by injection or infusion (e.g., intravenous, intraarterial, intramuscular, intracardiac, subcutaneous, intradermal, intrathecal, intraperitoneal), and/or parenteral other than injection (e.g., transdermal, transmucosal, or by inhalation).

Although the administered dosage of a compound of the invention will differ depending on severity of symptoms, age, gender, body weight, form of administration, and type of disease, etc., dosages may fall between about 0.01 mg/kg/day to about 100 mg/kg/day for an adult, and such dosages may be administered once or divided over several days. In certain embodiments, a therapeutically effective amount of a compound of formula (I) is between about 0.01 mg/kg/day to about 100 mg/kg/day. In certain embodiments, a therapeutically effective amount of a compound of formula (I) is at least 0.01 mg/kg/day, 0.05 mg/kg/day, 0.10 mg/kg/day, 1.0 mg/kg/day, 5.0 mg/kg/day, 10 mg/kg/day, 15 mg/kg/day, 20 mg/kg/day, 30 mg/kg/day, 40 mg/kg/day, 50 mg/kg/day, 60 mg/kg/day, 70 mg/kg/day, 80 mg/kg/day, 90 mg/kg/day, or 100 mg/kg/day.

The present invention is also directed to kits, comprising at least one compound of formula (I), or pharmaceutically acceptable salts, prodrugs, isomers, or tautomers thereof. A kit of the invention can be particularly useful if it provides additional solvents, buffers, or excipients for pre-mixing before administration to a subject, or if it provides a means for oral or parental administration (e.g., syringes or graduated measurement cups). A kit of the invention can also be particularly useful if it contains additional chemotherapeutic agents for use in combination with a compound of formula (I). For instance, a physician may wish to administer to a subject one or more compounds of formula (I) in combination with one or more additional chemotherapeutic agents.

Exemplary additional chemotherapeutic agents include, but are not limited to, 13-cis-Retinoic Acid, 2-CdA (2-Chlorodcoxyadcnosinc), 5-Fluorouracil (5-FU), 6-Mercaptopurine, 6-MP, 6-TG, 6-Thioguanine, Abraxane, ACCUTANE®, ACTINOMYCIN-D, ADRIAMYON®, ADRUCIL®, AGRYLIN®, ALA-CORT®, Aldesleukin, Alemtuzumab, ALIMTA, Alitretinoin, ALKABAN-AQ®, ALKERAN®, All-transretinoic acid Alpha interferon, Altretamine, Amethopterin, Amifostine, Aminoglutethimide, Anagrelide, ANANDRON®, Anastrozole, Arabinosylcytosine, Ara-C ARANESP®, AREDIA®, ARIMIDEX®, AROMASIN®, ARRANON®, Arsenic trioxide, Asparaginase, ATRA, AVASTIN®, Azacitidine, BCG, BCNU, Bevacizumab, Bexarotene, BEXXAR®, Bicalutamidc, BiCNU, BLENOXANE®, Bleomycin, Bortczomib, Busulfan, BUSULFEX®, C225, Calcium Leucovorin, CAMPATH®, CAMPTOSAR®, Camptothecin-11, Capecitabine, CARAC™, Carboplatin, Carmustine, Carmustine wafer, CASODEX®, CC-5013, CCNU, CDDP, CeeNU, CERUBIDINE®, Cetuximab, Chlorambucil, Cisplatin, Citrovorum Factor, Cladribine, Cortisone, COSMEGEN®, CPT-11, Cyclophosphamide, CYTADREN®, Cytarabine, Cytarabine liposomal, CYTOSAR-U®, CYTOXAN®, Dacarbazine, Dacogen, Dactinomycin, Darbepoetin alfa, Daunomycin, Daunorubicin, Daunorubicin hydrochloride, Daunorubicin liposomal, DAUNOXOME®, Decadron, Decitabine, DELTA-CORTEF®, DELTASONE®, Denileukin diftitox, DEPOCYT™, Dexamethasone, Dexamethasone acetate, Dexamethasone Sodium Phosphate, Dexasone, Dexrazoxane, DHAD, DIC, Diodex, Docetaxel, DOXIL®, Doxorubicin, Doxorubicin liposomal, DROXIA™, DTIC, DTIC-DOME®, DURALONE®, EFUDEX®, ELIGARD™, ELLENCE™, ELOXATIN™, ELSPAR®, EMCYT®, Epirubicin, Epoetin alfa, ERBITUXT™, Erlotinib, Erwinia L-asparaginase, Estramustine, Ethyol, ETOPOPHOS®, Etoposide, Etoposide Phosphate, EULEXIN®, Evista®, Exemestane, FARESTON®, FASLODEX®, FEMARA®, Filgrastim, Floxuridine, FLUDARA®, Fludarabine, FLUOROPLEX®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, GEMZAR®, GLEEVEC™, Gliadel wafer, GM-CSF, Goserelin granulocyte-colony stimulating factor, Granulocyte macrophage colony stimulating factor, Halotestin, Herceptin, Hexadrol, Hexylen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, IDAMYCIN®, Idarubicin, IFEX®, IFN-alpha, Ifosfamide, IL-11, IL-2, Imatinib mesylate, Imidazole Carboxamide, Interferon alfa, Interferon Alfa-2b (PEG conjugate), Interleukin-2 (t), Interleukin-11, INTRON A® (interferon alfa-2b), IRESSA®, Irinotecan, Isotretinoin, Kidrolase, Lanacort, L-asparaginase, LCR, Lenalidomide, Letrozole, Leucovorin, Leukeran, Leukine, Leuprolide, Leurocristine, Leustatin, Liposomal Ara-C, Liquid Pred, Lomustine, L-PAM, L-Sarcolysin, Lupron, LUPRON DEPOT®, Matulane, Maxidex, Mechlorethamine, Mechlorethamine Hydrochloride, Medralone, MEDROL®, Megace, Megestrol, Megestrol Acetate, Melphalan, Mercaptopurine, Mesna, Mesnex, Methotrexate, Methotrexate Sodium, Methylprednisolone, Meticorten, Mitomycin, Mitomycin-C, Mitoxantrone, M-Prednisol, MTC, MTX, Mustargen, Mustine, Mutamycin, Myleran, Mylocel, Mylotarg, NAVELBINE®, Nelarabine, Neosar, Neulasta, Neumega, NEUPOGEN®, NEXAVAR®, Nilandron®, Nilutamide, NIPENT®, Nitrogen Mustard, Novaldex, Novantrone, Octreotide, Octreotide acetate, Oncospar, Oncovin, Ontak, Onxal, Oprevelkin, Orapred, Orasone, Oxaliplatin, Paclitaxel, Paclitaxel Protein-bound, Pamidronate, Panretin, Paraplatin, Pediapred, PEG Interferon, Pegaspargase, Pegfilgrastim, PEG-INTRON, PEG-L-asparaginase, PEMETREXED, Pentostatin, Phenylalanine Mustard, Platinol, Platinol-AQ, Prednisolone, Prednisone, Prelone, Procarbazine, PROCRIT®, Proleukin, Prolifeprospan 20 with Carmustine implant, PURINETHOL®, Raloxifene, REVLIMID®, Rheumatrex, Rituxan, Rituximab, ROFERON-A® (interferon alfa-2a), Rubex, Rubidomycin hydrochloride, SANDOSTATIN®, Sandostatin LAR, Sargramostim, Solu-Cortef, Solu-Medrol, Sorafenib, STI-571, Streptozocin, SU11248, Sunitinib, SUTENT®, Tamoxifen, TARCEVA®, Targretin, TAXOL®, TAXOTERE®, TEMODAR®, Temozolomide, Teniposide, TESPA, Thalidomide, THALOMID®, TheraCys, Thioguanine, THIOGUANINE TABLOID®, Thiophosphoamide, Thioplex, Thiotepa, TICE®, Toposar, Topotecan, Toremifene, Tositumomab, Trastuzumab, Tretinoin, Trexall, Trisenox, TSPA, VCR, Velban, VELCADE®, VePesid, Vesanoid, Viadur, Vidaza, Vinblastine, Vinblastine Sulfate, Vincasar Pfs, Vincristine, Vinorelbine, Vinorelbine tartrate, VLB, VM-26, VP-16, Vumon, XELODA®, Zanosar, ZEVALIN™, Zinecard, ZOLADEX Zolcdronic acid, and ZOMETA®.

Methods of Preparation of Compounds of Formula (I)

The present invention also provides a method of synthesizing compounds of formula (I), as depicted in Scheme 1 below.

Scheme 1

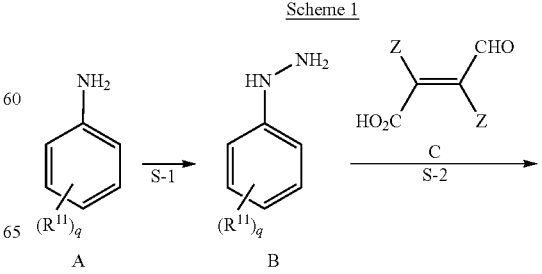

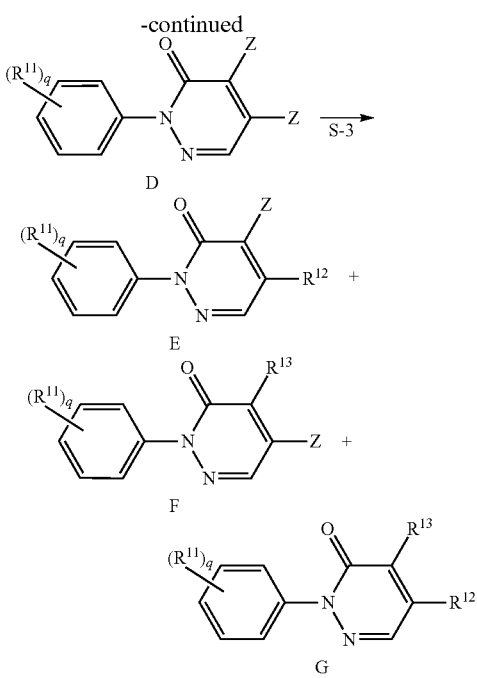

Compounds of formula (I) may be synthesized starting from an optionally substituted aniline (A), wherein $R^{11}$ is any substitutent, as is described herein, which results in a stable substituted aniline compound (A), and q is 0-5.

In step 1 (S-1), under standard hydrazine formation conditions, optionally substituted aniline (A) is converted to optionally substituted phenyl hydrazine (B).

In step 2 (S-2), reaction of compound (B) with compound (C), wherein Z is, independently, hydrogen or halo (—Cl, —Br, —I, —F), generates an optionally substituted pyridazin-3-one derivative (D).

Reaction of compound (D) in step 3 (S-3) with different nucleophiles can generate a wide variety of compounds with different substitutions and/or substitution patterns (for example, compounds (E), (F), and/or (G), as depicted above). In certain embodiments, $R^{12}$ and $R^{13}$, are, independently, optionally substituted aliphaticoxy, aliphaticthioxy, aliphaticamino, dialiphaticamino, trialiphaticamino, arylamino, diarylamino, isocyano, amino, azido, hydrazino, hydroxy, thio, halo, aryloxy, arylthioxy, arylamino, heteroaryloxy, heteroarylamino, or heteroarylthiooxy.

In certain embodiments, compound (D) is treated with a mono- or di-substituted aliphaticamine to form compounds (E), and/or (F), and/or (G), wherein $R^{12}$ and $R^{13}$ are, independently, —N($R^N$)$_2$, and each instance of $R^N$ is, independently, hydrogen or optionally substituted aliphatic, heteroaliphatic, aryl, heteroaryl, or two $R^N$ groups form an optionally substituted 5- to 6-membered heteroaryl or heterocyclic ring.

In certain embodiments, compound (D) is treated with an optionally substituted hydroxy group to form compounds (E), and/or (F), and/or (G), wherein $R^{12}$ and $R^{13}$ are, independently, —O($R^o$), and each instance of $R^o$ is, independently, hydrogen or optionally substituted aliphatic, heteroaliphatic, aryl, heteroaryl, or two $R^o$ groups form an optionally substituted 5- to 6-membered heteroaryl or heterocyclic ring.

In certain embodiments, compound (D) is treated with an optionally substituted thio group to form compounds (E), and/or (F), and/or (G), wherein $R^{12}$ and $R^{13}$ are, independently, —S($R^s$), and each instance of $R^s$ is, independently, hydrogen or optionally substituted aliphatic, heteroaliphatic, aryl, heteroaryl, or two $R^s$ groups form an optionally substituted 5- to 6-membered heteroaryl or heterocyclic ring.

In certain embodiments, compound (D) is treated with a Brønstead acid (such as hydrogen chloride, hydrogen bromide, hydrogen bromide, hydrogen fluoride, nitric acid, sulfuric acid, phosphoric acid, and the like), or a halogenating reagent (such as NBS, Br$_2$, NCS, and the like) to form compounds (D), and/or (E), and/or (F), wherein $R^{12}$ and $R^{13}$ are, independently, hydrogen, bromo, iodo, fluoro, —NO$_2$, —SO$_3$, —OP(O)(OH)$_2$ and the like.

Alternatively, compounds of formula (I) can be synthesized according to the method as depicted in Scheme 2 below.

In step 4 (S-4), under suitable cyclization conditions, optionally substituted phenyl hydrazine (B) reacts with a compound of formula (H) wherein Z is, independently, hydrogen or halo, to generate an optionally substituted pyridazine-3,6-dionepyridazin-3-one derivative (J). Treatment of compound (J) under suitable reducing conditions or alkylation conditions, in step 5 (S-5), generates optionally substituted pyridazin-3-one derivative (K), wherein $R^o$ is hydrogen or optionally substituted aliphatic, respectively. Reaction of compound (K) in step 6 (S-6) with different nucleophiles (as described in certain embodiments for step 3 (S-3) above) can generate a wide variety of compounds with different substitutions and/or substitution patterns (for example, compounds (L), (M), and/or (N), as depicted below).

Scheme 2

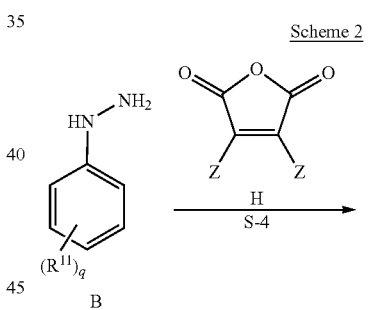

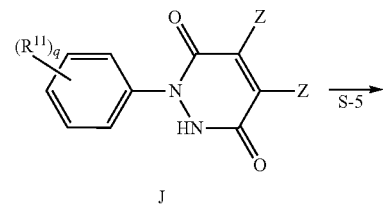

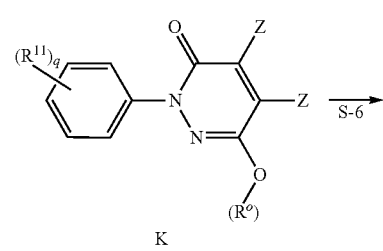

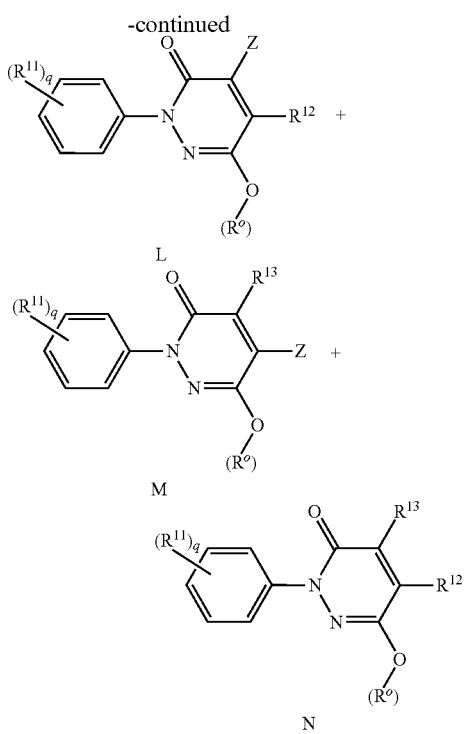

Compounds of Formula (II)

The present invention is also directed to compounds of formula (II):

(II)

wherein each instance of $R^1$, $R^2$, and $R^3$ is, independently, hydrogen, aliphatic, heteroaliphatic, hydroxy, thio, amino, heterocyclic, aryl, heteroaryl, acyl, amido, imido, sulfinyl, sulfonyl, carboxaldehyde, cyano, isocyano, azido, hydrazino, nitro, or halo; optionally substituted with oxo, thiooxo, imino, aliphatic, carbocyclic, hydroxy, aliphaticoxy, aryloxy, thio, aliphaticthioxy, arylthioxy, heteroaliphatic, heterocyclic, aryl, arylaliphatic, heteroaryl, heteroarylaliphatic, acyl, acyloxy, amido, imido, sulfinyl, sulfonyl, amino, aliphaticamino, dialiphaticamino, trialiphaticamino, arylamino, diarylamino, carboxaldehyde, cyano, isocyano, azido, hydrazino, nitro, or halo; or $R^1$ and $R^2$ are joined to form a 5- or 6-membered optionally substituted carbocyclic, optionally substituted heterocyclic, optionally substituted aryl, or optionally substituted heteroaryl ring, and $R^3$ is as defined above;

each instance of $R^4$ and $R^5$ is, independently, hydrogen, aliphatic, heteroaliphatic, hydroxy, thio, amino, heterocyclic, aryl, heteroaryl, acyl, amido, imido, sulfinyl, sulfonyl, carboxaldehyde, hydrazino; optionally substituted with oxo, thiooxo, imino, aliphatic, carbocyclic, hydroxy, aliphaticoxy, aryloxy, thio, aliphaticthioxy, arylthioxy, heteroaliphatic, heterocyclic, aryl, arylaliphatic, heteroaryl, heteroarylaliphatic, acyl, acyloxy, amido, imido, sulfinyl, sulfonyl, amino, aliphaticamino, dialiphaticamino, trialiphaticamino, arylamino, diarylamino, carboxaldehyde, cyano, isocyano, azido, hydrazino, nitro, or halo; or $R^4$ and $R^5$ are joined to form an 5- or 6-membered optionally substituted heterocyclic or optionally substituted heteroaryl ring; and J and J', together, form an oxo (=O), thiooxo (=S), or imino (=$NR^{N5}$) group, wherein $R^{N5}$ is hydrogen, optionally substituted hydroxy, optionally substituted amino, optionally substituted aryl, optionally substituted sulfonyl, optionally substituted heteroaryl, optionally substituted acyl, optionally substituted aliphatic, or optionally substituted heteroaliphatic; or each instance of J and J' is, independently, hydrogen, optionally substituted aliphatic or optionally substituted heteroaliphatic.

In certain embodiments, the compound 5-nitro-furan-2-carboxylic acid (4-chloro-phenyl)-amide (SKI-98698), as depicted below, is specifically excluded from compounds of formula (II):

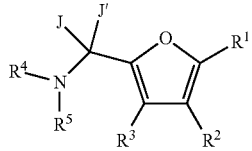

5-nitro-furan-2-carboxylic acid (4-chloro-phenyl)-amide (SKI-98698)

In certain embodiments, compounds of formula (II) have the structural formulae:

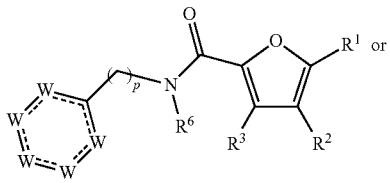

IIa

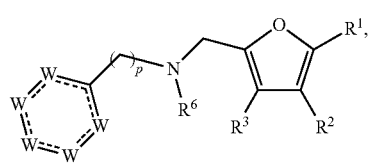

IIb wherein each instance of $R^6$ is, independently, hydrogen or optionally substituted aliphatic;

each W is, independently, —N—, —C(H)—, or —C($R^7$)—; wherein each instance of $R^7$ is, independently, aliphatic, heteroaliphatic, hydroxy, thio, amino, heterocyclic, aryl, heteroaryl, acyl, amido, imido, sulfinyl, sulfonyl, carboxaldehyde, cyano, isocyano, azido, hydrazino, nitro, halo; optionally substituted with oxo, thiooxo, imino, aliphatic, carbocyclic, hydroxy, aliphaticoxy, aryloxy, thio, aliphaticthioxy, arylthioxy, heteroaliphatic, heterocyclic, aryl, arylaliphatic, heteroaryl, heteroarylaliphatic, acyl, acyloxy, amido, imido, sulfinyl, sulfonyl, amino, aliphaticamino, dialiphaticamino, trialiphaticamino, arylamino, diarylamino, carboxaldehyde, cyano, isocyano, azido, hydrazino, nitro, or halo;

═══ is a single or double bond; and p is 0 or 1.

In certain embodiments, $R^6$ is hydrogen. In certain embodiments, $R^6$ is alkyl. In certain embodiments, $R^6$ is $C_{1-6}$ alkyl.

In certain embodiments, compounds of formula (II) have the structural formula IIa. Such compounds of formula IIa are exemplified in Table 4:

TABLE 4

Compounds of formula (II)

TABLE 4-continued

Compounds of formula (II)

TABLE 4-continued
Compounds of formula (II)
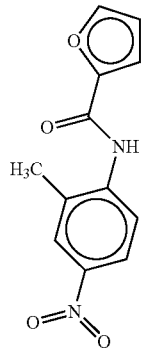
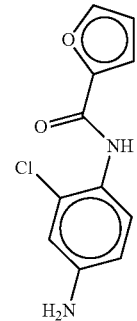
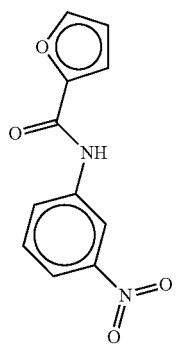
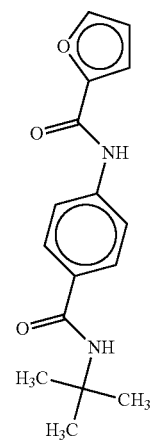
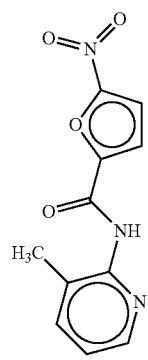
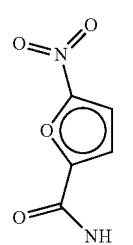
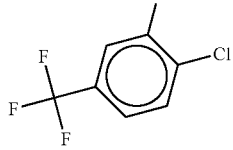
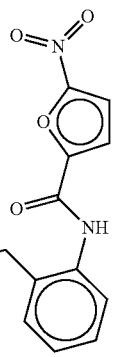
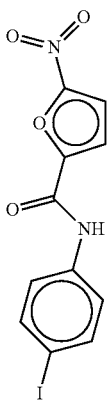
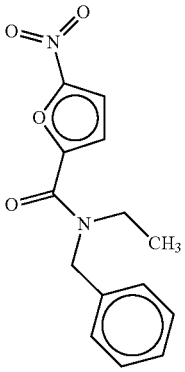
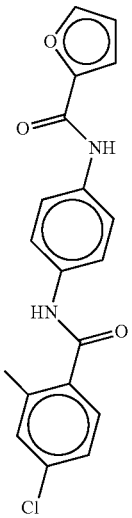
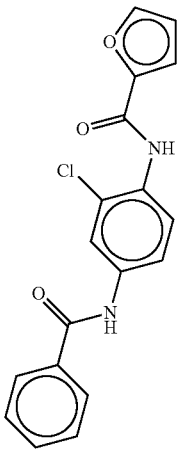

TABLE 4-continued
Compounds of formula (II)
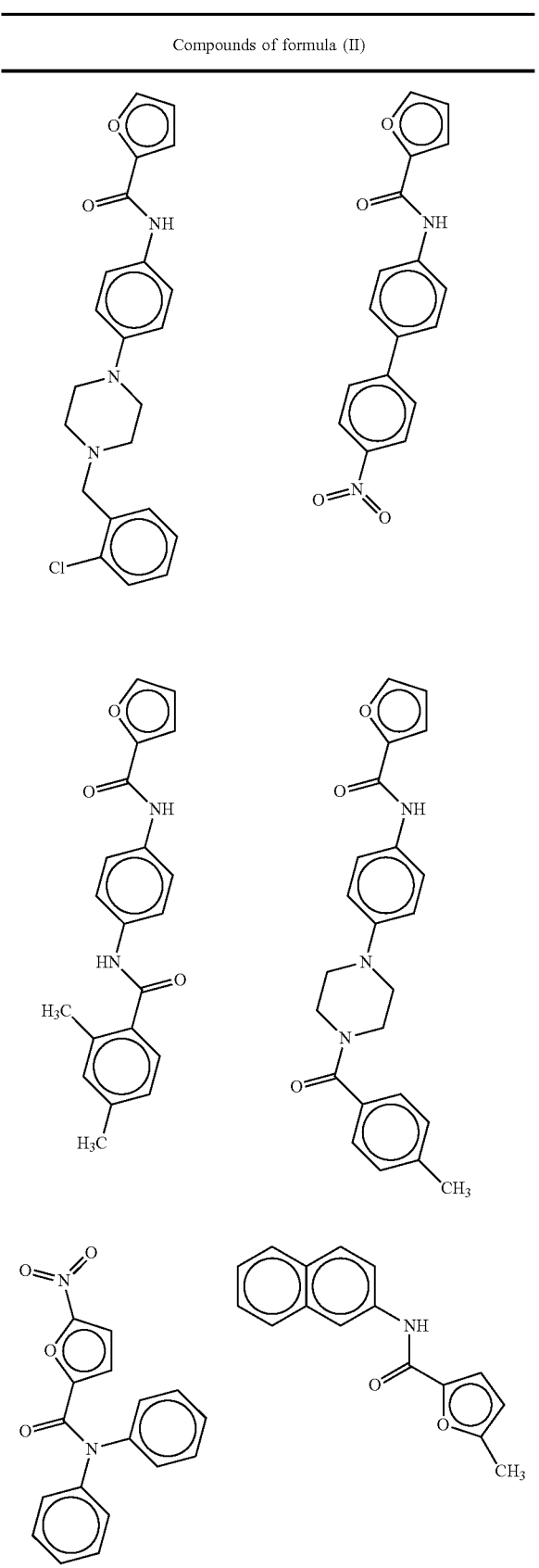
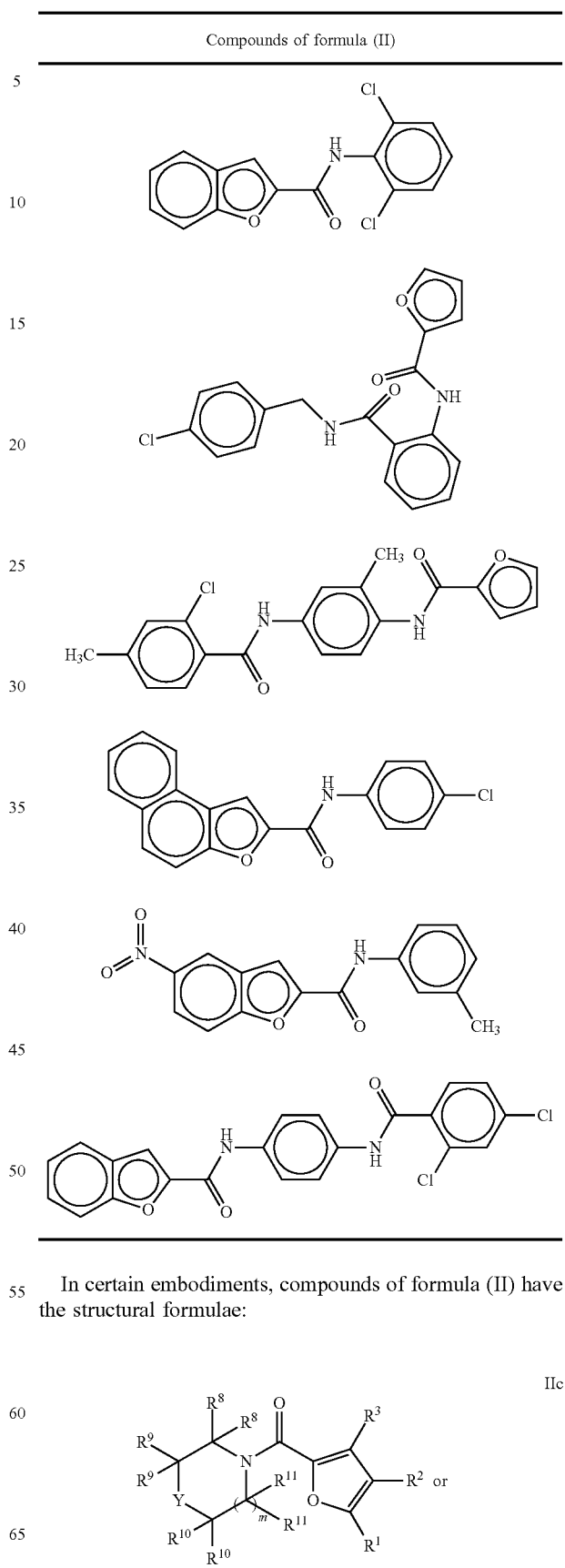
In certain embodiments, compounds of formula (II) have the structural formulae:
IIc -continued

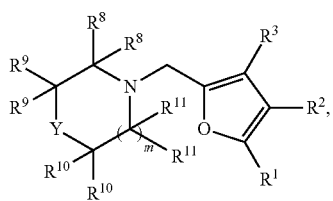

IId wherein Y is —O—, —N(R$^{12}$)—, or —C(R$^{12}$)$_2$—;

each instance of R$^8$, R$^9$, R$^{10}$, R$^{11}$, and R$^{12}$, is, independently, hydrogen, aliphatic, heteroaliphatic, hydroxy, thio, amino, heterocyclic, aryl, heteroaryl, acyl, amido, imido, sulfinyl, sulfonyl, carboxaldehyde, cyano, isocyano, azido, hydrazino, nitro, halo; optionally substituted with oxo, thiooxo, imino, aliphatic, carbocyclic, hydroxy, aliphaticoxy, aryloxy, thio, aliphaticthioxy, arylthioxy, heteroaliphatic, heterocyclic, aryl, arylaliphatic, heteroaryl, heteroarylaliphatic, acyl, acyloxy, amido, imido, sulfinyl, sulfonyl, amino, aliphaticamino, dialiphaticamino, trialiphaticamino, arylamino, diarylamino, carboxaldehyde, cyano, isocyano, azido, hydrazino, nitro, or halo; or R$^8$ and R$^9$ are joined to form a 5- to 6-membered optionally substituted aryl or optionally substituted heteroaryl ring, and R$^{10}$, R$^{11}$, and R$^{12}$ are as defined above; and m is 0 or 1.

In certain embodiments, compounds of formula (II) have the structural formula IIe. Such compounds of formula IIe are exemplified in Table 5:

TABLE 5

Compounds of formula (II)

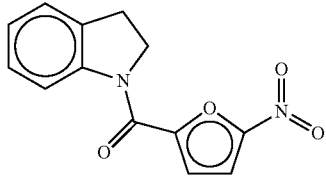

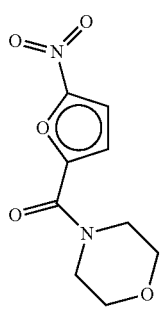

TABLE 5-continued

Compounds of formula (II)

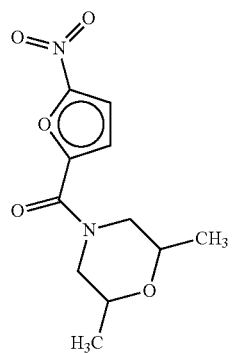

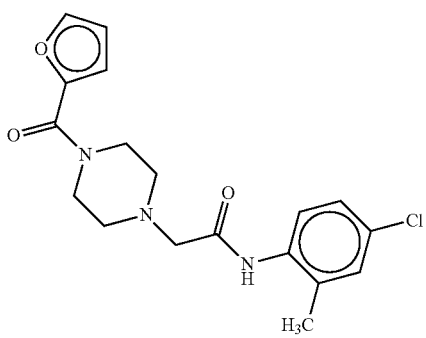

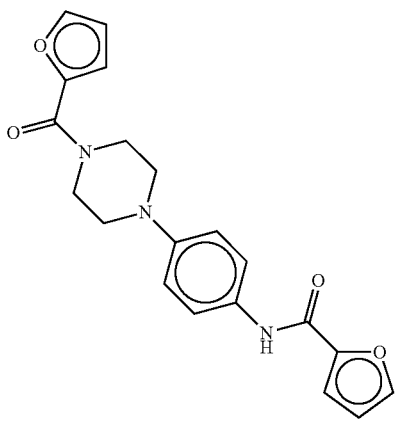

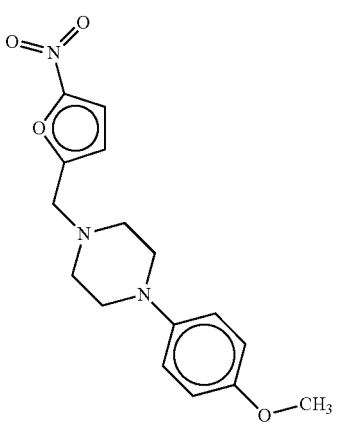

TABLE 5-continued

Compounds of formula (II)

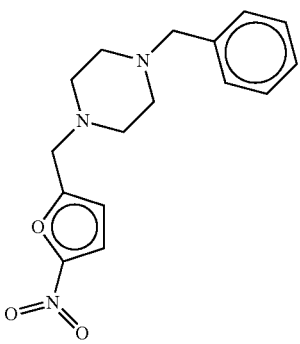

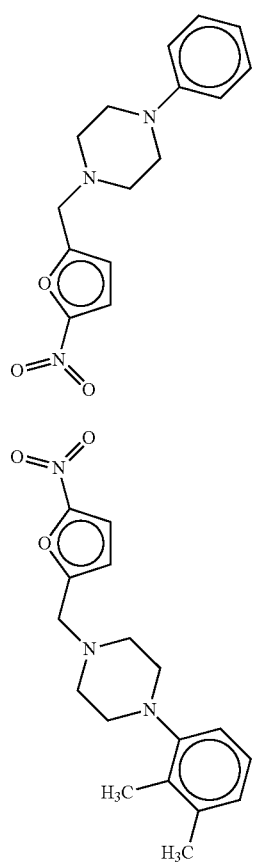

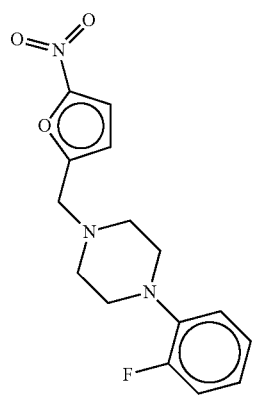

TABLE 5-continued

Compounds of formula (II)

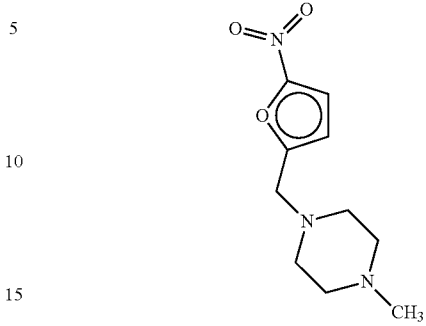

Pharmaceutical Compositions of Compounds of Formula (II)

The present invention is also directed to a pharmaceutical composition comprising a therapeutically effective amount of a compound of formula (II), as defined herein, or a pharmaceutically acceptable salt, prodrug, isomer or tautomer thereof, and at least one pharmaceutically acceptable excipient.

The present invention is also directed to methods of treating a proliferative disease in a subject by administering to a subject a therapeutically effective amount of a compound of formula (II), or a pharmaceutically acceptable salt, prodrug, isomer or tautomer thereof.

In certain embodiments, the proliferative disease is neoplasia. Neoplasia, as used herein, refers to the abnormal growth of tissue in a subject, and may be either benign or malignant. In certain embodiments, the neoplasia is a tumor. In certain embodiments, the neoplasia is cancer. In certain embodiments, the cancer is renal cancer, bladder cancer, liver cancer, testicular cancer, ovarian cancer, colorectal cancer, prostate cancer, pancreatic cancer, lung cancer, breast cancer, brain cancer, bone cancer, stomach cancer, oral cancer, skin cancer, blood cancer, or leukemia. In certain embodiments, the cancer is non-Hodgkin's lymphoma, Wilms' tumor, lymphomas, rhabdomyosarcoma (arising from muscle), retinoblastoma, osteosarcoma, or Ewing's sarcoma. In certain embodiments, the cancer is lung cancer. In certain embodiments, the lung cancer is human non-small cell lung cancer (adenocarcinoma, squamous cell carcinoma, and large cell carcinoma). In certain embodiments the cancer is associated with EGFR and/or KRAS mutations.

In certain embodiments, compounds of formula (II) are effective against a cancer or a tumor. In certain embodiments, compounds of formula (II) are effective against a cancer or a tumor associated with EGFR and/or KRAS mutations. In certain embodiments, compounds of formula (II) are effective against lung cancer or a lung tumor associated with EGFR and/or KRAS mutations.

The present invention is also directed to kits, comprising at least one compound of formula (II), or pharmaceutically acceptable salts, prodrugs, isomers, or tautomers, thereof. A kit of the invention can be particularly useful if it provides additional solvents, buffers, or excipients for pre-mixing before administration, or if it provides a means for oral or parental administration (e.g., syringes or graduated measurement cups). A kit of the invention can also be particularly useful if it contains additional chemotherapeutic agents, as described herein, for use in combination with one or more compounds of formula (II).

In certain embodiments, a therapeutically effective amount of a compound of formula (II) is between about 0.01 mg/kg/day to about 100 mg/kg/day. In certain embodiments, a therapeutically effective amount of a compound of formula (II) is at least 0.01 mg/kg/day, 0.05 mg/kg/day, 0.10 mg/kg/day, 1.0 mg/kg/day, 5.0 mg/kg/day, 10 mg/kg/day, 15 mg/kg/day, 20 mg/kg/day, 30 mg/kg/day, 40 mg/kg/day, 50 mg/kg/day, 60 mg/kg/day, 70 mg/kg/day, 80 mg/kg/day, 90 mg/kg/day, or 100 mg/kg/day.

The present invention will be more specifically illustrated by the following examples. However, it should be understood that the present invention is not limited by these examples in any manner.

EXAMPLES

Example 1

High Throughput Screening for Novel Agents that Block Proliferation of NSCLC Cell Lines There are a variety of well-documented human lung adenocarcinoma cell lines that have been used in the cell-based screens. Characteristics of these cell lines are shown in Table 6. Some of these cell lines have gain of function mutations in either exon 2 of KRAS (H2030) or in exons 18-21 of the EGFR(H1650, H1975 and H3255). The cell lines H11-18 and H3255 express EGFR with an L858R mutation and growth of these cells is inhibited by erlotinib at much lower concentrations than is required to attenuate growth in cells with wild type EGFR (Table 6). In H1650 there is a deletion of four amino acids (E746-A750) in the EGFR. Growth of this cell line is less sensitive to erlotinib than H11-18 and H3255. This may be due to the presence of additional mutations in proteins function downstream of the EGFR. Only the L858R mutation is present in the H1975 cell line. However, we sequenced exons 18-24 of EGFR in 8 adenocarcinoma cell lines and identified a second point mutation in the kinase domain of the EGFR. This C to T change at position 2369 in exon 20 results in a T790M substitution in the receptor and is believed to confer resistance to the EGFR tyrosine kinase inhibitors erlotinib and gefitinib. Indeed, growth of the H1975 cell line is more resistant to erlotinib than the cell lines carrying mutant KRAS such as H358 and H2030 (Table 6). Introduction of double stranded siRNA specific for the EGFR deletion mutant or the L858R mutant into H1650 or H1975 and H3255 induced apoptosis, suggesting that these lung adenocarcinoma cell lines require continuous expression of the EGFR oncogene for survival.

All of the adenocarcinoma cell lines with EGFR mutations shown in Table 6 express wild type KRAS. Conversely, the lines with wild type EGFR in Table 6 carry a mutation in exon 2 of KRAS, resulting in a missense amino acid substitution in codons 12 or 13. In H358 and H2030, this exon 2 mutation results in a G12C amino acid change in KRAS. In H1734, there is a G13C substitution in KRAS. introduction of a G12C-KRAS allele-specific siRNA into the H2030 cell line results in growth arrest, suggesting that this cell line is dependent on expression of mutant KRAS for growth. All adenocarcinoma cell lines with mutant KRAS in Table 6 are resistant to erlotinib and express wild type EGFR.

TABLE 6

| Cell Line | EGFR | KRAS | $IC_{50}$ (Erlotinib) |
|---|---|---|---|
| 11-18 | L858R | WT | 0.01 μM |
| H358 | WT | G12C | 10 μM |
| H1650 | DelE746-A750 | WT | 1 μM |
| H1734 | WT | G13C | 7 μM |
| H1975 | T790M/L858R | WT | 25 μM |
| H2030 | WT | G12C | 10 μM |
| H3255 | L858R | WT | 0.01 μM |
| HCC827 | DelE746-A750 | WT | 0.01 μM |
| HPL1D | WT | WT | 10 μM |
| NHBE | WT | WT | 10 μM |
| WI-38 | WT | WT | 10 μM |

Exons 18-24 of EGFR and exon 2 of KRAS were sequenced and mutations identified are shown. Sensitivity of cell proliferation to erlotinib is also shown. NHBE (normal human bronchiolar epithelial cells) are primary cells obtained from donor lungs and commercially available from Cambrex. The HPL1D (human peripheral lung epithelial) cell line has been immortalized with the SV40 large T-antigen. WI-38: human lung fibroblast cell line. HPL1D, NHBE and WI-38 cells will serve as controls in the chemical screens. WT: wildtype; WT*: over-expressed wildtype.

Methods

Cell cycle analysis. For cell cycle analysis, cells were plated at a density of 500,000 cells per well in 6-well plates. Attached cells were treated with drugs for 24 h. Cells were then collected, washed with PBS and fixed in 70% ethanol for 1 h. For FACS analysis, fixed cells were washed with cold PBS resuspended in PBS containing 200 μg/mL propidium iodide and 0.1% sodium citrate. Flow cytometry was performed on a Becton-Dickinson FACSCalibur flow cytometer and data the processed using FlowJo software.

Caspase 3/7 enzyme activity assay. Apoptosis was determined by measuring the enzymatic activity of caspase 3/7 in cell homogenates. Cells were plated at a density of 10,000 cells per well in 96-well plates and treated immediately with drugs for 24-72 h. Caspase 3/7 activity will be determined in cell extracts using Z-DEVD-R110 (rhodamine 110 conjugated to the caspase substrate Z-DEVD) as substrate (Promega). The fluorescence of the cleaved substrate was measured using a micro-titer fluorescence plate reader (Ex: 499 nm, Em: 521 nm).

[$^3$H]-thymidine incorporation assay. Cells were seeded in 12-well plates at a density of 100 000 cells/well and treated with inhibitors for 24 hours. H3-thymidine (3 μCi/mL) was then added for 3 hours. Cells were washed twice with PBS, fixed with cold 10% TCA (in PBS) for 30 min then lysed with 0.5% NaOH/0.5% SDS. DNA was scraped from the wells and the amount of H3-thymidine incorporated determined by liquid scintillation counting.

TABLE 7

Reagent/Assay Supplies

| Name | Supplier | Description |
| --- | --- | --- |
| Non-Small Cell Lung Cancer Cell Line | ATCC | Human lung cancer cell lines with various mutations in eGFR or kRas |
| RPMI 1640 | ATCC | Cell Culture Growth Media, Supplement with 10% FBS |
| Corning Cell Culture Flask | Fisher | 175 cm2 Flask, 600 ml capacity, sterile with Filter Caps |
| 384 Well Cell Culture Microplate | Corning | Sterile Black Plate w/ Clear Bottom and Lid, tissue culture treated |
| Staurosporine | LC Laboratories | Potent inhibitor of phospholipid/Ca++ dependent protein kinase and platelet aggregation, all PKC isoforms, all Akt isoforms |
| DMSO | Sigma-Aldrich | Dimethyl Sulfoxide |
| Alamar Blue | Serotech | Nontoxic aqueous dye for viability and proliferation measurements |

TABLE 8

Equipment used

| Name | Description |
| --- | --- |
| Biophile | Automated Compound Plate Management System |
| TPS-384 | Compound Dispensing System from Apricot Designs |
| CRS F3 Robot System | Linear Robotic Track System from Thermo Electron Corp. |
| Multidrop 384 | Liquid dispenser for 96/384 microplates |
| Cell Culture Incubator | Incubator at 37° C., humidified, 5% CO2 |
| FlexDrop | Precision liquid handling dispenser from Perkin Elmer |
| Wallac 1420 Victor V Plate Reader | Multi label PMT based reader for Prompt Fluorescence from Perkin Elmer |

Protocols

Growing & Maintaining Non Small Cell Lung Cancer Cell Line. Non Small Cell Lung Cancer cell lines are grown and maintained in Corning 175 $cm_2$ flasks in RPMI 1640 media supplemented with 10% FBS, 1% antibiotic solution, 1% additional glutamine and pyruvate. These cells have a doubling time of 1-2 days. All cell types are adherent and grow in colonies. The cells should be kept at a density between 50,000 cells/mL-500,000 cells/mL to provide for optimum growth and adequate nutrition. The cell line should be maintained at 37° C. in a humidified atmosphere with 5% CO2 in a sterile cell culture incubator.

Non Small Cell Lung Cancer Proliferation Assay. To perform the assay, the Non Small Cell Lung Cancer lines are diluted in media and plated into 384 well microplates at a final density of 250 cells in 45 µL. To ensure consistency and minimal pipetting error, the cells are plated using the Multidrop 384 with the following settings: Rocker Switch set at 384, Volume 45 and Column 24.

Low Controls for this assay are made by treating Non Small Cell Lung Cancer cells with 5 ul of staurosporine at 250 uM in 10% DMSO and 1% SDS. [Final concentration in this assay is 25 uM staurosporine in 1% DMSO and 0.1% SDS.]

High Controls for this assay are made by treating Non Small Cell Lung Cancer cells with 5 ul of 10% DMSO. [Final concentration in this assay is 1% DMSO].

The remaining wells of the 384 microplate may be treated with different compounds depending on the study. Important Note: All compounds for testing in this assay should be done at the final concentration of 1% DMSO.

After addition, the cells are placed in cell culture incubator at 37° C. for 48 hours for complete treatment.

After drug treatment, cytotoxicity is measured by Alamar Blue reduction. 5 µL of Alamar Blue is added to the 384 microplates using the Flexdrop.

The cells are incubated for 48 hours at 37° C. to complete the Alamar Blue reduction.

The final step in the assay is to measure the amount of Alamar Blue reduction. The cells are placed in the Wallac 1420 Victor V Plate Reader I and with the following program, DS Alamar Blue Prompt Fluo (#8). The Alamar Blue fluorescence is measured at an excitation of 530 nm and emission of 590 nm.

For the NSCLC project, the cell based assay was screened against a small molecule library of approximately 200,000 compounds. The compound library is stored in our automated robotic freezer (Biophile) at −20° C. in 100% DMSO. Compound freeze and thaw cycles are kept to a minimum. Compounds for use are diluted into the appropriate concentration and plated into 384 well microplates using our custom built low volume 384-well head tool (TPS 384, Apricot Designs Inc., CA, USA). This assay was performed on a fully automated linear track robotic platform (CRS F3 Robot System, Thermo Electron Corp., Ontario, Canada) utilizing several integrated peripherals for plate handling, liquid dispensing, and readout detection. First, non-small cell lung cancer cell lines are dispensed into 384 well microplates (Corning #3712 Tissue Culture Treated Plate, Corning, N.Y., USA) with 5 µL of test compounds at 100 uM in 10% DMSO for screening studies or 1 mM in 10% DMSO to 50 nM in 10% DMSO for dose response studies. The microplates are then placed at 37° C. for 48 hours to complete treatment of cells with compounds. Next, 5 ul of alamar blue was added using a liquid dispenser (FlexDrop Precision Dispenser, Perkin Elmer, Mass., USA) and incubated for 48 hours at 37° C. The alamar blue prompt fluorescence was measured on Victor V (Victor$^3$ V, Perkin Elmer, Mass., USA) and output data files were loaded into ORIS (Oncology Research Informatics System, MSKCC, NY, USA), a screening data acquisition and analysis platform.

A high throughput screening was performed using four established non small cell lung cancer cell lines (H1650, H1975, H2030, H3255) against a chemical library of 200,000 small molecules. Description of the assays is described herein. Several hits were identified inhibiting one or more cell line with the most potent one being 4,5-dichloro-2-m-tolyl-2H-pyridazin-3-one (SKI-104122).

4,5-dichloro-2-m-tolyl-2H-pyridazin-3-one (SKI-104122)

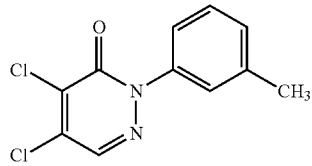 [SMILES: Cc1cccc(-n2ncc(Cl)c(Cl)c2=O)c1]

A substructure search was then performed against the SKI library and identified 115 derivatives of SKI-104122. Further analysis of the biological data for these derivatives reveals a coherent structure activity relationship for both active and inactive compounds with only 22 compounds identified as active during primary screening. Summary of the data is shown in Table 9. Data is expressed as percentage inhibition in the cell based assay; screening concentration of 10 μM compound in 1% DMSO (v/v).

TABLE 9

| Structure | SKI ID | H1650 | H1975 | H2030 | H3255 |
|---|---|---|---|---|---|
| 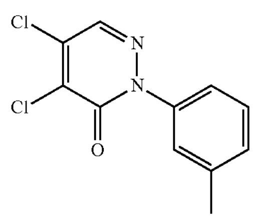 [SMILES: Cc1cccc(-n2ncc(Cl)c(Cl)c2=O)c1] | 104122 | 48 | 104 | 101 | 98 |
| 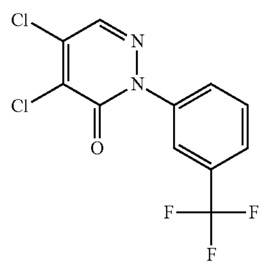 [SMILES: O=c1c(Cl)c(Cl)cnn1-c1cccc(C(F)(F)F)c1] | 176729 | 100 | 102 | −3 | 115 |
| 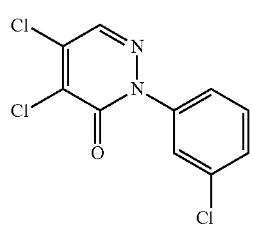 [SMILES: O=c1c(Cl)c(Cl)cnn1-c1cccc(Cl)c1] | 104188 | −13 | 102 | −4 | 4 |
| 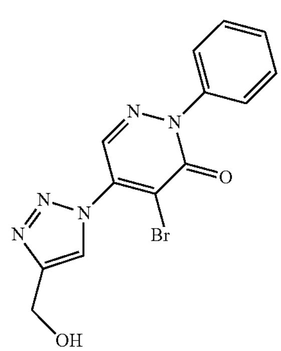 [SMILES: O=c1c(Br)c(-n2cc(CO)nn2)cnn1-c1ccccc1] | 224256 | 103 | 102 | 1 | 110 |

TABLE 9-continued

| Structure | SKI ID | H1650 | H1975 | H2030 | H3255 |
|---|---|---|---|---|---|
| 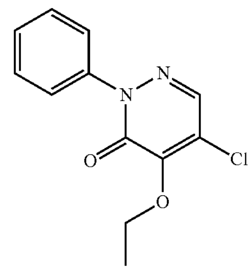 [SMILES: CCOc1c(Cl)cnn(-c2ccccc2)c1=O] | 104288 | −13 | 102 | 66 | 46 |
| 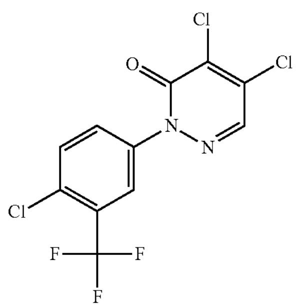 [SMILES: O=c1c(Cl)c(Cl)cnn1-c1ccc(Cl)c(C(F)(F)F)c1] | 103719 | 45 | 102 | 94 | 76 |
| 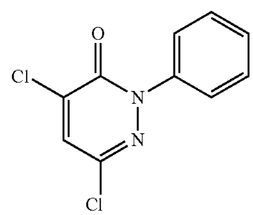 [SMILES: O=c1c(Cl)cc(Cl)nn1-c1ccccc1] | 196392 | 87 | 99 | −13 | 111 |
| 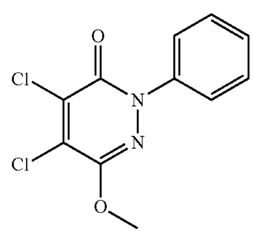 [SMILES: COc1nn(-c2ccccc2)c(=O)c(Cl)c1Cl] | 104322 | 51 | 99 | 87 | 82 |
| 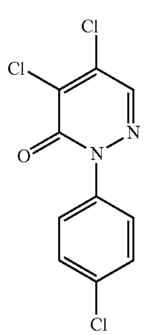 [SMILES: O=c1c(Cl)c(Cl)cnn1-c1ccc(Cl)cc1] | 104004 | 1 | 98 | 75 | 90 |

TABLE 9-continued

| Structure | SKI ID | H1650 | H1975 | H2030 | H3255 |
|---|---|---|---|---|---|
| (pyridazinone with N-phenyl, Cl, SEt) | 103997 | −15 | 98 | 9 | 2 |
| (pyridazinone with N-phenyl, Cl, pyrrolidinyl) | 104304 | 52 | 98 | 14 | 107 |
| (pyridazinone with N-(4-nitrophenyl), di-Cl) | 103529 | −13 | 97 | 15 | 1 |
| (pyridazinone with N-phenyl, SH, OMe) | 187118 | 101 | 96 | 7 | 108 |
| (pyridazinone with N-(4-bromophenyl), tri-Cl) | 202245 | 48 | 96 | −8 | 71 |

TABLE 9-continued

| Structure | SKI ID | H1650 | H1975 | H2030 | H3255 |
|---|---|---|---|---|---|
| 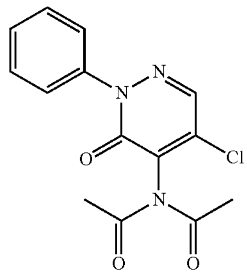 [SMILES: CC(=O)N(C(C)=O)c1c(Cl)cnn(-c2ccccc2)c1=O] | 187116 | 31 | 90 | 4 | 27 |
| 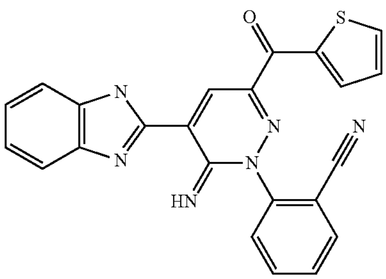 [SMILES: N#Cc1ccccc1-n1nc(C(=O)c2cccs2)cc(-c2nc3ccccc3[nH]2)c1=N] | 186926 | 27 | 81 | 2 | 52 |
| 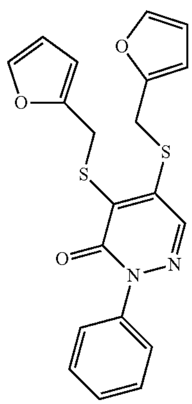 [SMILES: O=c1c(SCc2ccco2)c(SCc2ccco2)cnn1-c1ccccc1] | 195071 | 71 | 77 | 9 | 82 |
| 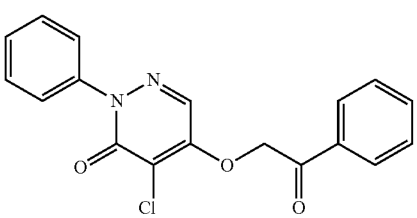 [SMILES: O=C(COc1cnn(-c2ccccc2)c(=O)c1Cl)c1ccccc1] | 199759 | 16 | 36 | 9 | 66 |
| 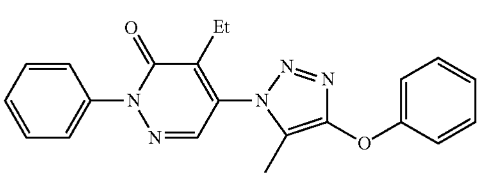 | 223337 | 13 | 5 | −14 | 61 |
| 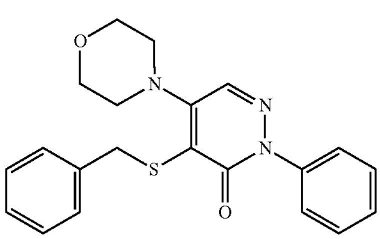 | 224770 | 65 | −8 | −8 | 24 |

TABLE 9-continued

| Structure | SKI ID | H1650 | H1975 | H2030 | H3255 |
|---|---|---|---|---|---|
| (2,4-dichlorostyryl cyano oxo dimethylphenyl pyridazine carboxylic acid) | 227626 | −15 | −14 | 0 | 71 |
| (phenyl pyridazinone bis(butylthio)) | 224766 | −12 | −29 | 95 | 24 |
| (phenyl pyridazinone chloro methylthio) | 104185 | −9 | 22 | −2 | 1 |
| (phenyl pyridazinone chloro ethoxy) | 104217 | −15 | −7 | 6 | −1 |

TABLE 9-continued
| Structure | SKI ID | H1650 | H1975 | H2030 | H3255 |
|---|---|---|---|---|---|
| 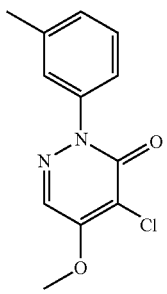 [SMILES: COc1cnn(-c2cccc(C)c2)c(=O)c1Cl] | 104325 | −31 | −12 | 2 | 4 |
| 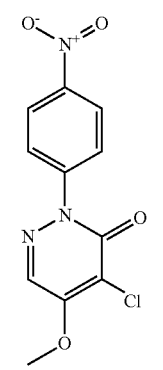 [SMILES: COc1cnn(-c2ccc([N+](=O)[O-])cc2)c(=O)c1Cl] | 104339 | −21 | −9 | −3 | 3 |
| 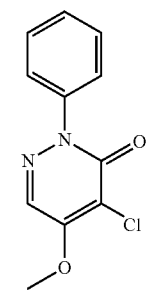 | 104386 | −12 | −11 | 6 | 0 |
| 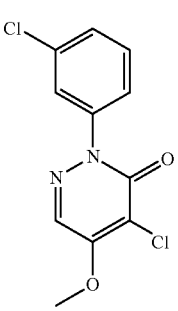 [SMILES: COc1cnn(-c2cccc(Cl)c2)c(=O)c1Cl] | 104390 | 15 | 4 | −6 | 34 |
| 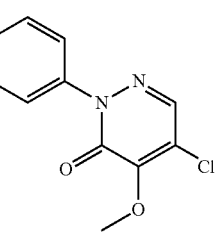 | 104415 | −20 | 15 | −3 | 9 |

TABLE 9-continued

| Structure | SKI ID | H1650 | H1975 | H2030 | H3255 |
|---|---|---|---|---|---|
| 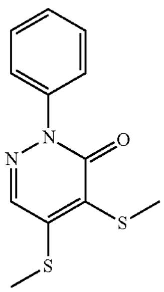 [SMILES: CSc1cnn(-c2ccccc2)c(=O)c1SC] | 104423 | −11 | −20 | −3 | 1 |
| 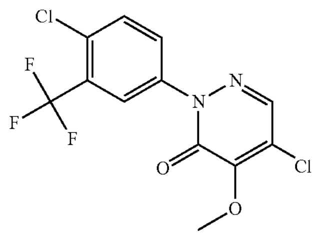 [SMILES: COc1c(Cl)cnn(-c2ccc(Cl)c(C(F)(F)F)c2)c1=O] | 174405 | 13 | 28 | −9 | 32 |
| 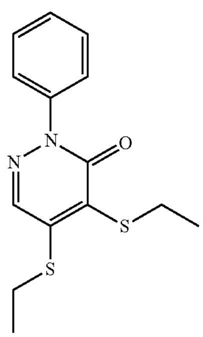 [SMILES: CCSc1cnn(-c2ccccc2)c(=O)c1SCC] | 174406 | 18 | 3 | −9 | 8 |
| 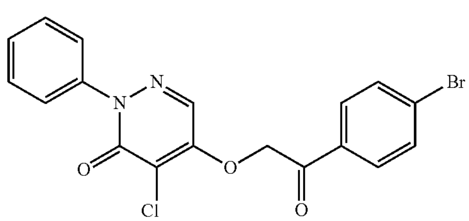 | 176702 | 29 | 26 | −14 | −21 |
| 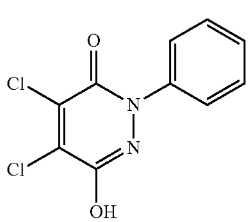 [SMILES: O=c1c(Cl)c(Cl)c(O)nn1-c1ccccc1] | 103751 | 6 | −4 | −4 | 0 |

TABLE 9-continued

| Structure | SKI ID | H1650 | H1975 | H2030 | H3255 |
|---|---|---|---|---|---|
| 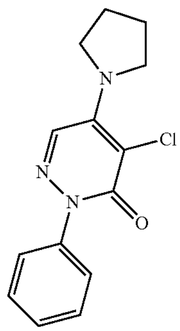 [SMILES: O=c1c(Cl)c(N2CCCC2)cnn1-c1ccccc1] | 103868 | −7 | −18 | −4 | −3 |
| 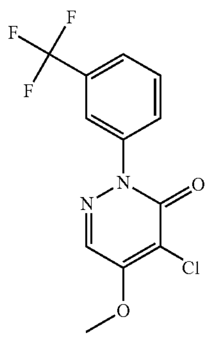 [SMILES: COc1cnn(-c2cccc(C(F)(F)F)c2)c(=O)c1Cl] | 103872 | 17 | 9 | 2 | −25 |
| 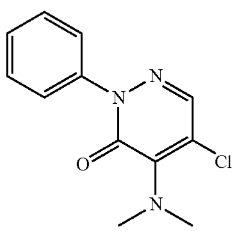 [SMILES: CN(C)c1c(Cl)cnn(-c2ccccc2)c1=O] | 103911 | −7 | −12 | −5 | −3 |
| 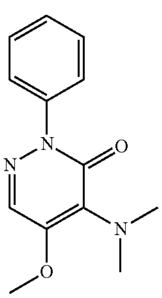 [SMILES: COc1cnn(-c2ccccc2)c(=O)c1N(C)C] | 103971 | 5 | −10 | 1 | −1 |
| 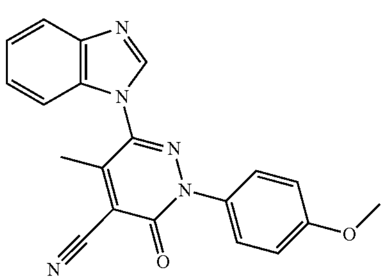 [SMILES: COc1ccc(-n2nc(-n3cnc4ccccc43)c(C)c(C#N)c2=O)cc1] | 176963 | 11 | −5 | 4 | 17 |

TABLE 9-continued

| Structure | SKI ID | H1650 | H1975 | H2030 | H3255 |
|---|---|---|---|---|---|
| 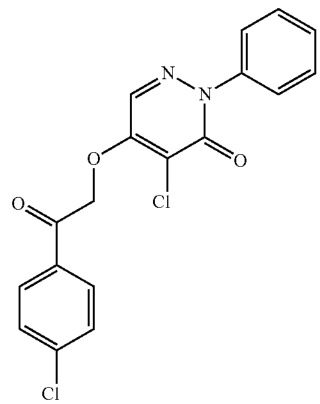 [SMILES: O=C(COc1cnn(-c2ccccc2)c(=O)c1Cl)c1ccc(Cl)cc1] | 177215 | 6 | 25 | −9 | 13 |
| 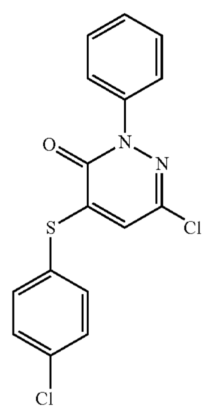 [SMILES: O=c1c(Sc2ccc(Cl)cc2)cc(Cl)nn1-c1ccccc1] | 177261 | 14 | 16 | −8 | 8 |
| 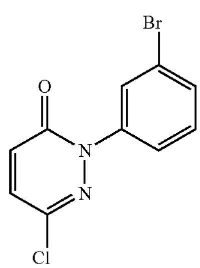 [SMILES: O=c1ccc(Cl)nn1-c1cccc(Br)c1] | 178393 | 8 | 3 | −11 | −4 |
| 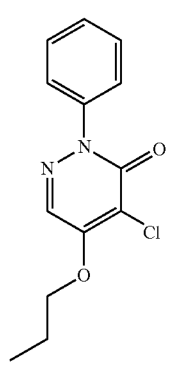 [SMILES: CCCOc1cnn(-c2ccccc2)c(=O)c1Cl] | 179389 | −3 | 1 | 8 | 28 |

TABLE 9-continued

| Structure | SKI ID | H1650 | H1975 | H2030 | H3255 |
|---|---|---|---|---|---|
| (phenylacetate ester of 1-phenyl-6-oxo-pyridazin-3-yl) | 180651 | 21 | 13 | 11 | 35 |
| (2-phenyl-4-chloro-5-(4-aminophenylthio)pyridazin-3(2H)-one) | 181612 | 7 | −11 | 11 | 11 |
| (5-(benzimidazol-2-yl)-3-(furan-2-carbonyl)-6-imino-1-phenylpyridazine) | 181801 | 13 | 24 | −7 | 7 |
| (5-(benzimidazol-2-yl)-3-(furan-2-carbonyl)-6-imino-1-(3-methylphenyl)pyridazine) | 181802 | −2 | 14 | −5 | 27 |

TABLE 9-continued

| Structure | SKI ID | H1650 | H1975 | H2030 | H3255 |
|---|---|---|---|---|---|
| 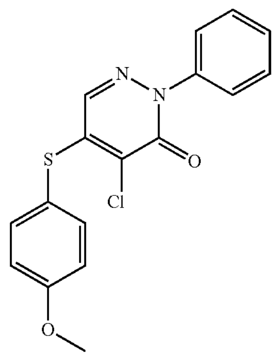 [SMILES: COc1ccc(Sc2cnn(-c3ccccc3)c(=O)c2Cl)cc1] | 181862 | 7 | 3 | 9 | 22 |
| 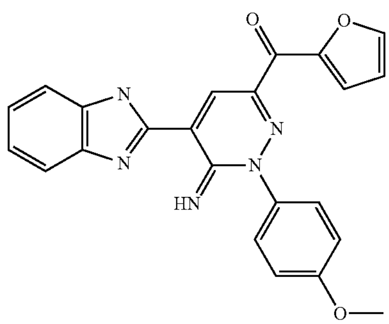 [SMILES: COc1ccc(-n2nc(C(=O)c3ccco3)cc(-c3nc4ccccc4[nH]3)c2=N)cc1] | 182721 | 8 | 9 | 11 | 4 |
| 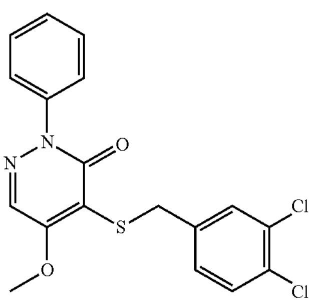 [SMILES: COc1cnn(-c2ccccc2)c(=O)c1SCc1ccc(Cl)c(Cl)c1] | 182729 | 10 | 23 | −14 | 1 |
| 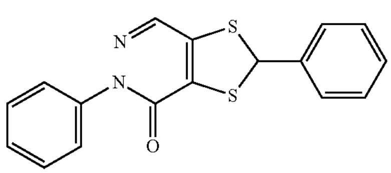 [SMILES: N=CC1=C(C(=O)Nc2ccccc2)SC(c2ccccc2)S1] | 182826 | 13 | 12 | −11 | −13 |
| 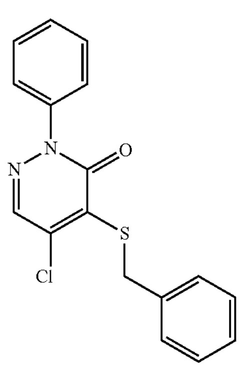 [SMILES: O=c1c(SCc2ccccc2)c(Cl)cnn1-c1ccccc1] | 182827 | −20 | 14 | −6 | −24 |

TABLE 9-continued

| Structure | SKI ID | H1650 | H1975 | H2030 | H3255 |
|---|---|---|---|---|---|
| 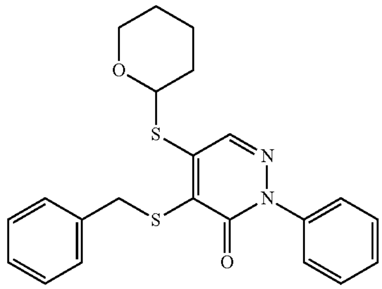 [SMILES: O=c1c(SCc2ccccc2)c(SC2CCCCO2)cnn1-c1ccccc1] | 182828 | 25 | −5 | −8 | 18 |
| 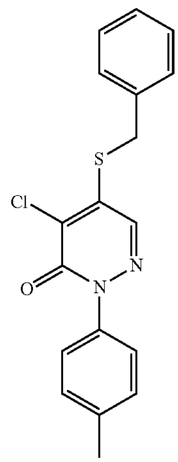 [SMILES: Cc1ccc(-n2ncc(SCc3ccccc3)c(Cl)c2=O)cc1] | 182830 | 20 | 10 | 3 | −4 |
| 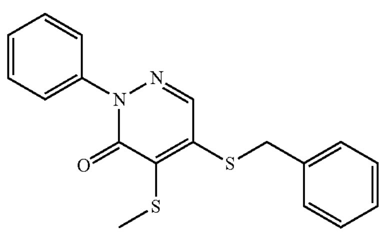 [SMILES: CSc1c(SCc2ccccc2)cnn(-c2ccccc2)c1=O] | 182831 | −4 | 5 | −12 | −18 |
| 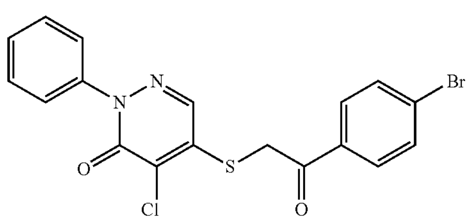 | 183073 | −3 | −6 | 8 | 30 |
| 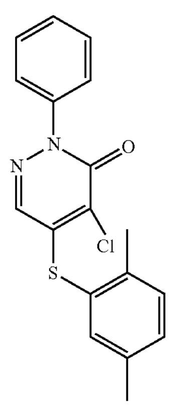 [SMILES: Cc1ccc(C)c(Sc2cnn(-c3ccccc3)c(=O)c2Cl)c1] | 183339 | 15 | 8 | −12 | −30 |

TABLE 9-continued

| Structure | SKI ID | H1650 | H1975 | H2030 | H3255 |
|---|---|---|---|---|---|
| 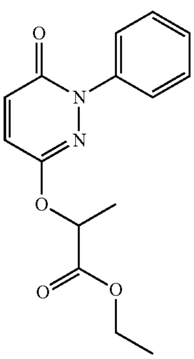 [SMILES: CCOC(=O)C(C)Oc1ccc(=O)n(-c2ccccc2)n1] | 185423 | 16 | −9 | 3 | 23 |
| 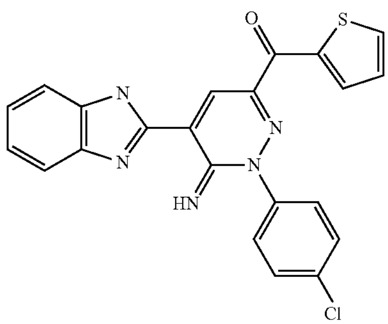 [SMILES: N=c1c(-c2nc3ccccc3[nH]2)cc(C(=O)c2cccs2)nn1-c1ccc(Cl)cc1] | 186017 | −12 | −6 | −4 | −13 |
| 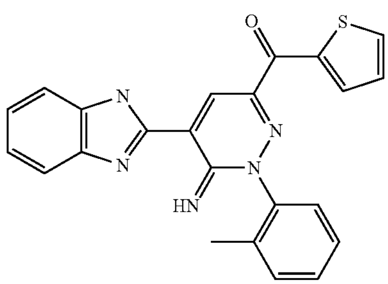 [SMILES: Cc1ccccc1-n1nc(C(=O)c2cccs2)cc(-c2nc3ccccc3[nH]2)c1=N] | 186018 | 42 | −4 | 4 | 35 |
| 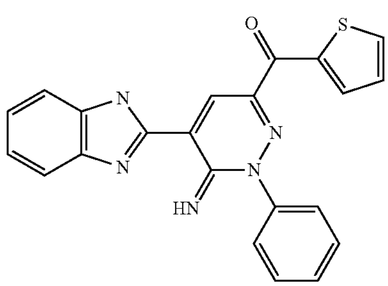 [SMILES: N=c1c(-c2nc3ccccc3[nH]2)cc(C(=O)c2cccs2)nn1-c1ccccc1] | 186924 | 7 | 14 | 1 | 8 |
| 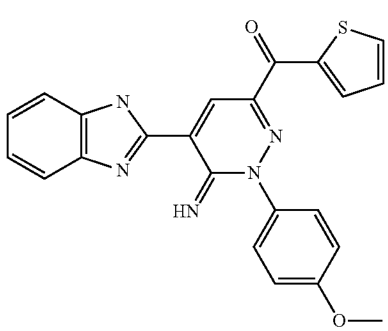 | 186925 | 6 | 3 | 1 | −28 |

TABLE 9-continued

| Structure | SKI ID | H1650 | H1975 | H2030 | H3255 |
|---|---|---|---|---|---|
| 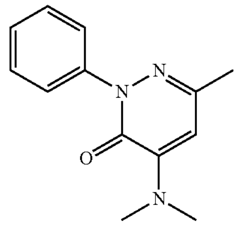 [SMILES: Cc1cc(N(C)C)c(=O)n(-c2ccccc2)n1] | 189015 | 21 | 29 | −4 | 32 |
| 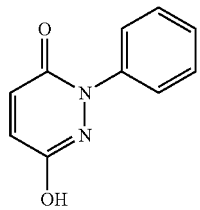 [SMILES: O=c1ccc(O)nn1-c1ccccc1] | 189286 | 0 | 9 | 5 | −15 |
| 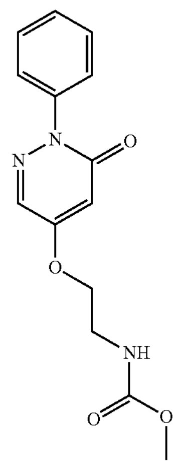 | 189493 | 2 | 12 | −8 | −25 |
| 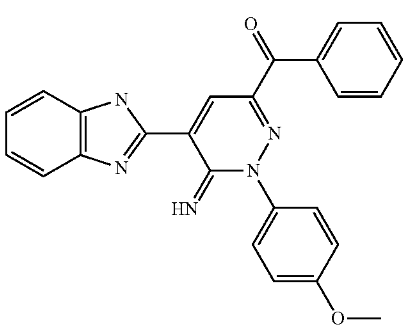 [SMILES: COc1ccc(-n2nc(C(=O)c3ccccc3)cc(-c3nc4ccccc4[nH]3)c2=N)cc1] | 193067 | −7 | 21 | 4 | −35 |
| 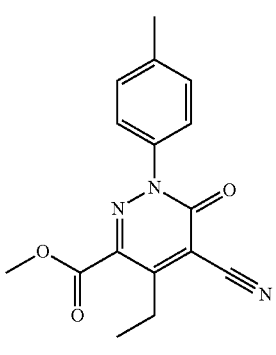 [SMILES: CCc1c(C(=O)OC)nn(-c2ccc(C)cc2)c(=O)c1C#N] | 193326 | −2 | −1 | −9 | −49 |

TABLE 9-continued
| Structure | SKI ID | H1650 | H1975 | H2030 | H3255 |
|---|---|---|---|---|---|
| 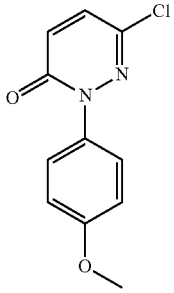 [SMILES: COc1ccc(-n2nc(Cl)ccc2=O)cc1] | 194491 | −2 | 0 | −12 | −32 |
| 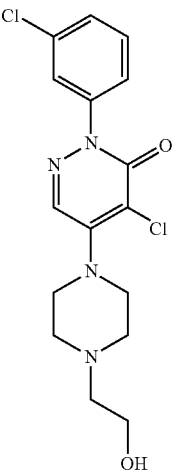 [SMILES: O=c1c(Cl)c(N2CCN(CCO)CC2)cnn1-c1cccc(Cl)c1] | 194617 | −9 | 9 | −4 | −5 |
| 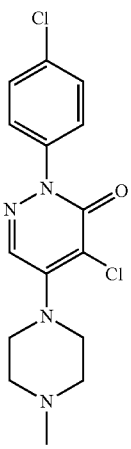 | 194618 | −15 | −3 | −6 | −48 |
| 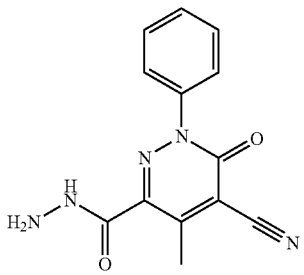 [SMILES: Cc1c(C(=O)NN)nn(-c2ccccc2)c(=O)c1C#N] | 194841 | −1 | −15 | −9 | −35 |

TABLE 9-continued

| Structure | SKI ID | H1650 | H1975 | H2030 | H3255 |
|---|---|---|---|---|---|
| 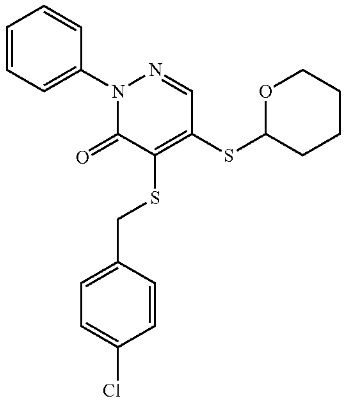 [SMILES: O=c1c(SCc2ccc(Cl)cc2)c(SC2CCCCO2)cnn1-c1ccccc1] | 195063 | 22 | 34 | −6 | −6 |
| 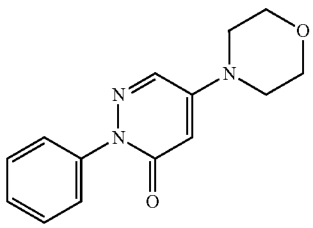 [SMILES: O=c1cc(N2CCOCC2)cnn1-c1ccccc1] | 195066 | 8 | −3 | 9 | −9 |
| 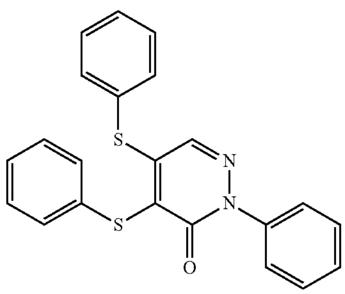 [SMILES: O=c1c(Sc2ccccc2)c(Sc2ccccc2)cnn1-c1ccccc1] | 195070 | 8 | 9 | −7 | −73 |
| 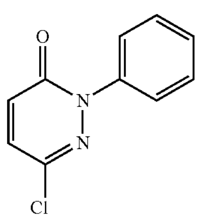 [SMILES: O=c1ccc(Cl)nn1-c1ccccc1] | 195149 | −4 | 11 | −5 | −19 |
| 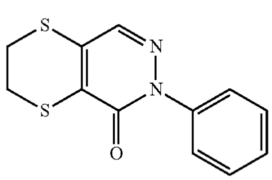 [SMILES: O=c1c2c(cnn1-c1ccccc1)SCCS2] | 195988 | 13 | −7 | 7 | −18 |
| 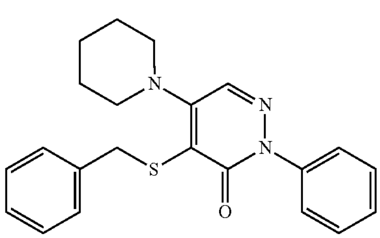 | 195989 | 21 | 35 | 6 | −27 |

TABLE 9-continued

| Structure | SKI ID | H1650 | H1975 | H2030 | H3255 |
|---|---|---|---|---|---|
| 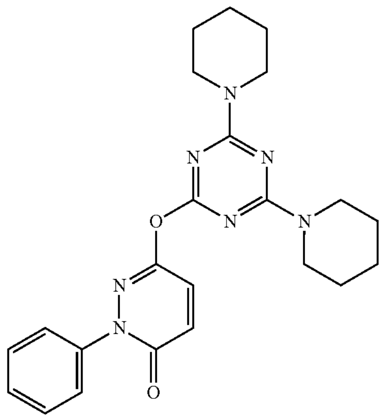 [SMILES: O=c1ccc(Oc2nc(N3CCCCC3)nc(N3CCCCC3)n2)nn1-c1ccccc1] | 196618 | 3 | −14 | 12 | −33 |
| 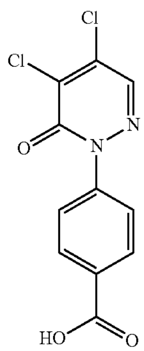 [SMILES: O=C(O)c1ccc(-n2ncc(Cl)c(Cl)c2=O)cc1] | 197940 | 11 | −6 | 2 | −37 |
| 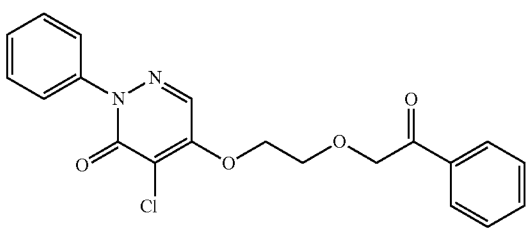 [SMILES: O=C(COCCOc1cnn(-c2ccccc2)c(=O)c1Cl)c1ccccc1] | 199760 | 12 | −22 | 21 | 6 |
| 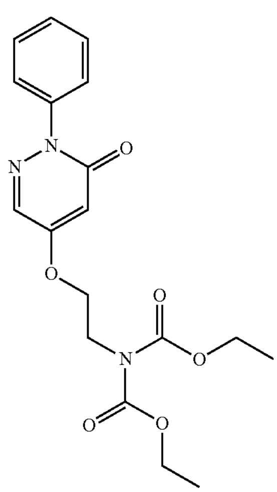 [SMILES: CCOC(=O)N(CCOc1cnn(-c2ccccc2)c(=O)c1)C(=O)OCC] | 199761 | −7 | −25 | 6 | 41 |

TABLE 9-continued

| Structure | SKI ID | H1650 | H1975 | H2030 | H3255 |
|---|---|---|---|---|---|
| (structure) | 199764 | −11 | −14 | −9 | 2 |
| (structure) | 200052 | −9 | 5 | 12 | −18 |
| (structure) | 201622 | 5 | −23 | 4 | 33 |
| (structure) | 206569 | −2 | 3 | 7 | 22 |

TABLE 9-continued

| Structure | SKI ID | H1650 | H1975 | H2030 | H3255 |
|---|---|---|---|---|---|
| 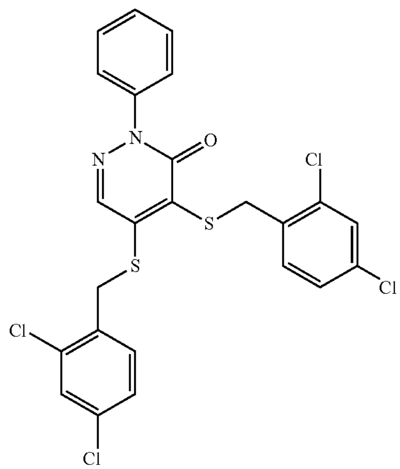 [SMILES: O=c1c(SCc2ccc(Cl)cc2Cl)c(SCc2ccc(Cl)cc2Cl)cnn1-c1ccccc1] | 208619 | −4 | 1 | −12 | −19 |
| 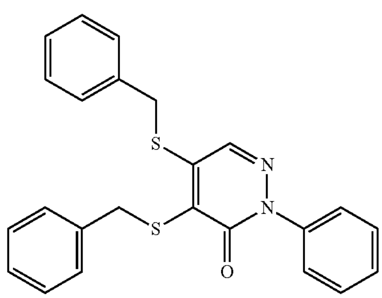 [SMILES: O=c1c(SCc2ccccc2)c(SCc2ccccc2)cnn1-c1ccccc1] | 208693 | −6 | −7 | −11 | 0 |
| 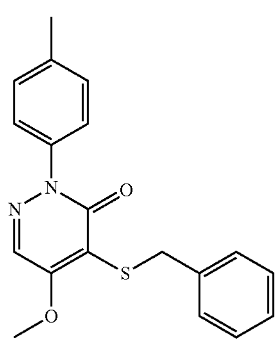 [SMILES: COc1cnn(-c2ccc(C)cc2)c(=O)c1SCc1ccccc1] | 208694 | −21 | −29 | 3 | −16 |
| 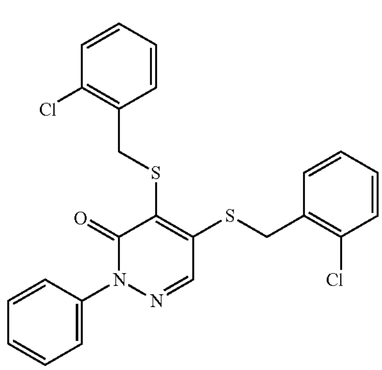 [SMILES: O=c1c(SCc2ccccc2Cl)c(SCc2ccccc2Cl)cnn1-c1ccccc1] | 208695 | −14 | −13 | −11 | −2 |

TABLE 9-continued
| Structure | SKI ID | H1650 | H1975 | H2030 | H3255 |
|---|---|---|---|---|---|
| 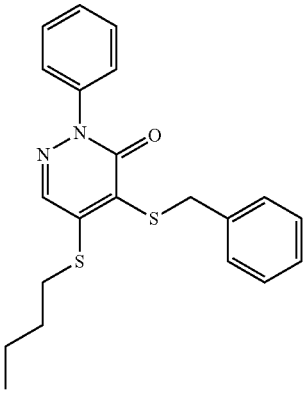 [SMILES: CCCCSc1cnn(-c2ccccc2)c(=O)c1SCc1ccccc1] | 208696 | −2 | −19 | 4 | 37 |
| 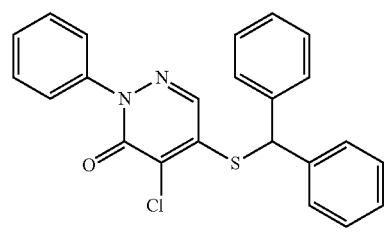 [SMILES: O=c1c(Cl)c(SC(c2ccccc2)c2ccccc2)cnn1-c1ccccc1] | 208697 | −3 | −16 | 4 | 31 |
| 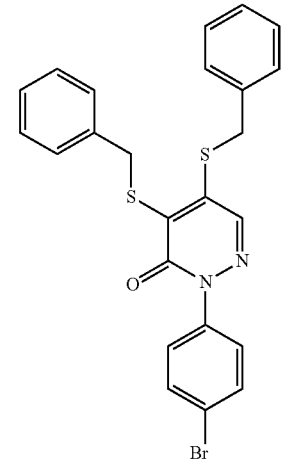 [SMILES: O=c1c(SCc2ccccc2)c(SCc2ccccc2)cnn1-c1ccc(Br)cc1] | 208699 | −12 | −22 | 10 | 19 |
| 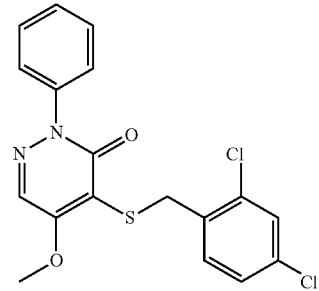 [SMILES: COc1cnn(-c2ccccc2)c(=O)c1SCc1ccc(Cl)cc1Cl] | 208701 | −4 | −25 | 7 | 7 |

TABLE 9-continued

| Structure | SKI ID | H1650 | H1975 | H2030 | H3255 |
|---|---|---|---|---|---|
| 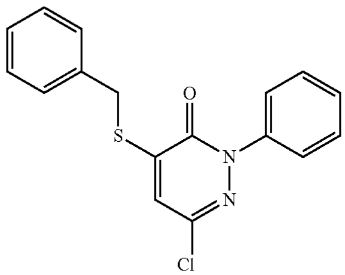 [SMILES: O=c1c(SCc2ccccc2)cc(Cl)nn1-c1ccccc1] | 208702 | 3 | −16 | −15 | 0 |
| 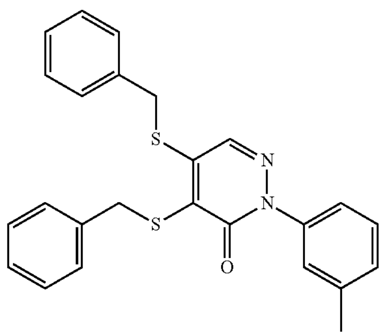 [SMILES: Cc1cccc(-n2ncc(SCc3ccccc3)c(SCc3ccccc3)c2=O)c1] | 208703 | 2 | −18 | 9 | 16 |
| 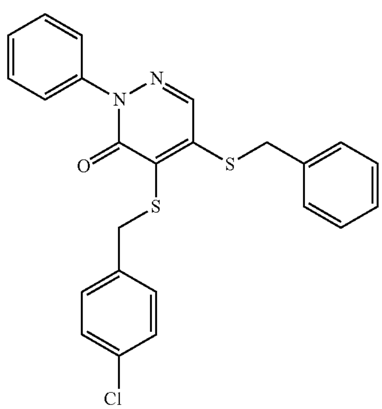 [SMILES: O=c1c(SCc2ccc(Cl)cc2)c(SCc2ccccc2)cnn1-c1ccccc1] | 208704 | −10 | −6 | −15 | −23 |
| 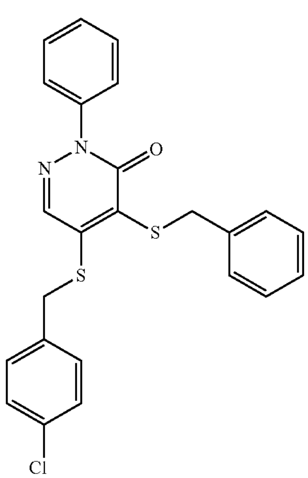 [SMILES: O=c1c(SCc2ccccc2)c(SCc2ccc(Cl)cc2)cnn1-c1ccccc1] | 208705 | −4 | −20 | 10 | 0 |

TABLE 9-continued

| Structure | SKI ID | H1650 | H1975 | H2030 | H3255 |
|---|---|---|---|---|---|
| 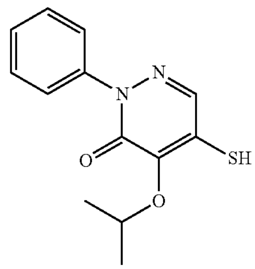 [SMILES: CC(C)Oc1c(S)cnn(-c2ccccc2)c1=O] | 213495 | 4 | −15 | −5 | 8 |
| 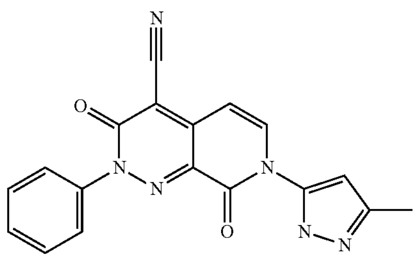 [SMILES: Cc1cc(-n2ccc3c(C#N)c(=O)n(-c4ccccc4)nc3c2=O)[nH]n1] | 216994 | 1 | 1 | 4 | −3 |
| 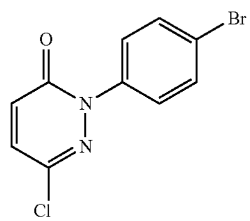 [SMILES: O=c1ccc(Cl)nn1-c1ccc(Br)cc1] | 222922 | −20 | 3 | −30 | −7 |
| 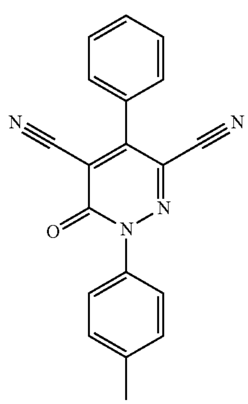 [SMILES: Cc1ccc(-n2nc(C#N)c(-c3ccccc3)c(C#N)c2=O)cc1] | 224358 | −4 | −9 | −2 | −14 |
| 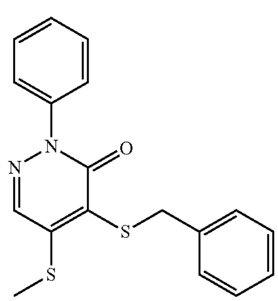 [SMILES: CSc1cnn(-c2ccccc2)c(=O)c1SCc1ccccc1] | 224764 | 21 | −5 | −10 | −32 |

TABLE 9-continued

| Structure | SKI ID | H1650 | H1975 | H2030 | H3255 |
|---|---|---|---|---|---|
| 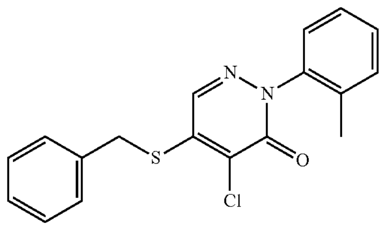 [SMILES: Cc1ccccc1-n1ncc(SCc2ccccc2)c(Cl)c1=O] | 224765 | 7 | 1 | −15 | −12 |
| 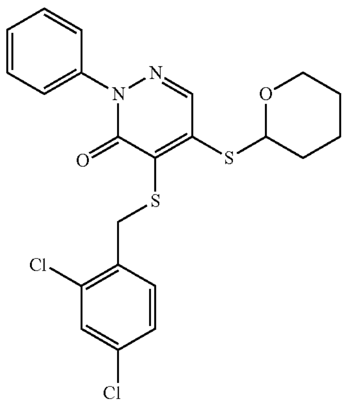 [SMILES: O=c1c(SCc2ccc(Cl)cc2Cl)c(SC2CCCCO2)cnn1-c1ccccc1] | 224771 | −12 | −21 | 3 | 30 |
| 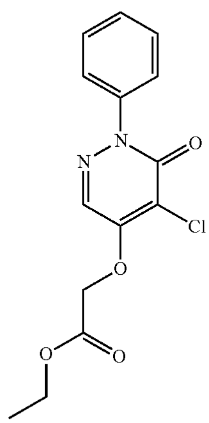 [SMILES: CCOC(=O)COc1cnn(-c2ccccc2)c(=O)c1Cl] | 225042 | −18 | 10 | 6 | 5 |
| 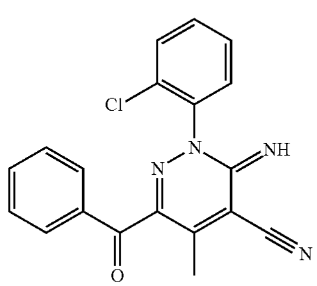 [SMILES: Cc1c(C(=O)c2ccccc2)nn(-c2ccccc2Cl)c(=N)c1C#N] | 227247 | −16 | −9 | −1 | 11 |
| 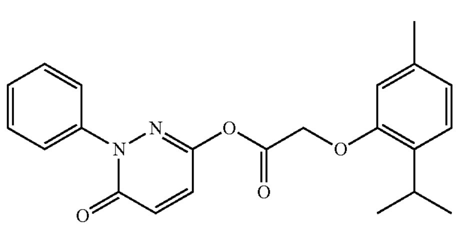 [SMILES: Cc1ccc(C(C)C)c(OCC(=O)Oc2ccc(=O)n(-c3ccccc3)n2)c1] | 228706 | −16 | −11 | 5 | −25 |

TABLE 9-continued

| Structure | SKI ID | H1650 | H1975 | H2030 | H3255 |
|---|---|---|---|---|---|
| (3-ethoxy-1-phenyl-pyridazin-6(1H)-one) | 251592 | ND | ND | ND | ND |
| (2-(3-chlorophenyl)-6-hydroxypyridazin-3(2H)-one) | 251603 | ND | ND | ND | ND |
| (5-cyano-1-(4-methoxyphenyl)-4-methyl-6-oxo-1,6-dihydropyridazine-3-carboxylic acid) | 254244 | ND | ND | ND | ND |
| (4-ethyl-6-oxo-1-phenyl-1,6-dihydropyridazine-3,5-dicarbonitrile) | 254254 | ND | ND | ND | ND |
| (ethyl 5-cyano-4-methyl-1-(2-methylphenyl)-6-oxo-1,6-dihydropyridazine-3-carboxylate) | 254262 | ND | ND | ND | ND |

TABLE 9-continued

| Structure | SKI ID | H1650 | H1975 | H2030 | H3255 |
|---|---|---|---|---|---|
| 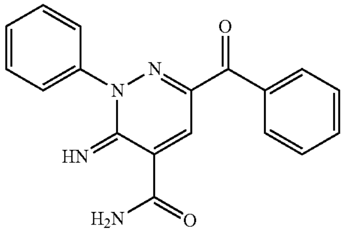 [SMILES: N=c1c(C(N)=O)cc(C(=O)c2ccccc2)nn1-c1ccccc1] | 254579 | ND | ND | ND | ND |
| 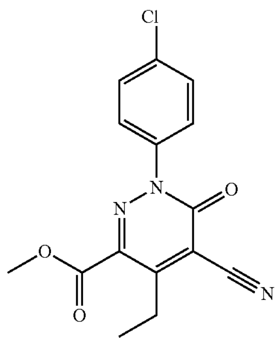 [SMILES: CCc1c(C(=O)OC)nn(-c2ccc(Cl)cc2)c(=O)c1C#N] | 254913 | ND | ND | ND | ND |
| 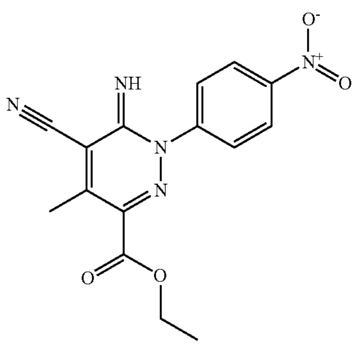 [SMILES: CCOC(=O)c1nn(-c2ccc([N+](=O)[O-])cc2)c(=N)c(C#N)c1C] | 255398 | ND | ND | ND | ND |

Example 2

SAR of Compound SKI-104122

Synthesis of Pyridazin-3(2H)-ones

Based on the obtained SAR results from primary screening and the observed affinities (see Example 1), the feasibility of identifying the molecular target for SKI-104122 was investigated. To achieve this, an SAR study was undertaken to identify potential sites on the molecule for linker addition without compromising biological activity. The linker will then be attached to sepharose beads generating an affinity chromatography column to be used for identifying molecular target.

The preparation of compounds screened is exemplified below.

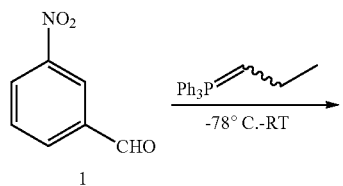

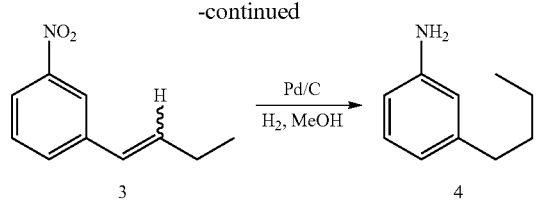

Preparation of 1-[(1E)-But-1-en-1-yl]-3-nitrobenzene (3). n-BuLi (2.5M/hexanes, 7.7 mL, 19.46 mmol) was added drop wise to a −78° C. cooled suspension of n-propyl triphenylphosphonium bromide (2) (7.5 g, 19.46 mmol) in THF (50 mL) and the reaction was warmed to room temperature over 1 h and cooled to −78° C. A solution of 3-nitrobenzaldehyde (1) (2.94 g, 19.46 mmol) in THF (10.0 mL) was then added and the reaction mixture was gradually warmed to room temperature. After 15 h, saturated NH$_4$Cl solution was added and diluted with water (25 mL). The organic layer was separated and aqueous layer was extracted with EtOAc (25 mL). The combined organic layers were dried (Na$_2$SO$_4$), filtered and concentrated in vacuo. The residue was purified by silica gel flash chromatography (10% EtOAc/hexanes) to afford (3) (2.5 g, 66%) as an oil. $^1$H NMR (300 MHz, CDCl$_3$): δ 1.09 (t, J=6.0 Hz, 3H), 2.25-2.42 (m, 2H), 5.75-5.90 (m, 1H), 6.39-6.49 (m, 1H), 7.40-7.64 (m, 2H), 7.95 (m, 2H).

Preparation of 3-(n-butyl)-phenylamine (4). A solution of (3) (2.5 g, 14.11 mmol) in methanol (20 mL) was added to a slurry of 10% Pd/C (300 mg) in ethyl acetate (1 mL) and stirred under hydrogen atmosphere for 5 h. The catalyst was filtered and the filtrate was concentrated to afford (4) (2.0 g, 96%). $^1$H NMR (300 MHz, CDCl$_3$): δ 0.90 (t, J=6.0 Hz, 3H), 1.25-1.42 (m, 2H), 1.50-1.65 (m, 2H), 2.52 (t, J=6.0 Hz, 2H J=6.0 Hz), 3.59 (br s, 2H), 6.45-6.62 (m, 3H), 7.05 (t, J=6.0 Hz, 1H).

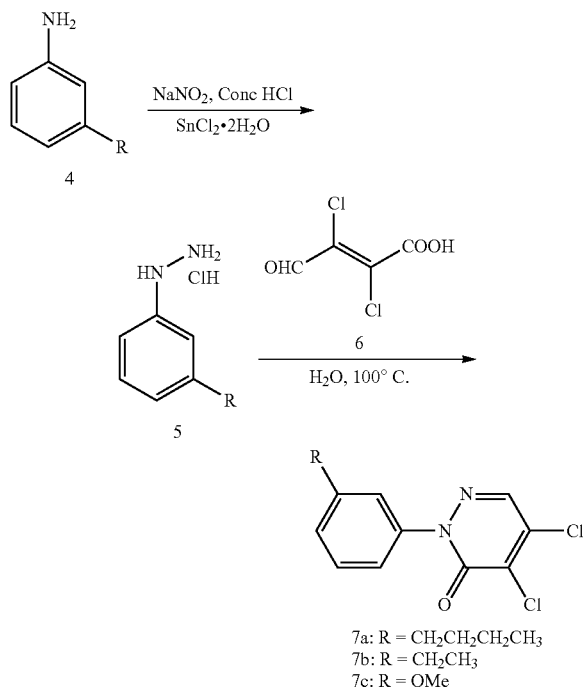

7a: R = CH$_2$CH$_2$CH$_2$CH$_3$
7b: R = CH$_2$CH$_3$
7c: R = OMe

Preparation of 2-(3-butylphenyl)-4,5-dichloropyridazin-3 (2H)-one (7a). A solution of NaNO$_2$ (510 mg, 7.39 mmol) in water (2 mL) was slowly added to a cooled (−15° C.) solution of (4) (1.0 g, 7.30 mmol) in Conc. HCl (5 mL) and water (5 mL). The reaction was warmed to 0° C. and slowly added to a vigorously stirred 0° C. cooled solution of SnCl$_2$.2H$_2$O (3.34 g) in con. HCl (15 mL). After 3 h of stirring at 0° C., crude 3-hydrazinophenyl hydrochloride (5) (300 mg) was collected by filtration and dried under vacuum. To a 90° C. stirred solution of crude 3-hydrazinophenyl hydrochloride (5) (50 mg, 0.21 mmol) in water (3 mL) was added mucochloric acid (6) (35 mg, 0.21 mmol) and stirred for 3 h. The reaction mixture was cooled to room temperature and the solid crystals were collected by filtration, washed with water (2×5 mL), dried under high vacuum at 40° C. to obtain (7a) (28.0 mg, 42%). $^1$H NMR (300 MHz, CDCl$_3$): δ 0.92 (t, 3H, J=6.0 Hz), 1.30-1.42 (m, 2H), 1.52-1.70 (m, 2H), 2.67 (t, 2H, J=6.0 Hz), 7.20-7.28 (m, 1H), 7.30-7.45 (m, 3H), 7.92 (s, 1H); ESI-MS m/z. 297.4 (M+1)$^+$.

Preparation of 4,5-dichloro-2-(3-ethylphenyl)pyridazin-3 (2H)-one (7b) was synthesized from 3-ethylaniline and mucochloric acid as described for 7a. Yield: 30 mg (53%). $^1$H NMR (300 MHz, CDCl$_3$): δ 1.27 (t, J=6.0 Hz, 3H), 2.70 (dd, J=15.0 Hz, 6.0 Hz, 2H), 7.13-7.19 (m, 1H), 7.28-7.43 (m, 3H), 7.95 (s, 1H); ESI-MS m/z. 269.0 (M+1)$^+$.

Preparation of 4,5-dichloro-2-(3-methoxyphenyl) pyridazin-3(2H)-one (7c) was synthesized from 3-methoxyaniline and mucochloric acid as described for 7a. Yield: 35 mg (62%). $^1$H NMR (300 MHz, CDCl$_3$): δ3.86 (s, 3H), 6.96-7.02 (m, 1H), 7.11-7.19 (m, 2H), 7.36-7.45 (m, 1H), 7.94 (s, 1H); ESI-MS m/z. 271.1 (M+1)$^+$.

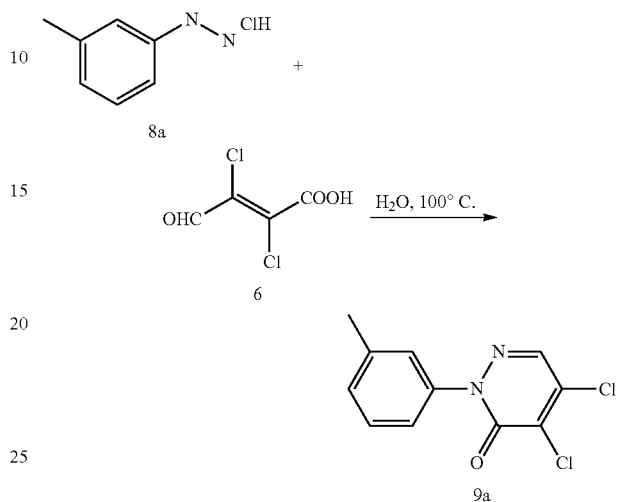

Preparation of 4,5-dichloro-2-(3-methylphenyl) pyridazin-3(2H)-one (9a): Mucochloric acid (6) (6.91 g, 40.92 mmol) was added to a 100° C. solution of 3-methyl-phenylhydrazine (8a) (5.0 g, 40.92 mmol) in 12% aqueous HCl water (34 mL). After 5 h, the reaction mixture was cooled to room temperature and the solid crystals were collected by filtration, washed with water (2×50 mL) and dried under high vacuum at 40° C. to obtain (9a) as light yellow solid (10.35 g, 99%). $^1$H NMR (300 MHz, CDCl$_3$): δ 2.41 (s, 3H), 7.26 (s, 1H), 7.36-7.40 (m, 3H), 7.90 (s, 1H); ESI-MS m/z. 255.4 (M+1)$^+$.

The following compounds were synthesized as described above for 9a using mucochloric acid and corresponding hydrazine.

4,5-Dichloro-2-(3-trifluoromethylphenyl)pyridazin-3 (2H)-one (9b) Yield: 64%. $^1$H NMR (300 MHz, CDCl$_3$) δ 7.60-7.75 (m, 2H), 7.80-7.86 (m, 1H), 7.93 (s, 1H), 7.97 (s, 1H) ESI-MS m/z. 309.1 (M+1)$^+$.

4,5-Dichloro-2-(2,3-dimethylphenyl)pyridazin-3(2H)-one (9c) Yield: 87%. $^1$H NMR (300 MHz, CDCl$_3$) δ 2.02 (s, 3H), 2.35 (s, 3H), 7.07-7.09 (m, 1H), 7.20-7.29 (m, 2H), 7.91 (s, 1H), ESI-MS m/z. 269.1 (M+1)$^+$.

4,5-Dichloro-2-(3,4-dimethylphenyl)pyridazin-3(2H)-one (9d) Yield: 90%. $^1$H NMR (300 MHz, CDCl$_3$) δ 2.31 (s, 3H), 2.34 (s, 3H), 7.22-7.32 (m, 3H), 7.90 (s, 1H); ESI-MS m/z. 269.0 (M+1)$^+$.

4,5-Dichloro-2-(3,5-dimethylphenyl)pyridazin-3(2H)-one (9e) Yield: 86%. $^1$H NMR (300 MHz, CDCl$_3$) δ 2.37 (s, 6H), 7.07 (s, 1H), 7.15 (s, 2H), 7.90 (s, 1H); ESI-MS m/z. 269.4 (M+1)$^+$.

4,5-Dichloro-2-(2-methylphenyl)pyridazin-3(2H)-one (9f) Yield: 85%. $^1$H NMR (300 MHz, CDCl$_3$): δ 2.17 (s, 3H), 7.22-7.26 (m, 1H), 7.31-7.42 (m, 3H), 7.91 (s, 1H); ESI-MS m/z. 255.1 (M+1)$^+$.

4,5-Dichloro-2-(4-bromo-3-methylphenyl)pyridazin-3 (2H)-one (9 g) Yield: 70%. $^1$H NMR (300 MHz, CDCl$_3$): δ 2.45 (s, 3H), 7.26-7.31 (m, 1H), 7.41-7.48 (m, 1H), 7.57 (d, 1H, J=6.0 Hz), 7.92 (s, 1H); ESI-MS m/z. 333.1 (M+1)$^+$ and 335.1 (M+2)$^+$.

4,5-Dichloro-2-(4-chloro-3-methylphenyl)pyridazin-3(2H)-one (9h) Yield: 71%. $^1$H NMR (300 MHz, CDCl$_3$): δ 2.43 (s, 3H), 7.29-7.38 (m, 1H), 7.44-7.59 (m, 2H), 7.94 (s, 1H); ESI-MS m/z. 291.0 (M+3)$^+$.

4,5-Dichloro-2-(2,3-dihydro-1H-inden-5yl)pyridazin-3(2H)-one (9i) Yield: 70%. $^1$H NMR (300 MHz, CDCl$_3$): δ 2.03-2.17 (m, 2H), 2.92-2.98 (m, 4H), 7.26-7.37 (m, 3H), 7.92 (s, 1H); ESI-MS m/z. 281.1 (M+1)$^+$ and 283.4 (M+3)

4,5-Dichloro-2-(2-methyl-1,3-benzothiazol-6-yl)pyridazin-3(2H)-one (9j) Yield: 15%. $^1$H NMR (300 MHz, CDCl$_3$): δ 2.96 (s, 3H), 7.59-7.69 (m, 1H), 7.95 (s, 1H), 8.08 (d, J=6.0 Hz, 1H), 8.12 (s, 1H); ESI-MS m/z. 312.4 (M+1)$^+$.

4,5-Dichloro-2-(2,3-dihydro-1,4-benzodioxin-6yl)pyridazin-3(2H)-one (9k) Yield: 75%. $^1$H NMR (300 MHz, CDCl$_3$): δ 4.26 (s, 4H), 6.93-6.98 (m, 1H), 7.02-7.12 (m, 2H), 7.88 (s, 1H); ESI-MS m/z. 299.3 (M+1)$^+$.

2-Benzyl-4,5-dichloropyridazin-3(2H)-one (9l) Yield: 78%. $^1$H NMR (300 MHz, CDCl$_3$): δ 5.32 (s, 2H), 7.28-7.38 (m, 3H), 7.40-7.46 (m, 2H), 7.86 (s, 1H); ESI-MS m/z. 255.1 (M+1)$^+$.

4,5-Dichloro-2-(3-chloro-4-methylphenyl)pyridazin-3(2H)-one (9m) Yield: 75%. $^1$H NMR (300 MHz, CDCl$_3$): δ 2.44 (s, 3H), 7.32-7.35 (m, 1H), 7.40-7.44 (m, 1H), 7.61 (s, 1H), 7.93 (s, 1H); ESI-MS m/z. 298.8 (M+1)$^+$.

4,5-Dichloro-2-pyridine-2-ylpyridazin-3(2H)-one (9n) Yield: 75%. $^1$H NMR (300 MHz, CDCl$_3$): δ 7.40-7.45 (m, 1H), 7.57-7.70 (m, 1H), 7.88-7.94 (m, 1H), 7.99 (s, 1H), 8.67-8.69 (m, 1H); ESI-MS m/z. 242.1 (W0$^+$.

The following compounds were synthesized as described for 9a using mucobromic acid and corresponding hydrazine.

4,5-Dibromo-2-(3-methylphenyl)pyridazin-3(2H)-one (12a) Yield: 75%. $^1$H NMR (300 MHz, CDCl$_3$): δ 2.36 (s, 3H), 7.23-7.28 (s, 1H), 7.33-7.37 (m, 3H), 7.95 (s, 1H); ESI-MS m/z. 343.0 (M+1)$^4$.

4,5-Dibromo-2-(3-trifluoromethylphenyl)pyridazin-3(2H)-one (12b) Yield: 70%. $^1$HNMR (300 MHz, CDCl$_3$): δ 7.59-7.67 (m, 2H), 7.84-8.01 (m, 3H), ESI-MS m/z. 397.0 (M+1)$^+$.

4,5-Dibromo-2-pyridine-2-ylpyridazin-3(2H)-one (12c) Yield: 75%. $^1$H NMR (300 MHz, CDCl$_3$): δ 7.41-7.46 (m, 1H), 7.55-7.83 (m, 1H), 7.87-7.95 (m, 1H), 8.00 (s, 1H), 8.65-8.67 (m, 1H); ESI-MS m/z. 330.1 (M+1)$^+$.

4,5-Dibromo-2-(3-methoxyphenyl)pyridazin-3(2H)-one (12d) Yield: 48%. $^1$H NMR (300 MHz, CDCl$_3$): δ 3.83 (s, 3H), 6.95-6.99 (m, 1H), 7.11-7.16 (m, 2H), 7.28-7.43 (m, 1H), 7.93 (s, 1H); ESI-MS m/z. 358.9 (M+1)$^+$.

4,5-Dibromo-2-(3-(1-methoxy)ethoxyphenyl)pyridazin-3(2H)-one (12e) Yield: 65%. $^1$H NMR (300 MHz, CDCl$_3$): δ 3.51 (s, 3H), 3.74-3.82 (m, 2H), 4.13-4.19 (m, 2H), 6.98-7.02 (m, 1H), 7.15-7.18 (m, 2H), 7.34-7.43 (m, 1H), 7.92 (s, 1H); ESI-MS m/z. 403.1 (M+1)$^+$.

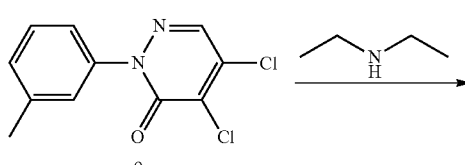

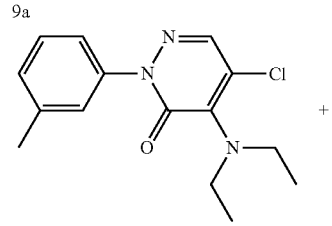

14

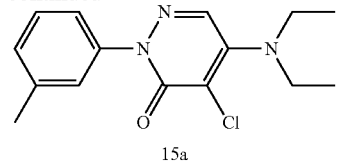

15a

Preparation of 5-Chloro-4-(diethylamino)-2-(3-methylphenyl) pyridazin-3(2H)-one (14) and 4-Chloro-5-(diethylamino)-2-(3-methylphenyl)pyridazin-3(2H)-one (15a). A mixture of (9a) (250 mg, 0.95 mmol) and N,N-diethylamine (143 mg, 1.95 mmol) in dioxane (3 mL) was heated at 100° C. for 10 h. The reaction mixture was cooled to room temperature and concentrated in vacuo. The products were separated by flash silica gel column chromatography.

5-Chloro-4-(diethylamino)-2-(3-methylphenyl)pyridazin-3(2H)-one (14): Oil (30.0 mg); R$_f$=0.45 (25% EtOAc/hexaness); $^1$H NMR (300 MHz, CDCl$_3$): δ 1.22 (t, J=6.0 Hz, 6H), 2.40 (s, 3H), 3.50 (q, J=6.0 Hz, 4H), 7.17-7.20 (m, 1H), 7.26-7.37 (m, 3H), 7.72 (s, 1H). ESI-MS m/z. 292.3 (M+1)$^+$.

4-Chloro-5-(diethylamino)-2-(3-methylphenyl)pyridazin-3(2H)-one (15a): Solid (120.0 mg); R$_f$=0.35 25% EtOAc/hexaness); $^1$H NMR (300 MHz, CDCl$_3$): δ 1.31 (t, J=6.0 Hz, 6H), 2.39 (s, 3H), 3.55 (q, J=6.0 Hz, 4H), 7.15-7.18 (m, 1H), 7.28-7.40 (m, 3H), 7.70 (s, 1H) ESI-MS m/z. 292.4 (M+1)$^+$.

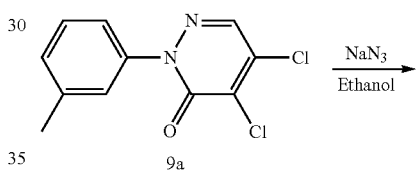

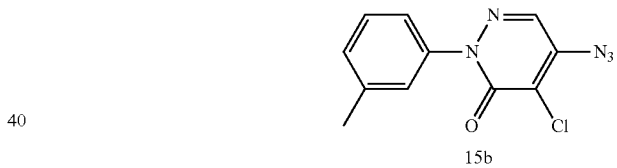

15b

Preparation of 5-Azido-4-chloro-2-(3-methylphenyl pyridazin-3(2H)-one (15b). This compound was prepared as described above for (15a) from (9a) and sodium azide using ethanol (2 mL) and water (2 mL). Yield 55%. $^1$HNMR (300 MHz, CDCl$_3$): δ 2.41 (s, 3H), 7.18-7.26 (m, 1H), 7.32-7.41 (m, 3H), 7.74 (s, 1H) ESI-MS m/z. 235.9 (M+1)$^+$.

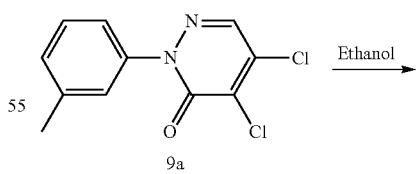

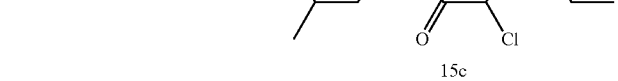

15c

Preparation of 4-Chloro-5-ethoxy-2-(3-methylphenyl)pyridazin-3(2H)-one (15c). This compound was prepared as described above for (15a) from (9a) and ethanol (5 mL). Yield 75%. $^1$H NMR (300 MHz, CDCl$_3$): δ 1.56 (t, J=6.0 Hz, 6H), 2.42 (s, 3H), 4.40 (q, J=6.0 Hz, 4H), 7.20-7.29 (m, 1H), 7.33-7.40 (m, 3H), 7.92 (s, 1H) ESI-MS m/z. 265.0 (M+1)$^+$.

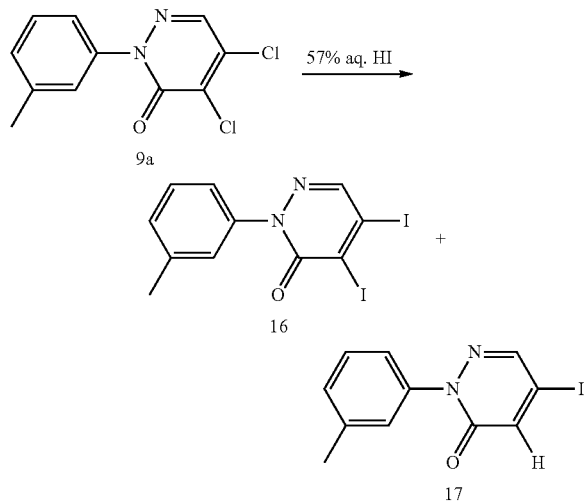 [SMILES: Cc1cccc(-n2ncc(Cl)c(Cl)c2=O)c1 ; Cc1cccc(-n2ncc(I)c(I)c2=O)c1 ; Cc1cccc(-n2ncc(I)cc2=O)c1]

Preparation of 4,5-Diiodo-2-(3-methylphenyl)pyridazin-3 (2H)-one (16) and 5-iodo-2-(3-methylphenyl)pyridazin-3 (2H)-one (17). A mixture of (9a) (700 mg, 2.74 mmol) and 57% aqueous HI (10 mL) was heated at 100° C. After 12 h, the reaction was cooled, diluted with water (30 mL) and extracted with ethyl acetate (2×25 mL). The organic extracts were washed with water (2×20 mL), dried (Na$_2$SO$_4$) and concentrated in vacuo. The pure products were separated on silica gel column using 20% ethyl acetate/hexanes.

4,5-Iodo-2-(3-methylphenyl)pyridazin-3(2H)-one (16): 200.0 mg, R$_f$=0.40; $^1$H NMR (300 MHz, CDCl$_3$): δ 2.40 (s, 3H), 7.17-7.26 (m, 1H), 7.32-7.37 (m, 3H), 7.95 (s, 1H) ESI-MS m/z. 439.1 (M+1)$^+$.

5-Iodo-2-(3-methylphenyl)pyridazin-3(2H)-one (17): 75.0 mg, R$_f$=0.20; $^1$H NMR (300 MHz, CDCl$_3$): δ 2.41 (s, 3H), 7.09-7.26 (m, 1H), 7.33-7.38, 7.60 (s, 1H), 8.04 (s, 1H). ESI-MS m/z. 313.1 (M+1)$^+$.

Preparation of 4,5-Dichloro-1-(3-methylphenyl)-1,2-dihydropyridazin-3,6-dione (19a). 3,4-Dichloromaleic anhydride (18a) (2.0 g, 12.27 mmol) was added to a solution 3-methylphenylhydrazine (5) (1.5 g, 12.27 mmol) in 20% aqueous HCl (12 mL) at 100° C. and stirred for 3 h. The reaction mixture was cooled to room temperature and diluted with water (15 mL) and extracted with ethyl acetate (3×20 mL). The combined extracts was dried, and concentrated in vacuo to afford a residue that was purified on silica gel column (20% EtOAc/hexanes) to afford (19a) (1.35 g, 40%). $^1$H NMR (300 MHz, DMSO-D$_6$): δ 2.36 (s, 3H), 7.22-7.25 (m, 1H), 7.33-7.41 (m, 3H); ESI-MS m/z. 271.2 (M-F1)$^1$.

Preparation of 4,5-Dichloro-6-methoxy-2-(3-methylphenyl)-pyridazin-3,6-dione (20a). A mixture of (19a) (1.5 g, 5.5 mmol) dimethyl sulfate (1.6 g, 6.9 mmol) and K$_2$CO$_3$ (2.28 g, 16.5 mmol) in acetone (20 mL) was stirred at reflux for 12 h. The reaction was cooled and the solids were filtered-off. The filtrate was concentrated and dissolved in ethyl acetate (30 mL), washed with water (2×15 mL), dried and concentrated under vacuum. The crude compound was purified on silica gel column using 25% ethyl acetate/hexanes to afford (20a) (1.8 g 76%). $^1$H NMR (300 MHz, CDCl$_3$): δ 2.24 (s, 3H), 3.96 (s, 3H), 7.17-7.28 (m, 1H), 7.34-7.53 (m, 3H); ESI-MS m/z. 285.3 (M+1)$^+$.

6-Methoxy-2-(3-methylphenyl)-pyridazin-3,6-dione (20b) This compound was prepared as described for (20a) using 19b [Data for 19b: Yield: 73%; $^1$H NMR (300 MHz, DMSO-Ds): δ 2.35 (s, 3H), 6.99-7.03 (m, 1H), 7.19 (d, 2H, J=6.0 Hz), 7.28-7.42 (m, 3H), 11.32 (s, 1H); ESI-MS m/z. 203.4 (M-1-1)$^+$.] Data for 20b: Yield: 82% $^1$H NMR (300 MHz, CDCl$_3$): δ 2.43 (s, 3H), 3.90 (s, 3H), 7.17-7.27 (m, 2H), 7.35-7.42 (m, 2H); ESI-MS m/z. 217.1 (M+1)$^+$.

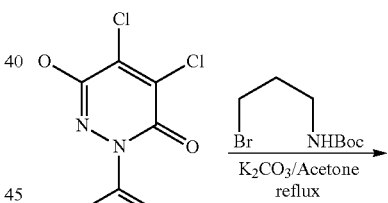

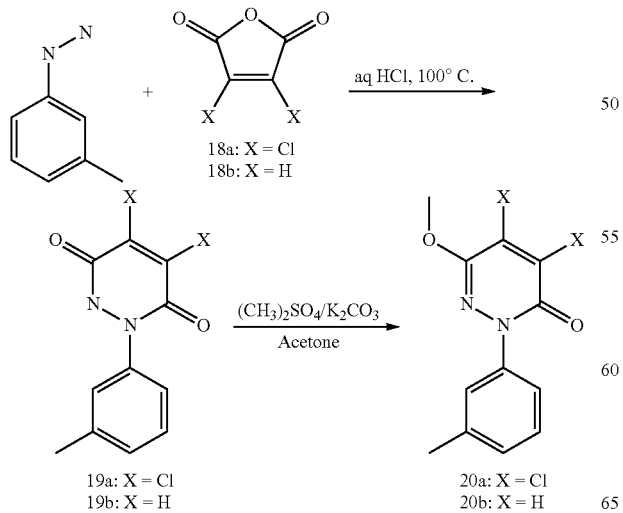

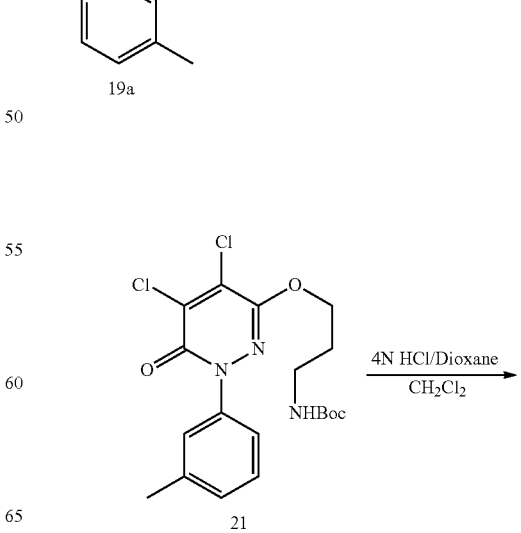

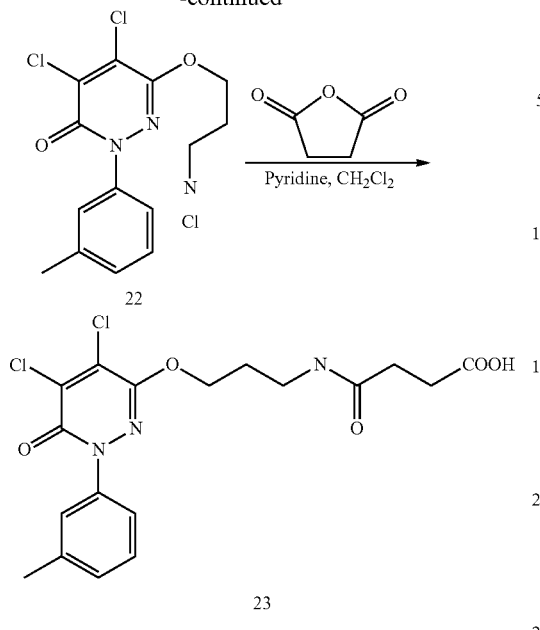
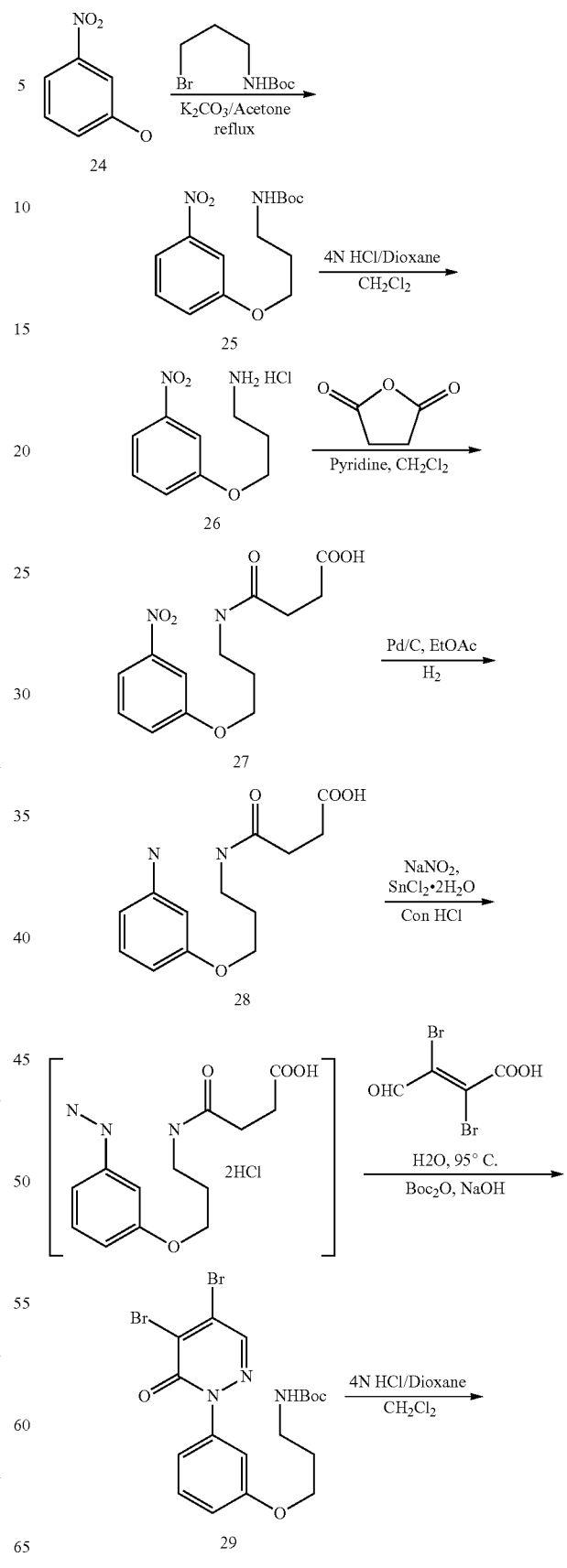

Preparation of tert-Butyl-3-{{4,5-dichloro-1-(3-methylphenyl)-6-oxo-1,6-dihydropyridazin-3-yl]oxy}propylcarbamate (21) A mixture of (19a) (1.5 g, 5.5 mmol), tert-butyl 3-bromopropylcarbamate (1.6 g, 6.9 mmol) and K$_2$CO$_3$ (2.28 g, 16.5 mmol) in acetone (20 mL) was refluxed for 12 h. The reaction was cooled and the solids were filtered-off. The filtrate was concentrated and dissolved in ethyl acetate (30 mL), washed with water (2×15 mL), dried and concentrated in vacuo. The crude compound was purified on silica gel column using 25% EtOAc/hexanes to afford (21) (1.8 g 76%). $^1$H NMR (300 MHz, CDCl$_3$): δ 1.43 (s, 9H), 1.97-2.05 (m, 2H), 2.41 (s, 3H), 3.30-3.36 (m, 2H), 4.29-5.32 (m, 2H), 4.82 (bs, 1H), 7.19-7.42 (m, 4H); ESI-MS m/z. 428.3 (M+1)$^+$.

Preparation of 6-(3-Aminopropoxy)-4,5-dichloro-2-(3-methylphenyl)pyridazin-3(2H)-one hydrochloride (22) To a solution of (21) (1.8 g, 4.20 mmol) was added 4 N HCl in dioxane (5.25 mL) and stirred at room temperature. After 15 h, the solid was filtered and washed with hexanes (2×25 mL) and dried in vacuo to afford (22) (1.32 g, 86%) as an off-white solid. $^1$H NMR (300 MHz, DMSO-D$_6$): δ 1.99-2.10 (m, 2H), 2.37 (s, 3H), 2.85-2.95 (2H), 4.20-4.36 (m, 2H), 7.15-7.27 (m, 1H), 7.39-7.59 (m, 3H), 8.03 (br s, 3H); ESI-MS m/z. 328.4 (M+1)$^+$.

Preparation of 4-[(3-{[4,5-Dichloro-1-(3-methylphenyl)-6-oxo-1,6-dihydropyridazin-3-yl]oxy}propyl)amino]-4-oxobutanoic acid (23) A mixture of (21) (1.30 g, 3.57 mmol) and succinic anhydride (357 mg, 3.57 mmol) in dichloromethane (10 mL) and pyridine (1.5 mL) was stirred at room temperature for 24 h. The mixture was concentrated and re-dissolved in ethyl acetate (20 mL) washed with 1 N HCl (2×5 mL) and with water (2×10 mL). The organic solution was dried over Na$_2$SO$_4$ and concentrated and the obtained syrup was stirred with 50% hexanes/CH$_2$Cl$_2$. The solid was collected by filtration and dried at 40° C. to afford (23) (1.4 g, 91%) as off-white solid. $^1$H NMR (300 MHz, DMSO-D$_6$): δ 1.84-1.90 (m, 2H), 2.26-2.30 (m, 2H), 2.37-2.43 (m, 5H), 3.18 (m, 2H), 4.20 (t, J=6.0 Hz, 2H) 7.24-7.26 (m, 1H), 7.30-7.41 (m, 3H), 7.90-7.96 (m, 1H), 12.12 (s, 1H); ESI-MS m/z. 428.3 (M+1)$^+$.

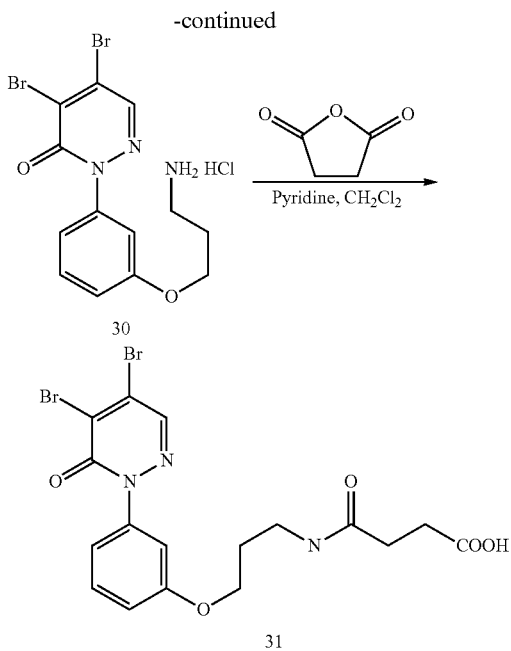

Preparation of tert-Butyl 3-(3-nitrophenoxy)propylcarbamate (25). A mixture of 3-nitrophenol (24) (7.0 g, 50.3 mmol), tert-butyl 3-bromopropylcarbamate (14.35 g, 60.3 mmol) and $K_2CO_3$ (13.90 g, 100.63 mmol) in acetone (150 mL) was stirred at reflux for 12 h. The reaction was cooled and the solids were filtered-off. The filtrate was concentrated, dissolved in EtOAc (250 mL), washed with water (2×15 mL), dried and concentrated in vacuo to afford (25) (14.25 g 95%) that was used without further purification. $^1H$ NMR (300 MHz, $CDCl_3$): δ 1.46 (s, 9H), 1.99-2.07 (m, 2H), 3.26-3.47 (m, 2H), 4.10 (t, J=6.0 Hz, 2H), 4.84 (bs, 1H), 7.20-7.24, 7.43 (t, J=6.0 Hz, 1H), 7.71 (s, 1H), 7.79-7.83 (m, 1H); ESI-MS m/z. 297.3 (M+1)$^+$.

Preparation of 3-(3-Nitrophenoxy)propan-1-amine hydrochloride (26). To a solution of (25) (14.25 g, 47.80 mmol) in dichloromethane (150 mL) was added 4 N HCl in dioxane (60 mL) and stirred at room temperature. After 7 h, the reaction was diluted with hexanes (200 mL). The solid was filtered, washed with hexanes (2×25 mL) and dried under vacuum to afford (26) (11.0 g, 98%) as off-white solid. ESI-MS m/z. 197.3 (M+1)$^+$.

Preparation of 4-{[3-(3-Nitrophenoxy)propyl]amino}-4-oxobutanoic acid (27). A mixture of (26) (11.0 g, 47.11 mmol) and succinic anhydride (4.71 g, 47.11 mmol) in dichloromethane (75 mL) and pyridine (18.63 g, 235.5 mmol) was stirred at room temperature for 24 h. The mixture was concentrated, re-dissolved in ethyl acetate (150 mL) and washed with 2 N HCl (2×50 mL). The precipitated solid product was collected by filtration and the filtrate was dried and concentrated to afford crude product. The combined solid was washed with 50% EtOAc/hexanes (25 mL) and dried under vacuum to afford (27) (13.5 g, 96%). $^1H$ NMR (300 MHz, DMSO-$D_6$): δ 1.80-1.92 (m, 2H), 2.27-2.31 (m, 2H), 2.36-2.43 (m, 2H), 3.19 (m, 2H), 4.09 (t, J=6.0 Hz, 2H) 7.38-7.41 (m, 1H), 7.54 (t, J=6.0 Hz, 3H), 7.67 (s, 1H), 7.78-7.81 (m, 1H), 7.94 (t, J=6.0 Hz, 1H); ESI-MS m/z. 297.3 (M+1)$^+$.

Preparation of 4-{[3-(3-Aminophenoxy)propyl]amino}-4-oxobutanoic acid (28). To a slurry of 10% Pd/C (1.75 g) in EtOAc (400 mL) was added (27) (13.5 g, 45.5 mmol) and stirred under hydrogen atmosphere (30 Psi). After 5 h, the catalyst was filtered-off and filtrate was concentrated to afford (28) (11.75, 96%) that was used for next reaction without further purification. ESI-MS m/z. 267.4 (M+H)$^+$.

Preparation of tert-Butyl 3-[3-(4,5-dibromo-6-oxopyridazin-1(6H)-yl)phenoxy]propylcarbamate (29). A solution of $NaNO_2$ (1.29 g, 18.77 mmol) in water (3 mL) was slowly added to a cooled (0° C.) solution of (28) (5.0 g, 18.77 mmol) in conc. HCl (15 mL) and water (5 mL). After 30 min, the reaction mixture was added to cooled (0° C.) slurry of $SnCl_2.2H_2O$ (10.72 g, 47.5 mmol) in conc. HCl (10 mL) with vigorous stirring. The resulting mixture was stirred for 3 h at 0° C. and crude 4-{[3-(3-hydrazinophenoxy)propyl]amino}4-oxobutanoic acid hydrochloride was collected by filtration and dried under vacuum (6.5 g). To a stirred solution of the crude acid (6.5 g, 18.35 mmol) in water (10 mL) at 90° C. was added mucobromic acid (4.73 g, 18.35 mmol). After 3 h, the reaction mixture was cooled to room temperature, basified with 1 N NaOH (pH=6.0) and treated with $(Boc)_2O$ (5.0 g, 22.9 mmol) for overnight at room temperature. The reaction was extracted with EtOAc (3×50 mL) and organic solution was washed with water (2×25 mL) and dried over $Na_2SO_4$ and concentrated under vacuum. The obtained residue was purified on silica gel using 25% EtOAc/hexanes to afford (29) (1.8 g, 19.0% 3 steps). $^1H$ NMR (300 MHz, $CDCl_3$): δ 1.46 (s, 3H), 1.94-2.06 (m, 2H), 3.31 (t, J=6.0 Hz, 2H), 4.04 (t, J=6.0 Hz, 2H), 4.75 (br s, 1H), 6.94-6.98 (m, 1H), 7.11-7.17 (m, 2H), 7.35-7.42 (m, 1H), 7.93 (s, 1H); ESI-MS m/z 502.1 (M+1)$^+$.

Preparation of 2-[3-(3-Aminopropoxy)phenyl]-4,5-dibromopyridazin-3(2H)-one hydrochloride (30). To a solution of (29) (1.75 g, 3.4 mmol) in dichloromethane (30 mL) was added 4 N HCl in dioxane (5 mL) and stirred at room temperature. After 7 h, the reaction was diluted with hexanes (20 mL). The solid was filtered, washed with hexanes (2×15 mL) and dried under vacuum to afford (30) (1.40 g, 94%) as off-white solid. $^1H$ NMR (300 MHz, $CDCl_3$): δ 1.96-2.10 (m, 2H), 2.94 (t, J=6.0 Hz, 2H), 4.10 (t, J=6.0 Hz, 2H), 7.05-7.13 (m, 2H), 7.43 (t, J=6.0 Hz, 1H), 8.26 (s, 1H); ESI-MS m/z 402.1 (M+1)$^+$.

Preparation of 4-({3-[3-(4,5-Dibromo-6-oxopyridazin-[(6H)-yl)phenoxy]propyl}amino)-4-oxobutanoic acid (31) A mixture of (30) (1.30 g, 2.95 mmol) and succinic anhydride (310.0 mg, 3.10 mmol) in dichloromethane (15 mL) and pyridine (3.5 mL) was stirred at room temperature for 15 h. The mixture was concentrated, re-dissolved in EtOAc (30 mL) and washed with 1 N HCl (3×10 mL) and then with water (2×15 mL). The organic solution was dried ($Na_2SO_4$) and concentrated to afford crude product. The obtained solid was stirred with 50% EtOAC/hexanes (10 mL), collected by filtration and dried under vacuum to afford (31) (1.2 g, 87%). $^1H$ NMR (300 MHz, DMSO-Ds): δ 1.81-1.86 (m, 2H), 2.30 (t, J=6.0 Hz, 2H), 2.4 (t, J=6.0 Hz, 2H), 3.19 (m, 2H), 4.00 (m, 2H) 7.01-7.03 (m, 1H), 7.07-7.10 (m, 2H), 7.40 (t, J=3.0 Hz, 1H), 7.93 (t, J=3.0 Hz, 1H), 8.26 (s, 1H), 12.05 (br s, 1H); ESI-MS m/z. 502.3 (M+1)$^+$.

Example 3

SAR of compound SKI-104122

Screening of pyridazin-3(2H)-ones

We undertook a SAR study to identify potential sites on the compound SKI-104122 for linker addition without compromising biological activity. Exemplary syntheses of compounds screened are detailed above in Example 2. The screening results of these compounds are summarized in Tables 10, 11, and 13 below. Compounds were tested in dose response studies from 10 μM to 5 nM against several non small cell lung cancer lines: H358, H827, H1118, H1650, H1734, H1975, H2030, and H3255, and were also studied in a 72 hour cytotoxicity assay against the NHBE and WI-38 cell lines. Additionally, Tables 12 and 14 summarize similar screenings of gefitinib (IRESSA™, Astra-Zeneca) and erlotinib (TARCEVA™, OSI Pharmaceuticals, Genentech).

In FIGS. 4(A-E) to 10(A-E), $IC_{50}$ curves are shown for all experiments performed on SKI 104122 including primary HTS and resynthesis. FIGS. 11 to 40 depict $IC_{50}$ curves for active pyridazinone compounds against the H3255 cell line.

TABLE 10

Summary of SKI-104122 against H1650, H1975, H2030, H3255, NHBE and WI-38 cell lines

| Structure | SKI ID | H1650 | H1975 | H2030 | H3255 | NHBE | WI-38 |
|---|---|---|---|---|---|---|---|
| | | Dose Response (uM) | | | | CytoTox (uM) | |
| 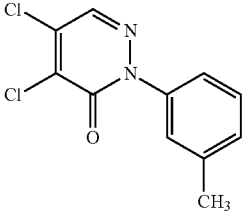 [SMILES: Cc1cccc(-n2ncc(Cl)c(Cl)c2=O)c1] | 104122 | 0.04 | 0.01 | 0.001 | 0.04 | 0.80 | ND |
| | 104122 | 0.97 | 0.14 | 0.30 | 0.38 | ND | ND |
| | 104122 | 1.24 | 0.14 | 0.27 | 0.64 | 2.64 | 3.70 |
| | 104122 | 2.71 | 0.31 | 0.58 | 1.33 | ND | ND |
| | 104122 | 3.80 | 0.28 | 0.65 | 0.38 | 3.40 | 6.06 |
| | 104122 | 1.18 | 0.29 | 0.82 | 0.53 | 1.59 | 6.86 |
| | 104122 | 1.88 | 0.29 | 0.45 | 0.84 | 1.97 | 8.95 |

ND = No Data, Assay Not Performed with this Cell Line

TABLE 11

Summary of Pyridazinone Compounds against H1650, H1975, H2030, H3255, NHBE, and WI-38 Cell Lines

| Structure | SKI ID | H1650 | H1975 | H2030 | H3255 | NHBE | WI-38 |
|---|---|---|---|---|---|---|---|
| | | Dose Response (uM) | | | | CytoTox (uM) | |
| 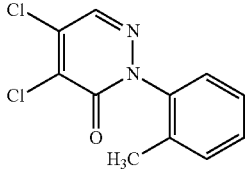 [SMILES: Cc1ccccc1-n1ncc(Cl)c(Cl)c1=O] | 257017 | 2.74 | 0.47 | 1.08 | 2.95 | 5.17 | 7.52 |
| 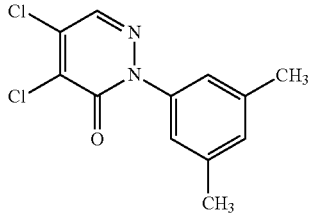 [SMILES: Cc1cc(C)cc(-n2ncc(Cl)c(Cl)c2=O)c1] | 257020 | 2.10 | 0.27 | 0.56 | 0.92 | 3.18 | 6.78 |
| 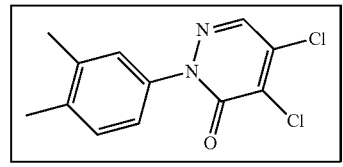 [SMILES: Cc1ccc(-n2ncc(Cl)c(Cl)c2=O)cc1C] | 257019 | 2.40 | 0.29 | 0.53 | 1.23 | 3.24 | 7.02 |
| 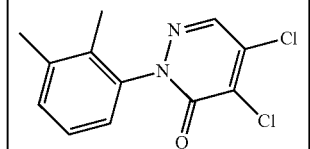 | 257018 | 2.42 | 0.35 | 0.89 | 1.63 | 3.89 | 7.35 |

TABLE 11-continued
Summary of Pyridazinone Compounds against H1650, H1975, H2030, H3255, NHBE, and WI-38 Cell Lines
| Structure | SKI ID | H1650 | H1975 | H2030 | H3255 | NHBE | WI-38 |
|---|---|---|---|---|---|---|---|
| | | | | Dose Response (uM) | | CytoTox (uM) | |
| 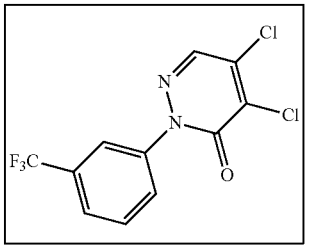 [SMILES: O=c1c(Cl)c(Cl)cnn1-c1cccc(C(F)(F)F)c1] | 176729 | 1.44 | 0.16 | 0.34 | 0.73 | 2.76 | 3.42 |
| 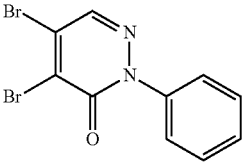 | 257015 | 1.14 | 0.16 | 0.39 | 0.62 | 2.38 | 3.03 |
| 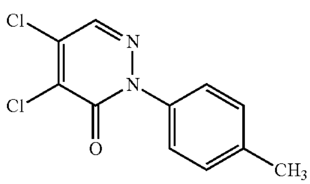 [SMILES: Cc1ccc(-n2ncc(Cl)c(Cl)c2=O)cc1] | 257016 | 2.73 | 0.32 | 0.65 | 1.32 | 3.29 | 6.43 |
| 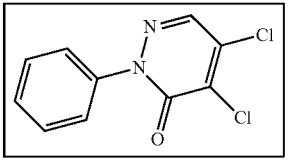 [SMILES: O=c1c(Cl)c(Cl)cnn1-c1ccccc1] | 257014 | 3.18 | 0.29 | 0.55 | 1.36 | 3.29 | 6.93 |
| 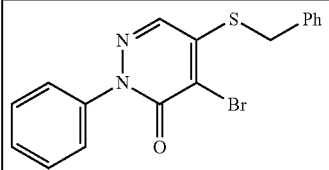 | 257021 | >10 | >10 | >10 | >10 | >10 | >10 |
| 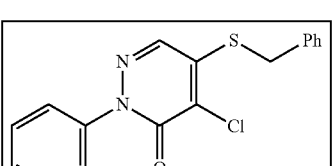 | 257022 | >10 | >10 | >10 | >10 | >10 | >10 |
| 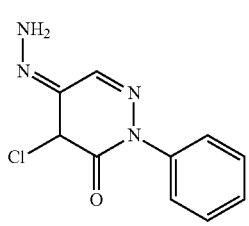 [SMILES: N/N=C1\C=NN(c2ccccc2)C(=O)C1Cl] | 257023 | >10 | >10 | >10 | >10 | >10 | >10 |

TABLE 11-continued
Summary of Pyridazinone Compounds against H1650, H1975, H2030, H3255, NHBE, and WI-38 Cell Lines
| Structure | SKI ID | H1650 | H1975 | H2030 | H3255 | NHBE | WI-38 |
|---|---|---|---|---|---|---|---|
| | | Dose Response (uM) | | | | CytoTox (uM) | |
| 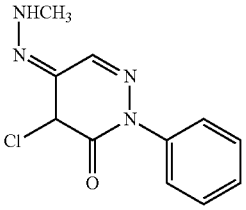 [SMILES: CN/N=C1\C=NN(c2ccccc2)C(=O)C1Cl] | 257024 | >10 | >10 | >10 | >10 | >10 | >10 |
| 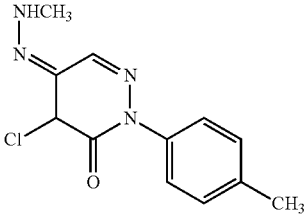 [SMILES: CN/N=C1\C=NN(c2ccc(C)cc2)C(=O)C1Cl] | 257025 | >10 | >10 | >10 | >10 | >10 | >10 |
| 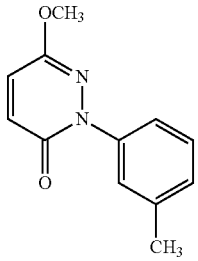 [SMILES: COc1ccc(=O)n(-c2cccc(C)c2)n1] | 257029 | >10 | >10 | >10 | >10 | >10 | >10 |
| 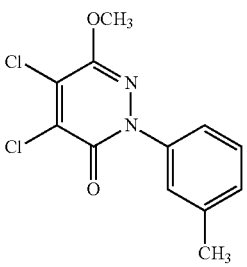 [SMILES: COc1nn(-c2cccc(C)c2)c(=O)c(Cl)c1Cl] | 257028 | 2.04 | 0.65 | 1.26 | 1.76 | 5.24 | 7.52 |
| 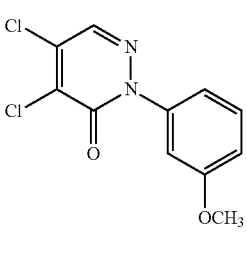 [SMILES: COc1cccc(-n2ncc(Cl)c(Cl)c2=O)c1] | 267061 | 3.52 | 0.37 | 0.72 | 1.34 | 1.70 | 3.91 |
| 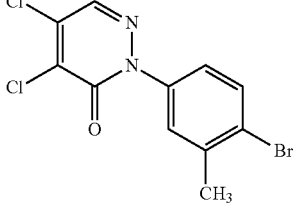 | 267064 | 2.83 | 0.71 | 0.88 | 2.47 | 4.04 | >10 |

TABLE 11-continued
Summary of Pyridazinone Compounds against H1650, H1975, H2030, H3255, NHBE, and WI-38 Cell Lines
| Structure | SKI ID | H1650 | H1975 | H2030 | H3255 | NHBE | WI-38 |
|---|---|---|---|---|---|---|---|
| | | | Dose Response (uM) | | | CytoTox (uM) | |
| 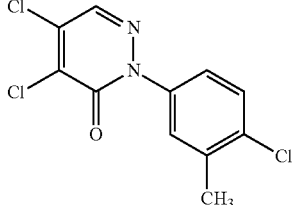 | 267065 | >10 | 1.89 | >10 | >10 | >10 | >10 |
| 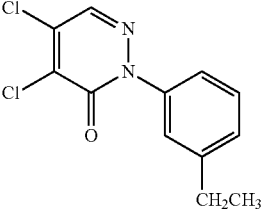 [SMILES: CCc1cccc(-n2ncc(Cl)c(Cl)c2=O)c1] | 267062 | 2.48 | 0.46 | 0.72 | 1.50 | 1.85 | 6.44 |
| 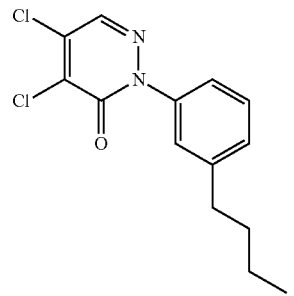 [SMILES: CCCCc1cccc(-n2ncc(Cl)c(Cl)c2=O)c1] | 267063 | 5.82 | 1.93 | 2.75 | 3.89 | 5.34 | >10 |
| 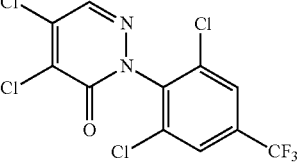 | 267059 | >10 | >10 | >10 | >10 | >10 | >10 |
| 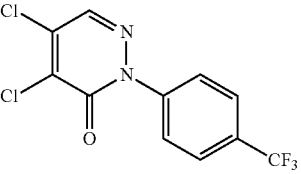 [SMILES: O=c1c(Cl)c(Cl)cnn1-c1ccc(C(F)(F)F)cc1] | 267060 | 3.92 | 0.69 | 1.09 | 2.27 | 3.44 | >10 |
| 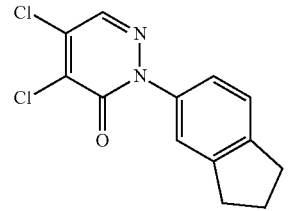 [SMILES: O=c1c(Cl)c(Cl)cnn1-c1ccc2c(c1)CCC2] | 267066 | 1.69 | 0.19 | 1.41 | 1.35 | 1.74 | 5.37 |
| 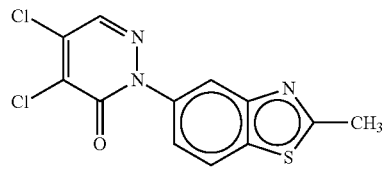 | 267067 | 4.47 | 0.45 | 3.04 | 3.64 | >10 | >10 |

TABLE 11-continued

Summary of Pyridazinone Compounds against H1650, H1975, H2030, H3255, NHBE, and WI-38 Cell Lines

| Structure | SKI ID | H1650 | H1975 | H2030 | H3255 | NHBE | WI-38 |
|---|---|---|---|---|---|---|---|
| | | | Dose Response (uM) | | | CytoTox (uM) | |
| 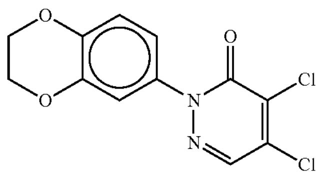 | 267068 | 2.33 | 0.25 | 1.23 | 1.20 | 1.56 | 3.96 |
| 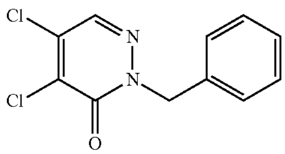 [SMILES: O=c1c(Cl)c(Cl)cnn1Cc1ccccc1] | 267069 | >10 | 2.16 | 6.83 | 6.50 | 7.32 | >10 |
| 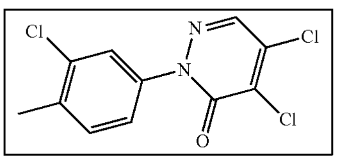 [SMILES: Cc1ccc(-n2ncc(Cl)c(Cl)c2=O)cc1Cl] | 267070 | >10 | 0.91 | 5.18 | 3.10 | >10 | >10 |
| 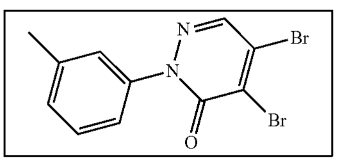 [SMILES: Cc1cccc(-n2ncc(Br)c(Br)c2=O)c1] | 267071 | 0.74 | 0.22 | 1.22 | 0.81 | 1.61 | 2.61 |
| 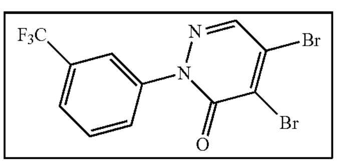 [SMILES: O=c1c(Br)c(Br)cnn1-c1cccc(C(F)(F)F)c1] | 267072 | 0.54 | 0.20 | 1.42 | 1.00 | 1.43 | 2.17 |
| 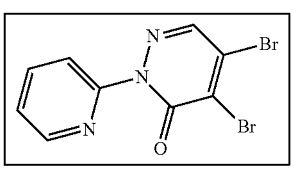 [SMILES: O=c1c(Br)c(Br)cnn1-c1ccccn1] | 267073 | 0.80 | 0.09 | 0.76 | 0.66 | 1.33 | 0.89 |
| 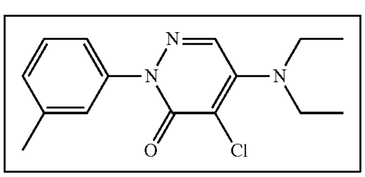 [SMILES: CCN(CC)c1cnn(-c2cccc(C)c2)c(=O)c1Cl] | 267074 | >10 | >10 | >10 | >10 | >10 | >10 |
| 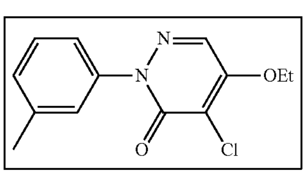 [SMILES: CCOc1cnn(-c2cccc(C)c2)c(=O)c1Cl] | 267075 | >10 | >10 | >10 | >10 | >10 | >10 |

TABLE 11-continued
Summary of Pyridazinone Compounds against H1650, H1975, H2030, H3255, NHBE, and WI-38 Cell Lines
| Structure | SKI ID | H1650 | H1975 | H2030 | H3255 | NHBE | WI-38 |
|---|---|---|---|---|---|---|---|
| | | | | Dose Response (uM) | | CytoTox (uM) | |
| 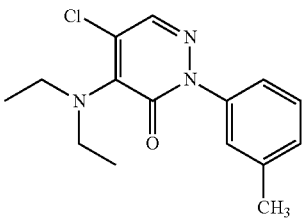 [SMILES: CCN(CC)c1c(Cl)cnn(-c2cccc(C)c2)c1=O] | 267076 | >10 | >10 | >10 | >10 | >10 | >10 |
| 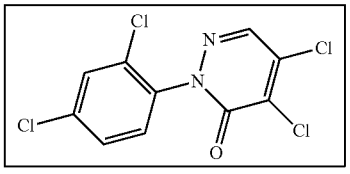 [SMILES: O=c1c(Cl)c(Cl)cnn1-c1ccc(Cl)cc1Cl] | 267077 | 0.56 | 0.05 | 1.27 | 1.11 | 1.10 | 1.74 |
| 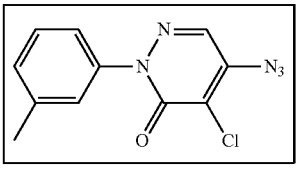 [SMILES: Cc1cccc(-n2ncc(N=[N+]=[N-])c(Cl)c2=O)c1] | 267082 | >10 | >10 | >10 | >10 | >10 | >10 |
| 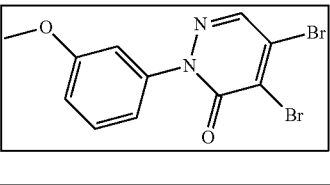 | 267083 | 1.06 | 0.23 | 0.57 | 0.35 | 1.85 | 2.60 |
| 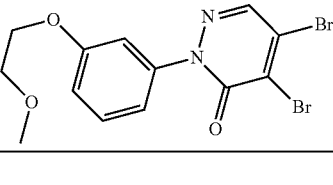 | 267084 | 1.51 | 0.23 | 0.61 | 0.38 | 2.56 | 2.33 |
| 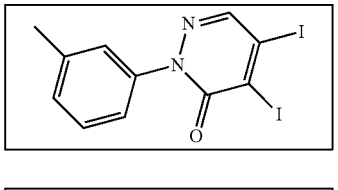 | 267085 | 1.93 | 0.50 | 0.99 | 0.71 | 2.88 | 5.51 |
| 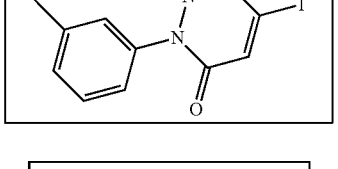 | 267086 | >10 | 6.76 | >10 | >10 | >10 | >10 |
| 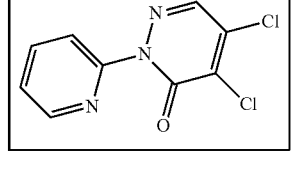 | 267090 | 1.29 | 0.20 | 0.41 | 0.50 | 1.43 | 1.19 |

TABLE 11-continued

Summary of Pyridazinone Compounds against H1650, H1975, H2030, H3255, NHBE, and WI-38 Cell Lines

| Structure | SKI ID | H1650 | H1975 | H2030 | H3255 | NHBE | WI-38 |
|---|---|---|---|---|---|---|---|
| | | Dose Response (uM) | | | | CytoTox (uM) | |
| [structure] | 273632 | >10 | >10 | >10 | >10 | >10 | >10 |
| [structure] | 273633 | >10 | >10 | >10 | >10 | >10 | >10 |
| [structure] | 273634 | 1.36 | 0.44 | 0.67 | 1.11 | 2.94 | 4.53 |

TABLE 12

Iressa and Tarceva against H1650, H1975, H2030, H2030, H3255, NHBE, and WI-38

| Structure | SKI ID | Original ID | H1650 | H1975 | H2030 | H3255 | NHBE | WI-38 |
|---|---|---|---|---|---|---|---|---|
| | | | \multicolumn{4}{c}{Dose Response (uM)} | \multicolumn{2}{c}{CytoTox (uM)} | |
| [structure] | 267079 | Iressa | >10 | >10 | >10 | <1.0 | ND | ND |
| [structure] | 267080 | Tarceva | >10 | >10 | >10 | <1.0 | ND | ND |
| [structure] | 267079 | Iressa | >10 | >10 | >10 | <0.01 | 5.44 | >10 |
| [structure] | 267080 | Tarceva | >10 | >10 | >10 | 0.02 | >10 | >10 |
| [structure] | 267079 | Iressa | >10 | 6.74 | 4.55 | <0.01 | 8.27 | 6.96 |

TABLE 12-continued

Iressa and Tarceva against H1650, H1975, H2030, H2030, H3255, NHBE, and WI-38

| Structure | SKI ID | Original ID | H1650 | H1975 | H2030 | H3255 | NHBE | WI-38 |
|---|---|---|---|---|---|---|---|---|
| | | | Dose Response (uM) | | | | CytoTox (uM) | |
| [structure] | 267080 | Tarceva | >10 | >10 | >10 | 0.02 | >10 | >10 |

TABLE 13

Summary of Pyridazinone Compounds against H358, H827, H1118, and H1734

| Structure | SKI ID | H358 | H827 | H1118 | H1734 |
|---|---|---|---|---|---|
| | | Dose Response (uM) | | | |
| [structure] | 104122 | 0.15 | 0.09 | 0.11 | 2.21 |
| [structure] | 104122 | ND | ND | ND | 1.73 |
| [structure] | 104122 | 0.21 | ND | ND | 2.17 |
| [structure] | 104122 | 0.10 | ND | ND | 1.17 |
| [structure] | 104122 | 0.12 | ND | ND | 1.17 |
| [structure] | 257017 | 0.74 | 0.71 | 0.49 | 3.20 |

TABLE 13-continued
Summary of Pyridazinone Compounds against H358, H827, H1118, and H1734
| Structure | SKI ID | H358 | H827 | H1118 | H1734 |
|---|---|---|---|---|---|
| | | | Dose Response (uM) | | |
| 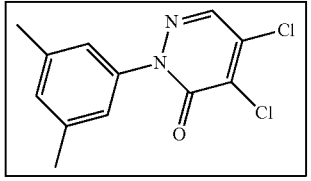 [SMILES: Cc1cc(C)cc(-n2ncc(Cl)c(Cl)c2=O)c1] | 257020 | 0.22 | 0.30 | 0.34 | 1.83 |
| 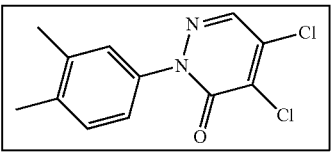 [SMILES: Cc1ccc(-n2ncc(Cl)c(Cl)c2=O)cc1C] | 257019 | 0.24 | 0.32 | 0.29 | 2.01 |
| 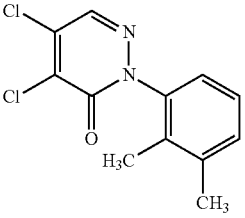 [SMILES: Cc1cccc(-n2ncc(Cl)c(Cl)c2=O)c1C] | 257018 | 0.55 | 0.50 | 0.44 | 2.12 |
| 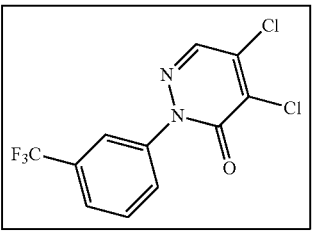 [SMILES: O=c1c(Cl)c(Cl)cnn1-c1cccc(C(F)(F)F)c1] | 176729 | 0.12 | 0.17 | 0.20 | 0.61 |
| 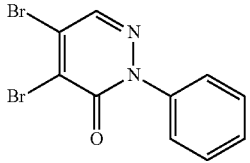 | 257015 | 0.16 | 0.17 | 0.22 | 0.87 |
| 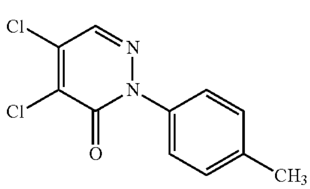 [SMILES: Cc1ccc(-n2ncc(Cl)c(Cl)c2=O)cc1] | 257016 | 0.35 | 0.29 | 0.38 | 3.37 |
| 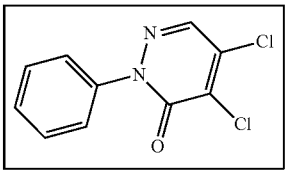 [SMILES: O=c1c(Cl)c(Cl)cnn1-c1ccccc1] | 257014 | 0.31 | 0.24 | 0.27 | 4.11 |

TABLE 13-continued

Summary of Pyridazinone Compounds against H358, H827, H1118, and H1734

| Structure | SKI ID | H358 | H827 | H1118 | H1734 |
|---|---|---|---|---|---|
| | | \multicolumn{4}{c}{Dose Response (uM)} | | | |
| (2-phenyl-4-bromo-5-(benzylthio)pyridazin-3(2H)-one) | 257021 | >10 | >10 | >10 | >10 |
| (2-phenyl-4-chloro-5-(benzylthio)pyridazin-3(2H)-one) | 257022 | >10 | >10 | >10 | >10 |
| (4-hydrazinyl-5-chloro-2-phenyl-pyridazin-3-one, NH2) | 257023 | >10 | >10 | >10 | >10 |
| (4-(methylhydrazinyl)-5-chloro-2-phenyl-pyridazin-3-one) | 257024 | >10 | >10 | >10 | >10 |
| (4-(methylhydrazinyl)-5-chloro-2-(4-methylphenyl)-pyridazin-3-one) | 257025 | >10 | >10 | >10 | >10 |
| (6-methoxy-2-(3-methylphenyl)pyridazin-3(2H)-one) | 257029 | >10 | ND | ND | >10 |

TABLE 13-continued

Summary of Pyridazinone Compounds against H358, H827, H1118, and H1734

| Structure | SKI ID | H358 | H827 | H1118 | H1734 |
| --- | --- | --- | --- | --- | --- |
| | | | Dose Response (uM) | | |
| (4,5-dichloro-6-methoxy-2-(m-tolyl)pyridazin-3(2H)-one) | 257028 | 0.94 | ND | ND | 2.42 |
| (4,5-dichloro-2-(3-methoxyphenyl)pyridazin-3(2H)-one) | 267061 | 0.24 | ND | ND | 2.41 |
| (2-(4-bromo-3-methylphenyl)-4,5-dichloropyridazin-3(2H)-one) | 267064 | 0.47 | ND | ND | 1.21 |
| (4,5-dichloro-2-(4-chloro-3-methylphenyl)pyridazin-3(2H)-one) | 267065 | 1.24 | ND | ND | >10 |
| (4,5-dichloro-2-(3-ethylphenyl)pyridazin-3(2H)-one) | 267062 | 0.24 | ND | ND | 1.75 |
| (2-(3-butylphenyl)-4,5-dichloropyridazin-3(2H)-one) | 267063 | 0.76 | ND | ND | 3.25 |

TABLE 13-continued
Summary of Pyridazinone Compounds against H358, H827, H1118, and H1734
| Structure | SKI ID | H358 | H827 | H1118 | H1734 |
| --- | --- | --- | --- | --- | --- |
| | | | Dose Response (uM) | | |
| 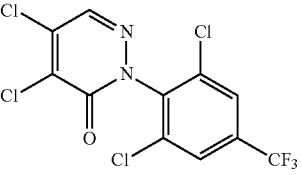 [SMILES: O=c1c(Cl)c(Cl)cnn1-c1c(Cl)cc(C(F)(F)F)cc1Cl] | 267059 | >10 | ND | ND | >10 |
| 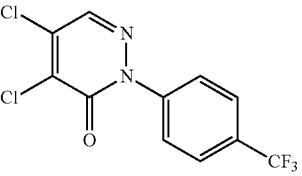 [SMILES: O=c1c(Cl)c(Cl)cnn1-c1ccc(C(F)(F)F)cc1] | 267060 | 0.29 | ND | ND | 1.60 |
| 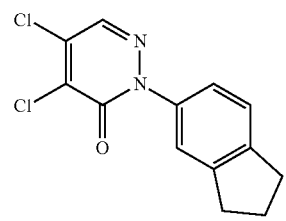 [SMILES: O=c1c(Cl)c(Cl)cnn1-c1ccc2c(c1)CCC2] | 267066 | 0.42 | ND | ND | 1.45 |
| 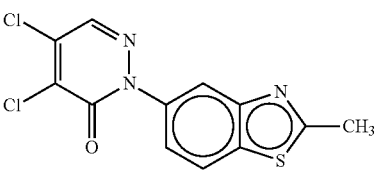 | 267067 | 1.38 | ND | ND | 2.57 |
| 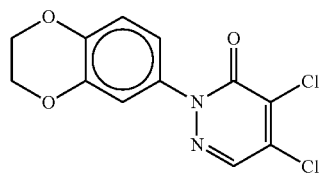 | 267068 | 0.43 | ND | ND | 2.12 |
| 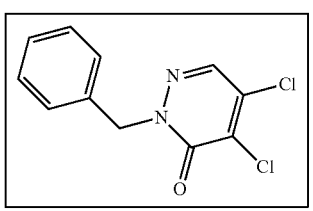 [SMILES: O=c1c(Cl)c(Cl)cnn1Cc1ccccc1] | 267069 | 4.76 | ND | ND | 6.86 |
| 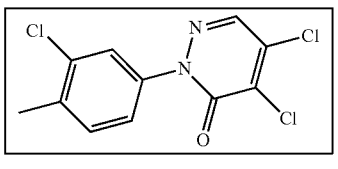 [SMILES: Cc1ccc(-n2ncc(Cl)c(Cl)c2=O)cc1Cl] | 267070 | 0.97 | ND | ND | 2.69 |
| 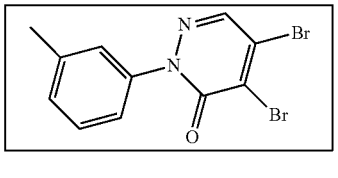 [SMILES: Cc1cccc(-n2ncc(Br)c(Br)c2=O)c1] | 267071 | 0.21 | ND | ND | 0.80 |

TABLE 13-continued
Summary of Pyridazinone Compounds against H358, H827, H1118, and H1734
| Structure | SKI ID | H358 | H827 | H1118 | H1734 |
|---|---|---|---|---|---|
| | | | Dose Response (uM) | | |
| 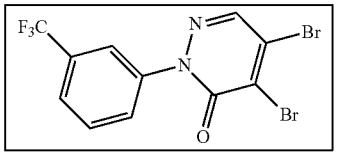 [SMILES: O=c1c(Br)c(Br)cnn1-c1cccc(C(F)(F)F)c1] | 267072 | 0.15 | ND | ND | 0.51 |
| 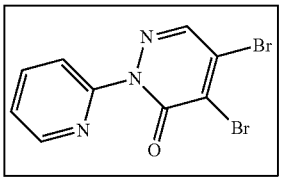 [SMILES: O=c1c(Br)c(Br)cnn1-c1ccccn1] | 267073 | 0.07 | ND | ND | 0.72 |
| 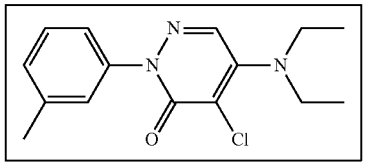 [SMILES: CCN(CC)c1cnn(-c2cccc(C)c2)c(=O)c1Cl] | 267074 | >10 | ND | ND | >10 |
| 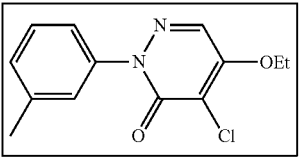 | 267075 | >10 | ND | ND | >10 |
| 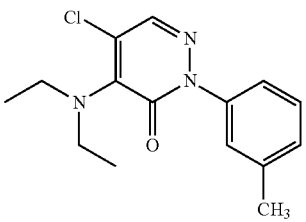 [SMILES: CCN(CC)c1c(Cl)cnn(-c2cccc(C)c2)c1=O] | 267076 | >10 | ND | ND | >10 |
| 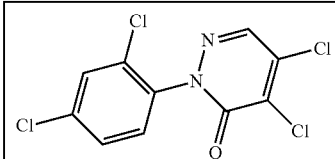 | 267077 | 0.14 | ND | ND | 0.52 |
| 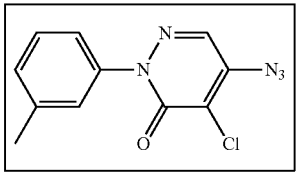 [SMILES: Cc1cccc(-n2ncc(N=[N+]=[N-])c(Cl)c2=O)c1] | 267082 | >10 | ND | ND | >10 |
| 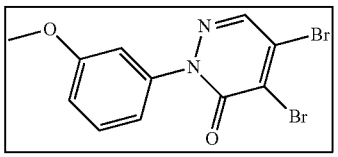 [SMILES: COc1cccc(-n2ncc(Br)c(Br)c2=O)c1] | 267083 | 0.13 | ND | ND | 1.31 |

TABLE 13-continued

Summary of Pyridazinone Compounds against H358, H827, H1118, and H1734

| Structure | SKI ID | H358 | H827 | H1118 | H1734 |
|---|---|---|---|---|---|
| | | | Dose Response (uM) | | |
| (structure) | 267084 | 0.13 | ND | ND | 1.63 |
| (structure) | 267085 | 0.30 | ND | ND | 1.94 |
| (structure) | 267086 | >10 | ND | ND | >10 |
| (structure) | 267090 | 0.06 | ND | ND | 1.10 |
| (structure) | 273632 | >10 | ND | ND | >10 |
| (structure) | 273633 | >10 | ND | ND | >10 |

TABLE 13-continued
Summary of Pyridazinone Compounds against H358, H827, H1118, and H1734
| Structure | SKI ID | H358 | H827 | H1118 | H1734 |
| --- | --- | --- | --- | --- | --- |
| | | Dose Response (uM) | | | |
| 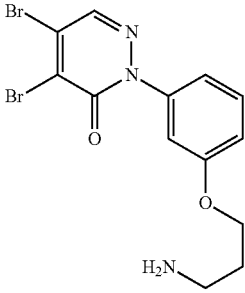 [SMILES: NCCCOc1cccc(-n2ncc(Br)c(Br)c2=O)c1] | 273634 | 0.24 | ND | ND | 0.93 |
TABLE 14
Iressa and Tarceva against H358 and H1734
| Structure | SKI ID | Original ID | H358 | H827 | H1118 | H1734 |
| --- | --- | --- | --- | --- | --- | --- |
| | | | Dose Response (uM) | | | |
| 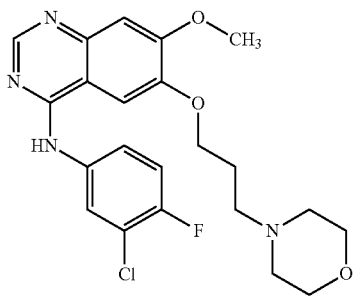 [SMILES: COc1cc2ncnc(Nc3ccc(F)c(Cl)c3)c2cc1OCCCN1CCOCC1] | 267079 | Iressa | >10 | ND | ND | 3.01 |
| 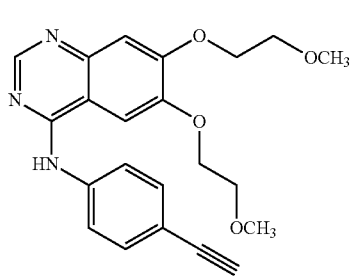 [SMILES: C#Cc1ccc(Nc2ncnc3cc(OCCOC)c(OCCOC)cc23)cc1] | 267080 | Tarceva | >10 | ND | ND | >10 |
| 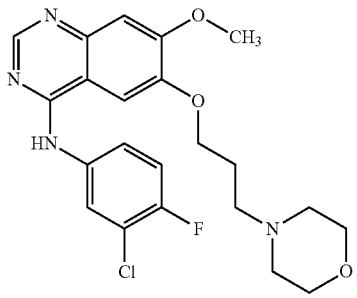 [SMILES: COc1cc2ncnc(Nc3ccc(F)c(Cl)c3)c2cc1OCCCN1CCOCC1] | 267079 | Iressa | >10 | ND | ND | 4.48 |

TABLE 14-continued

Iressa and Tarceva against H358 and H1734

| Structure | SKI ID | Original ID | H358 | H827 | H1118 | H1734 |
|---|---|---|---|---|---|---|
| | | | Dose Response (uM) | | | |
| (structure) | 267080 | Tarceva | >10 | ND | ND | >10 |
| (structure) | 267079 | Iressa | 7.33 | ND | ND | 2.67 |
| (structure) | 267080 | Terceva | >10 | ND | ND | >10 |

Example 4

High Throughput Screening for Novel Agents that Block Proliferation of NSCLC Cell Lines We have performed high throughput screening campaigns using four established non small cell lung cancer cell lines (H1650, H1975, H2030, H3255) against a chemical library of 200,000 small molecules. Description of the assays is described herein. We have identified several hits inhibiting one or more cell line with the most potent one being 5-nitro-furan-2-carboxylic acid (4-chloro-phenyl)-amide (SKI-98698). We then performed a substructure search against the library and identified 51 close derivatives of SKI-98698 (Table 15). Further analysis of the biological data for these derivatives reveals a coherent structure activity relationship for both active and inactive compounds with only 8 compounds identified as active during primary screening (Table 16). Data is expressed as percentage inhibition in the cell based assay; screening concentration of 10 µM compound in 1% DMSO (v/v).

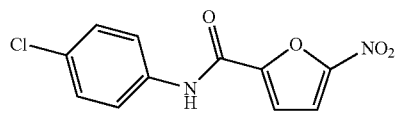 [SMILES: O=C(Nc1ccc(Cl)cc1)c1ccc([N+](=O)[O-])o1]

5-nitro-furan-2-carboxylic acid (4-chloro-phenyl)-amide (SKI-98698)

TABLE 15 pre-SAR summary for substituted furan derivatives

| Structure | SKI ID | R1650 | R1975 | H2030 | H3255 |
|---|---|---|---|---|---|
| | | | PRIMARY HTS [%] | | |
| 5-nitro-furan-2-carboxamide with 3-chloro-4-fluorophenyl | 87200 | 103 | 67 | 23 | 6 |
| 5-nitro-furan-2-carboxamide with 4-methylphenyl | 98697 | 103 | 70 | 62 | 83 |
| 5-nitro-furan-2-carboxamide with 4-chlorophenyl | 98698 | 101 | 74 | 17 | 20 |

TABLE 15-continued pre-SAR summary for substituted furan derivatives

| Structure | SKI ID | R1650 | R1975 | H2030 | H3255 |
|---|---|---|---|---|---|
| | | \multicolumn{4}{c}{PRIMARY HTS [%]} | | | |
| [5-nitrofuran-2-carboxamide, N-(3-methylphenyl)] | 71762 | 104 | 74 | 101 | 100 |
| [5-nitrofuran-2-carboxamide, N-(3-methylphenyl)] | 71762 | 104 | 74 | 101 | 100 |
| [5-nitrofuran-2-carboxamide, N-(4-chloro-2-trifluoromethylphenyl)] | 64228 | 87 | 82 | 93 | 91 |
| [5-nitrofuran-2-carboxamide, N-cyclohexyl] | 71763 | 87 | 61 | 82 | 77 |

TABLE 15-continued
pre-SAR summary for substituted furan derivatives
| Structure | SKI ID | R1650 | R1975 | H2030 | H3255 |
|---|---|---|---|---|---|
| | | | PRIMARY HTS [%] | | |
| 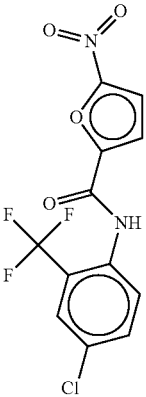 | 64228 | 87 | 82 | 93 | 91 |
| 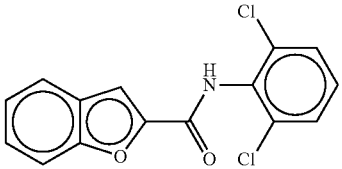 | 60998 | 10 | 19 | 1 | 1 |
| 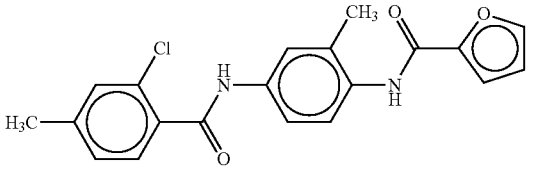 | 61302 | 13 | 16 | −2 | 2 |
| 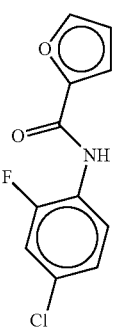 | 66598 | 8 | 8 | 0 | 1 |
| 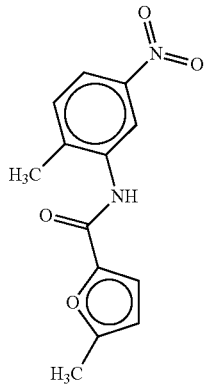 | 66776 | 13 | 2 | −3 | 2 |

TABLE 15-continued pre-SAR summary for substituted furan derivatives

| Structure | SKI ID | R1650 | R1975 | H2030 | H3255 |
|---|---|---|---|---|---|
| | | \multicolumn{4}{c}{PRIMARY HTS [%]} | | | |
| | 72456 | 12 | 9 | 8 | 7 |
| | 75072 | 13 | 0 | 5 | 1 |
| | 76739 | 13 | −9 | 3 | 5 |

TABLE 15-continued
pre-SAR summary for substituted furan derivatives
| Structure | SKI ID | R1650 | R1975 | H2030 | H3255 |
|---|---|---|---|---|---|
| | | | PRIMARY HTS [%] | | |
| 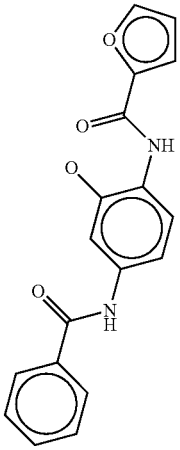 | 76839 | 20 | 3 | −6 | 2 |
| 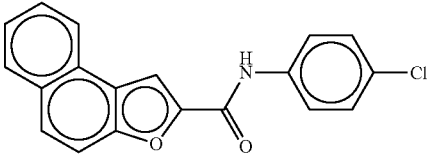 | 77021 | 16 | −11 | −1 | 4 |
| 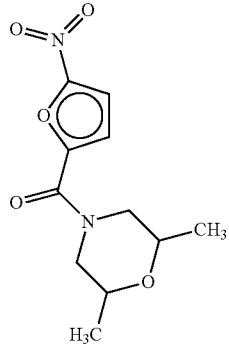 | 77942 | 14 | −2 | 6 | 7 |
| 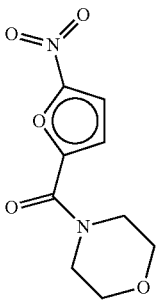 | 77953 | 12 | −1 | −6 | 0 |

TABLE 15-continued pre-SAR summary for substituted furan derivatives

| Structure | SKI ID | R1650 | R1975 | H2030 | H3255 |
|---|---|---|---|---|---|
| | | | PRIMARY HTS [%] | | |
| (furan-2-carboxamide, N-(3-chlorophenyl)) | 78107 | 14 | −14 | 4 | 6 |
| (furan-3-carboxamide, N-(4-chlorophenyl)) | 78158 | 20 | −2 | 6 | 4 |
| (5-nitrofuran-2-carboxamide, N-benzyl-N-ethyl) | 78535 | 41 | −2 | 26 | 8 |
| (furan-2-carboxamide, N-(2-methyl-4-nitrophenyl)) | 79434 | 4 | −7 | 0 | 4 |

TABLE 15-continued
pre-SAR summary for substituted furan derivatives
| Structure | SKI ID | R1650 | R1975 | H2030 | H3255 |
|---|---|---|---|---|---|
| | | | PRIMARY HTS [%] | | |
| 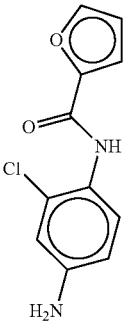 | 82456 | 6 | −15 | −2 | 2 |
| 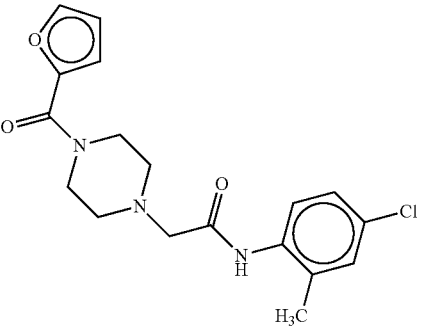 | 83809 | 22 | −10 | 2 | 2 |
| 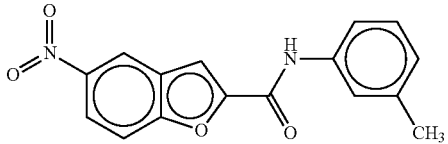 | 84487 | 27 | −5 | 5 | 3 |
| 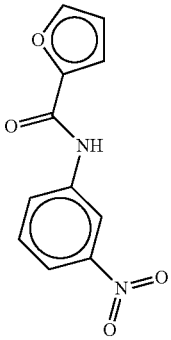 | 87246 | 8 | −3 | 9 | 5 |
| 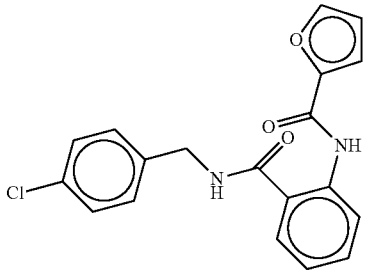 | 88935 | −4 | −10 | −1 | −2 |

TABLE 15-continued pre-SAR summary for substituted furan derivatives

| Structure | SKI ID | R1650 | R1975 | H2030 | H3255 |
|---|---|---|---|---|---|
| | | | PRIMARY HTS [%] | | |
| (structure) | 91753 | −3 | −22 | −5 | −1 |
| (structure) | 92553 | 2 | −3 | 5 | 1 |
| (structure) | 93911 | −4 | −22 | −3 | −1 |

TABLE 15-continued
pre-SAR summary for substituted furan derivatives
| Structure | SKI ID | R1650 | R1975 | H2030 | H3255 |
|---|---|---|---|---|---|
| | | | PRIMARY HTS [%] | | |
| 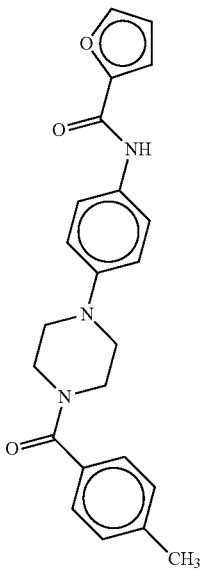 | 95436 | 2 | −12 | 2 | −3 |
| 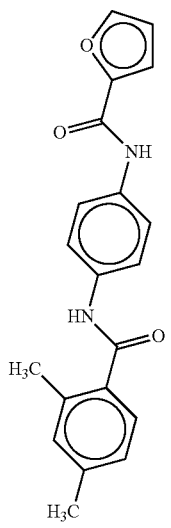 | 97216 | −1 | −4 | −4 | 3 |
| 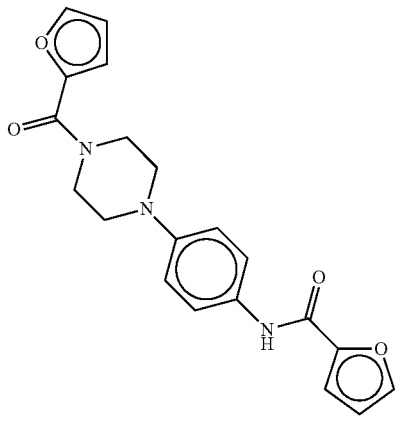 | 97253 | −2 | −15 | −5 | −3 |

TABLE 15-continued pre-SAR summary for substituted furan derivatives

| Structure | SKI ID | R1650 | R1975 | H2030 | H3255 |
|---|---|---|---|---|---|
| | | | PRIMARY HTS [%] | | |
| (structure) | 98705 | −8 | 14 | 8 | 9 |
| (structure) | 100403 | −13 | −13 | 3 | 2 |
| (structure) | 100483 | −1 | −8 | −1 | 1 |
| (structure) | 100507 | −3 | −15 | 7 | 1 |

TABLE 15-continued pre-SAR summary for substituted furan derivatives

| Structure | SKI ID | R1650 | R1975 | H2030 | H3255 |
|---|---|---|---|---|---|
| | | | PRIMARY HTS [%] | | |
| (structure) | 100588 | −5 | −14 | 5 | 4 |
| (structure) | 100652 | −12 | −2 | −6 | −3 |
| (structure) | 100792 | −5 | −9 | 43 | 1 |

TABLE 15-continued pre-SAR summary for substituted furan derivatives

| Structure | SKI ID | R1650 | R1975 | H2030 | H3255 |
|---|---|---|---|---|---|
| | | | PRIMARY HTS [%] | | |
| (structure with nitrofuran-CH2-piperazine-2,3-dimethylphenyl) | 101070 | 2 | −18 | 5 | 1 |
| (furan-2-carboxamide-biphenyl-4-nitro) | 102031 | −2 | −11 | −1 | 3 |
| (5-nitrofuran-2-carboxamide-4-iodophenyl) | 103710 | 33 | 17 | −5 | 4 |

TABLE 15-continued pre-SAR summary for substituted furan derivatives

| Structure | SKI ID | R1650 | R1975 | H2030 | H3255 |
|---|---|---|---|---|---|
| | | | PRIMARY HTS [%] | | |
| 5-nitrofuran-2-carboxamide with 2-ethylphenyl | 103960 | 62 | 41 | 73 | 68 |
| 5-nitrofuran-2-carboxamide with N-methyl-N-phenyl | 104003 | −3 | 18 | 0 | 5 |
| 5-nitrofuran-2-carboxamide with 2-chloro-5-(trifluoromethyl)phenyl | 104039 | 61 | 69 | 13 | 6 |
| 5-methylfuran-2-carboxamide with naphthalen-2-yl | 105503 | −10 | −13 | −7 | 0 |

TABLE 15-continued pre-SAR summary for substituted furan derivatives

| Structure | SKI ID | R1650 | R1975 | H2030 | H3255 |
|---|---|---|---|---|---|
| | | | PRIMARY HTS [%] | | |
| (structure) | 107911 | 8 | −15 | 2 | 7 |
| (structure) | 108321 | 38 | −7 | 6 | 2 |
| (structure) | 109007 | −6 | −3 | 3 | 1 |

TABLE 16

SAR summary for substituted phenylfuran-2-carboxamide derivatives

| Structure | SKI ID | 1650 | 1975 | 2030 | 3255 | 1650 | 1975 | 2030 | 3255 | NHBE |
|---|---|---|---|---|---|---|---|---|---|---|
| | | CONFIRMATION [%] | | | | $IC_{50}$ (uM) | | | | |
| (structure) | 87200 | 112 | 95 | 107 | 103 | 0.29 | 0.44 | 1.01 | 0.69 | ND |

TABLE 16-continued
SAR summary for substituted phenylfuran-2-carboxamide derivatives
| Structure | SKI ID | 1650 | 1975 | 2030 | 3255 | 1650 | 1975 | 2030 | 3255 | NHBE |
|---|---|---|---|---|---|---|---|---|---|---|
| | | CONFIRMATION [%] | | | | IC$_{50}$ (uM) | | | | |
| 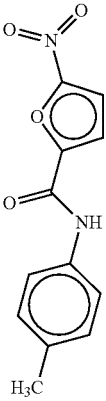 | 98697 | 136 | 70 | 101 | 130 | 0.44 | 1.09 | 1.06 | 0.91 | 29.40 |
| 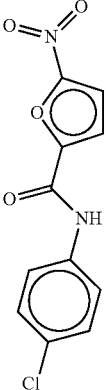 | 98698 | 133 | 57 | 98 | 118 | 0.38 | 0.63 | 1.12 | 0.95 | 21.36 |
| 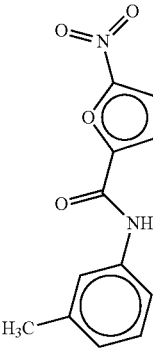 | 71762 | 135 | 59 | 101 | 122 | 0.43 | 1.24 | 1.43 | 0.95 | 15.77 |
| 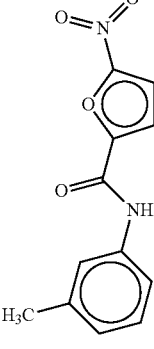 | 71762 | 106 | 76 | 103 | 97 | 0.41 | 1.23 | 1.46 | 1.01 | 14.75 |

TABLE 16-continued

SAR summary for substituted phenylfuran-2-carboxamide derivatives

| Structure | SKI ID | 1650 | 1975 | 2030 | 3255 | 1650 | 1975 | 2030 | 3255 | NHBE |
|---|---|---|---|---|---|---|---|---|---|---|
| | | CONFIRMATION [%] | | | | IC$_{50}$ (uM) | | | | |
| 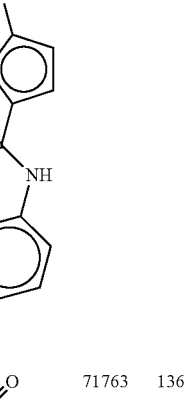 | 64228 | 111 | 70 | 90 | 97 | 1.60 | 2.24 | 1.12 | 2.54 | 13.20 |
| 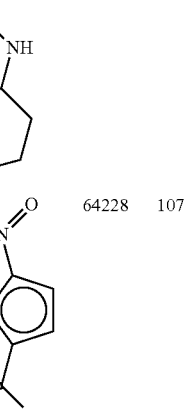 | 71763 | 136 | 74 | 97 | 135 | 1.39 | 3.54 | 3.79 | 2.98 | 24.90 |
| 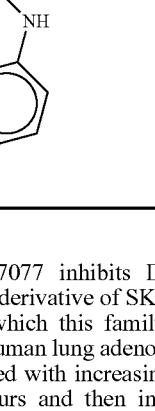 | 64228 | 107 | 97 | 105 | 97 | 2.31 | 5.46 | 6.23 | 7.51 | ND |

SK1-267077 inhibits DNA synthesis. We used SKI-267077, a derivative of SKI-104122 to elucidate the mechanism by which this family of compounds caused growth arrest of human lung adenocarcinoma cell lines. H2030 cells were treated with increasing concentrations of SKI-267077 for 24 hours and then incorporation of $^3$H-thymide into DNA determined (FIG. 1). As shown in FIG. 1, SKI-267077 caused a dose-dependent decrease in DNA synthesis.

Figure 2A:
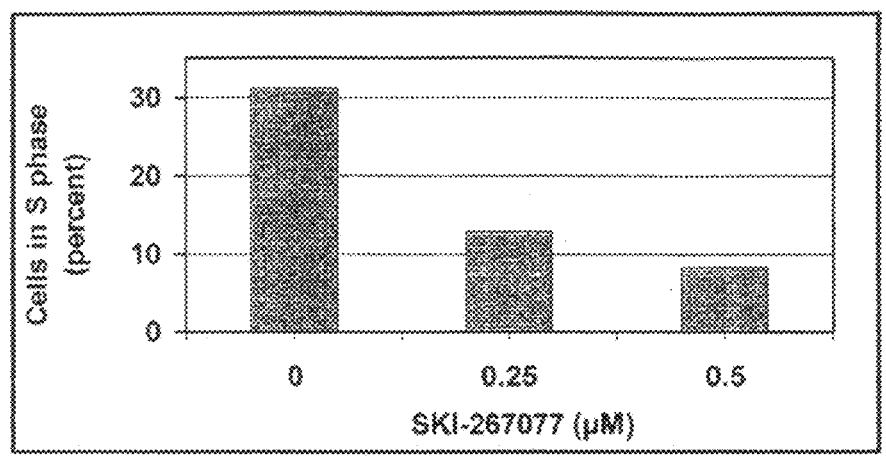
FIG. 2A: Percent of cells in S-phase.
Figure 2B:
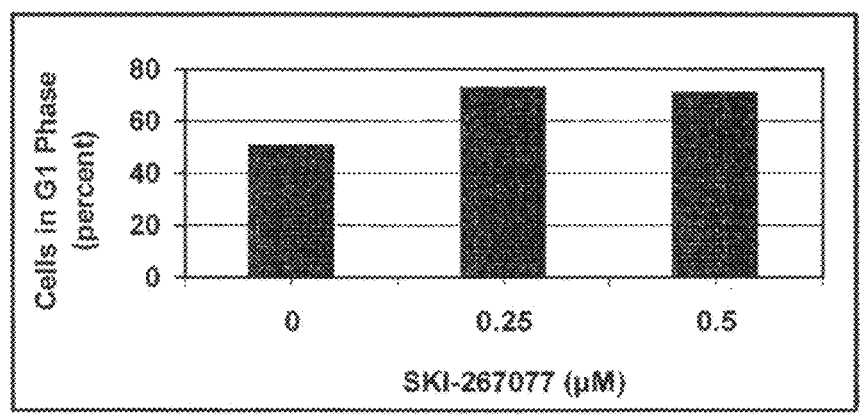
FIG. 2B: percent of cells in G1 phase.

SKI-267077 induces cell cycle arrest at the G1 phase. Cell cycle progression in the presence of SKI-267077 was determined by FACS analysis of H2030 cells that were treated for 24 hours. SKI-267077 treatment resulted in a reduction of the percent of cells in the S phase (FIG. 2A) of the cell cycle and a concomitant increase in the percent of cells in the induce G1 phase (FIG. 2B).

Figure 3:
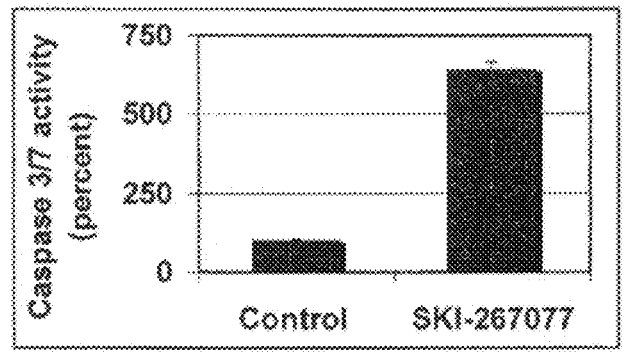
FIG. 3. Activation of caspase 3/7 by SKI-267077. H2030 cells were treated with 1 µM SKI-267077 for 48 h and then caspase 3/7 activity measured in whole cell extracts.
Figure 11:
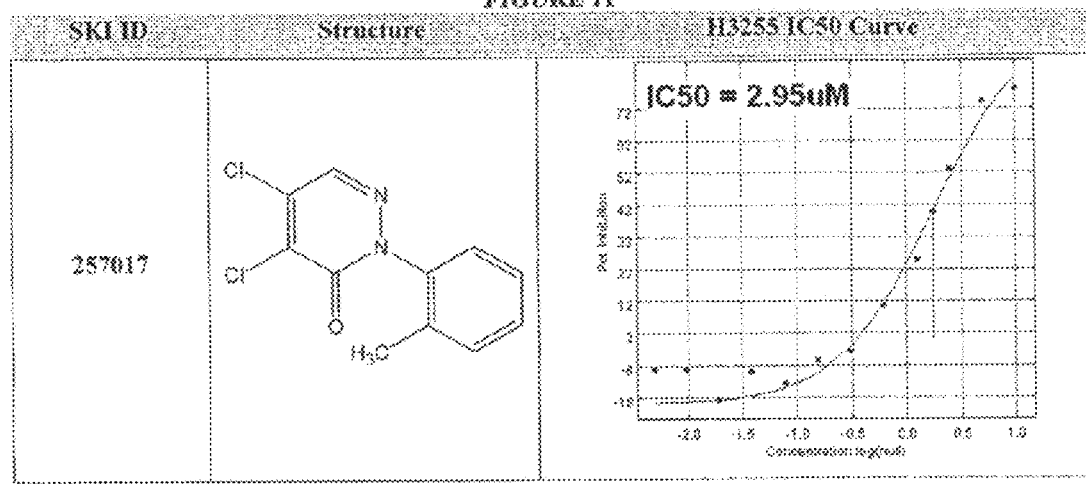
Figure 12:
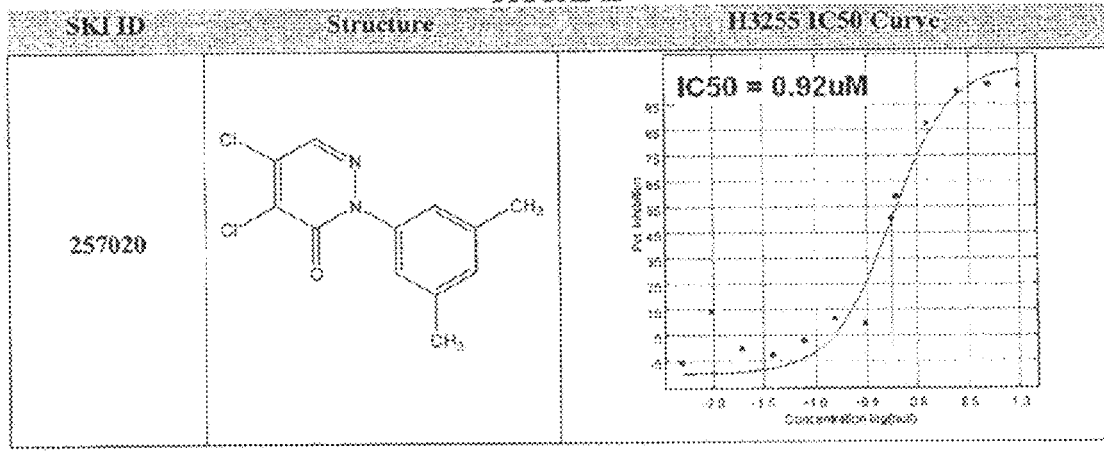
Figure 25:
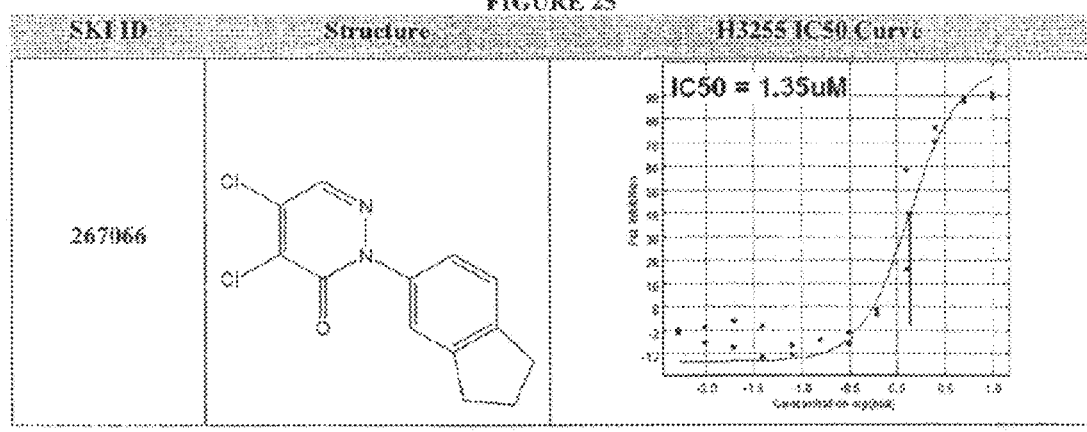
Figure 26:
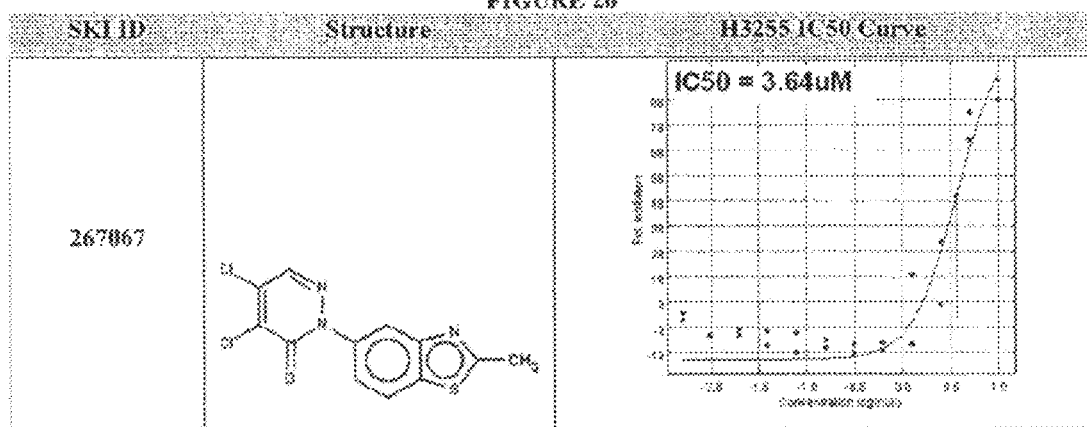
Figure 29:
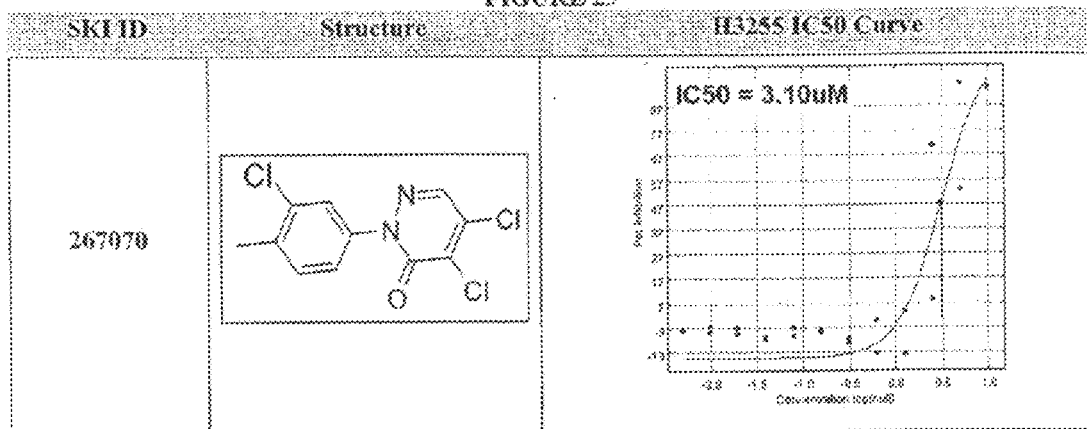
Figure 30:
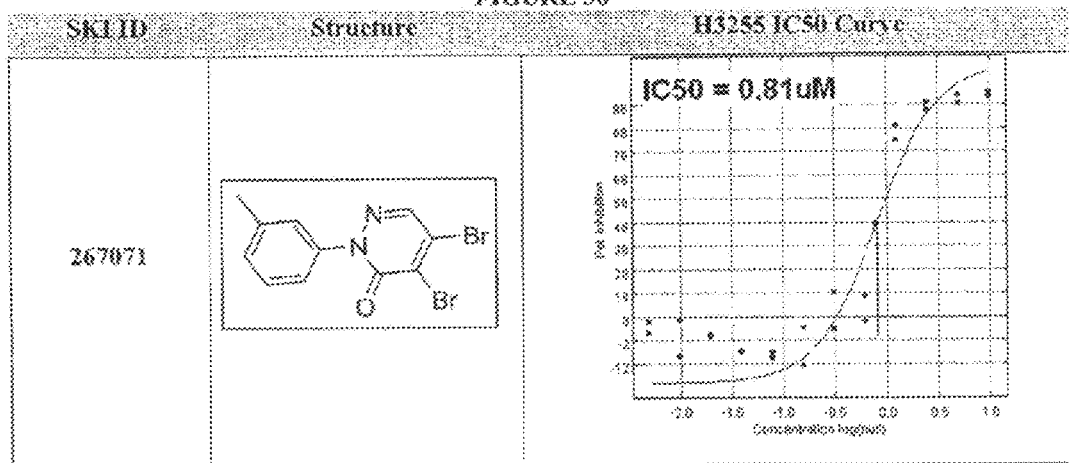
Figure 35:
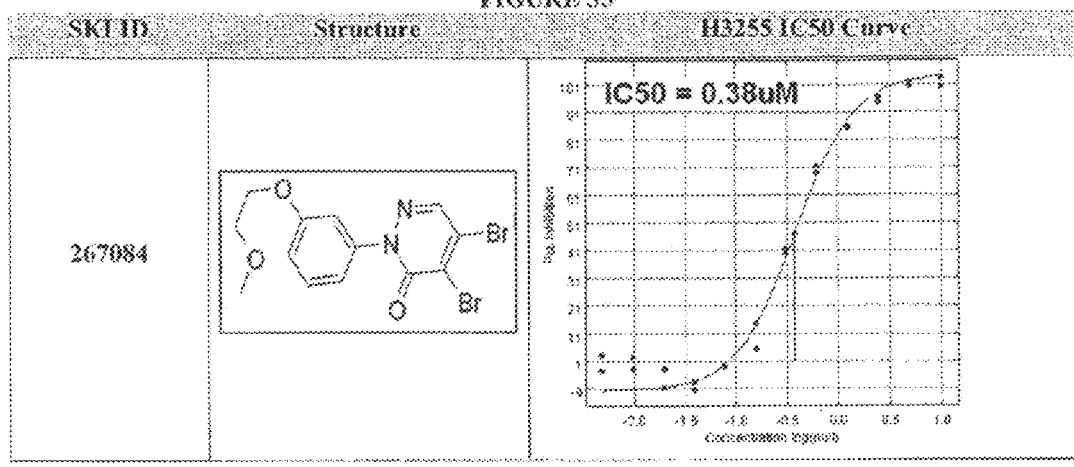
Figure 36:
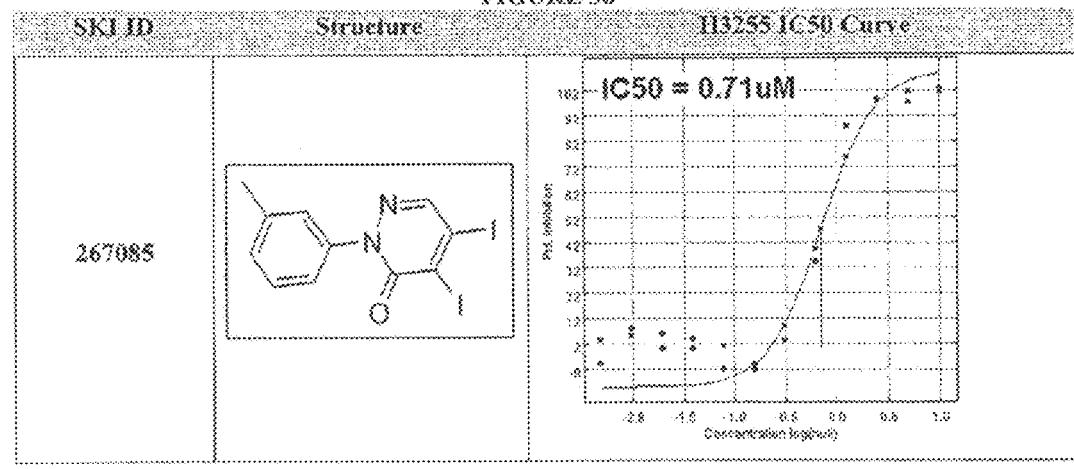
Figure 37:
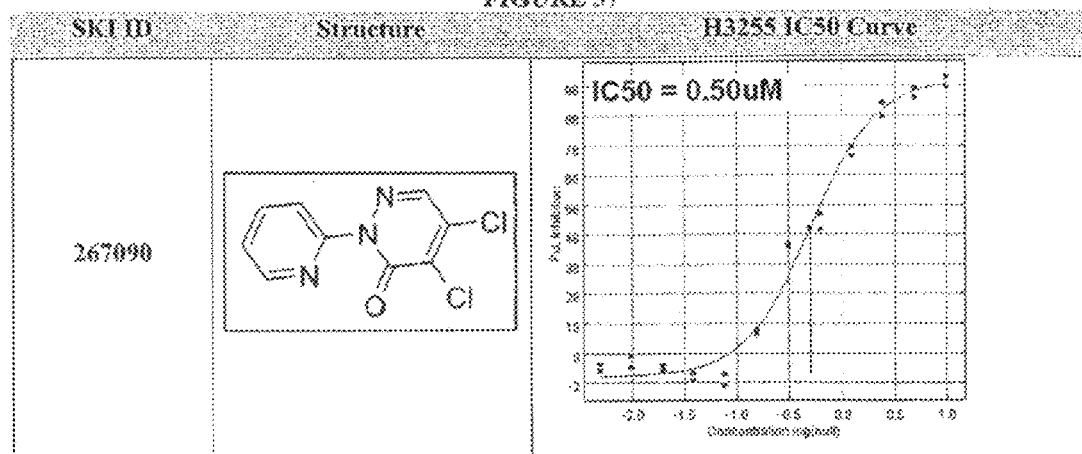
Figure 38:
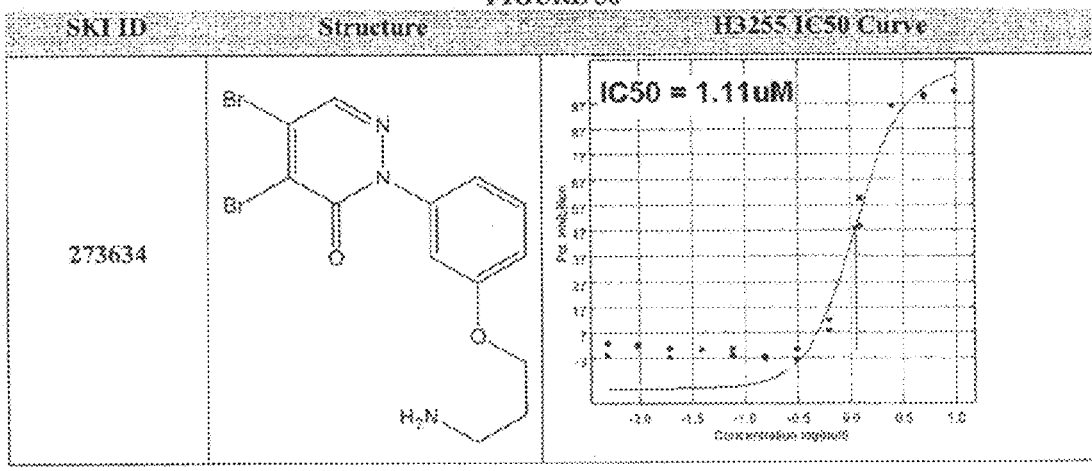
Figure 41A:
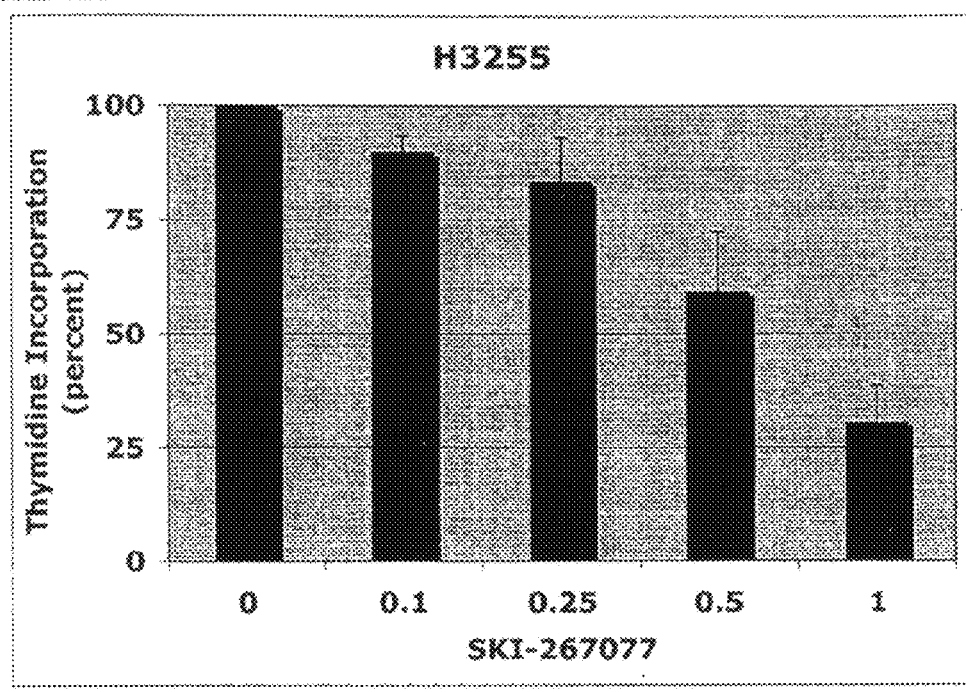
FIGS. 41A-41B. SKI-267077 inhibits DNA synthesis. SKI-267077 was used to elucidate the mechanism by which this agent inhibits cell growth. Treatment of adenocarcinoma cell lines with either mutant EGFR (H1975 and H3255) resulted in a dose-dependent reduction in DNA synthesis.
Figure 41B:
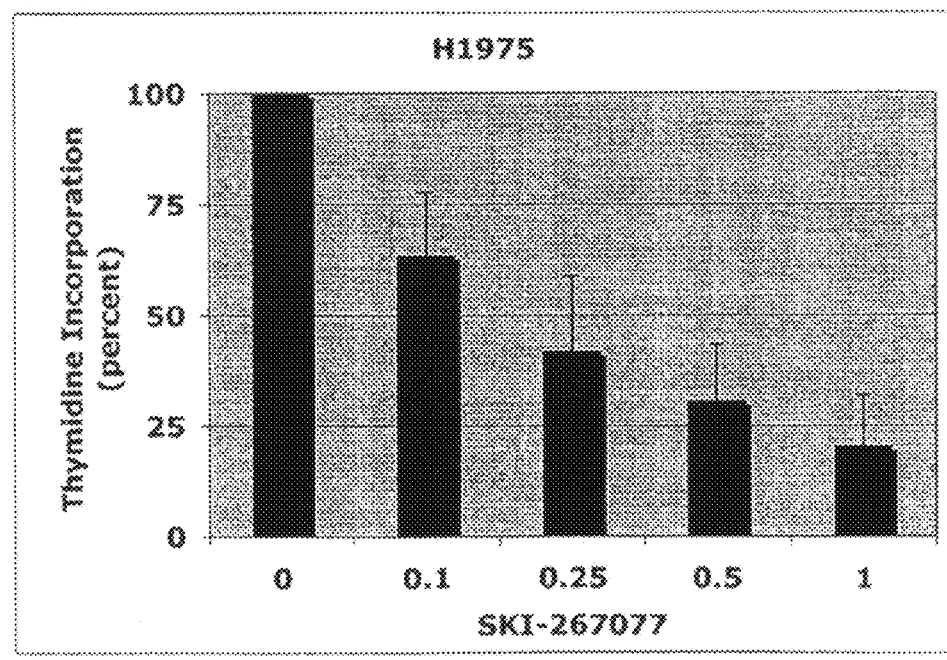
Figure 42:
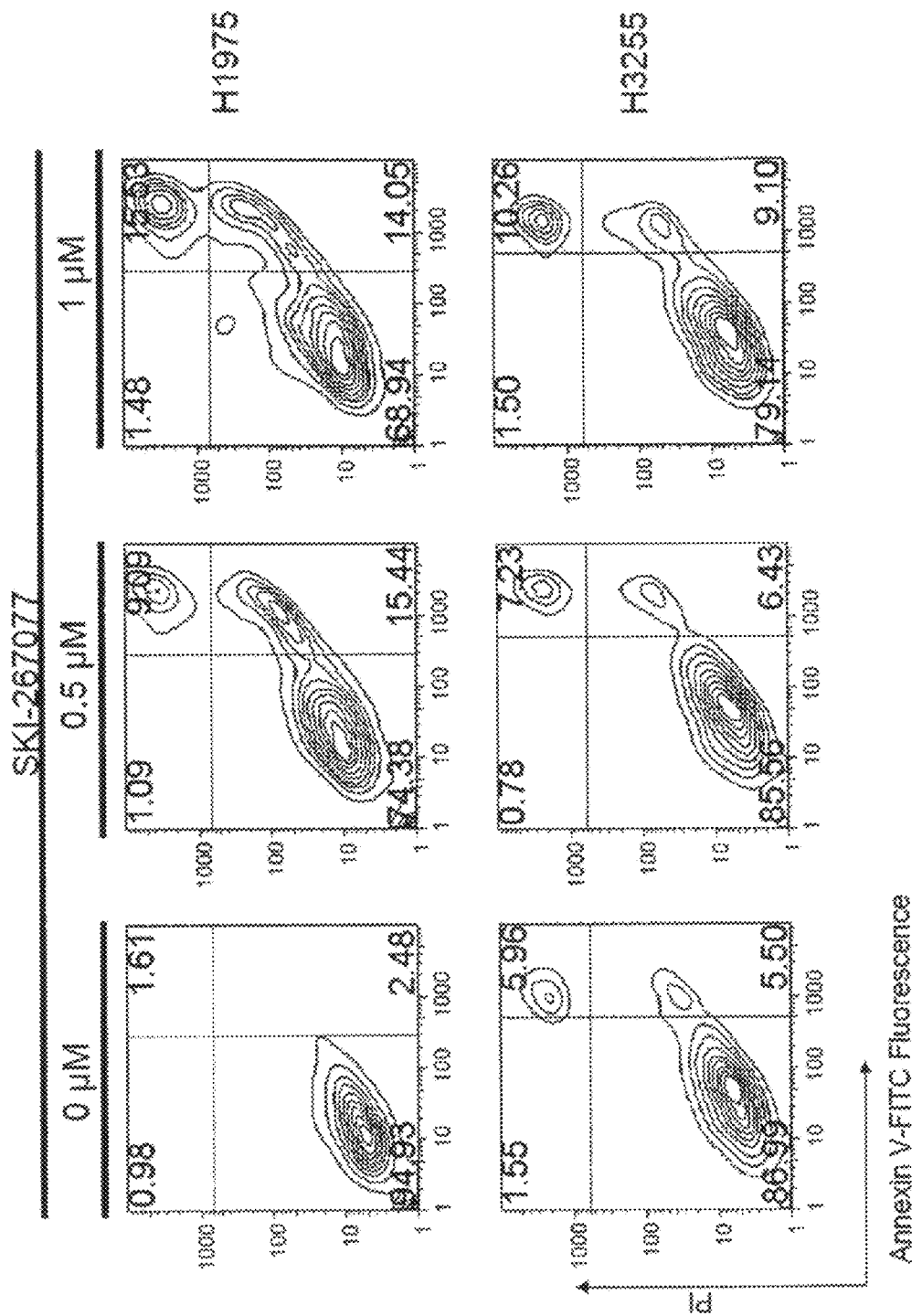
FIG. 42. SKI-267077 induces apoptosis. Cells were treated for 48 hours with SKI-267077 and then binding of FITC-labeled annexin V to cells determined FACS analysis was used to determine the amount of annexin V-positive cells. There was an induction of apoptosis, as measured by binding of annexin-V to the cell surface.
Figure 43A:
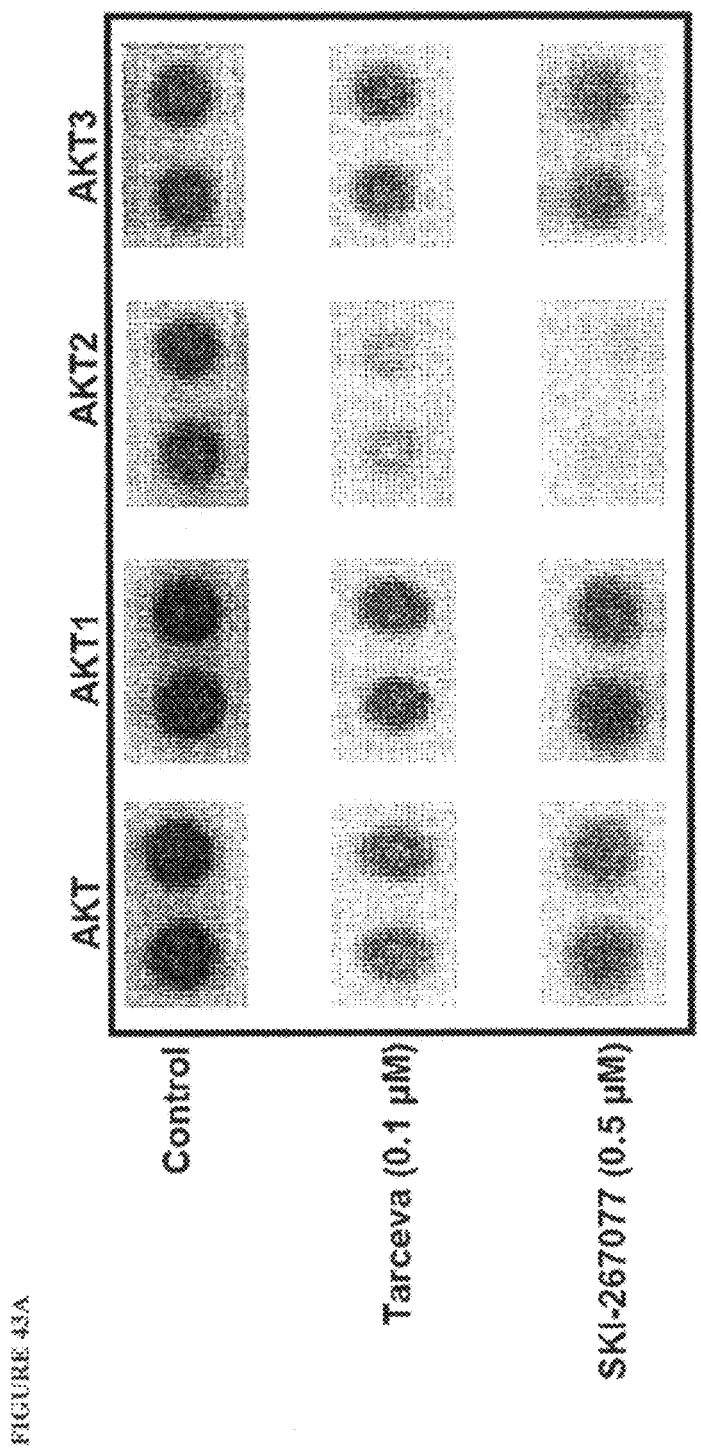
FIG. 43A-43C. A phosphoprotein array was used to determine which signaling pathways were affected by treatment of cells with SKI-267077. To detect protein phosphorylation using phosphoprotein arrays (R and D Systems), cells were treated for 24 hours with SKI-267077 or erlotinib (Tarceva). A phosphoprotein array (R and D Systems) was used to measure the level of phosphorylation of cellular proteins. Protein phosphorylation was determined according to the manufacturer's instructions. SKI-267077 blocked phosphorylation of all three AKT isoforms (FIG. 43A) and p70 S6 kinase (FIG. 43B) (PI-3kinase signaling pathway). In addition, SKI-267077 treatment also reduced phosphorylation of the MAPK isoforms ERK1 and ERK2 (FIG. 43C) (MAPK signaling pathway). Erolotinib was used as a control in these experiments and a similar pattern of inhibition of the PI-3 kinase and MAPK pathways was observed.
Figure 43B:
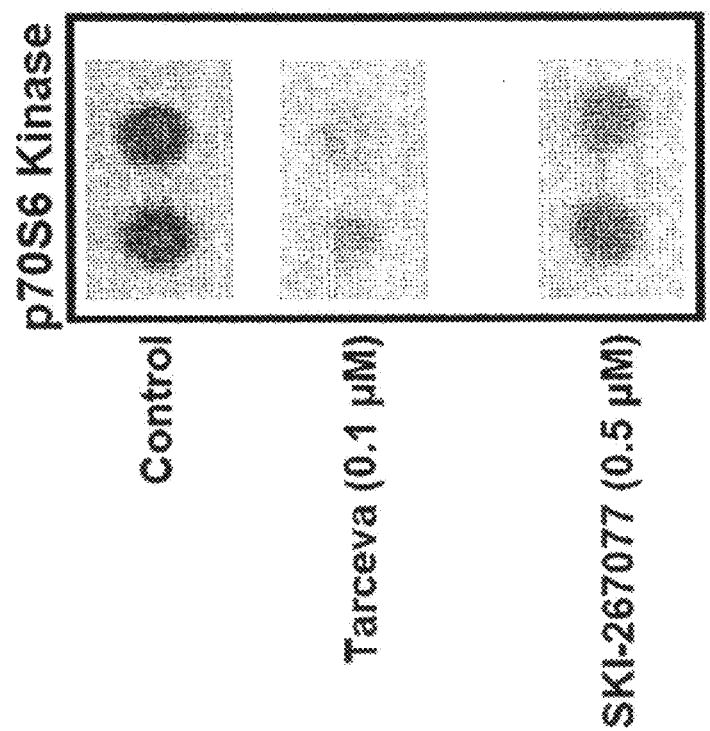
Figure 43C:
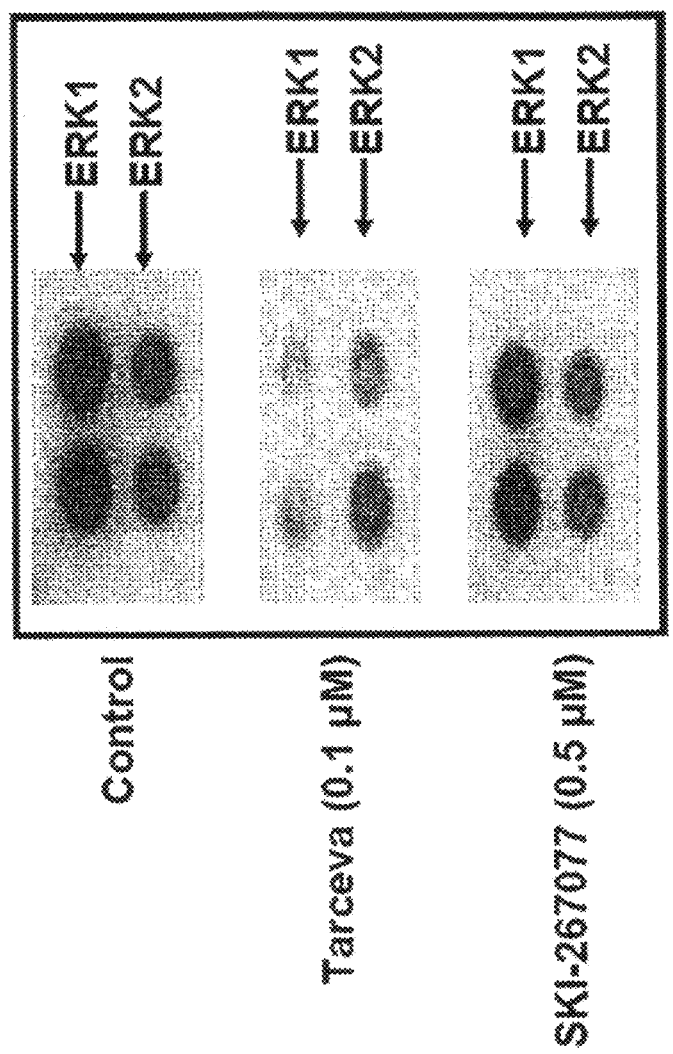

SKI-267077 stimulates the enzymatic activity of caspase 3/7. Treatment of H2030 with SKI-267077 for 48 hours lead to an increase in the activity of caspase 3/7 (FIG. 3).

Example 5

Dose Response Studies

Dose response studies against 34 compounds from the pyridazinone and phenylfuran-carboxamide class were conducted. The 34 compounds were run in a 12 point doubling dilution from 10 uM to 5 nM for IC50 determination against 15 non small cell lung cancer lines representing various EGFR and KRAS mutations (see Table 17). In addition, Tarceva was included in these dose response studies.

TABLE 17

Non Small Cell Lung Cancer Cell Lines

| Cell line | EGFR | KRAS | P53 | PTEN |
|---|---|---|---|---|
| H1118 | L858R | WT | K164X | |
| H820 | T790M/DelE746-A750 | WT | | |
| H1650 | DelE746-A750 | WT | | No protein |
| H1975 | T7980M/L858R | WT | | |
| H3255 | L858R | WT | WT | |
| PC9 | DelE746-A750 | WT | | |
| A549 | WT | G12S | | |
| H23 | WT | G12C | I246M | |
| H358 | WT | G12C | R273H | |
| H460 | WT | Q61H | | |
| H1734 | WT | G13C | | |
| H2030 | WT | G12C | | |
| H2122 | WT | G12C | G262V | WT |

TABLE 17-continued

Non Small Cell Lung Cancer Cell Lines

| Cell line | EGFR | KRAS | P53 | PTEN |
|---|---|---|---|---|
| H2444 | WT | G12V | | |
| HPL1D* | WT | WT | | |

*SV40-immortalized human lung epithelian cells

The dose response studies were done with the following standard procedure. First, the cells were counted and dispensed at 250 cells/well into 384-well microplates with compound. The cells were incubated for 48 hours at 37 C to complete treatment, and then alamar blue was added for an additional 48 hours. Finally, alamar blue reduction was measured and the data was loaded into ORIS, our data screening acquisition platform. Table 18 provides a summary of these experiments.

TABLE 18

Compound Metric Summary of 15 NSCLC Lines ($IC_{50}$ in uM)

| Structure | SKI ID | H1118 | H820 | H1650 | H1975 | H3255 | PC9 | A549 | H23 |
|---|---|---|---|---|---|---|---|---|---|
| 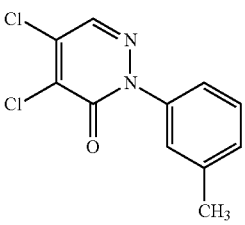 [SMILES: Cc1cccc(-n2ncc(Cl)c(Cl)c2=O)c1] | 104122 | 0.34 | 0.18 | 1.41 | 0.29 | 0.87 | 0.65 | 1.45 | 0.21 |
| 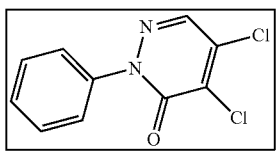 [SMILES: O=c1c(Cl)c(Cl)cnn1-c1ccccc1] | 257014 | 0.45 | 0.24 | 1.64 | 0.36 | 1.50 | 0.83 | 1.68 | 0.26 |
| 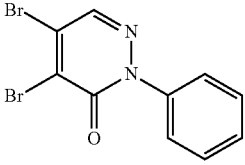 [SMILES: O=c1c(Br)c(Br)cnn1-c1ccccc1] | 257015 | 0.37 | 0.22 | 0.92 | 0.32 | 0.76 | 0.71 | 1.20 | 0.23 |
| 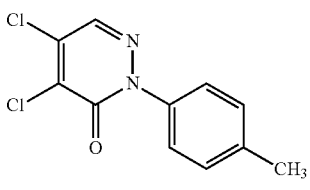 | 257016 | 0.54 | 0.37 | 2.49 | 0.47 | 1.53 | 1.13 | 2.63 | 0.32 |

| Structure | SKI ID | H358 | H460 | H1734 | H2030 | H2122 | H2444 | HPL1D |
|---|---|---|---|---|---|---|---|---|
| 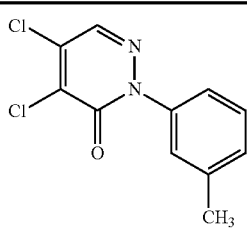 | 104122 | 0.41 | 1.56 | 2.14 | 0.29 | 1.15 | 0.24 | 0.28 |

TABLE 18-continued
Compound Metric Summary of 15 NSCLC Lines (IC$_{50}$ in uM)
| Structure | SKI ID | | | | | | |
|---|---|---|---|---|---|---|---|
| 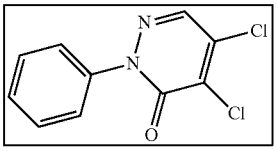 [SMILES: O=c1c(Cl)c(Cl)cnn1-c1ccccc1] | 257014 | 0.68 | 2.01 | 2.28 | 0.41 | 1.16 | 0.34 | 0.38 |
| 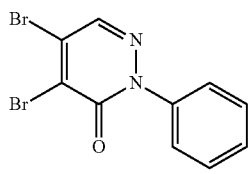 [SMILES: O=c1c(Br)c(Br)cnn1-c1ccccc1] | 257015 | 0.43 | 1.30 | 1.62 | 0.31 | 1.26 | 0.30 | 0.30 |
| 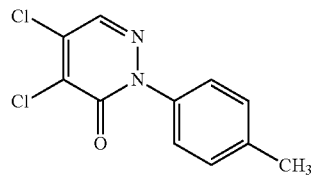 [SMILES: Cc1ccc(-n2ncc(Cl)c(Cl)c2=O)cc1] | 257016 | 0.78 | 2.55 | 3.22 | 0.51 | 2.07 | 0.41 | 0.48 |
| Structure | SKI ID | H1118 | H820 | H1650 | H1975 | H3255 | PC9 | A549 | H23 |
|---|---|---|---|---|---|---|---|---|---|
| 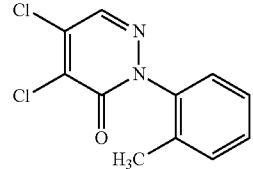 | 257017 | 0.83 | 0.47 | 1.67 | 0.76 | 3.16 | 2.00 | 2.13 | 0.31 |
| 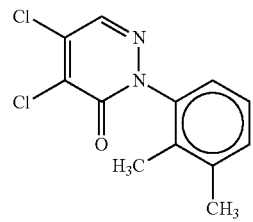 | 257018 | 0.54 | 0.34 | 1.69 | 0.54 | 1.86 | 1.57 | 2.27 | 0.24 |
| 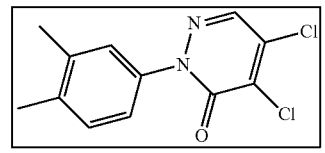 [SMILES: Cc1ccc(-n2ncc(Cl)c(Cl)c2=O)cc1C] | 257019 | 0.94 | 0.67 | 4.15 | 0.89 | 2.01 | 1.98 | 4.20 | 0.69 |
| 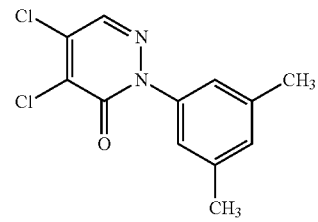 | 257020 | 0.58 | 0.45 | 2.58 | 0.58 | 1.35 | 1.55 | 2.87 | 0.46 |
| Structure | SKI ID | H358 | H460 | H1734 | H2030 | H2122 | H2444 | HPL1D |
|---|---|---|---|---|---|---|---|---|
| 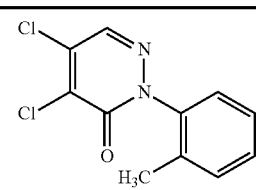 | 257017 | 1.70 | 3.68 | 3.20 | 1.38 | 2.16 | 1.05 | 1.14 |

TABLE 18-continued
Compound Metric Summary of 15 NSCLC Lines (IC$_{50}$ in uM)
| Structure | SKI ID | | | | | | | |
|---|---|---|---|---|---|---|---|---|
| 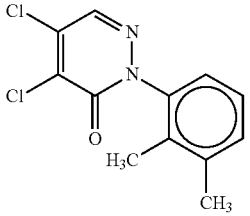 | 257018 | 1.13 | 3.51 | 2.51 | 0.90 | 2.16 | 0.85 | 1.30 |
| 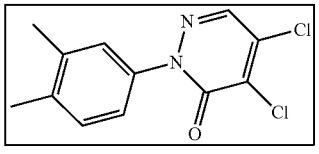 [SMILES: Cc1ccc(-n2ncc(Cl)c(Cl)c2=O)cc1C] | 257019 | 0.79 | 4.09 | 4.65 | 0.80 | 4.38 | 0.82 | 0.62 |
| 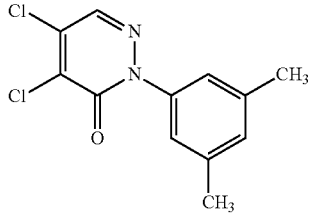 [SMILES: Cc1cc(C)cc(-n2ncc(Cl)c(Cl)c2=O)c1] | 257020 | 0.62 | 2.93 | 2.62 | 0.57 | 2.21 | 0.40 | 0.41 |
| Structure | SKI ID | H1118 | H820 | H1650 | H1975 | H3255 | PC9 | A549 | H23 |
|---|---|---|---|---|---|---|---|---|---|
| 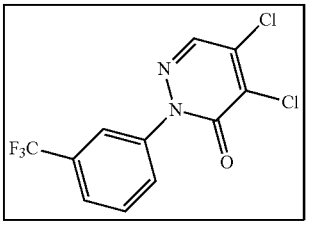 [SMILES: O=c1c(Cl)c(Cl)cnn1-c1cccc(C(F)(F)F)c1] | 176729 | 0.31 | 0.28 | 0.80 | 0.31 | 0.66 | 0.90 | 1.19 | 0.23 |
| 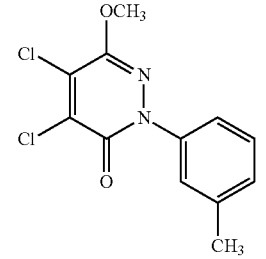 [SMILES: COc1nn(-c2cccc(C)c2)c(=O)c(Cl)c1Cl] | 257028 | 1.10 | 0.77 | 3.04 | 1.18 | 2.38 | 2.40 | 3.76 | 0.68 |
| 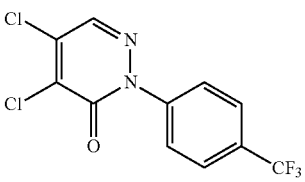 | 267060 | 1.66 | 1.48 | 3.95 | 1.27 | 2.29 | 3.49 | 5.31 | 1.07 |
| 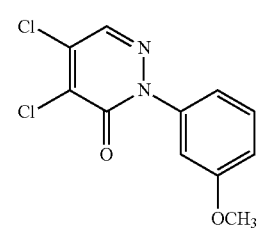 [SMILES: COc1cccc(-n2ncc(Cl)c(Cl)c2=O)c1] | 267061 | 0.40 | 0.26 | 1.96 | 0.31 | 1.20 | 0.85 | 1.76 | 0.28 |

TABLE 18-continued
Compound Metric Summary of 15 NSCLC Lines (IC$_{50}$ in uM)
| Structure | SKI ID | H358 | H460 | H1734 | H2030 | H2122 | H2444 | HPL1D |
|---|---|---|---|---|---|---|---|---|
| 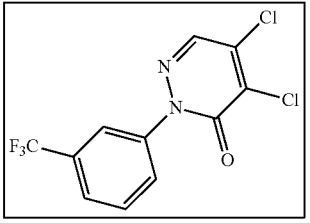 [SMILES: O=c1c(Cl)c(Cl)cnn1-c1cccc(C(F)(F)F)c1] | 176729 | 0.32 | 1.26 | 1.22 | 0.32 | 1.50 | 0.21 | 0.25 |
| 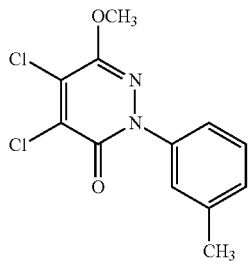 [SMILES: COc1nn(-c2cccc(C)c2)c(=O)c(Cl)c1Cl] | 257028 | 1.83 | 5.23 | 3.87 | 1.79 | 4.04 | 1.17 | 1.93 |
| 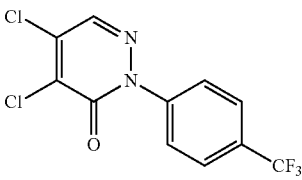 [SMILES: O=c1c(Cl)c(Cl)cnn1-c1ccc(C(F)(F)F)cc1] | 267060 | 1.39 | 4.26 | 5.23 | 1.11 | 6.00 | 1.26 | 0.56 |
| 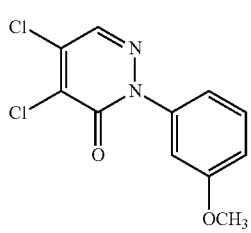 [SMILES: COc1cccc(-n2ncc(Cl)c(Cl)c2=O)c1] | 267061 | 0.46 | 1.63 | 3.04 | 0.36 | 1.20 | 0.37 | 0.29 |
| Structure | SKI ID | H1118 | H820 | H1650 | H1975 | H3255 | PC9 | A549 | H23 |
|---|---|---|---|---|---|---|---|---|---|
| 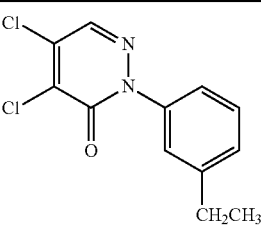 | 267062 | 0.67 | 0.45 | 1.91 | 0.47 | 1.51 | 1.51 | 2.81 | 0.39 |
| 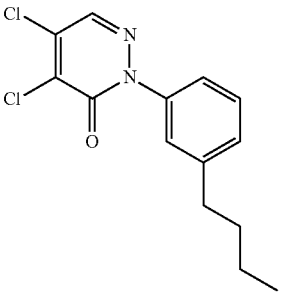 [SMILES: CCCCc1cccc(-n2ncc(Cl)c(Cl)c2=O)c1] | 267063 | 6.41 | 6.24 | >10 | 6.57 | 8.35 | 8.89 | >10 | 5.47 |

TABLE 18-continued
Compound Metric Summary of 15 NSCLC Lines (IC$_{50}$ in uM)
| Structure | SKI ID | | | | | | | |
|---|---|---|---|---|---|---|---|---|
| 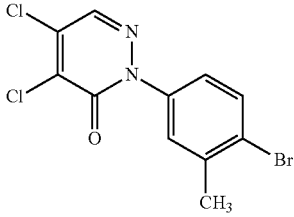 [SMILES: Cc1cc(-n2ncc(Cl)c(Cl)c2=O)ccc1Br] | 267064 | >10 | 6.72 | >10 | 7.58 | >10 | >10 | >10 | 5.75 |
| Structure | SKI ID | H358 | H460 | H1734 | H2030 | H2122 | H2444 | HPL1D |
|---|---|---|---|---|---|---|---|---|
| 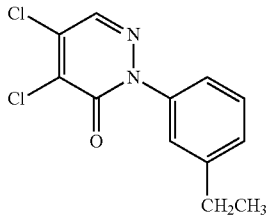 [SMILES: CCc1cccc(-n2ncc(Cl)c(Cl)c2=O)c1] | 267062 | 0.66 | 2.88 | 2.89 | 0.54 | 2.55 | 0.43 | 0.38 |
| 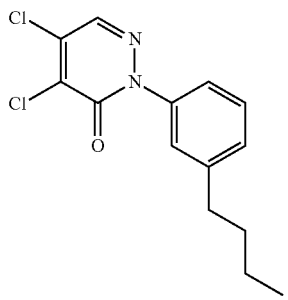 [SMILES: CCCCc1cccc(-n2ncc(Cl)c(Cl)c2=O)c1] | 267063 | 6.66 | >10 | >10 | 6.43 | >10 | 5.28 | 7.04 |
| 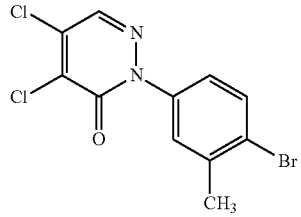 [SMILES: Cc1cc(-n2ncc(Cl)c(Cl)c2=O)ccc1Br] | 267064 | 7.65 | >10 | >10 | 7.80 | >10 | 6.41 | 4.72 |
| Structure | SKI ID | H1118 | H820 | H1650 | H1975 | H3255 | PC9 | A549 | H23 |
|---|---|---|---|---|---|---|---|---|---|
| 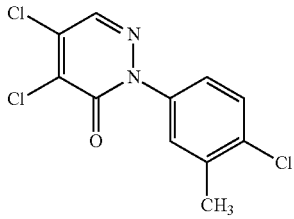 [SMILES: Cc1cc(-n2ncc(Cl)c(Cl)c2=O)ccc1Cl] | 267065 | >10 | >10 | >10 | >10 | >10 | >10 | >10 | 6.96 |
| 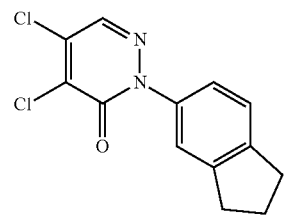 [SMILES: O=c1c(Cl)c(Cl)cnn1-c1ccc2c(c1)CCC2] | 267066 | 2.73 | 2.80 | >10 | 2.23 | 4.61 | 5.87 | 7.52 | 2.04 |

TABLE 18-continued

Compound Metric Summary of 15 NSCLC Lines (IC$_{50}$ in uM)

| Structure | SKI ID | | | | | | | |
|---|---|---|---|---|---|---|---|---|
| (4,5-dichloropyridazinone-N-(2-methylbenzothiazol-5-yl)) | 267067 | >10 | 8.25 | >10 | >10 | >10 | >10 | >10 | 5.68 |
| (2,3-dihydrobenzodioxin-6-yl dichloropyridazinone) | 267068 | 0.48 | 0.32 | 2.26 | 0.37 | 1.23 | 0.88 | 1.93 | 0.29 |

| Structure | SKI ID | H358 | H460 | H1734 | H2030 | H2122 | H2444 | HPL1D |
|---|---|---|---|---|---|---|---|---|
| (4,5-dichloro-N-(4-chloro-3-methylphenyl)pyridazinone) | 267065 | >10 | >10 | >10 | >10 | >10 | 6.37 | 6.66 |
| (4,5-dichloro-N-(indan-5-yl)pyridazinone) | 267066 | 2.81 | 6.56 | 8.85 | 2.34 | 8.72 | 1.53 | 1.66 |
| (4,5-dichloro-N-(2-methylbenzothiazol-5-yl)pyridazinone) | 267067 | >10 | >10 | >10 | 9.19 | >10 | 6.92 | 7.01 |
| (2,3-dihydrobenzodioxin-6-yl dichloropyridazinone) | 267068 | 0.78 | 1.97 | 2.83 | 0.47 | 1.59 | 0.41 | 0.42 |

| Structure | SKI ID | H1118 | H820 | H1650 | H1975 | H3255 | PC9 | A549 | H23 |
|---|---|---|---|---|---|---|---|---|---|
| (4,5-dichloro-N-benzylpyridazinone) | 267069 | 3.21 | 2.57 | >10 | 3.60 | >10 | 6.21 | 7.39 | 2.53 |
| (3,4,5-trichloro-N-(3-chloro-4-methylphenyl)pyridazinone) | 267070 | >10 | >10 | >10 | >10 | >10 | >10 | >10 | >10 |

TABLE 18-continued

Compound Metric Summary of 15 NSCLC Lines (IC$_{50}$ in uM)

| Structure | SKI ID | | | | | | | |
|---|---|---|---|---|---|---|---|---|
| (3-methylphenyl-4,5-dibromopyridazinone) | 267071 | 0.41 | 0.27 | 1.10 | 0.36 | 0.76 | 0.86 | 1.62 | 0.26 |
| (3-trifluoromethylphenyl-4,5-dibromopyridazinone) | 267072 | 1.21 | 0.82 | 2.09 | 0.93 | 1.64 | 2.59 | 3.42 | 0.84 |
| (2-pyridyl-4,5-dibromopyridazinone) | 267073 | 0.10 | 0.10 | 0.79 | 0.16 | 0.45 | 0.42 | 0.31 | 0.07 |

| Structure | SKI ID | H358 | H460 | H1734 | H2030 | H2122 | H2444 | HPL1D |
|---|---|---|---|---|---|---|---|---|
| (benzyl-4,5-dichloropyridazinone) | 267069 | 6.66 | >10 | >10 | 4.01 | 9.04 | 4.13 | 5.25 |
| (3-chloro-4-methylphenyl-4,5-dichloropyridazinone) | 267070 | >10 | >10 | >10 | >10 | >10 | >10 | >10 |
| (3-methylphenyl-4,5-dibromopyridazinone) | 267071 | 0.40 | 1.43 | 1.72 | 0.37 | 1.26 | 0.31 | 0.24 |
| (3-trifluoromethylphenyl-4,5-dibromopyridazinone) | 267072 | 0.85 | 2.76 | 3.19 | 0.85 | 4.61 | 1.05 | 0.51 |
| (2-pyridyl-4,5-dibromopyridazinone) | 267073 | 0.14 | 0.42 | 1.23 | 0.12 | 0.78 | 0.13 | 0.11 |

| Structure | SKI ID | H1118 | H820 | H1650 | H1975 | H3255 | PC9 | A549 | H23 |
|---|---|---|---|---|---|---|---|---|---|
| (2,4-dichlorophenyl-4,5-dichloropyridazinone) | 267077 | 3.73 | 2.68 | >10 | 2.08 | 8.75 | >10 | >10 | 1.72 |

TABLE 18-continued
Compound Metric Summary of 15 NSCLC Lines (IC$_{50}$ in uM)
| Structure | SKI ID | | | | | | | |
|---|---|---|---|---|---|---|---|---|
| 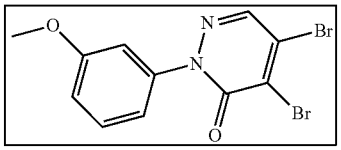 [SMILES: COc1cccc(-n2ncc(Br)c(Br)c2=O)c1] | 267083 | 0.27 | 0.20 | 1.08 | 0.24 | 0.65 | 0.74 | 1.07 | 0.21 |
| 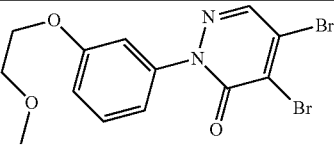 | 267084 | 0.23 | 0.18 | 1.04 | 0.21 | 0.71 | 0.68 | 0.84 | 0.17 |
| 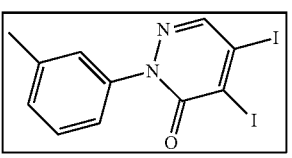 [SMILES: Cc1cccc(-n2ncc(I)c(I)c2=O)c1] | 267085 | 1.03 | 0.41 | 3.16 | 0.80 | 2.13 | 2.24 | 3.27 | 0.72 |
| 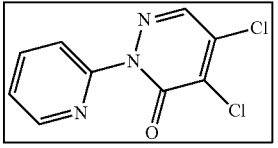 [SMILES: O=c1c(Cl)c(Cl)cnn1-c1ccccn1] | 267090 | 0.15 | 0.41 | 1.42 | 0.16 | 0.70 | 0.47 | 0.54 | 0.08 |
| Structure | SKI ID | H358 | H460 | H1734 | H2030 | H2122 | H2444 | HPL1D |
|---|---|---|---|---|---|---|---|---|
| 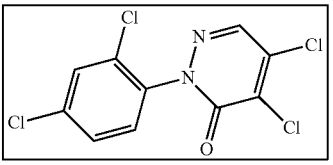 [SMILES: O=c1c(Cl)c(Cl)cnn1-c1ccc(Cl)cc1Cl] | 267077 | 3.22 | >10 | >10 | 3.55 | >10 | 4.68 | 4.95 |
| 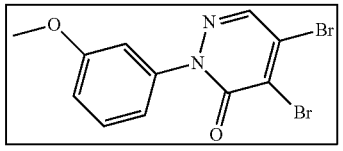 [SMILES: COc1cccc(-n2ncc(Br)c(Br)c2=O)c1] | 267083 | 0.30 | 0.91 | 1.36 | 0.26 | 1.15 | 0.28 | 0.22 |
|  | 267084 | 0.27 | 0.89 | 1.50 | 0.22 | 1.12 | 0.23 | 0.18 |
| 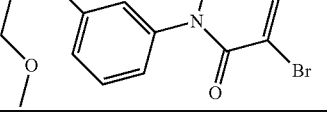 | 267085 | 1.33 | 3.49 | 2.99 | 0.81 | 2.34 | 0.53 | 0.68 |
| 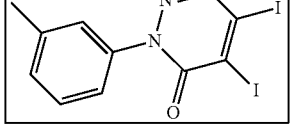 | 267090 | 0.21 | 0.79 | 2.47 | 0.17 | 0.89 | 0.22 | 0.17 |

TABLE 18-continued
Compound Metric Summary of 15 NSCLC Lines (IC$_{50}$ in uM)
| Structure | SKI ID | H1118 | H820 | H1650 | H1975 | H3255 | PC9 | A549 | H23 |
|---|---|---|---|---|---|---|---|---|---|
| 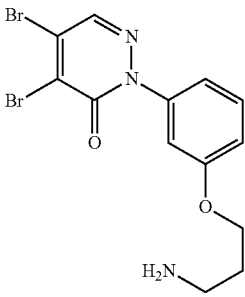 [SMILES: NCCCOc1cccc(-n2ncc(Br)c(Br)c2=O)c1] | 273634 | 0.57 | 0.29 | 0.51 | 0.41 | 0.99 | 0.97 | 1.65 | 0.38 |
| 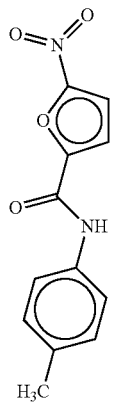 | 98697 | 0.56 | 3.53 | 0.60 | 4.57 | 2.72 | 2.17 | 1.81 | 0.91 |
| Structure | SKI ID | H358 | H460 | H1734 | H2030 | H2122 | H2444 | HPL1D |
|---|---|---|---|---|---|---|---|---|
| 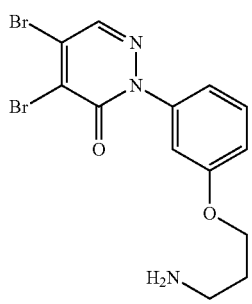 [SMILES: NCCCOc1cccc(-n2ncc(Br)c(Br)c2=O)c1] | 273634 | 0.69 | 1.47 | 1.23 | 0.47 | 1.42 | 0.40 | 0.35 |
| 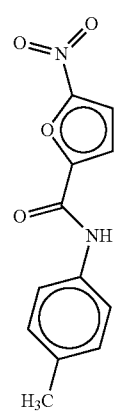 | 98697 | 1.20 | 2.20 | 4.42 | 1.18 | 5.20 | 4.79 | >10 |

TABLE 18-continued

Compound Metric Summary of 15 NSCLC Lines (IC$_{50}$ in uM)

| Structure | SKI ID | H1118 | H820 | H1650 | H1975 | H3255 | PC9 | A549 | H23 |
|---|---|---|---|---|---|---|---|---|---|
| (5-nitrofuran-2-carboxamide, 4-chlorophenyl) | 98698 | 0.53 | 1.83 | 0.47 | 2.63 | 1.77 | 1.58 | 1.33 | 0.60 |
| (5-nitrofuran-2-carboxamide, 3-methylphenyl) | 71762 | 0.38 | 3.61 | 0.63 | 4.23 | 2.41 | 1.89 | 1.46 | 0.83 |

| Structure | SKI ID | H358 | H460 | H1734 | H2030 | H2122 | H2444 | HPL1D |
|---|---|---|---|---|---|---|---|---|
| (5-nitrofuran-2-carboxamide, 4-chlorophenyl) | 98698 | 0.81 | 1.62 | 3.47 | 0.91 | 3.09 | 2.43 | >10 |
| (5-nitrofuran-2-carboxamide, 3-methylphenyl) | 71762 | 1.27 | 1.85 | 4.88 | 0.99 | 4.83 | 3.80 | >10 |

TABLE 18-continued

Compound Metric Summary of 15 NSCLC Lines (IC$_{50}$ in uM)

| Structure | SKI ID | H1118 | H820 | H1650 | H1975 | H3255 | PC9 | A549 | H23 |
|---|---|---|---|---|---|---|---|---|---|
| (5-nitrofuran-2-carboxamide with 3-chloro-4-fluoroaniline) | 87200 | 4.33 | >10 | 7.49 | >10 | >10 | 8.67 | >10 | 4.55 |
| Tarceva | 267080 | >10 | >10 | >10 | >10 | 0.03 | >10 | >10 | >10 |

| Structure | SKI ID | H358 | H460 | H1734 | H2030 | H2122 | H2444 | HPL1D |
|---|---|---|---|---|---|---|---|---|
| (5-nitrofuran-2-carboxamide with 3-chloro-4-fluoroaniline) | 87200 | 7.17 | >10 | >10 | 8.51 | >10 | >10 | >10 |
| Tarceva | 267080 | >10 | >10 | >10 | >10 | >10 | >10 | >10 |

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A method of inhibiting proliferation of a tumor cell carrying or expressing a cancer-associated epidermal growth factor receptor (EGFR) and/or Kirsten rat sarcoma viral oncogene homolog (KRAS) mutation comprising contacting the cell with a compound having the formula:

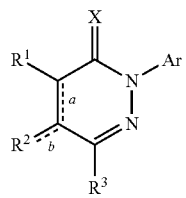

wherein
X is oxygen or $NR^x$;
$R^x$ is hydrogen;
===== designates a single or double bond represented by a and b;
a is a double bond;
b is a single bond;
$R^1$ is selected from hydrogen, aliphaticoxy, aliphaticthioxy optionally substituted with aryl or heteroaryl, thio, amino, heterocyclyl, heteroaryl, amido, cyano, and halo;
$R^2$ is selected from hydrogen, optionally substituted aliphatic, optionally substituted aliphaticoxy, optionally substituted aliphaticthioxy, heterocyclyl, optionally substituted heteroaryl, halo, and optionally substituted arylthioxy; wherein an optionally substituted group is optionally substituted with aliphatic, aliphaticoxy, aryloxy, hydroxyaliphatic, aryl, heteroaryl, acyl, or amido;
$R^3$ is selected from hydrogen, aliphatic, optionally substituted aliphaticoxy, optionally substituted acyl, optionally substituted acyloxy, and halo, wherein an optionally substituted group is optionally substituted with heteroaryl, aryl or acyl; and
Ar is selected from phenyl, indanyl, benzyl, benzothiazolyl, 1,4-benzodioxanyl and pyridinyl, each optionally and independently substituted with aliphaticoxy, aliphatic, cyano, nitro, perfluoroaliphatic, or halo;
or a pharmaceutically acceptable salt thereof.

2. The method according to claim 1, wherein the cancer-associated EGFR and/or KRAS mutation is selected from delE746-A750, T790M/L858R, L858R, G12C and G13C.

3. The method according to claim 2, wherein the cancer-associated EGFR mutation is selected from delE746-A750, T790M/L858R and L858R.

4. The method according to claim 2, wherein the cancer-associated KRAS mutation is selected from G12C and G13C.

5. The method according to claim 1, wherein the compound is applied to a tumor cell which is resistant to erlotinib.

6. The method according to claim 1, wherein the compound is applied to a tumor cell which is resistant to gefitinib.

7. The method according to claim 1, wherein the compound is applied to a tumor cell which is resistant to both erlotinib and gefitinib.

8. The method according to claim 1, wherein $R^1$ and $R^2$ are the same, and $R^3$ is selected from hydrogen, halo, and acyl.

9. The method according to claim 8, wherein $R^1$ and $R^2$ are both hydrogen.

10. The method according to claim 8, wherein $R^1$ and $R^2$ are both chloro, bromo, iodo, or fluoro.

11. The method according to claim 8, wherein $R^1$ and $R^2$ are both aliphaticthioxy optionally substituted with heteroaryl or aryl.

12. The method according to claim 1, wherein $R^1$ and $R^2$ are different, and $R^3$ is selected from hydrogen, halo, and acyl.

13. The method according to claim 12, wherein $R^1$ and $R^2$ are independently selected from hydrogen, aliphaticoxy, aliphaticthioxy optionally substituted with heteroaryl or aryl, heterocyclyl, heteroaryl, and halo.

14. The method according to claim 1, wherein Ar is selected from:

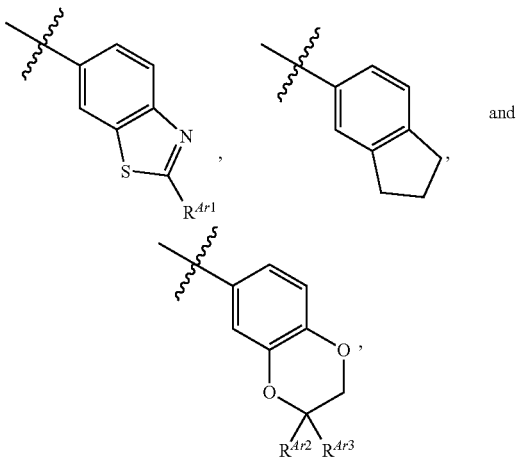

wherein $R^{Ar1}$, $R^{Ar2}$, and $R^{Ar3}$ are independently selected from hydrogen, methyl, and ethyl.

15. The method according to claim 1, wherein Ar is selected from:

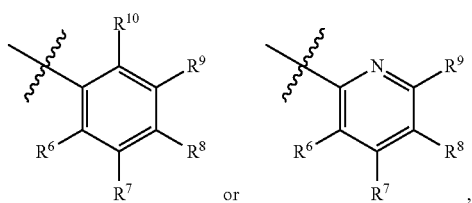

wherein each $R^6$, $R^7$, $R^8$, $R^9$, and $R^{10}$ is independently selected from hydrogen, aliphaticoxy, aliphatic, cyano, nitro, perfluoroaliphatic, and halo.

16. The method according to claim 15, wherein Ar is:

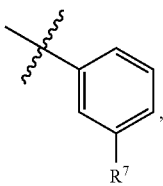

wherein $R^7$ is selected from aliphaticoxy, aliphatic, perfluoroaliphatic, and halo.

17. The method according to claim 16, wherein $R^7$ is selected from methoxy, methyl, ethyl, n-propyl, n-butyl, trifluoromethyl, bromo, chloro, and iodo.

18. The method according to claim 15, wherein Ar is:

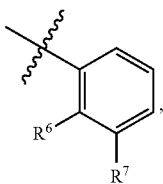

wherein $R^6$ and $R^7$ are both aliphatic.

19. The method according to claim 15, wherein Ar is:

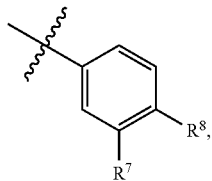

wherein $R^7$ and $R^8$ are independently selected from aliphatic, perfluoroaliphatic, and halo.

20. The method according to claim 19, wherein $R^7$ is selected from methyl, ethyl, n-propyl, n-butyl, trifluoromethyl, bromo, chloro, and iodo, and $R^8$ is selected from methyl, ethyl, n-propyl, n-butyl, trifluoromethyl, bromo, chloro, and iodo.

21. The method according to claim 15, wherein Ar is:

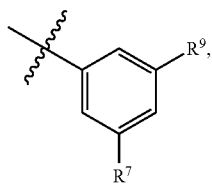

wherein $R^7$ and $R^9$ are both aliphatic.

22. The method according to claim 21, wherein $R^7$ and $R^9$ are independently selected from methyl, ethyl, n-propyl, and n-butyl.

23. The method according to claim 15, wherein $R^7$ is not hydrogen.

24. The method according to claim 15, wherein when $R^8$ is not hydrogen, $R^7$ is not hydrogen.

25. The method according to claim 15, wherein when $R^6$ is not hydrogen, $R^8$ is hydrogen.

26. The method according to claim 1, wherein Ar is selected from benzothiazolyl, 1,4-benzodioxanyl, and pyridinyl.

27. The method according to claim 26, wherein Ar is selected from benzothiazolyl and pyridinyl.

28. The method according to claim 27, wherein Ar is pyridinyl.

29. The method according to claim 1, wherein Ar is phenyl.

30. The method according to claim 1, wherein the compound is not 4,5-dichloro-2-m-tolyl-2H-pyridazin-3-one.

31. The method according to claim 1, wherein X is oxygen.

32. The method according to claim 31, wherein the compound is selected from:

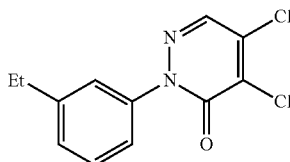

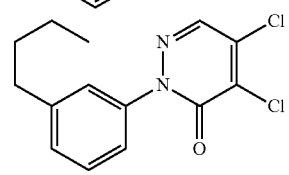

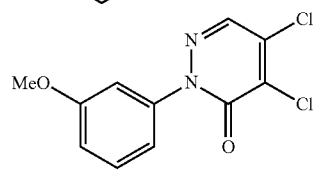

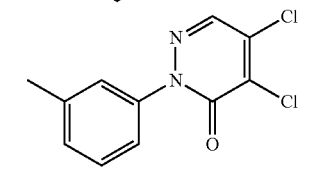

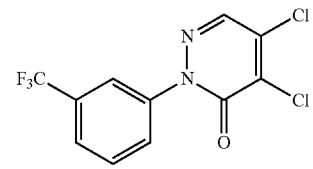

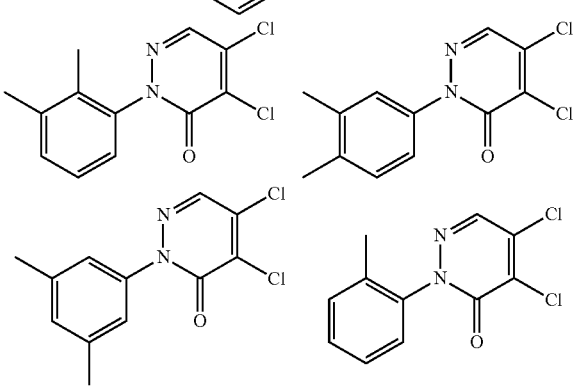

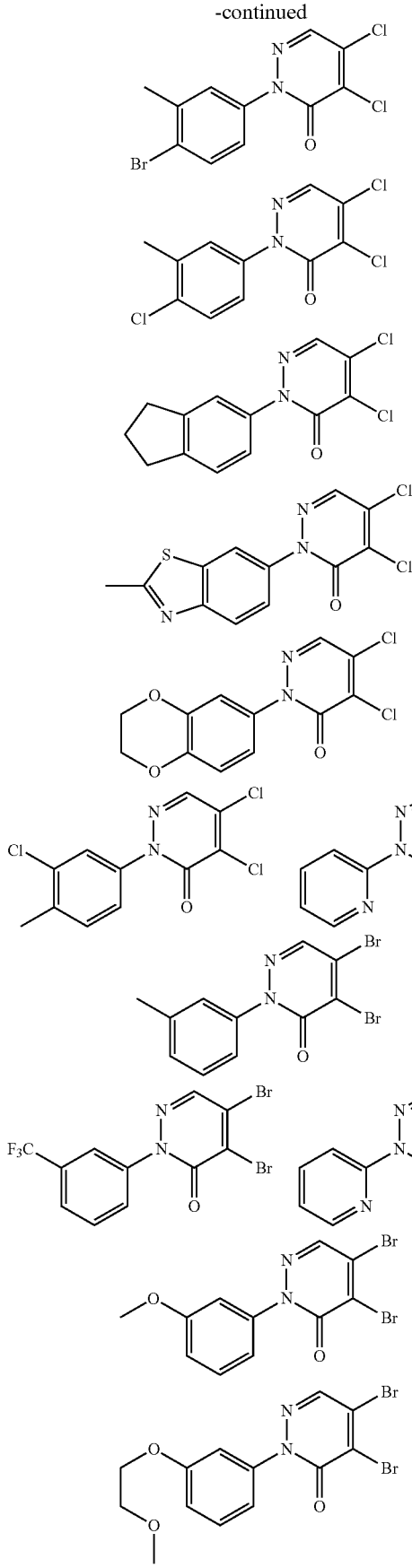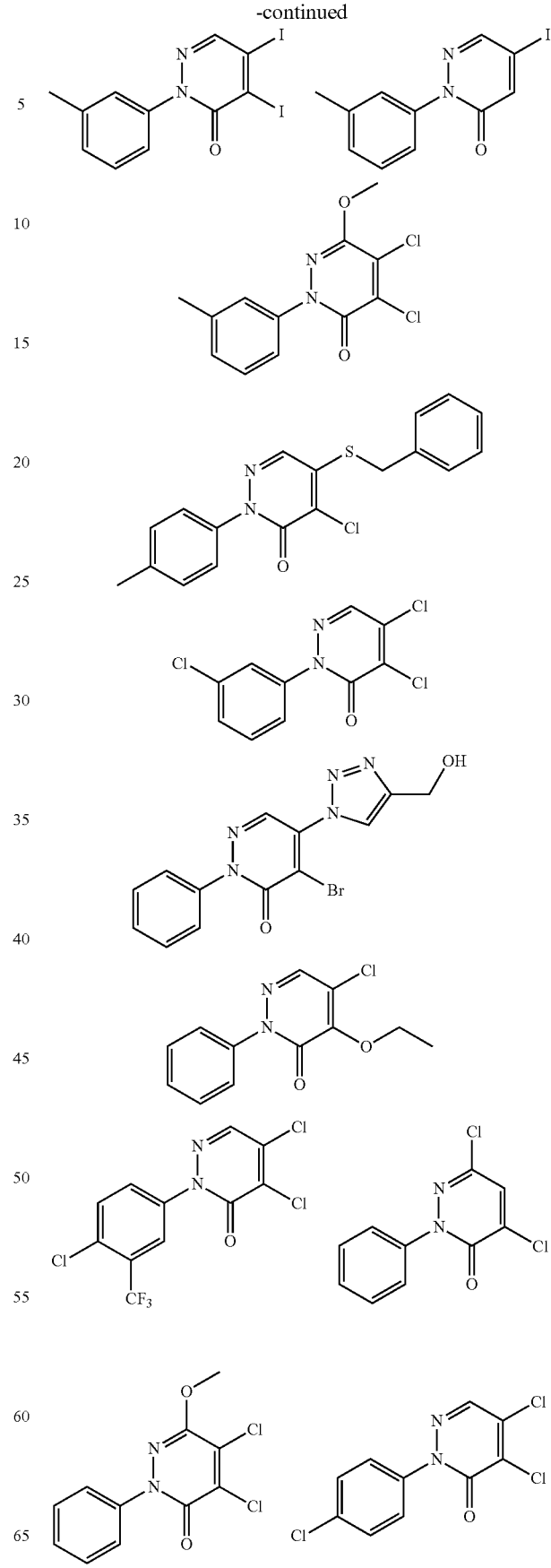

231
-continued
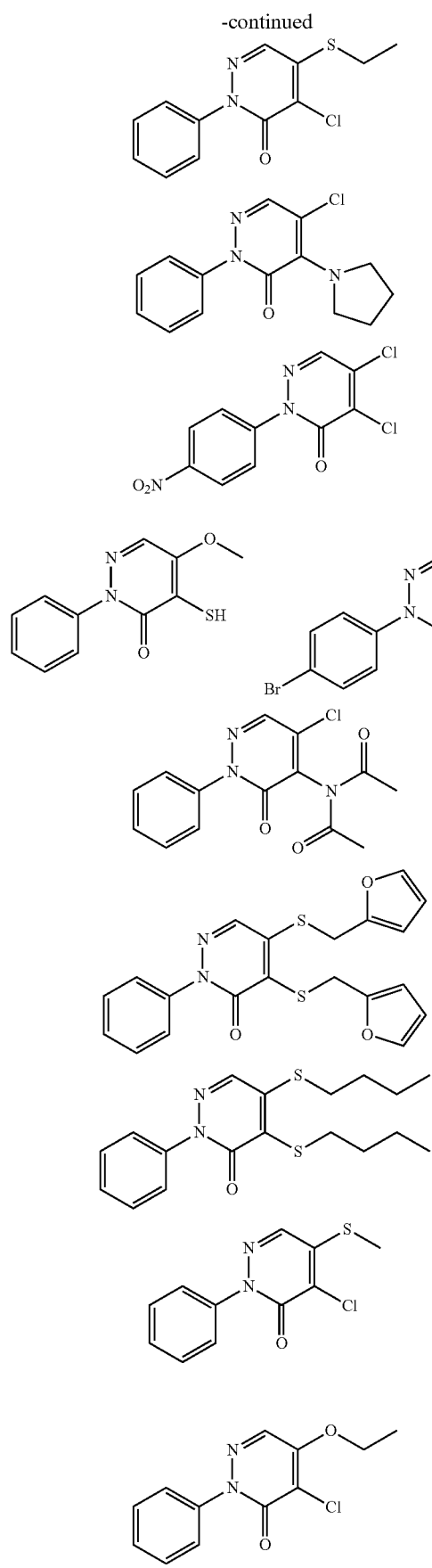
232
-continued
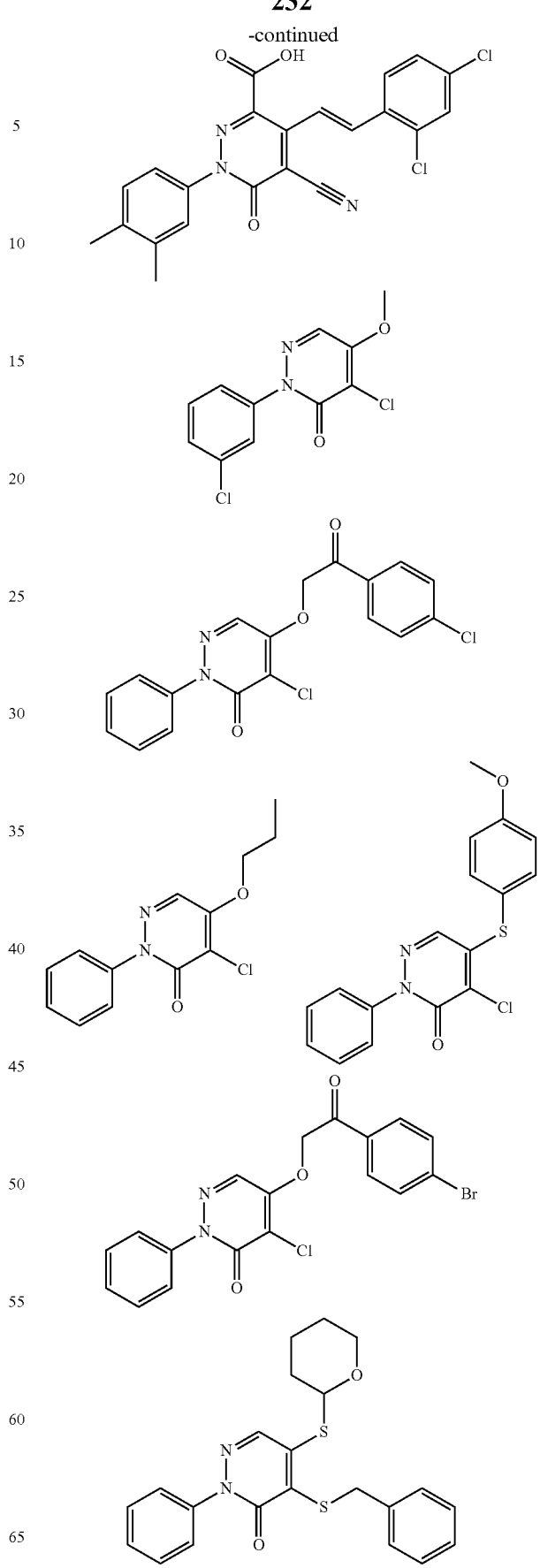

233
-continued
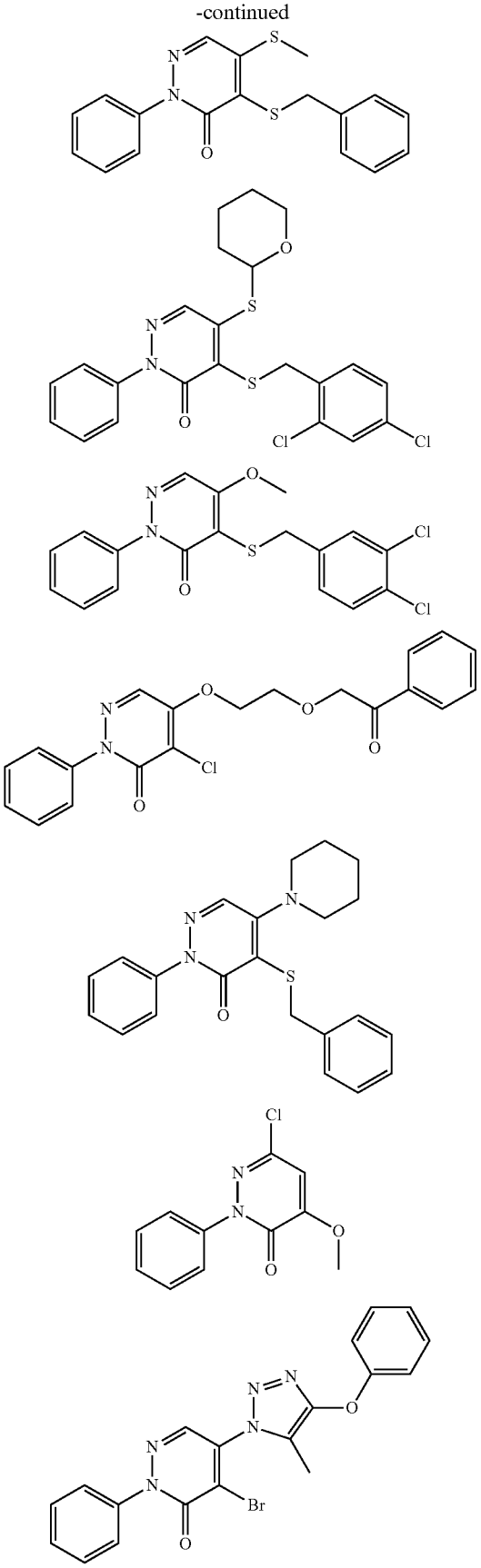
234
-continued
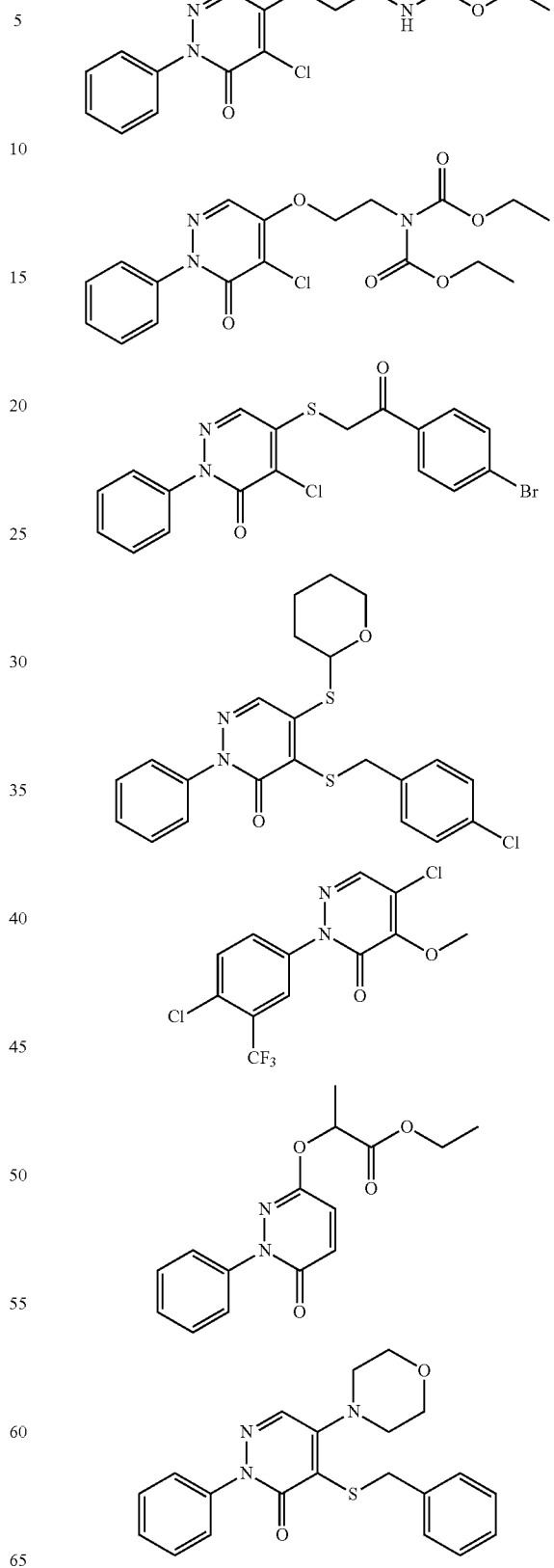

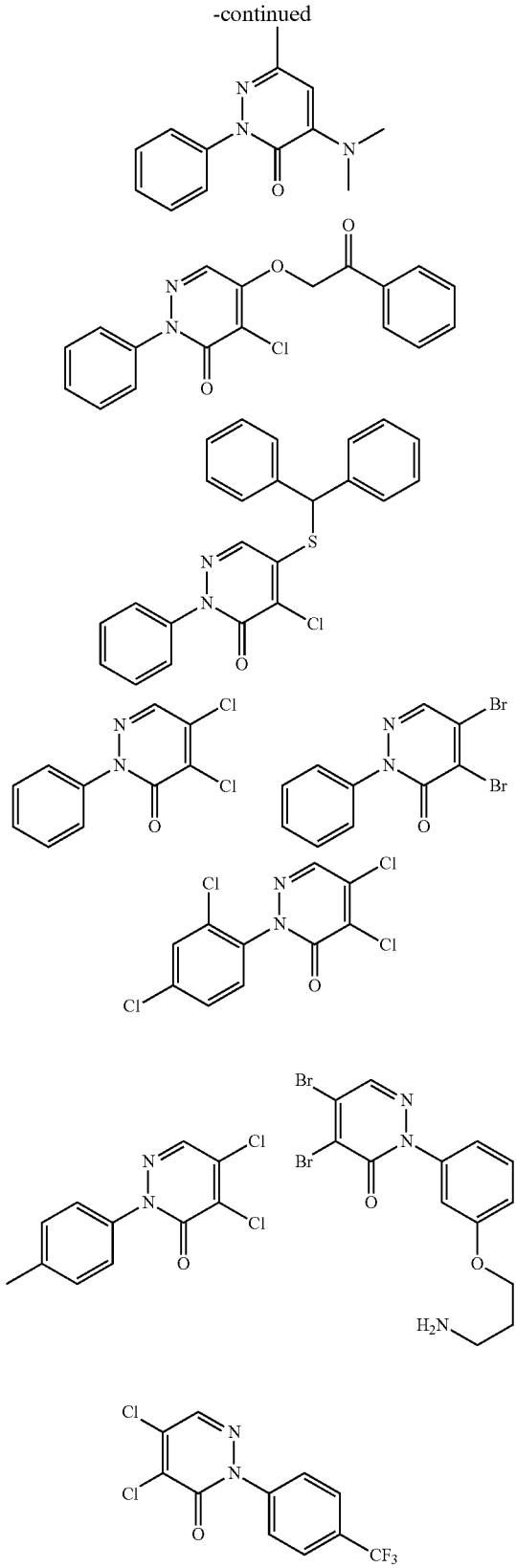
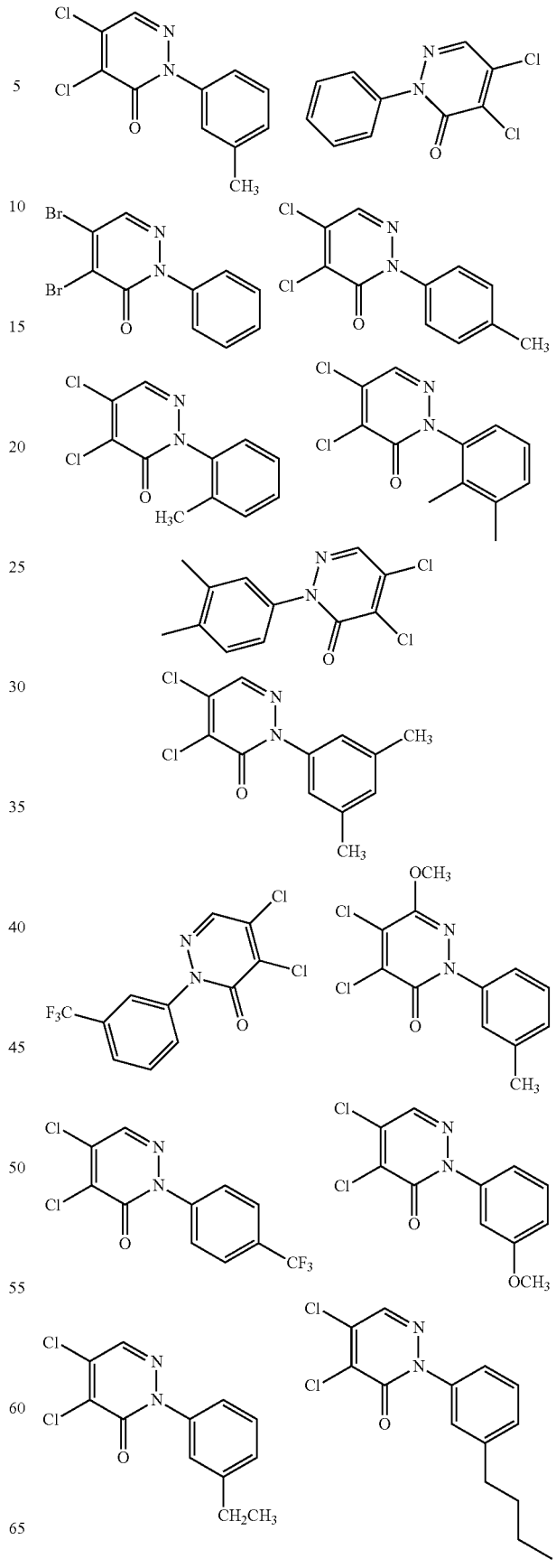
or a pharmaceutically acceptable salt thereof.
33. The method according to claim 32, wherein the compound is selected from:

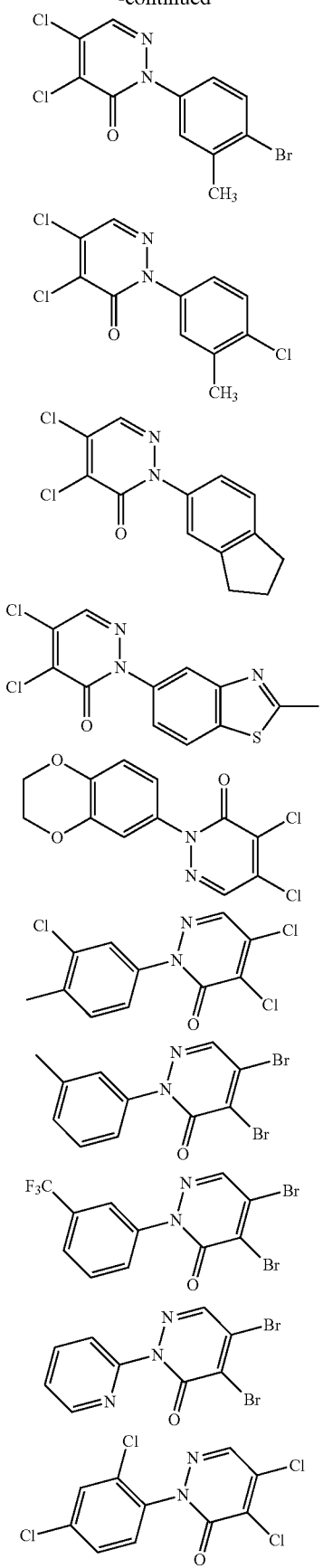
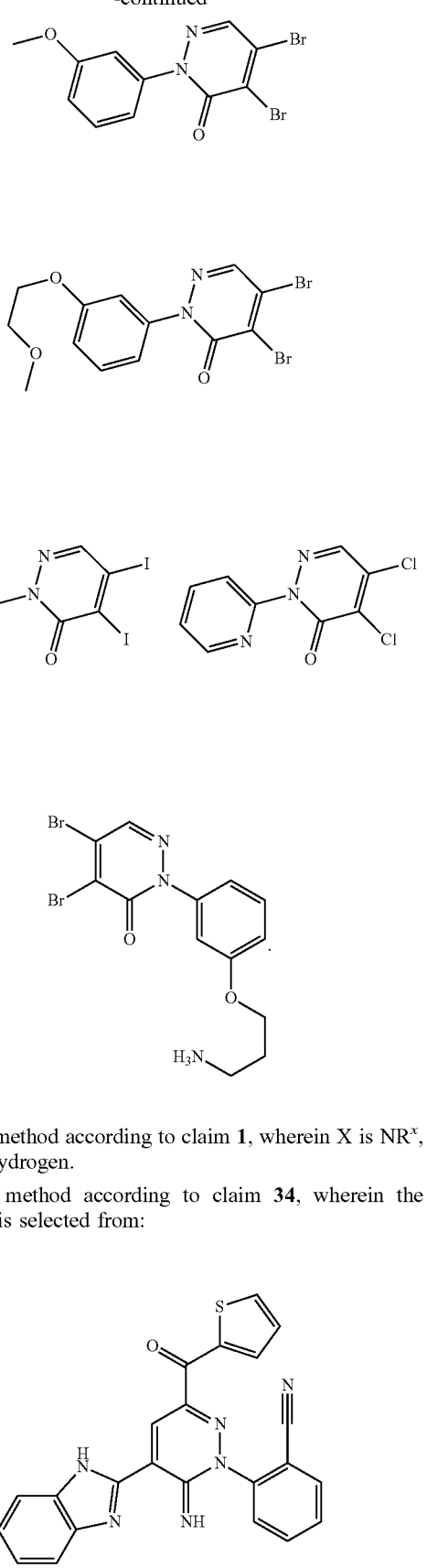
34. The method according to claim 1, wherein X is NR$^x$, and R$^x$ is hydrogen.
35. The method according to claim 34, wherein the compound is selected from:
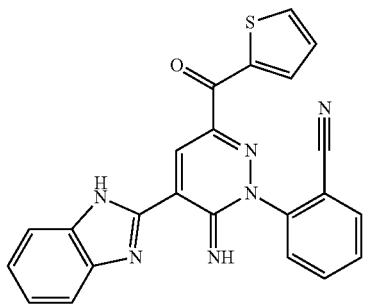

-continued
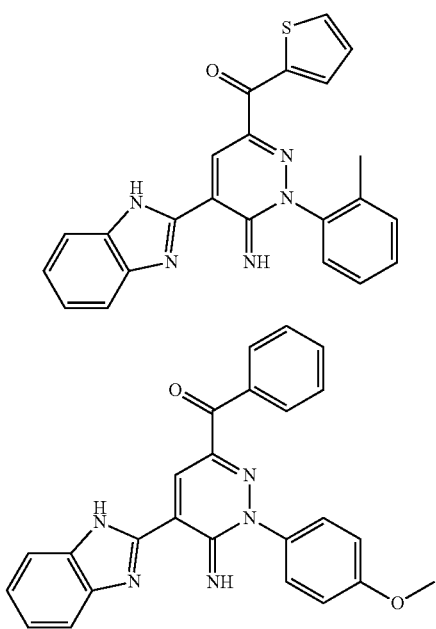
-continued
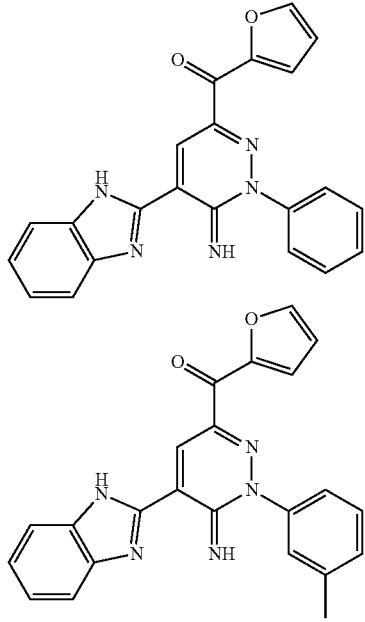
or a pharmaceutically acceptable salt thereof.
* * * * *